US011666653B2

United States Patent
Manoharan et al.

(10) Patent No.: US 11,666,653 B2
(45) Date of Patent: *Jun. 6, 2023

(54) CARBOHYDRATE CONJUGATES AS DELIVERY AGENTS FOR OLIGONUCLEOTIDES

(71) Applicant: ALNYLAM PHARMACEUTICALS, INC., Cambridge, MA (US)

(72) Inventors: Muthiah Manoharan, Cambridge, MA (US); Kallanthottathil G. Rajeev, Cambridge, MA (US); Jayaprakash K. Nair, Cambridge, MA (US); Martin Maier, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/533,559

(22) Filed: Nov. 23, 2021

(65) Prior Publication Data

US 2022/0143189 A1 May 12, 2022

Related U.S. Application Data

(63) Continuation of application No. 17/368,246, filed on Jul. 6, 2021, which is a continuation of application No. 16/861,494, filed on Apr. 29, 2020, now Pat. No. 11,110,174, which is a continuation of application No. 16/196,628, filed on Nov. 20, 2018, now Pat. No. 10,806,791, which is a continuation of application No. 15/817,473, filed on Nov. 20, 2017, now abandoned, which is a continuation of application No. 14/835,272, filed on Aug. 25, 2015, now Pat. No. 9,867,882, which is a continuation of application No. 14/329,540, filed on Jul. 11, 2014, now Pat. No. 9,370,581, which is a continuation of application No. 13/693,478, filed on Dec. 4, 2012, now Pat. No. 8,828,956, which is a continuation of application No. 13/326,203, filed on Dec. 14, 2011, now Pat. No. 8,450,467, which is a continuation of application No. 12/328,528, filed on Dec. 4, 2008, now Pat. No. 8,106,022.

(60) Provisional application No. 61/097,261, filed on Sep. 16, 2008, provisional application No. 61/091,093, filed on Aug. 22, 2008, provisional application No. 61/127,751, filed on May 14, 2008, provisional application No. 61/013,597, filed on Dec. 13, 2007, provisional application No. 60/992,309, filed on Dec. 4, 2007.

(51) Int. Cl.

| A61K 47/28 | (2006.01) |
|---|---|
| A61K 31/7004 | (2006.01) |
| A61K 31/7052 | (2006.01) |
| A61K 31/70 | (2006.01) |
| A61K 47/60 | (2017.01) |
| A61K 47/54 | (2017.01) |
| C07H 21/02 | (2006.01) |
| A61K 31/7088 | (2006.01) |
| A61K 31/713 | (2006.01) |
| A61K 47/16 | (2006.01) |
| A61K 47/22 | (2006.01) |
| A61K 48/00 | (2006.01) |

(52) U.S. Cl.
CPC .............. *A61K 47/28* (2013.01); *A61K 31/70* (2013.01); *A61K 31/7004* (2013.01); *A61K 31/7052* (2013.01); *A61K 31/7088* (2013.01); *A61K 31/713* (2013.01); *A61K 47/16* (2013.01); *A61K 47/22* (2013.01); *A61K 47/543* (2017.08); *A61K 47/549* (2017.08); *A61K 47/60* (2017.08); *C07H 21/02* (2013.01); *A61K 48/00* (2013.01); *Y02A 50/30* (2018.01); *Y02P 20/55* (2015.11)

(58) Field of Classification Search
CPC ..... A61K 47/28; A61K 47/543; A61K 47/549
See application file for complete search history.

(56) References Cited

U.S. PATENT DOCUMENTS

| 5,994,517 A | 11/1999 | Ts'o et al. |
|---|---|---|
| 6,906,182 B2 * | 6/2005 | Ts'o ..................... A61P 35/00 |
| | | 536/23.1 |
| 7,109,165 B2 | 9/2006 | Matulic-Adamic et al. |
| 7,491,805 B2 | 2/2009 | Vargeese et al. |
| 7,626,014 B2 | 12/2009 | Manoharan et al. |

(Continued)

FOREIGN PATENT DOCUMENTS

| EP | 0957107 A1 | 11/1999 |
|---|---|---|
| WO | 1990012096 A1 | 10/1990 |

(Continued)

OTHER PUBLICATIONS

Delaney; Antimicrobial agents and Chemotherapy; Sep. 2002, p. 3057-3060.*

(Continued)

*Primary Examiner* — Pancham Bakshi
(74) *Attorney, Agent, or Firm* — Jeffrey N. Townes; Cozen O'Connor

(57) ABSTRACT

The present invention provides a modified RNAi agent comprising a sense strand and an antisense strand, wherein the antisense strand targets an HBV mRNA; all of the nucleotide sugars of the RNAi agent are 2'-modified; and at least one of the sense and antisense strands is conjugated to at least one targeting ligand that comprises two or more building blocks connected to a biantennary or triantennary branched linker, optionally via one or more linking groups.

22 Claims, 44 Drawing Sheets

Specification includes a Sequence Listing.

(56) References Cited

U.S. PATENT DOCUMENTS

| | | | |
|---|---|---|---|
| 8,106,022 B2* | 1/2012 | Manoharan | A61P 35/00 536/18.7 |
| 8,450,467 B2* | 5/2013 | Manoharan | A61K 47/60 536/18.7 |
| 8,828,956 B2* | 9/2014 | Manoharan | A61K 47/28 536/23.1 |
| 9,370,581 B2* | 6/2016 | Manoharan | A61K 47/56 |
| 9,867,882 B2* | 1/2018 | Manoharan | A61K 31/70 |
| 10,806,791 B2* | 10/2020 | Manoharan | A61K 31/7004 |
| 2002/0086356 A1 | 7/2002 | Tuschl et al. | |
| 2003/0148928 A1 | 8/2003 | Beigelman et al. | |
| 2004/0110296 A1 | 6/2004 | Vargeese et al. | |
| 2004/0259247 A1 | 12/2004 | Tuschl et al. | |
| 2006/0148740 A1 | 7/2006 | Platenburg | |
| 2009/0325297 A1 | 12/2009 | Tian et al. | |

FOREIGN PATENT DOCUMENTS

| | | |
|---|---|---|
| WO | 1999052932 A1 | 10/1999 |
| WO | 1999065925 A1 | 12/1999 |
| WO | 2000044914 A1 | 8/2000 |
| WO | 2002085908 A1 | 10/2002 |
| WO | 2002094185 A2 | 11/2002 |
| WO | 2004024757 A2 | 3/2004 |
| WO | 2004080406 A2 | 9/2004 |
| WO | 2004090108 A2 | 10/2004 |
| WO | 2004094595 A2 | 11/2004 |
| WO | 2006020768 A2 | 2/2006 |
| WO | 2006078278 A2 | 7/2006 |

OTHER PUBLICATIONS

Dorwald F. A. Side Reactions in Organic Synthesis, 2005, Wiley: VCH, Weinheim p. IX of Preface.*

Barder et al., "Catalysts for Suzuki-Miyaura Coupling Processes: Scope and Studies of the Effect of Ligand Structure", J. Am. Chem. Soc. 127:4685-96 (2005).

Trost et al., "Effect of Ligand Structure on the Zinc-Catalyzed Henry Reaction. Asymmetric Syntheses of (−)-Denopamine and (−)-Arbutamine", Org. Lett. 4(16): 2621-23 (2002).

Biessen et al., "The Cholesterol Derivative of a Triantennary Galactoside with High Affinity for Hepatic Asialoglycoprotein Receptor: A Potent Cholesterol Lowering Agent" J. Med. Chem. 38(11): 1846-52 (1995).

Biessen et al., "Synthesis of Cluster Galactosides with High Affinity for the Hepatic Asialoglycoprotien Receptor," J. Med. Chem. 38(9): 1538-46 (1995).

Chiu et al., "RNAi in Human Cells: Basic Structural and Functional Features of Small Interfering RNA," Mol. Cell 10:549-61 (2002).

Choi et al., "Targeting Cancer Cells with DNA-Assembled Dendrimers: A Mix and Match Strategy for Cancer," Cell Cycle 4(5):669-71 (2005).

Connolly et al., "Binding and Endocytosis of Cluster Glycosides by Rabbit Hepatocytes" J. Biol. Chem. 257(2): 939-45(1982).

Crossman et al., "Synthesis of Some Second-Generation Substrate Analogues of Early Intermediates in the Biosynthetic Pathway of Glycosylphosphatidylinositol Membrane Anchors," Carbohyd. Res. 321 (1-2):42-51 (1999).

Dubber et al., "Solid-Phase Synthesis of Multivalent Glycoconjugates on a DNA Synthesizer," Bioconjugate Chem. 14(1):239-46 (2003).

Guo et al., "Construction of Folate-Conjugated pRNA of Bateriophase phi29 DNA Packaging Motor for Delivery of Chimeric siRNA to Nasopharyngeal Carcinoma Cells," Gene Ther. 13(10):814-20 (2006).

Hamzavi et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers," Bioconjugate Chem. 14:941-54 (2003).

Ikeda et al., "Ligand-Targeted Delivery of Therapeutic siRNA," Pharm. Res. 23(8): 1631-40 (2006).

Karskela et al., "Synthesis and Cellular Uptake of Fluorecently Labeled Multivalent Hyaluronan Disacharide Conjugates of Oligonucleotide Phosphorothioates," Bioconjugate Chem. 19(12): 2549-58 (2008).

Katajisto et al., "An Aminooxy-Functionalized Non-Nucleosidic Phosphormadite for the Construction of Multiantennary Oligonucleotide Glycoconjugates on a Solid Support," Current Protocols in Nucleic Acid Chemistry 4.26.1-16 (2005).

Katajisto et al., "Solid-Phase Synthesis of Oligonucleotide Glycoconjugates Bearing Three Different Glycosyl Groups: Orthoganally Protected Bis (Hydroxymethyl)-N, N'-bis(3-Hydroxyproply)Malondiamide Phosphoramidites as Key Building Block," J. Org. Chem. 69(22):7609-15 (2004).

Katajisto et al., "Solid-Phase Synthesis of Multiantennary Oligonucleotide Glycoconjugates Utilizing On-Support Oximation," Bioconjugate Chem. 15(4)890-96 (2004).

Krapcho et al., "Mono-Protected Diamines. N-tert-Butoxycarbonyl-a, ω-Alkanediamines from a, ω-Alkanediamines," Synthetic Commun. 2559-64 (1990).

Li et al., "Folate-Mediated Targeting of Antisense Oligodeoxynucleotides to Ovarian Cancer Cells," Pharm. Res. 15 (10):1540-45 (1998).

Liu et al., "Targeted Drug Delivery to Chemoresistant Cells: Folic Acid Derivatization of FdUMP [10] Enhances Cytotoxicity Toward 5-FU-Resistant Human ColorectorTumor Cells," J. Org. Chem. 66(17):5655-63 (2001).

Mahato et al., "Modulation of Gene Expression by Antisense and Antigene Oligodeoxynucleotides and Small Interfering RNA" Expert Opin. Durg Del. 2(1):3-28 (2005).

Mahato et al., "Physicochemical and Disposition Characteristics of Antisense Oligonucleotides Complexed with Glycosylated Poly(L-lysine)," Biochem. Pharmacol. 53:887-95 (1997).

Maier et al., "Synthesis of Antisense Oligonucleotides Conjugated to a Multivalent Carbohydrate Cluster for Cellular Targeting," Bioconjugate Chem. 14:18-29 (2003).

Murata et al., "Design of Quaternary Chitosan Conjugate Having Antennary Galactose Residues as a Gene Delivery Tool," Carbohyd. Polym, 32(2):105-9 (1997).

Resin et al., "Design and Synthesis of Novel N-Acetylgalactosamine-Terminated Glycolipids for Targeting of Lipoproteins to the Hepatic Asialoglycoprotein Receptor," J. Med. Chem. 47(23):5798-5808 (2004).

Sioud, "On the Delivery of Small Interfering RNA's into Mammalian Cells," Expert Opin. Drug Del. 2(4):639-51 (2005).

Six et al., "An Efficient and Stereoselective Synthesis of 1, 2-0-Dialkyl-3-0-Beta-D-Glycosyl-SN-Glycerols," Tetrahedron Lett 24(12): 1229-32 (1983).

Six et al., "Influence of Carbohydrate Moities on Monolayer Properties of Dialkylglycerylethergylcosides, Simple Model Compounds of the Glycolipids of Halophilic Bacteria." J. Colloid Intert Sci. 93(1): 109-14 (1983).

Sliedregt et al., "Design and Synthesis of Novel Amphiphilic Dendritic Galactosides for Selective Targeting of Liposomes to the Hepatic Asialoglycoprotein Receptor," J Med. Chem. 42(4):609-18 (1999).

Vaino et al., "Synthesis of a D-Lactosyl Cluster-Nucleoside Conjugate," Chem. Commun. 19: 1871-72 (1997).

Wolfrum et al., "Mechanisms and Optimization of In Vivo Delivery of Lipophilic siRNAs," Nature Biotechnology 25 (10): 1149-57 (2007).

Wong et al., "Lipid, Sugar and Liposaccharide Based Delivery Systems," Curr. Med, Chem. 8(9): 1123-36 (2001).

Zatsepin et al., "Synthesis and Applications of Oligonucleotide-Carbohydrate Conjugates," Chem. Biodivers. 1 (10):1401-17 (2004).

Zheng et al., "Distrubution and Anti-HBV Effects of Antisense Oligodeoxynucleotides Conjugated to Galactosylated Poly-L-Lysine," World J. Gastroentero 9(6) 1251-55 (2003).

Zimmerman et al., "RNAi-Mediated Gene Silencing in Non-Human Primates," Nature 441 (7089): 111-14 (2006).

(56) References Cited

OTHER PUBLICATIONS

Dorwarld, "Side Reaction in Organic Synthesis: A Guide to Successful Synthesis Design," Wiley-VCH Verlag GmbH & Co. KGaA: Weinheim (2005).

* cited by examiner

Figure 3
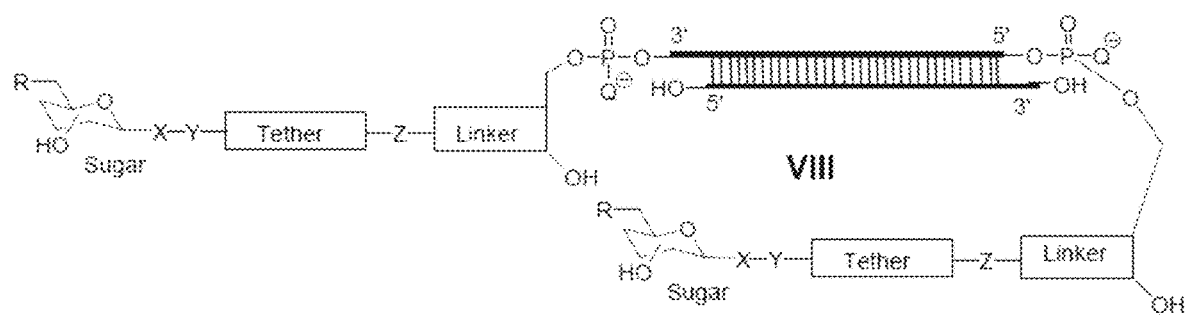
Figure 4
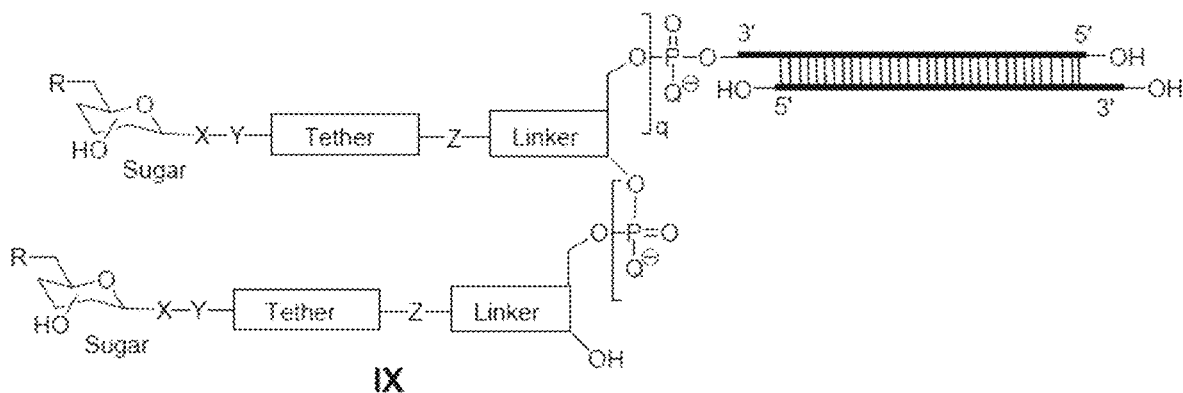
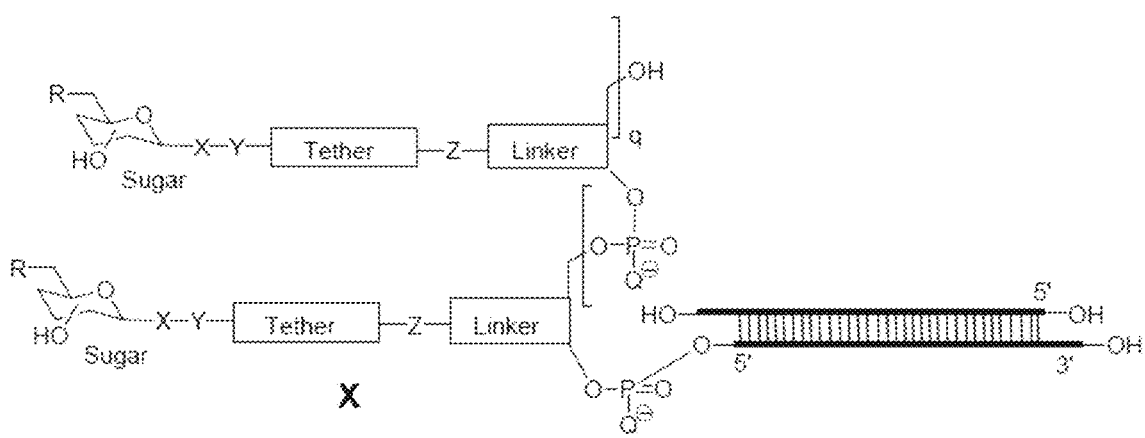

Figure 8

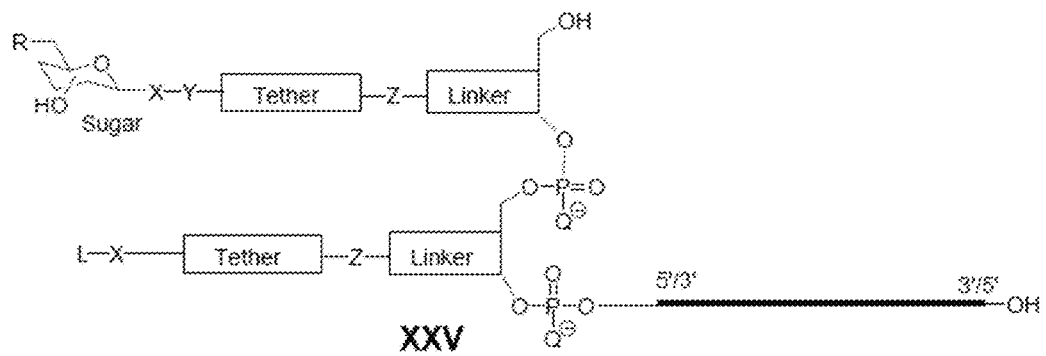

Figure 9

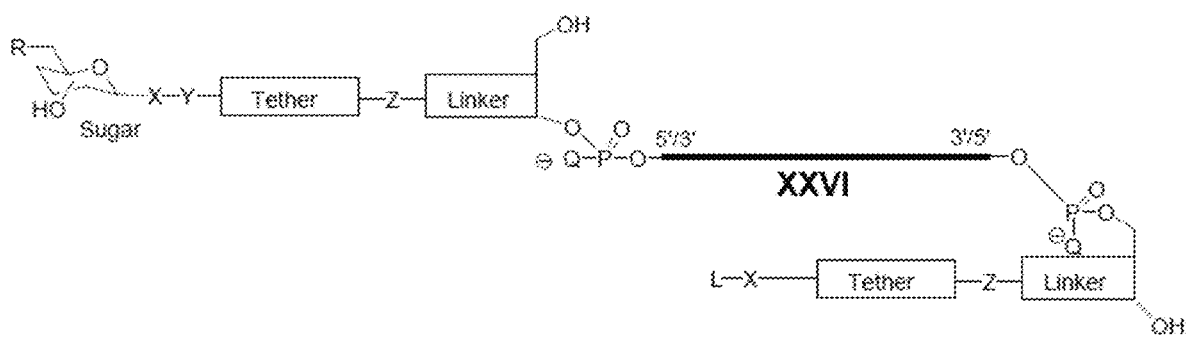

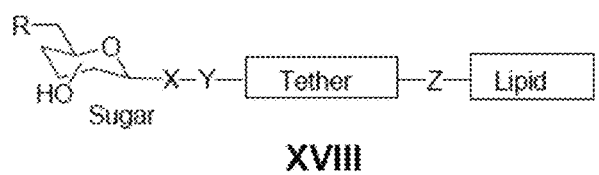

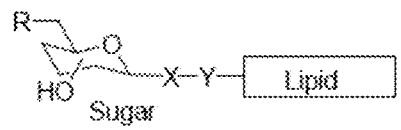

R' = OH, SH, NH$_2$, NH(Alkyl = Me, Et, Pr, isoPr, Bu, Bn), N(diAlkyl = Me$_2$, Et$_2$, Bn$_2$), H
R" = OH, SH, NH$_2$, H, NH(Alkyl = Me, Et, Pr, isoPr, Bu, Bn), N(diAlkyl = Me$_2$, Et$_2$, Bn$_2$)
R = COOH, H, CONH$_2$, CONHMe, CONMe$_2$, CONH(CH$_2$)$_m$NH$_2$, CONH(CH$_2$)$_m$OH, CONH(CH$_2$)$_m$COOH
    CONH(CH$_2$)$_m$SH, CONH(CH$_2$)$_m$CONH$_2$, CONH(CH$_2$)$_m$CONHMe, CONH(CH$_2$)$_m$CONH(CH$_2$CH$_2$O)$_l$H
    CONH(CH$_2$)$_m$CONH(CH$_2$CH$_2$O)$_l$NH$_2$, CONH(CH$_2$)$_m$CONH(CH$_2$CH$_2$O)$_l$CH$_3$,
    CONH(CH$_2$)$_m$CONH(CH$_2$CH$_2$O)$_l$COOH, CONH(CH$_2$)$_m$CONH(CH$_2$CH$_2$O)$_l$SH
X = CO, NH, O, S, OC(O), NHC(O), CH$_2$ Y = NH, O, S, CO, CH$_2$, C(O)O, C(O)NH, 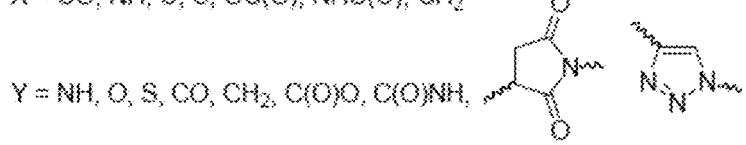

Figure 12
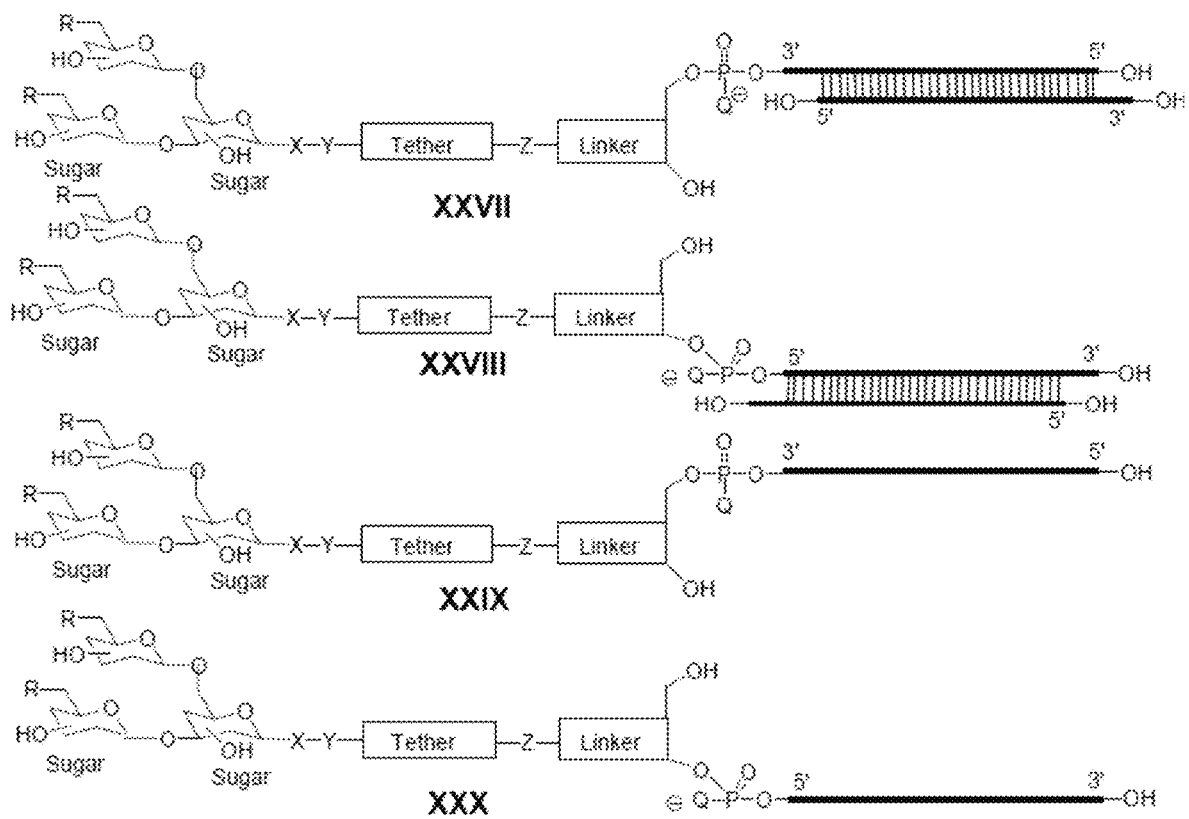
R = H, OH, SH, PO$_4^{2-}$
X = CO, NH, O, S, OC(O), NHC(O), CH$_2$,
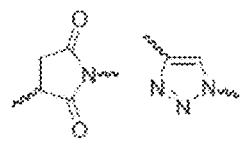
Y = NH, O, S, CO, CH$_2$, C(O)O, C(O)NH,
Z = C(O)NH, NHC(O), C(O)O, OC(O), NHC(O)O, OC(O)NH, NHC(O)NH, S-S, O, NH, NMe, CH$_2$,
n = 1-6, m = 0-32, l = 0-50

Figure 15. In vivo apoB gene silencing of galactose-siRNA conjugate
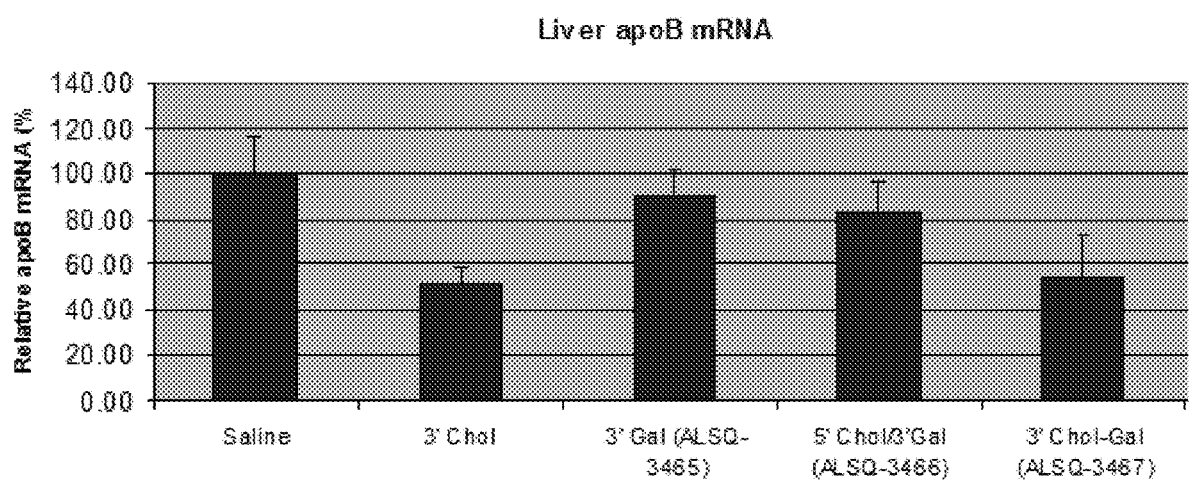
Figure 16. Q11L96. Cholesterol and (GalNAc)3 (Q11L96) linked via phosphate and attached to siRNA at the 3'-end
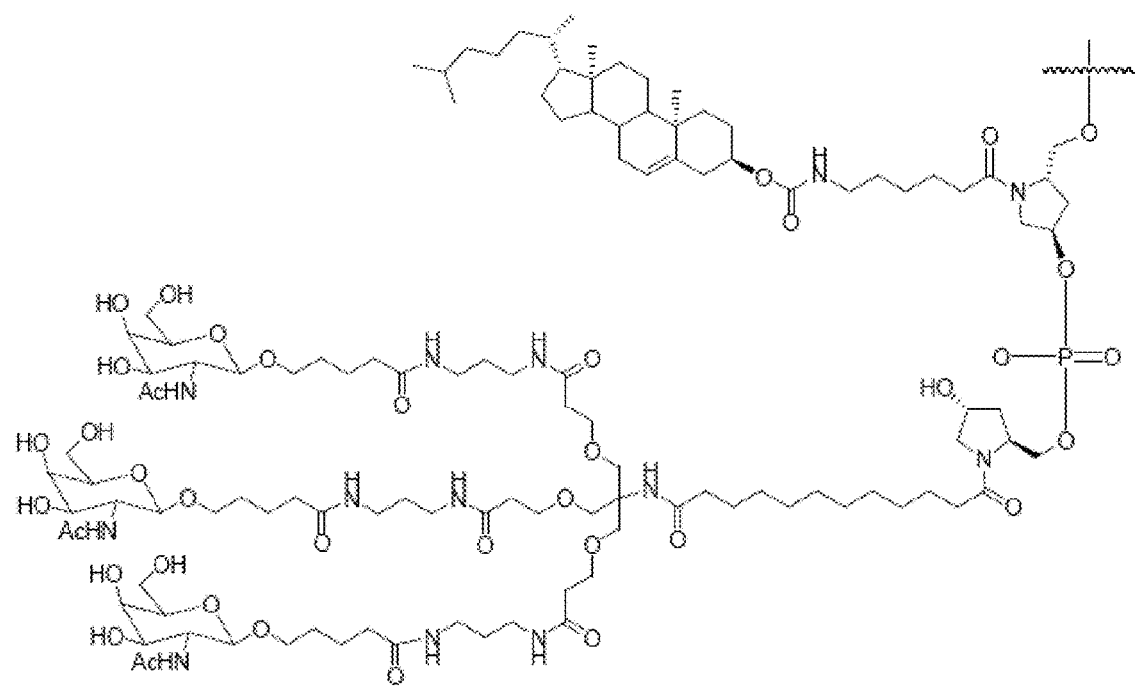

Figure 17. Glycolipid-siRNA conjugate strategies
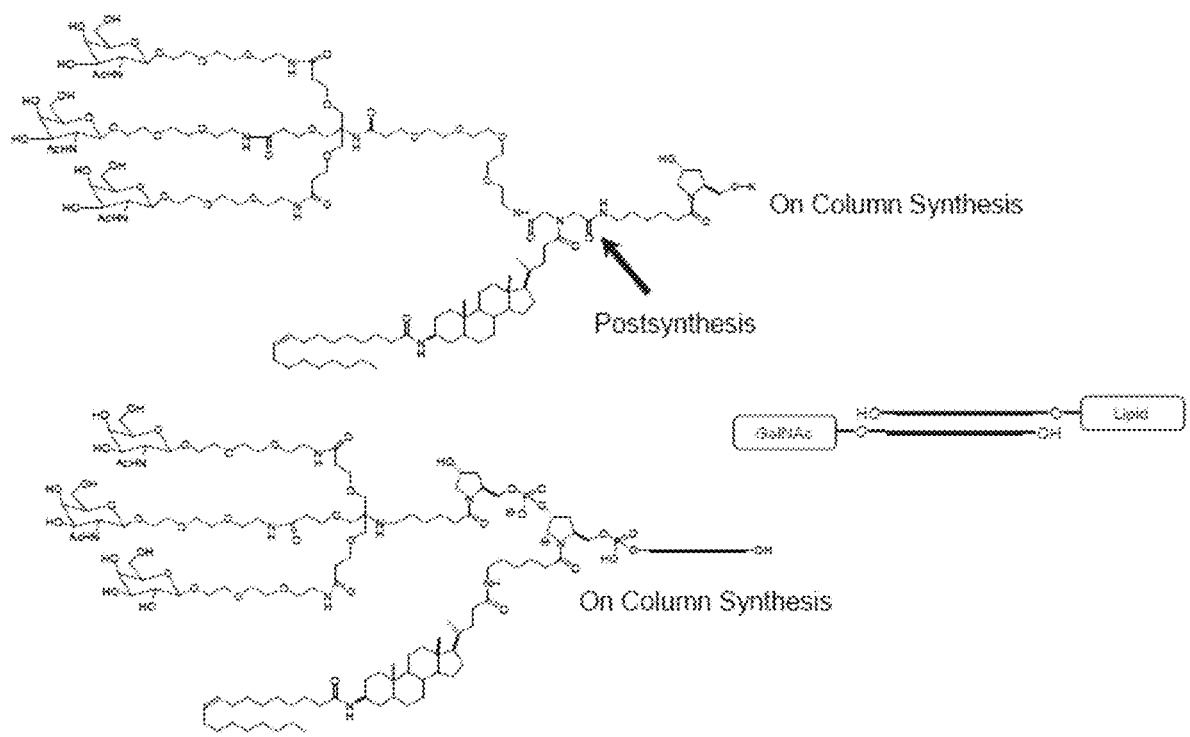

Figure 18. Binding Affinity and Multivalency of the Asialoglycoprotein Receptor
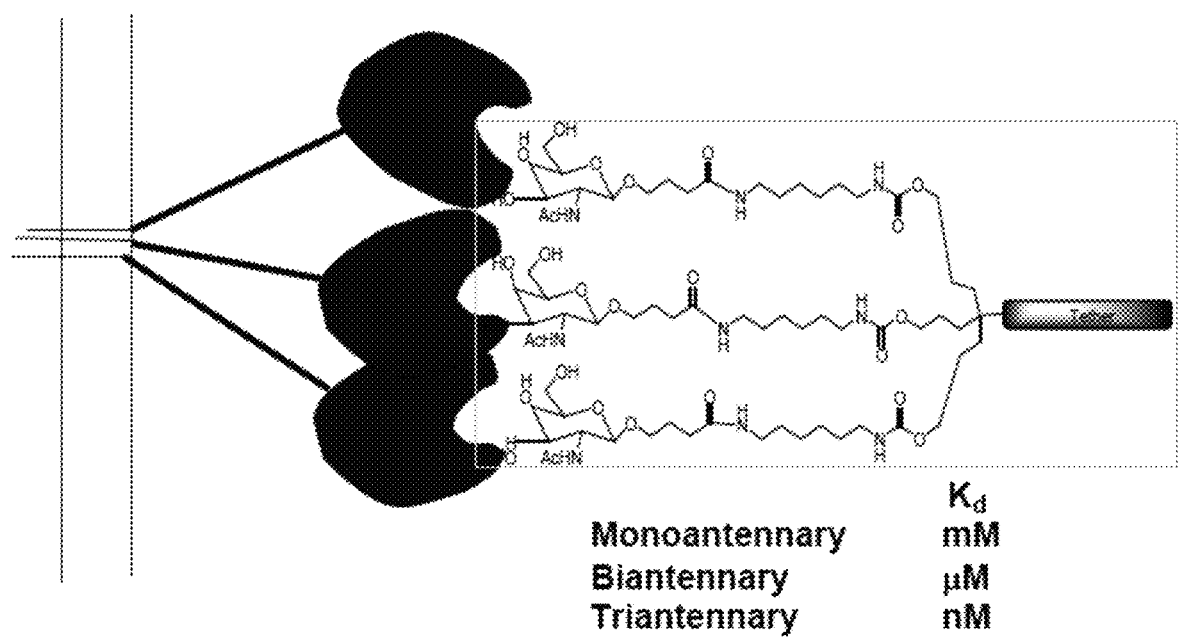

Figure 19. Synthesis of multiantennary conjugates from simple monomers
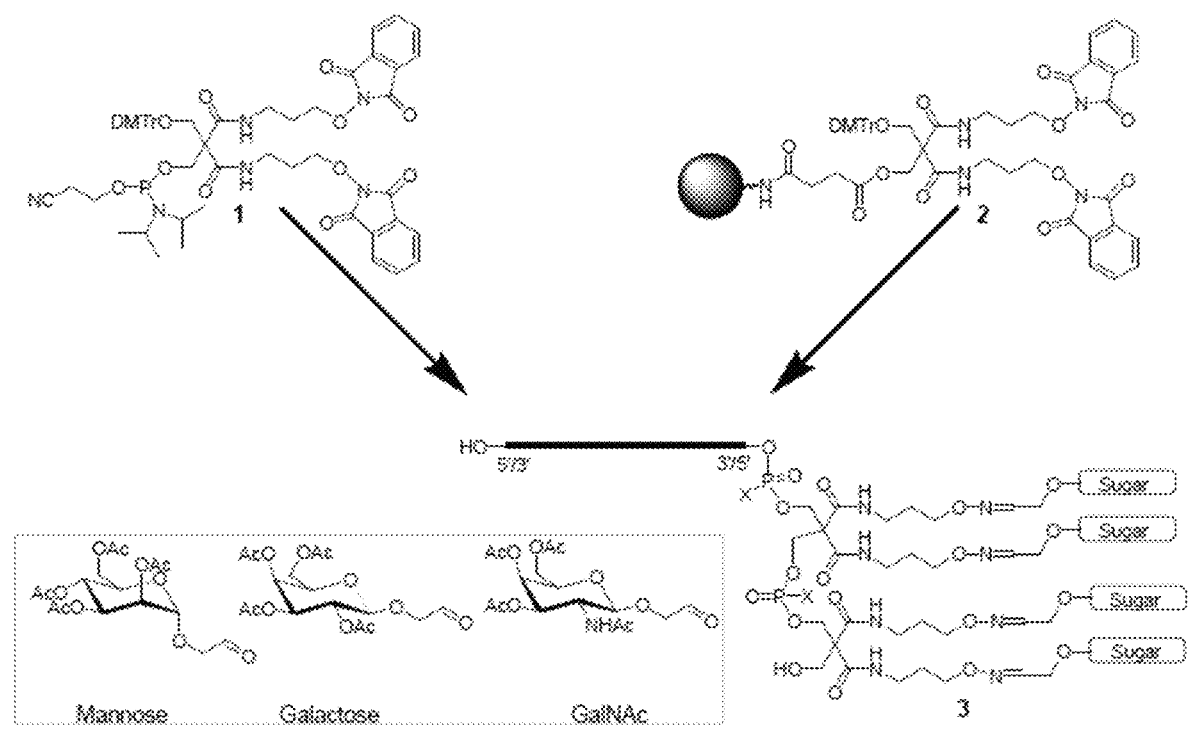

Figure 20. Glycolipid – siRNA conjugate for LDL and HDL packing and liver targeting
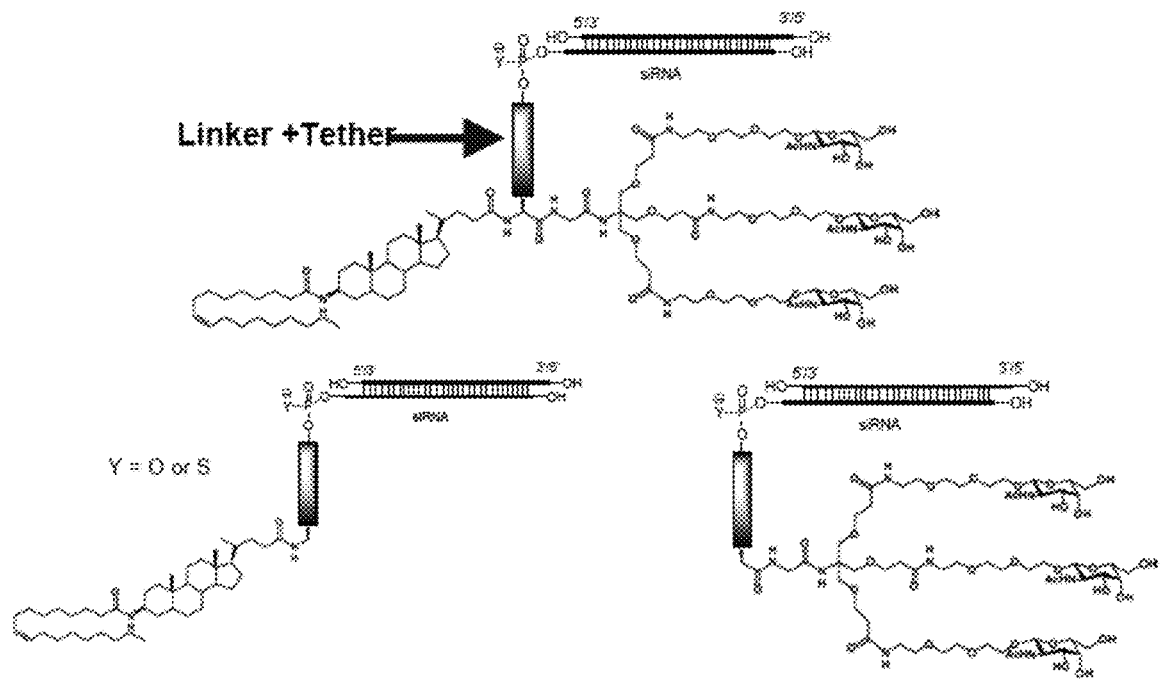

Figure 21. Glycolipid-siRNA Conjugate: Synthesis
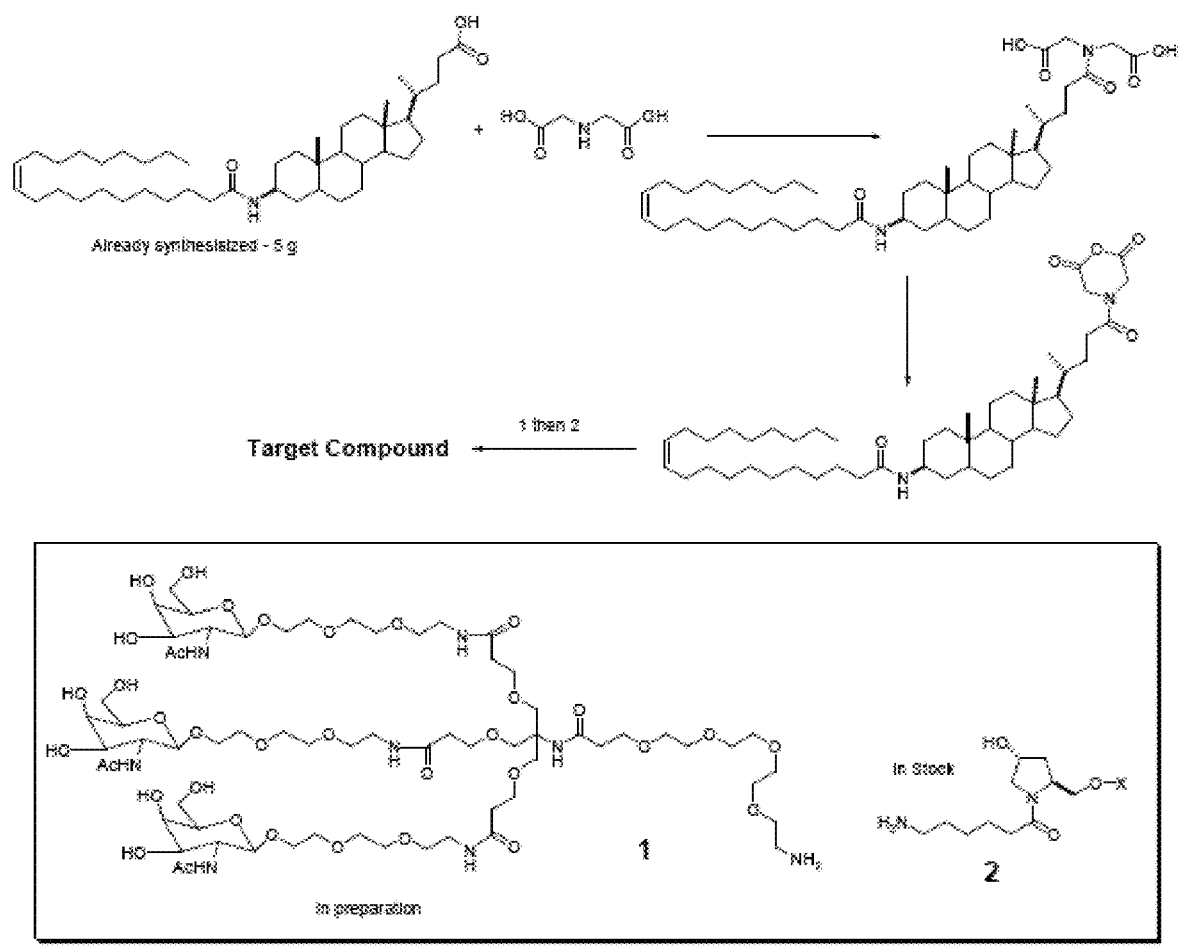

Figure 22. Monomers for carbohydrate conjugation to siRNA
(A)
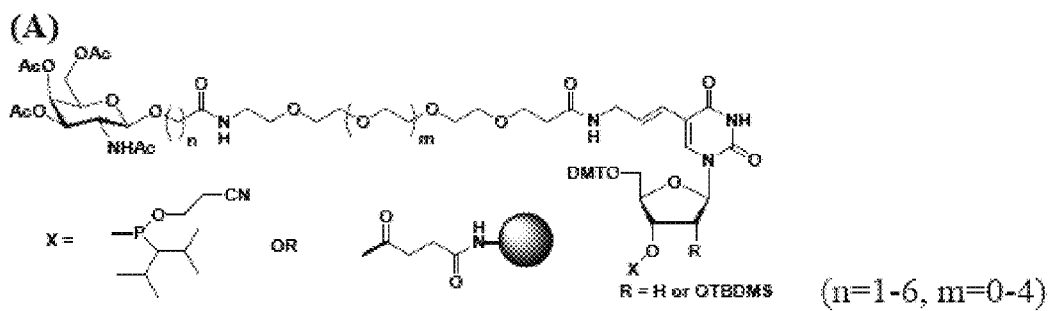
(B)
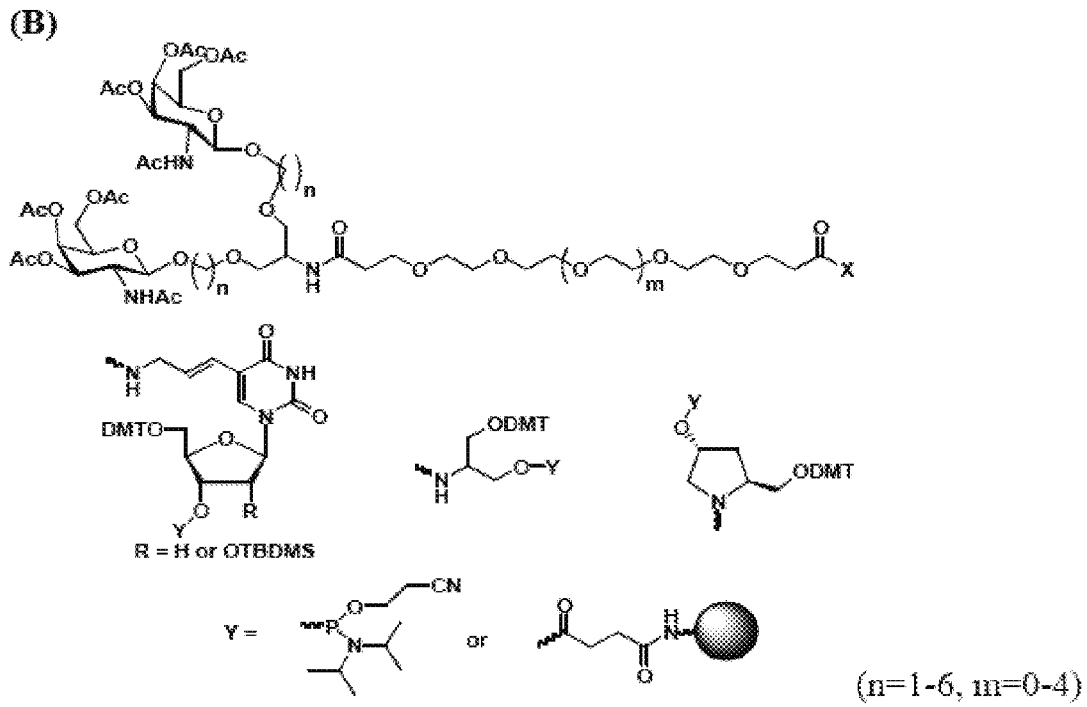
(C)
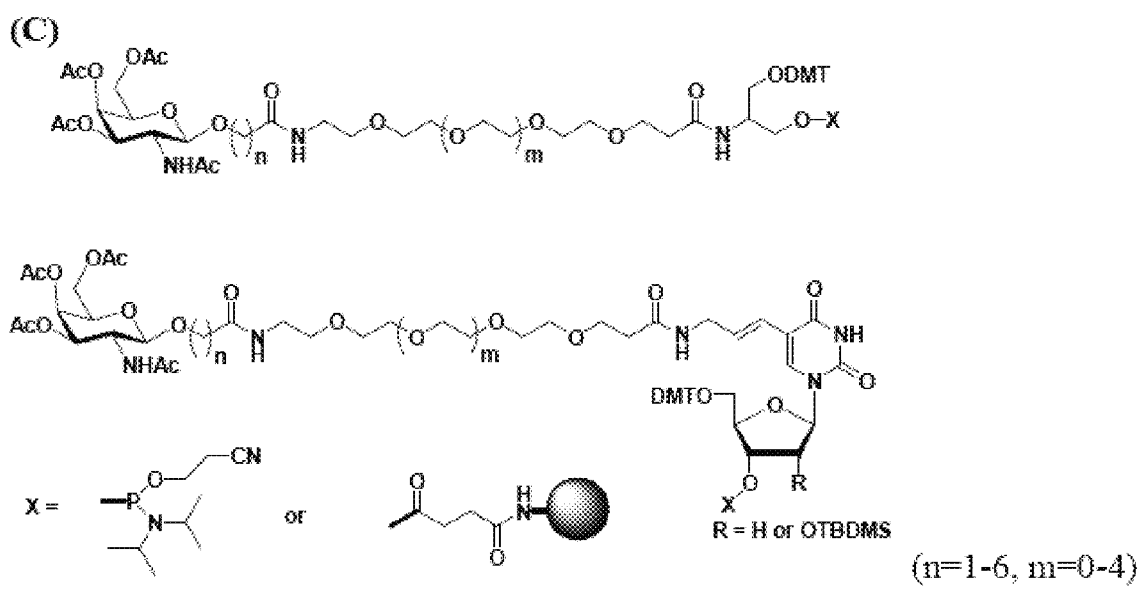

Figure 23. Synthesis of GalNAc building blocks
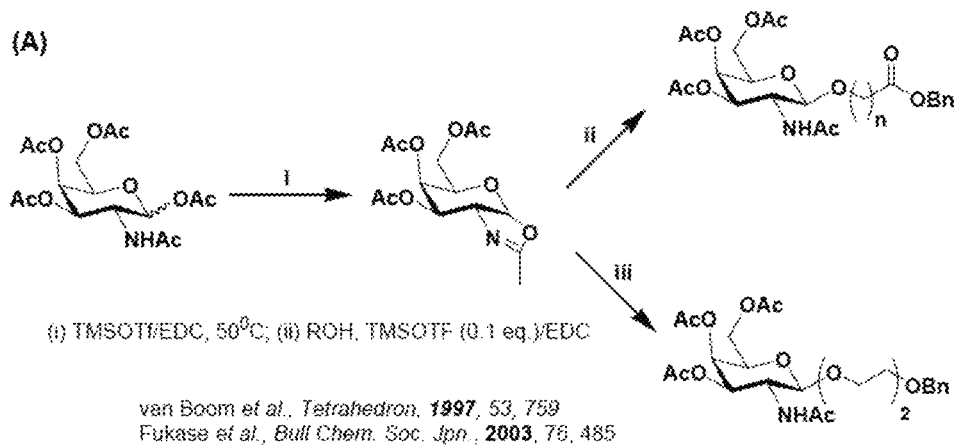
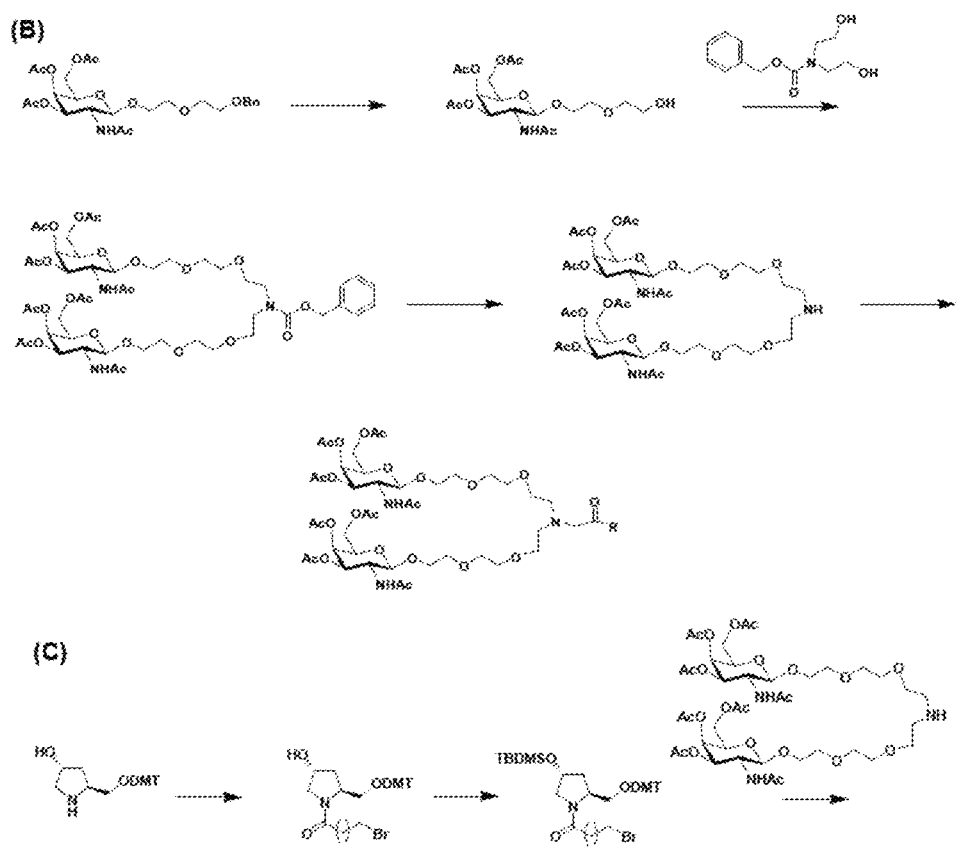
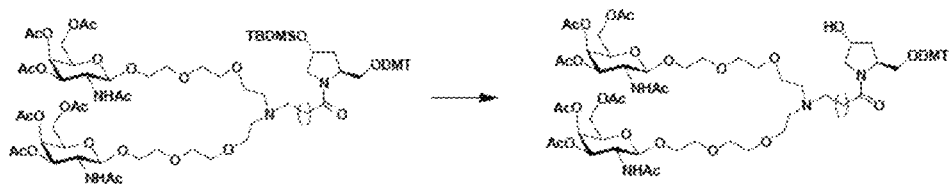

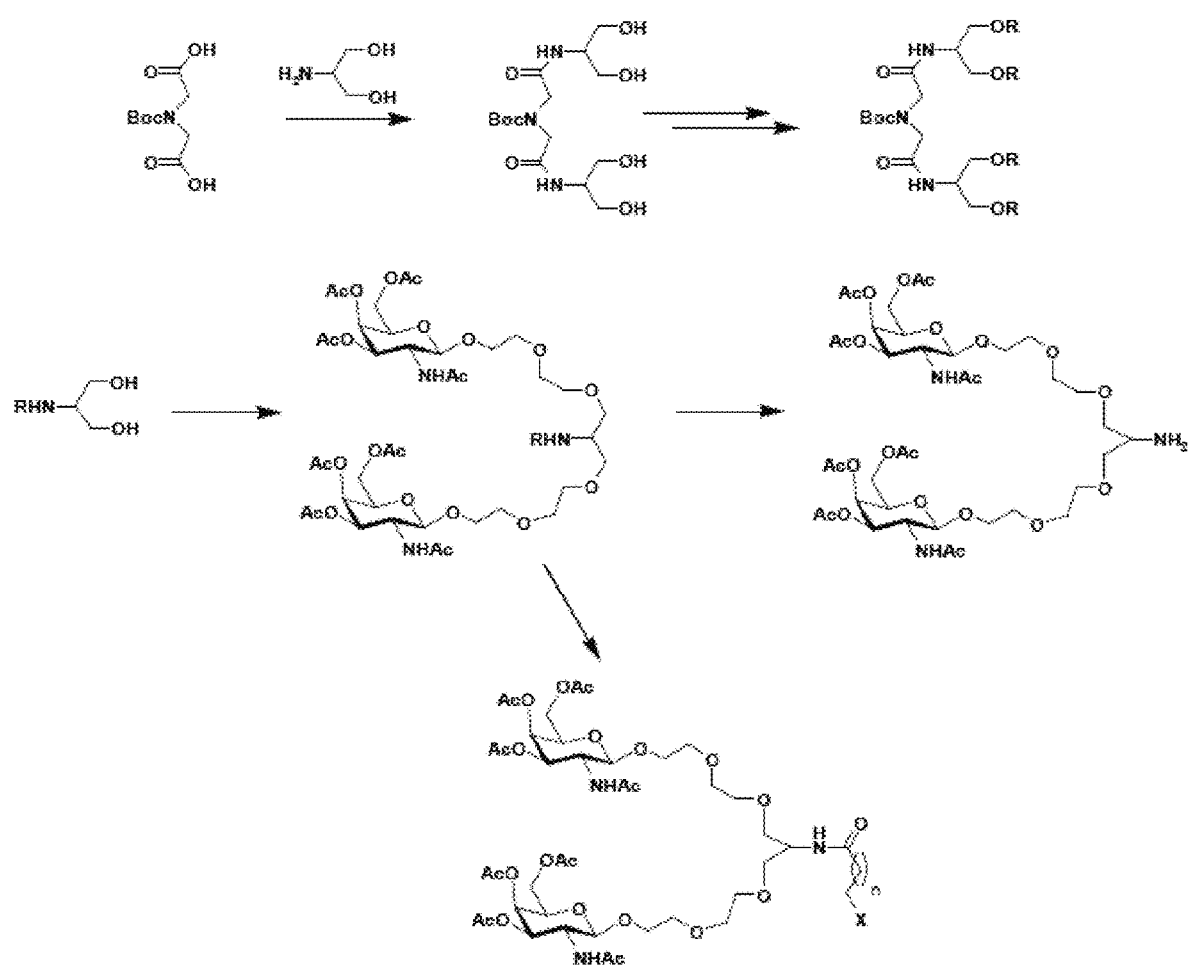
Figure 24. Synthesis of GalNAc building blocks (II)

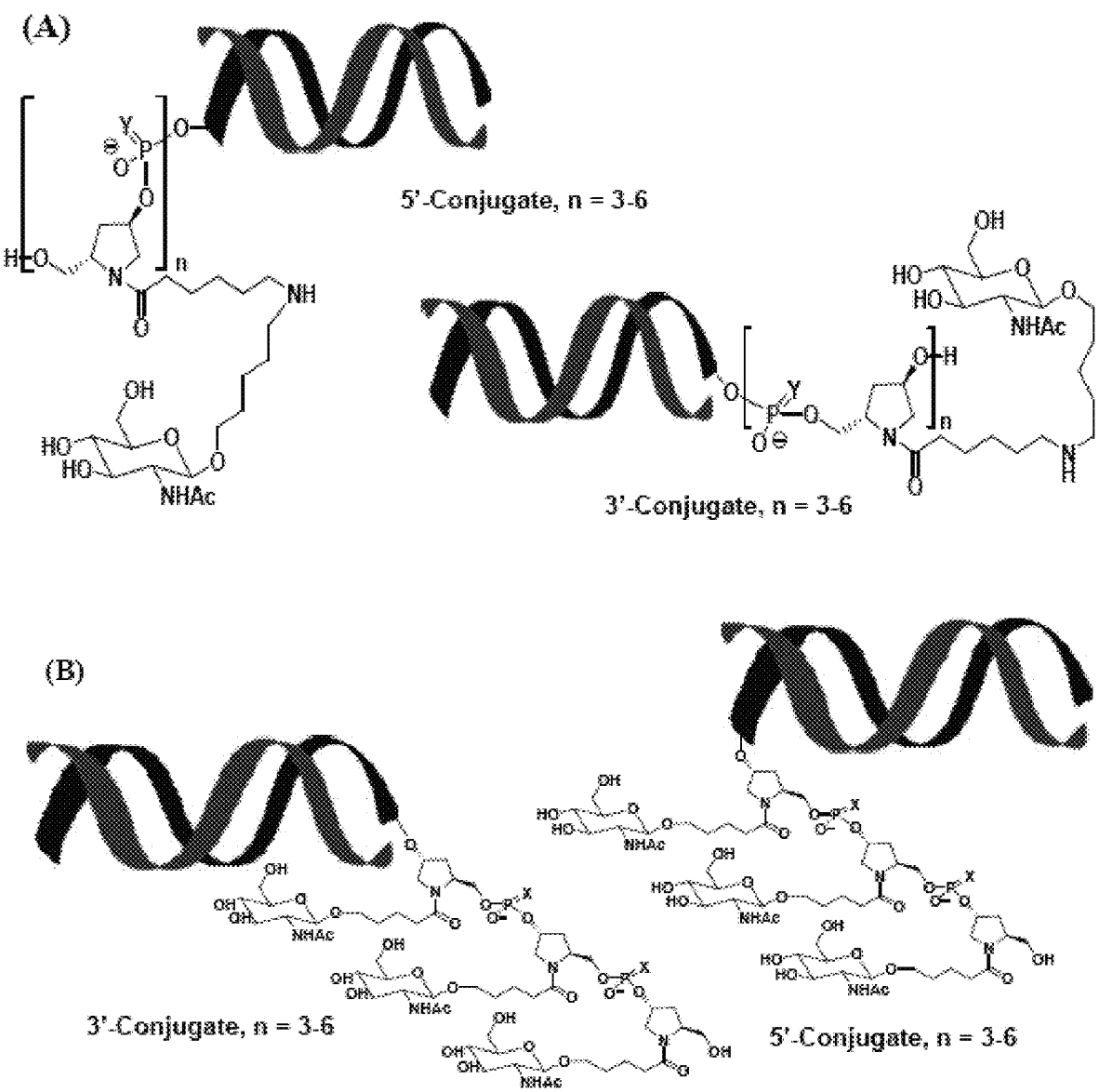
Figure 25. GalNAc custers for hepatic targeting

Figure 26. Carbohydrate (GalNAC) clusters for conjugation to siRNA
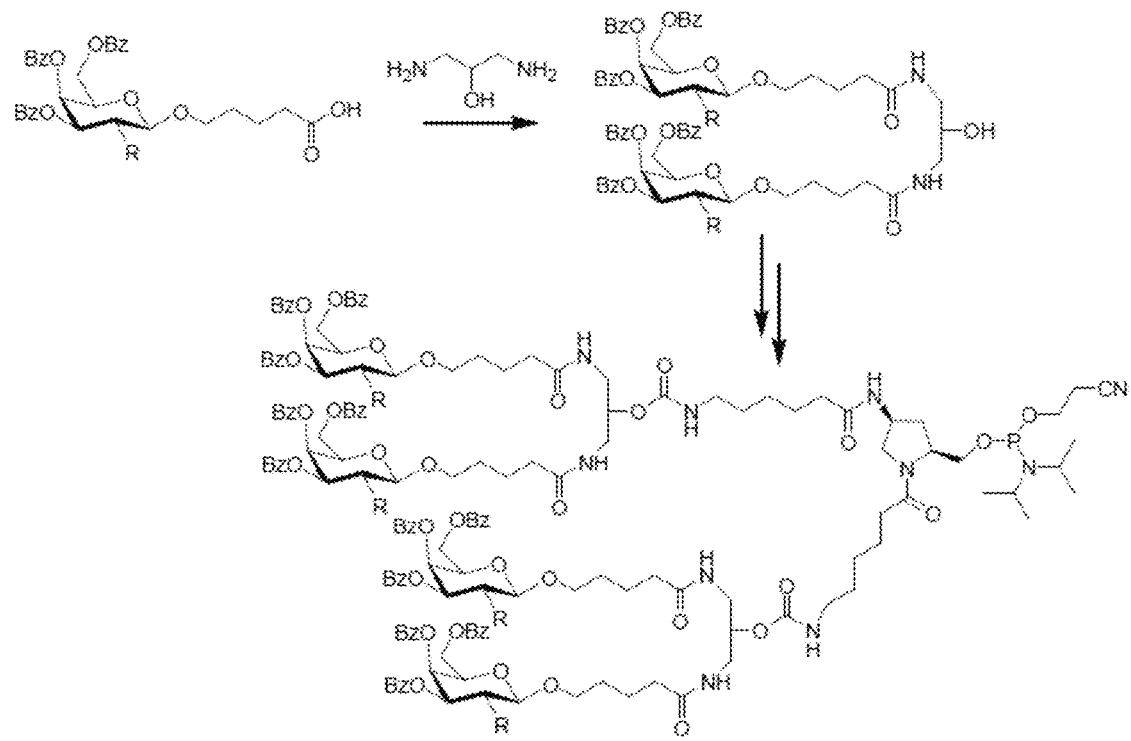
Figure 27. Multivalent GalNAC-siRNA conjugates
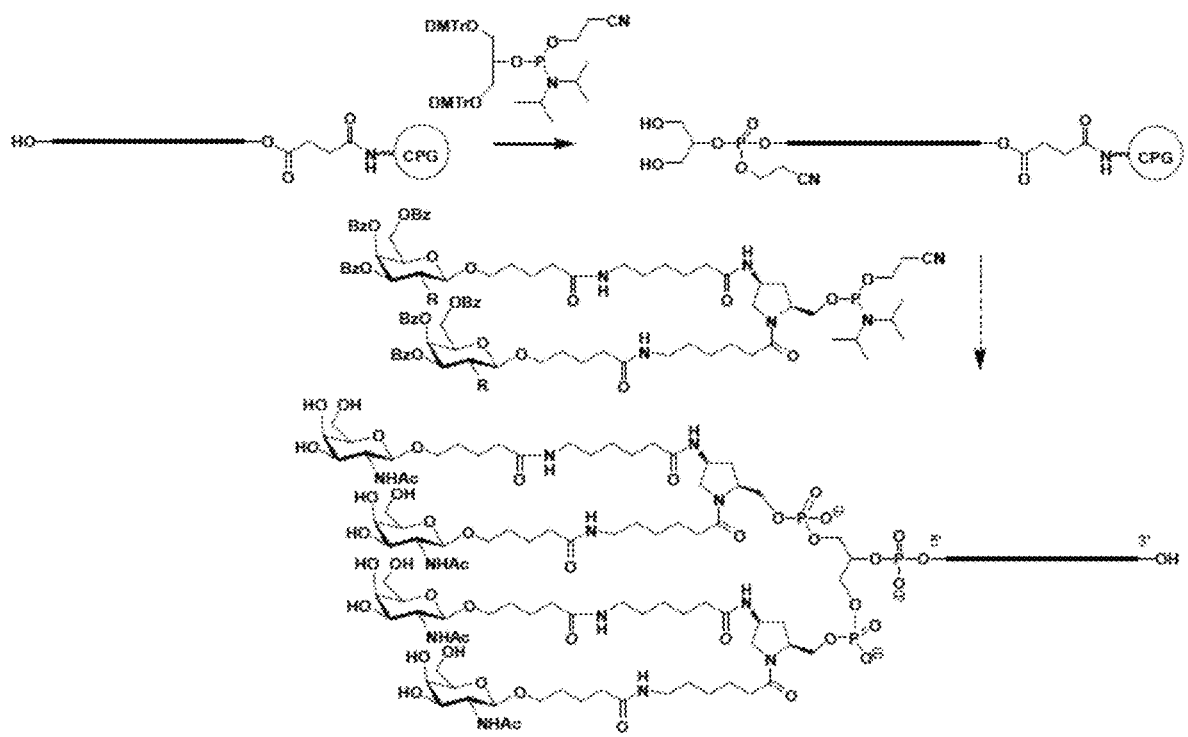

Figure 28. Carbohydrate building blocks for 5'-conjugation
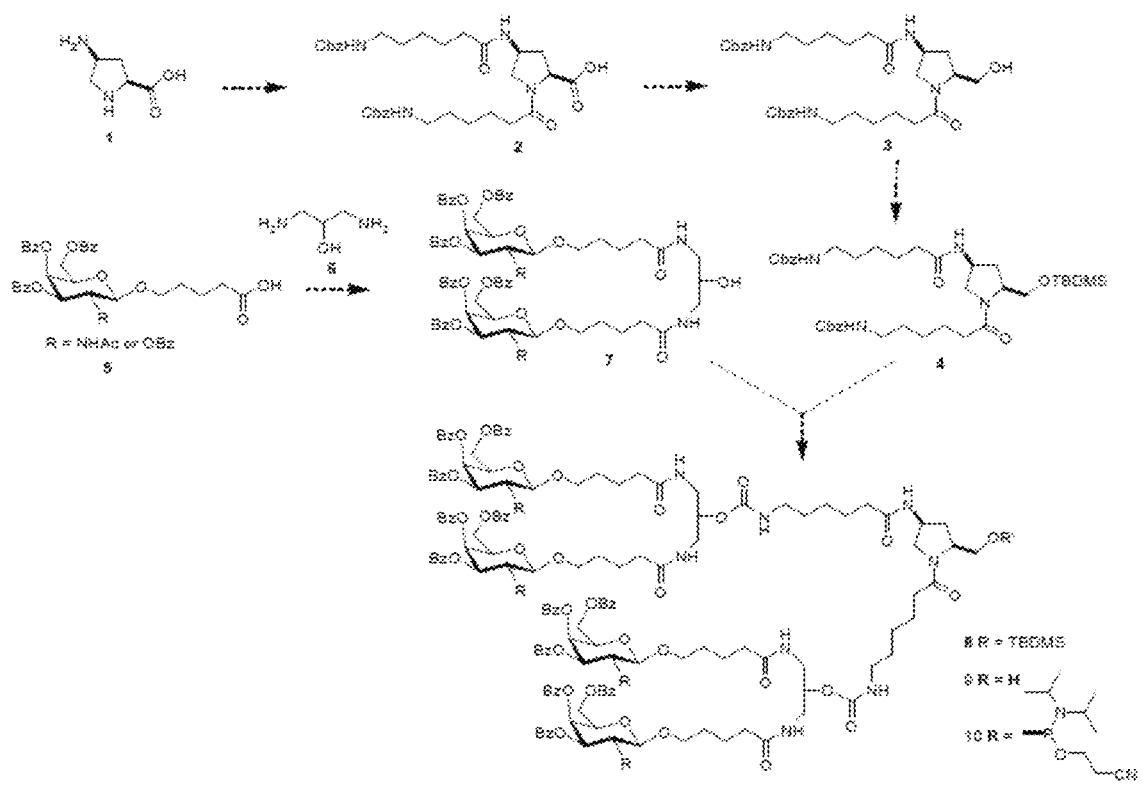
Figure 29. Synthesis of Mannose conjugate building blocks
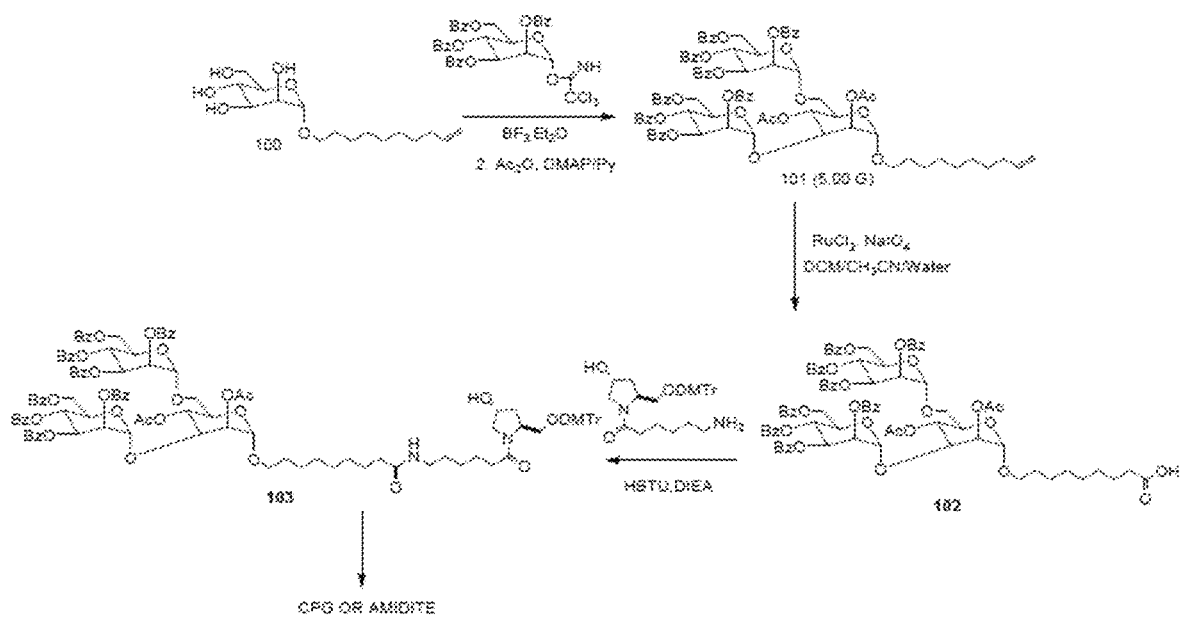

Figure 30. Post-synthetic carbohydrate conjugate building blocks
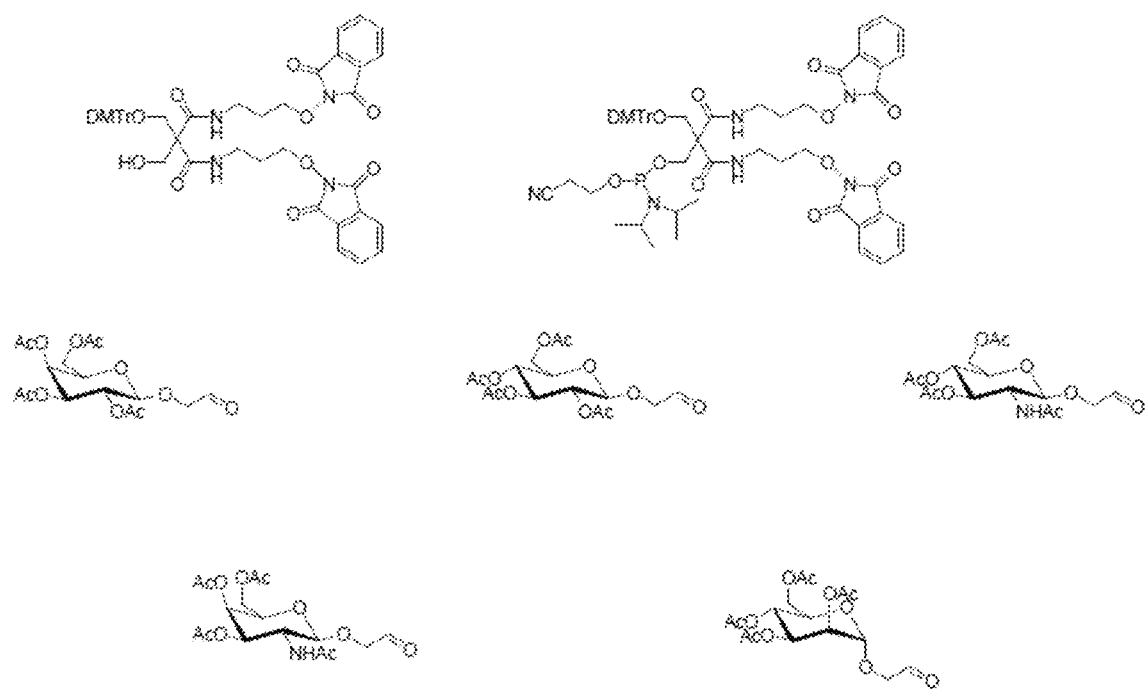

Figure 31. Comparison of gene silencing with cholesterol conjugated siRNA versus cholesterol-(GalNAc)3 conjugated siRNA
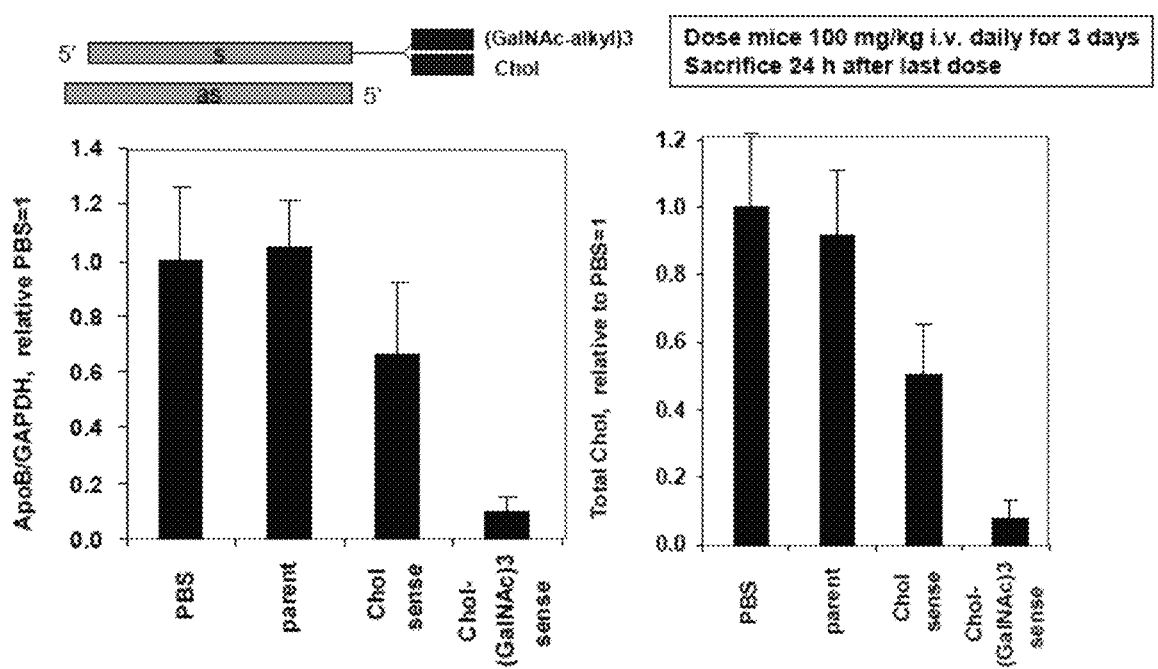

Figure 32. Comparison of duration of effect on serum cholesterol levels with cholesterol conjugated siRNA versus cholesterol-(GalNAc)3 conjugated siRNA
- Groups (n = 5): PBS, AD-5544 (Chol), AD-3698 (GalNAc-Chol)
- Dose: 3 x 100 mg/kg
- Plasma Chol levels: pre-dose and d1, d2, d5, d8, d11, d15 after last inj.
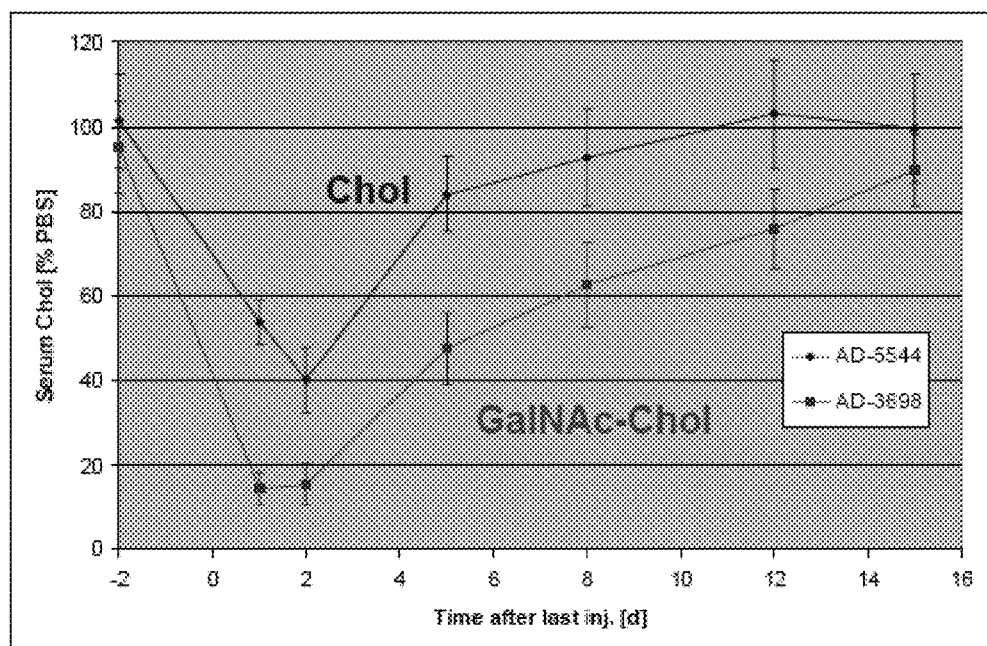

Figure 33. Comparison of uptake of Cy3 labeled siRNA with cholesterol conjugated siRNA versus cholesterol-(GalNAc)3 conjugated siRNA
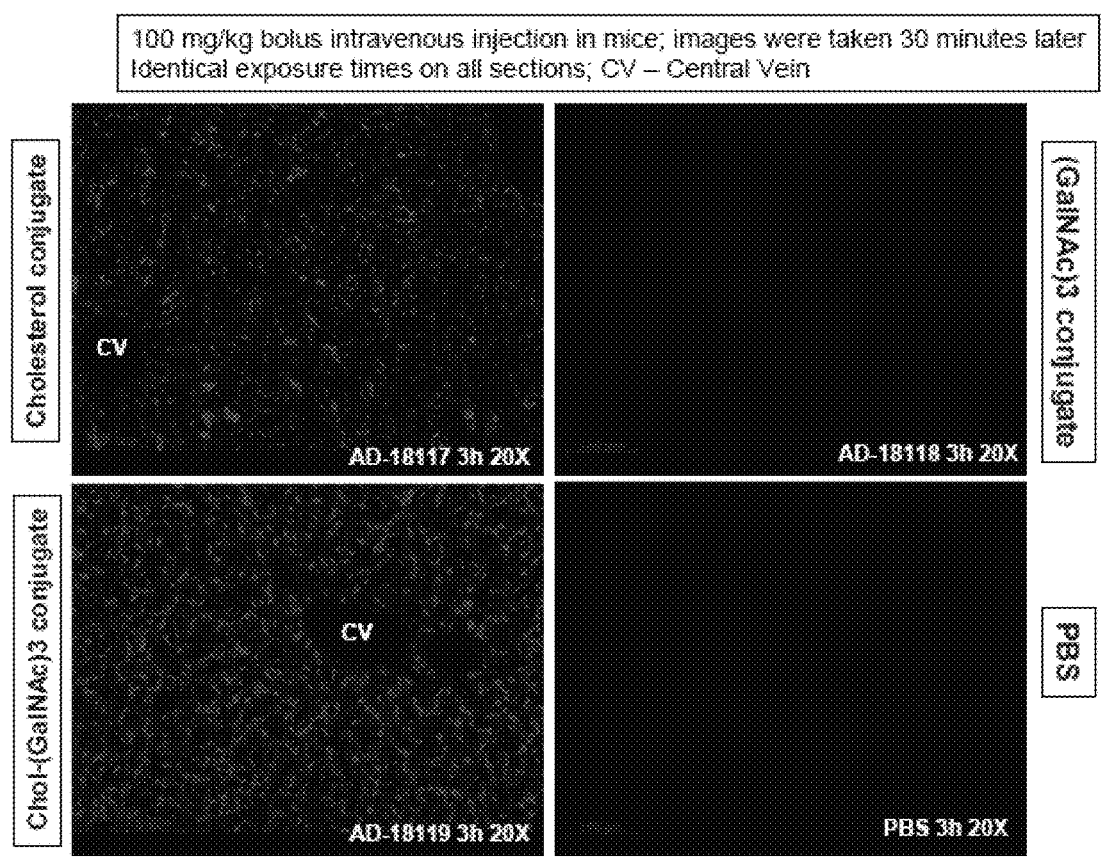

I (Triantennary)　　　　　　　II (Biantennary)

Figure 37
(A)
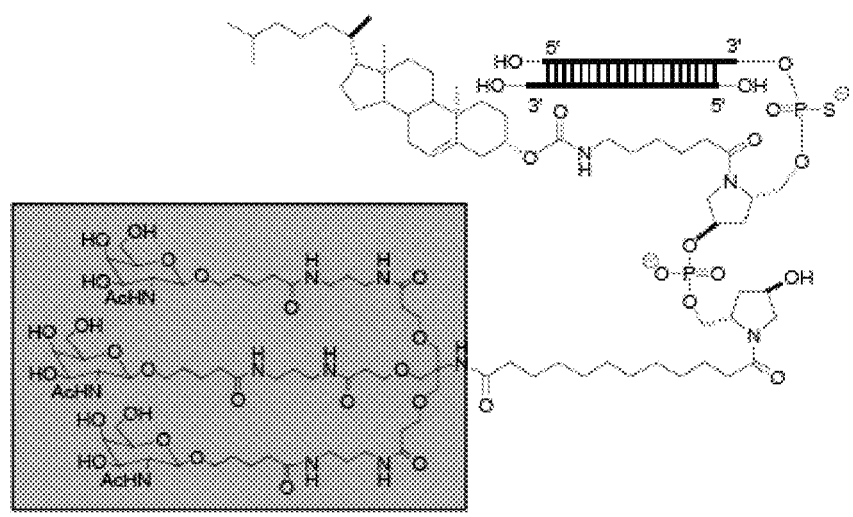
I (AD-3698)
(B)
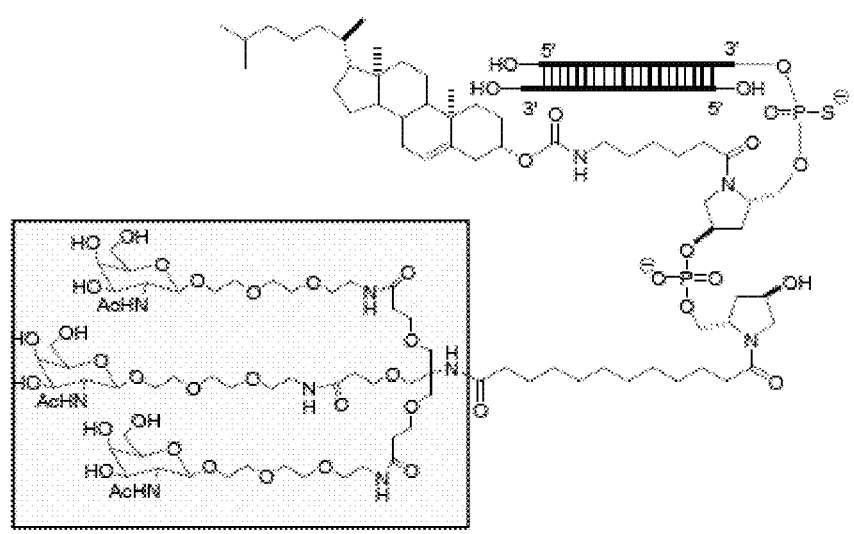
II (AD-31644)

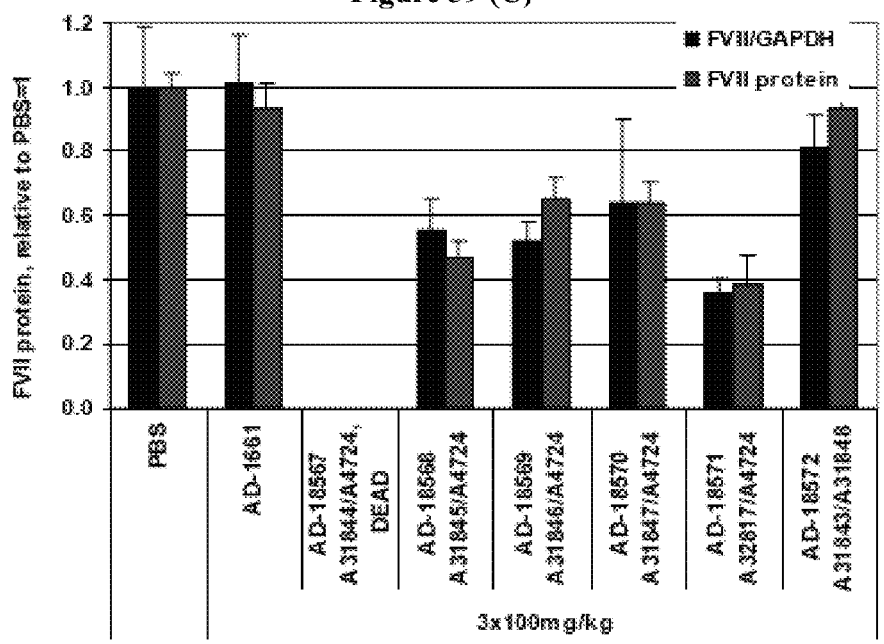

Figure 42
(A)
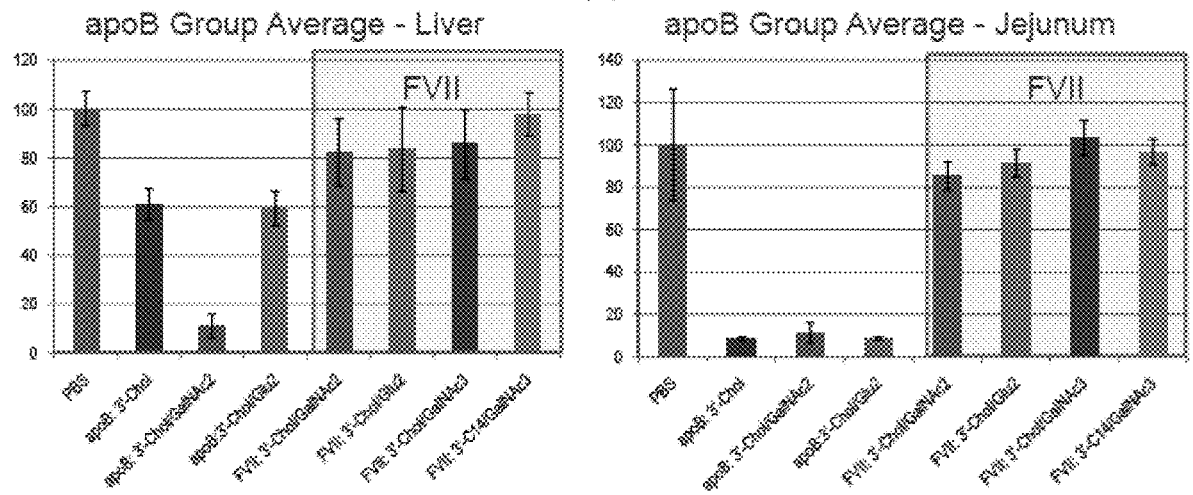
(B)
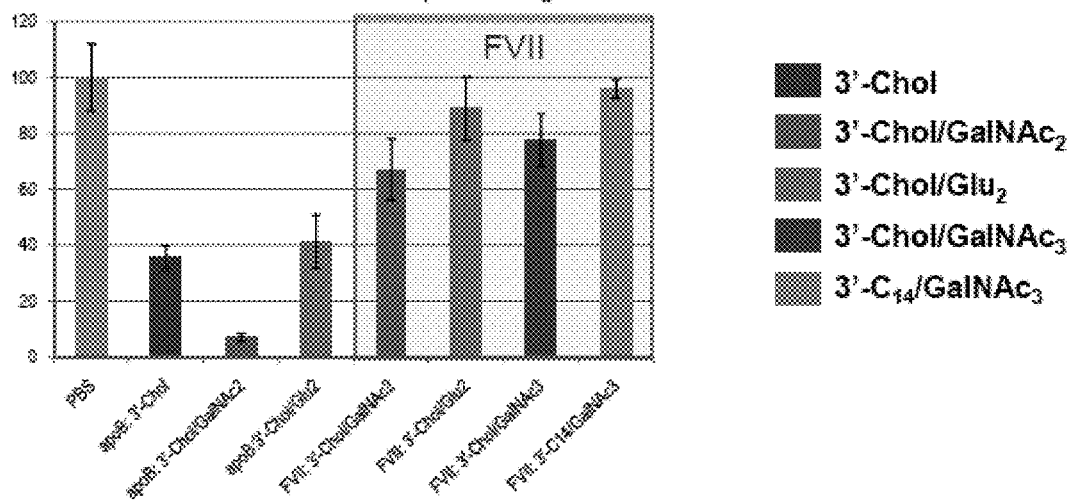
- 3'-Chol
- 3'-Chol/GalNAc$_2$
- 3'-Chol/Glu$_2$
- 3'-Chol/GalNAc$_3$
- 3'-C$_{14}$/GalNAc$_3$

Figure 46
(A)
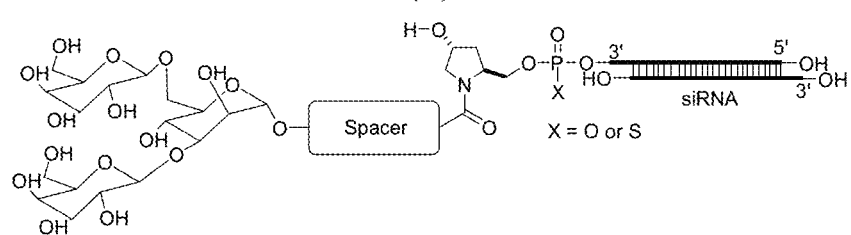
(B)
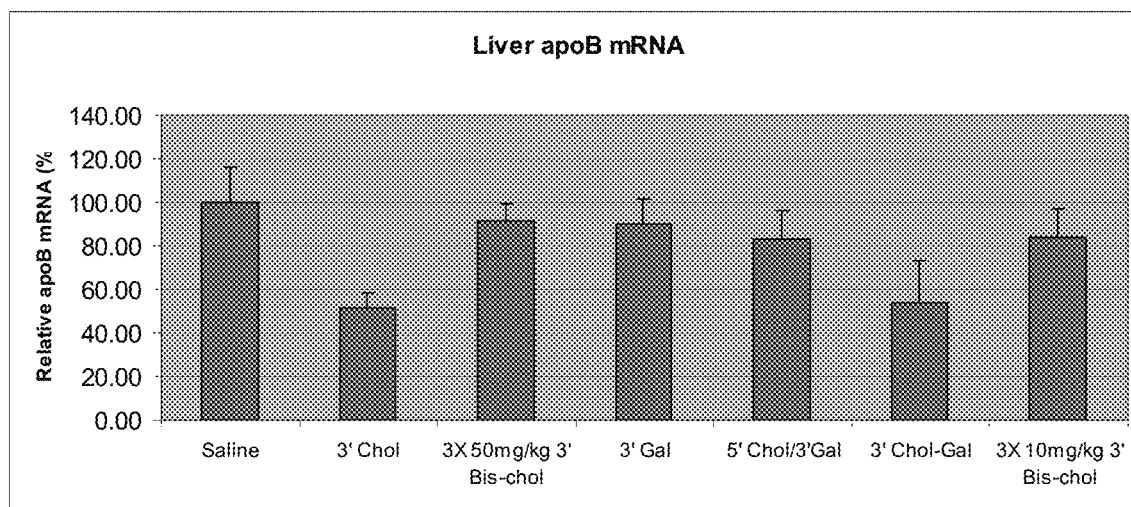

SEQUENCE LISTING

<160> NUMBER OF SEQ ID NOS: 136

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ala Leu Ala
1

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Glu Ala Leu Ala Glu Ala Leu Glu Ala Leu Glu Ala
1               5                   10                  15

Leu Glu Ala Leu Ala Glu Ala Ala Ala Ala Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 16
<212> TYPE: PRT
<213> ORGANISM: Drosophila sp.

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 13
<212> TYPE: PRT
<213> ORGANISM: Human immunodeficiency virus 1

<400> SEQUENCE: 6

Gly Arg Lys Lys Arg Arg Gln Arg Arg Arg Pro Pro Gln
1               5                   10

<210> SEQ ID NO 7
<211> LENGTH: 27
<212> TYPE: PRT
<213> ORGANISM: Human immunodeficiency virus 1

<400> SEQUENCE: 7

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 8
<211> LENGTH: 18
<212> TYPE: PRT
<213> ORGANISM: Mus sp.

<400> SEQUENCE: 8

Leu Leu Ile Ile Leu Arg Arg Arg Ile Arg Lys Gln Ala His Ala His
1               5                   10                  15

Ser Lys

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25
```

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Lys Leu Ala Leu Lys Leu Ala Leu Lys Ala Leu Lys Ala Ala Leu Lys
1               5                   10                  15

Leu Ala
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Arg Arg Arg Arg Arg Arg Arg Arg Arg
1               5
```

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Lys Phe Phe Lys Phe Phe Lys Phe Phe Lys
1               5                   10
```

<210> SEQ ID NO 13
<211> LENGTH: 37
<212> TYPE: PRT
<213> ORGANISM: Homo sapiens

<400> SEQUENCE: 13

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

```
<210> SEQ ID NO 14
<211> LENGTH: 31
<212> TYPE: PRT
<213> ORGANISM: Ascaris suum

<400> SEQUENCE: 14

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 15
<211> LENGTH: 30
<212> TYPE: PRT
<213> ORGANISM: Homo sapiens

<400> SEQUENCE: 15

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 16
<211> LENGTH: 36
<212> TYPE: PRT
<213> ORGANISM: Homo sapiens

<400> SEQUENCE: 16

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 17
<211> LENGTH: 12
<212> TYPE: PRT
<213> ORGANISM: Unknown
<220> FEATURE:
<223> OTHER INFORMATION: Description of Unknown: Unknown bactenecin
      sequence

<400> SEQUENCE: 17

Arg Lys Cys Arg Ile Val Val Ile Arg Val Cys Arg
1               5                   10

<210> SEQ ID NO 18
<211> LENGTH: 42
<212> TYPE: PRT
<213> ORGANISM: Sus scrofa

<400> SEQUENCE: 18

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 19
```

```
<211> LENGTH: 13
<212> TYPE: PRT
<213> ORGANISM: Unknown
<220> FEATURE:
<223> OTHER INFORMATION: Description of Unknown: Unknown indolicidin
      sequence

<400> SEQUENCE: 19

Ile Leu Pro Trp Lys Trp Pro Trp Trp Pro Trp Arg Arg
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Val Ala Leu Leu Pro Ala Val Leu Leu Ala Leu Leu Ala Pro
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Leu Leu Pro Val Leu Leu Ala Ala Pro
1               5                   10

<210> SEQ ID NO 22
<211> LENGTH: 23
<212> TYPE: DNA
<213> ORGANISM: Mus sp.

<400> SEQUENCE: 22
aagctggccc tggacatgga gat                                           23

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 23
gccuggaguu uauucggaat t                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide
```

<400> SEQUENCE: 24
uuccgaauaa acuccaggct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 25
gccuggaguu uauucggaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 26
uuccgaauaa acuccaggct t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 27
gccuggaguu uauucggaat t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 28
uuccgaauaa acuccaggct t                                              21

<210> SEQ ID NO 29
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 29
gccuggaguu uauucggaat t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 30
uuccgaauaa acuccaggct t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 31
gccuggaguu uauucggaat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 32
uuccgaauaa acuccaggct t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 33
gccuggaguu uauucggaat t                                              21
```

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 34
uuccgaauaa acuccaggct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 35
gccuggaguu uauucggaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 36
uuccgaauaa acuccaggct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 37
gccuggaguu uauucggaat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic oligonucleotide

<400> SEQUENCE: 38
gccuggaguu uauucggaat t                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ggaaucuuau auugaucca a                                               21

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uuggaucaaa uauaagauuc ccu                                            23

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaaucuuau auugaucca a                                               21

<210> SEQ ID NO 42
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uuggaucaaa uauaagauuc ccu                                            23

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggaaucuuau auugaucca a                                               21

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 44
uuggaucaaa uauaagauuc ccu                                          23

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggaaucuuau auuugaucca a                                            21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uuggaucaaa uauaagauuc ccu                                          23

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ggaaucuuau auuugaucca a                                            21

<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uuggaucaaa uauaagauuc ccu                                          23

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaaucuuau auuugaucca a                                            21

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 50
uuggaucaaa uauaagauuc ccu                                           23

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ggaaucuuau auuugaucca a                                             21

<210> SEQ ID NO 52
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uuggaucaaa uauaagauuc ccu                                           23

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ggaaucuuau auuugaucca a                                             21

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuggaucaaa uauaagauuc ccu                                           23

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ggaaucuuau auuugaucca a                                             21

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
```

```
uuggaucaaa uauaagauuc ccu                                            23

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ggaaucuuau auuugaucca a                                              21

<210> SEQ ID NO 58
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uuggaucaaa uauaagauuc ccu                                            23

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ggaaucuuau auuugaucca a                                              21

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uuggaucaaa uauaagauuc ccu                                            23

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ggaaucuuau auuugaucca a                                              21

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
```
uuggaucaaa uauaagauuc ccu                                          23

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggaaucuuau auugaucca a                                             21

<210> SEQ ID NO 64
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uuggaucaaa uauaagauuc ccu                                          23

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ggaaucuuau auugaucca a                                             21

<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuggaucaaa uauaagauuc ccu                                          23

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ggaaucuuau auugaucca a                                             21

<210> SEQ ID NO 68
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuggaucaaa uauaagauuc ccu                                          23

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ggaaucuuau auuugaucca a                                              21

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uuggaucaaa uauaagauuc ccu                                            23

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaaucuuau auuugaucca a                                              21

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uuggaucaaa uauaagauuc ccu                                            23

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ggaaucuuau auuugaucca a                                              21

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uuggaucaaa uauaagauuc ccu                                            23

```
<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaaucuuau auuugaucca a                                                21

<210> SEQ ID NO 76
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuggaucaaa uauaagauuc ccu                                              23

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ggaaucuuau auuugaucca a                                                21

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuggaucaaa uauaagauuc ccu                                              23

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggaaucuuau auuugaucca a                                                21

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uuggaucaaa uauaagauuc ccu                                              23
```

```
<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ggaaucuuau auugaucca a                                                    21

<210> SEQ ID NO 82
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uuggaucaaa uauaagauuc ccu                                                 23

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ggaaucuuau auugaucca a                                                    21

<210> SEQ ID NO 84
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uuggaucaaa uauaagauuc ccu                                                 23

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 85
ggaucaucuc aagucuuact t                                                   21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
``` oligonucleotide

<400> SEQUENCE: 86
guaagacuug agaugaucct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 87
ggaucaucuc aagucuuact t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 88
guaagacuug agaugaucct t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 89
ggaucaucuc aagucuuact t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 90
guaagacuug agaugaucct t                                              21

<210> SEQ ID NO 91
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 91
ggaucaucuc aagucuuact t                                         21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 92
guaagacuug agaugaucct t                                         21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 93
ggaucaucuc aagucuuact t                                         21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 94
guaagacuug agaugaucct t                                         21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 95
ggaucaucuc aagucuuact t                                         21
```

-continued

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 96
guaagacuug agaugaucct t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 97
ggaucaucuc aagucuuact t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 98
guaagacuug agaugaucct t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 99
ggaucaucuc aagucuuact t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:

-continued

<223> OTHER INFORMATION: Description of Artificial Sequence: Synthetic
      oligonucleotide

<400> SEQUENCE: 100
guaagacuug agaugaucct t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 101
ggaucaucuc aagucuuact t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 102
guaagacuug agaugaucct t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 103
ggaucaucuc aagucuuact t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 104
guaagacuug agaugaucct t                                              21

<210> SEQ ID NO 105
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 105
ggaucaucuc aagucuuact t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 106
guaagacuug agaugaucct t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 107
ggaucaucuc aagucuuact t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 108
guaagacuug agaugaucct t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 109
```
ggaucaucuc aagucuuact t                                                  21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 110
guaagacuug agaugaucct t                                                  21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 111
ggaucaucuc aagucuuact t                                                  21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 112
guaagacuug agaugaucct t                                                  21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 113
ggaucaucuc aagucuuact t                                                  21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide

```
<220> FEATURE:
<223> OTHER INFORMATION: Description of Artificial Sequence: Synthetic
      oligonucleotide

<400> SEQUENCE: 114
guaagacuug agaugaucct t                                                    21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 115
ggaucaucuc aagucuuact t                                                    21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 116
guaagacuug agaugaucct t                                                    21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 117
ggaucaucuc aagucuuact t                                                    21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 118
guaagacuug agaugaucct t                                                    21

<210> SEQ ID NO 119
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gucaucacac ugaauaccaa u                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gucaucacac ugaauaccaa u                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gucaucacac ugaauaccaa u                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 122
cugaagaccu gaagacaaut t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 123
cugaagaccu gaagacaaut t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
```

```
<220> FEATURE:
<223> OTHER INFORMATION: Description of Artificial Sequence: Synthetic
      oligonucleotide

<400> SEQUENCE: 124
cuuacgcuga guacuucgat t                                                    21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 125
cuuacgcuga guacuucgat t                                                    21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic
      oligonucleotide
<220> FEATURE:
<223> OTHER INFORMATION: Description of Artificial Sequence: Synthetic
      oligonucleotide

<400> SEQUENCE: 126
cuggcugaau uucagagcat t                                                    21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ggaaucuuau auugaucca a                                                     21

<210> SEQ ID NO 128
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uuggaucaaa uauaagauuc ccu                                                  23

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
```
ggaaucuuau auuugaucca a 21

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 130
uuggaucaaa uauaagauuc ccu 23

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 131
ggaaucuuau auuugaucca a 21

<210> SEQ ID NO 132
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 132
uuggaucaaa uauaagauuc ccu 23

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 133
ggaaucuuau auuugaucca a 21

<210> SEQ ID NO 134
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 134
uuggaucaaa uauaagauuc ccu 23

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 135
ggaaucuuau auuugaucca a 21

<210> SEQ ID NO 136
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uuggaucaaa uauaagauuc ccu                                              23

CARBOHYDRATE CONJUGATES AS DELIVERY AGENTS FOR OLIGONUCLEOTIDES

RELATED APPLICATIONS

This application is a continuation of U.S. patent application Ser. No. 17/368,246, filed Jul. 6, 2021, which is a continuation of U.S. patent application Ser. No. 16/861,494, filed Apr. 29, 2020, now U.S. Pat. No. 11,110,174, which is a continuation of U.S. patent application Ser. No. 16/196,628, filed Nov. 20, 2018, now U.S. Pat. No. 10,806,791, which is a continuation of U.S. application Ser. No. 15/817,473, filed Nov. 20, 2017, which is a continuation application of U.S. application Ser. No. 14/835,272, filed Aug. 25, 2015, now U.S. Pat. No. 9,867,882, which is a continuation application of U.S. application Ser. No. 14/329,540, filed Jul. 11, 2014, now U.S. Pat. No. 9,370,581, which is a continuation of U.S. application Ser. No. 13/693,478, filed Dec. 4, 2012, now U.S. Pat. No. 8,828,956, which is a continuation of U.S. application Ser. No. 13/326,203, filed Dec. 14, 2011, now U.S. Pat. No. 8,450,467, which is a continuation application of U.S. application Ser. No. 12/328,528, filed Dec. 4, 2008, now U.S. Pat. No. 8,106,022, which claims the benefit of priority to U.S. Provisional Patent Application No. 60/992,309, filed Dec. 4, 2007; U.S. Provisional Patent Application No. 61/013,597, filed Dec. 13, 2007; U.S. Provisional Patent Application No. 61/127,751, filed May 14, 2008; U.S. Provisional Patent Application No. 61/091,093, filed Aug. 22, 2008; and U.S. Provisional Patent Application No. 61/097,261, filed Sep. 16, 2008; all of which are herein incorporated by reference in their entirety.

FIELD OF INVENTION

The present invention relates to the field of therapeutic agent delivery using carbohydrate conjugates. In particular, the present invention provides novel carbohydrate conjugates and iRNA agents comprising these conjugates, which are advantageous for the in vivo delivery of these iRNA agents, as well as iRNA compositions suitable for in vivo therapeutic use. Additionally, the present invention provides methods of making these compositions, as well as methods of introducing these iRNA agents into cells using these compositions, e.g., for the treatment of various disease conditions.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

RNA interference or "RNAi" is a term initially coined by Fire and co-workers to describe the observation that double-stranded RNA (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

siRNA has been shown to be extremely effective as a potential anti-viral therapeutic with numerous published examples appearing recently. siRNA molecules directed against targets in the viral genome dramatically reduce viral titers by orders of magnitude in animal models of influenza (Ge et al., (2004) *Proc. Natl. Acd. Sci. USA*, 101, 8676-8681; Tompkins et al. (2004) *Proc. Natl. Acd. Sci. USA*, 101, 8682-8686; Thomas et al. (2005) *Expert Opin. Biol. Ther.* 5, 495-505), respiratory synctial virus (RSV) (Bitko et al. (2005) *Nat. Med.* 11, 50-55), hepatitis B virus (HBV) (Morrissey et al. (2005) *Nat. Biotechnol.* 23, 1002-1007), hepatitis C virus (Kapadia et al. (2003) *Proc. Natl. Acad. Sci. USA*, 100, 2014-2018; Wilson et al. (2003) *Proc. Natl. Acad. Sci. USA*, 100, 2783-2788) and SARS coronavirus (Li et al. (2005) *Nat. Med.* 11, 944-951).

Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that alter the expression level of the target sequence, discussed by Cohen (*Oligonucleotides: Antisense Inhibitors of Gene Expression*, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller et al. (1987) *Anti-Cancer Drug Design*, 2, 117-128), and α-anomer oligonucleotides are the two most extensively studied antisense agents which are thought to disrupt nucleic acid function by hybridization arrest.

Another means by which antisense oligonucleotides alter the expression level of target sequences is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

The opportunity to use these and other nucleic acid based therapies holds significant promise, providing solutions to medical problems that could not be addressed with current, traditional medicines. The location and sequences of an increasing number of disease-related genes are being identified, and clinical testing of nucleic acid-based therapeutics for a variety of diseases is now underway.

Despite the advances in application of oligonucleotides and oligonucleotide analogs as therapeutics, the need exists for oligonucleotides having improved pharmacological properties, e.g. serum stability, delivery to the right organ or cell and transmemebrane delivery. Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport.

Efficient delivery to cells in vivo requires specific targeting and substantial protection from the extracellular environment, particularly serum proteins. One method of achieving specific targeting is to conjugate a targeting moiety to the iRNA agent. The targeting moiety helps in targeting the iRNA agent to the required target site. One way a targeting moiety can improve delivery is by receptor mediated endocytotic activity. This mechanism of uptake involves the movement of iRNA agent bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve nM affinity, while spacing among sugars is also crucial.

The Mannose receptor, with its high affinity to D-mannose represents another important carbohydrate-based ligand-receptor pair. The mannose receptor is highly expressed on specific cell types such as macrophages and possibly dendritic cells Mannose conjugates as well as mannosylated drug carriers have been successfully used to target drug molecules to those cells. For examples, see Biessen et al. (1996) *J. Biol. Chem.* 271, 28024-28030; Kinzel et al. (2003) *J. Peptide Sci.* 9, 375-385; Barratt et al. (1986) *Biochim. Biophys. Acta* 862, 153-64; Diebold et al. (2002) *Somat. Cell Mol. Genetics* 27, 65-74.

Lipophilic moieties, such as cholesterol or fatty acids, when attached to highly hydrophilic molecules such as nucleic acids can substantially enhance plasma protein binding and consequently circulation half life. In addition, binding to certain plasma proteins, such as lipoproteins, has been shown to increase uptake in specific tissues expressing the corresponding lipoprotein receptors (e.g., LDL-receptor HDL-receptor or the scavenger receptor SR-B1). For examples, see Bijsterbosch, M. K., Rump, E. T. et al. (2000) *Nucleic Acids Res.* 28, 2717-25; Wolfrum, C., Shi, S. et al. (2007) 25, 1149-57. Lipophilic conjugates can also be used in combination with the targeting ligands in order to improve the intracellular trafficking of the targeted delivery approach.

There is a clear need for new receptor specific ligand conjugated iRNA agents and methods for their preparation, that address the shortcomings of the in vivo delivery of oligonucleotide therapeutics as described above. The present invention is directed to this very important end.

SUMMARY

In one aspect, the invention provides an iRNA agent that is conjugated with at least one carbohydrate ligand, e.g., monosaccharide, disaccharide, trisaccharide, tetrasaccharide, oligosaccharide, polysaccharide. These carbohydrate-conjugated iRNA agents target, in particular, the parenchymal cells of the liver. In one embodiment, the iRNA agent includes more than one carbohydrate ligand, preferably two or three. In one embodiment, the iRNA agent comprises one or more galactose moiety. In another embodiment, the iRNA agent includes at least one (e.g., two or three or more) lactose molecules (lactose is a glucose coupled to a galactose). In another embodiment, the iRNA agent includes at least one (e.g., two or three or more) N-Acetyl-Galactosamine (GalNAc), N—Ac-Glucosamine (GluNAc), or mannose (e.g., mannose-6-phosphate). In one embodiment, iRNA agent comprises at least one mannose ligand, and the iRNA agent targets macrophages.

In one aspect, the invention features an iRNA agent comprising a carbohydrate ligand, and the presence of the carbohydrate ligand can increase delivery of the iRNA agent to the liver. Thus an iRNA agent comprising a carbohydrate ligand can be useful for targeting a gene for which expression is undesired in the liver. For example, an iRNA agent comprising a carbohydrate ligand can target a nucleic acid expresses by a hepatitis virus (e.g., hepatitis C, hepatitis B, hepatitis A, hepatitis D, hepatitis E, hepatitis F, hepatitis G, or hepatitis H).

In one embodiment, the carbohydrate-conjugated iRNA agent targets a gene of the hepatitis C virus. In another embodiment, the iRNA agent that targets a gene of the hepatitis C virus can be administered to a human having or at risk for developing hepatitis, e.g., acute or chronic hepatitis, or inflammation of the liver. A human who is a candidate for treatment with a carbohydrate-conjugated iRNA agent, e.g., an iRNA agent that targets a gene of HCV, can present symptoms indicative of HCV infection, such as jaundice, abdominal pain, liver enlargement and fatigue.

In one embodiment, a carbohydrate-conjugated iRNA agent targets the 5' core region of HCV. This region lies just downstream of the ribosomal toe-print straddling the initiator methionine. In another embodiment, an iRNA agent targets any one of the nonstructural proteins of HCV, such as NS3, NS4A, NS4B, NS5A, or NS5B. In another embodiment, an iRNA agent targets the E1, E2, or C gene of HCV.

In another embodiment, the carbohydrate-conjugated iRNA agent targets a hepatitis B virus (HBV), and the iRNA agent has a sequence that is substantially similar to a sequence of a gene of HBV, e.g., the protein X (HBx) gene of HBV.

Carbohydrate-conjugated iRNA agents can also be used to treat other liver disorders, including disorders characterized by unwanted cell proliferation, hematological disorders, metabolic disorders, and disorders characterized by inflammation. A proliferation disorder of the liver can be, for example, a benign or malignant disorder, e.g., a cancer, e.g, a hepatocellular carcinoma (HCC), hepatic metastasis, or hepatoblastoma. A hepatic hematology or inflammation disorder can be a disorder involving clotting factors, a complement-mediated inflammation or a fibrosis, for example. Metabolic diseases of the liver include dyslipidemias and irregularities in glucose regulation. In one embodiment, a liver disorder is treated by administering one or more iRNA agents that have a sequence that is substantially identical to a sequence in a gene involved in the liver disorder.

In one embodiment, a carbohydrate-conjugated iRNA agent targets a nucleic acid expressed in the liver, such as an ApoB RNA, c-jun RNA, beta-catenin RNA, or glucose-6-phosphatase mRNA.

An iRNA that targets glucose-6-phosphatase can be administered to a subject to inhibit hepatic glucose production, e.g., for the treatment of glucose-metabolism-related disorders, such as diabetes, e.g., type-2-diabetes mellitus. The iRNA agent can be administered to an individual at risk for the disorder to delay onset of the disorder or a symptom of the disorder.

BRIEF DESCRIPTION OF THE DRAWINGS

FIG. 3. Conjugation of sugars (monosaccharides) to nucleic acids. Conjugation of Galactose, N-acetylgalactosamine, mannose, glucose, glucosamone, fucose, lactose etc to: 3'- and 5'-ends of one strand (sense or antisense/guide strands). Double stranded nucleic acids can have two 3'-overhangs, one overhang at 3'-end of sense or antisense or with no overhangs.

FIG. 4. Conjugation of sugars (monosaccharides) to nucleic acids. Conjugation of Galactose, N-acetylgalactosamine, mannose, glucose, glucosamone, fucose, lactose etc to: 3'-end (IX) and 5'-end (X) of sense or antisense strand; q=0-10. Double stranded nucleic acids can have two 3'-overhangs, one overhang at 3'-end of sense or antisense or with no overhangs.

FIG. 8. Hybrid conjugates of sugars (monosaccharides) to nucleic acids. Conjugation of Galactose, N-acetylgalactosamine, mannose, glucose, glucosamone, fucose, lactose etc and a second ligand of choice to single stranded nucleic acids: XXV—3'- or 5-end serial conjugation; XXVI 3'- or 5-end ligand and 5'- or 3-end pteroic acid analogues. L is ligand of choice.

FIG. 9. Conjugates of sugars (monosaccharides) to nucleic acids. Conjugation of Galactose, N-acetylgalactosamine, mannose, glucose, glucosamone, fucose, lactose etc to lipid or lipid like molecule with (XVIII) and without spacer/tether (XIX).

FIG. 12. Conjugation of oligosaccharides to nucleic acids. Conjugation of analogues or derivates of galactose, N-acetylgalactosamine, mannose, glucose, glucosamone, fucose, lactose etc to 3'—(XXVII) and 5'-ends (XXVIII) of double stranded nucleic acids and 3'—(XXIX) and 5'-ends (XXX) of single stranded nucleic acids. Double stranded nucleic acids can have two 3'-overhangs, one overhang at 3'-end of sense or antisense or with no overhangs; Q is O or S. Similarly the sugar moiety or moieties in FIGS. 2-9 are replaced with oligosaccharides moieties described in FIG. 12.

FIG. 15. In vivo apoB gene silencing of galactose-siRNA conjugate.

FIG. 16. Structure of cholesterol and (GalNAc)$_3$ linked together via a phosphate linkage.

FIG. 17. Glycolipid-siRNA conjugate strategies.

FIG. 18. Binding Affinity and Multivalency of the Asialoglycoprotein Receptor.

FIG. 19. Synthesis of multiantennary conjugates from simple monomers.

FIG. 20. Glycolipid-siRNA conjugate for LDL and HDL packing and liver targeting.

FIG. 21. Glycolipid-siRNA Conjugate: Synthesis.

FIG. 22. Monomers for carbohydrate conjugation to siRNA. (A) shows one monomer for carbohydrate conjugation to siRNA; (B) shows another monomer for carbohydrate conjugation to siRNA; and (C) shows another monomer for carbohydrate conjugation to siRNA.

FIG. 23. Synthesis of GalNAc building blocks. (A) shows the synthesis of one GalNAc building block; (B) shows the synthesis of another GalNAc building block; and (C) shows the synthesis of another GalNAc building block FIG. 24. Synthesis of GalNAc building blocks (II).

FIG. 25. GalNAc clusters for hepatic targeting. (A) shows GalNAc conjugate; and (B) shows conjugate of GalNAc clusters.

FIG. 26. Carbohydrate (GalNAC) clusters for conjugation to siRNA.

FIG. 27. Multivalent GalNAC-siRNA conjugates.

FIG. 28. Carbohydrate building blocks for 5'-conjugation.

FIG. 29. Syntheses of Mannose conjugate building blocks.

FIG. 30. Post-synthetic carbohydrate conjugate building blocks.

FIG. 31. Comparison of gene silencing with cholesterol conjugated siRNA versus cholesterol-(GalNAc)3 conjugated siRNA.

FIG. 32. Comparison of duration of effect on serum cholesterol levels with cholesterol conjugated siRNA versus cholesterol-(GalNAc)3 conjugated siRNA.

FIG. 33. Comparison of uptake of Cy3 labeled siRNA with cholesterol conjugated siRNA versus cholesterol-(GalNAc)3 conjugated siRNA.

FIG. 37. Two different conjugates of this invention. (A) shows a conjugate represented by AD-3698 (GalNAc+Chol/Cy3); and (B) shows a conjugate represented by AD-31644 (Q11+L90).

FIG. 38A shows a scheme of placement of disulfide linkage in conjugates as 3'—Chol-S—S-(GalNAc)₃; and FIG. 38B shows a scheme of placement of disulfide linkage in conjugates as 3'-S—S-Chol-(GalNAc)₃.

FIG. 39A shows the experimental design for in vivo silencing of FVII with carbohydrate conjugated siRNAs; FIG. 39B shows the results of in vivo silencing of FVII with various carbohydrate-conjugated siRNAs; and FIG. 39C shows the results of in vivo silencing of FVII with various carbohydrate-conjugated siRNAs.

FIG. 41A shows the results of in vivo silencing of ApoB with various carbohydrate-conjugated siRNAs samples in liver and jejunum; and FIG. 41B shows the results of total cholesterol in liver.

FIG. 42. In vivo silencing of ApoB with carbohydrate conjugated siRNAs. (A) shows the results of in vivo silencing of ApoB with various carbohydrate-conjugated siRNAs samples in liver and jejunum, comparing GalNAc to Glucose; and (B) shows the results of total cholesterol in liver.

FIG. 46. Galactose conjugate (A) and in vivo gene silencing (B).

DETAILED DESCRIPTION

Figure 1:
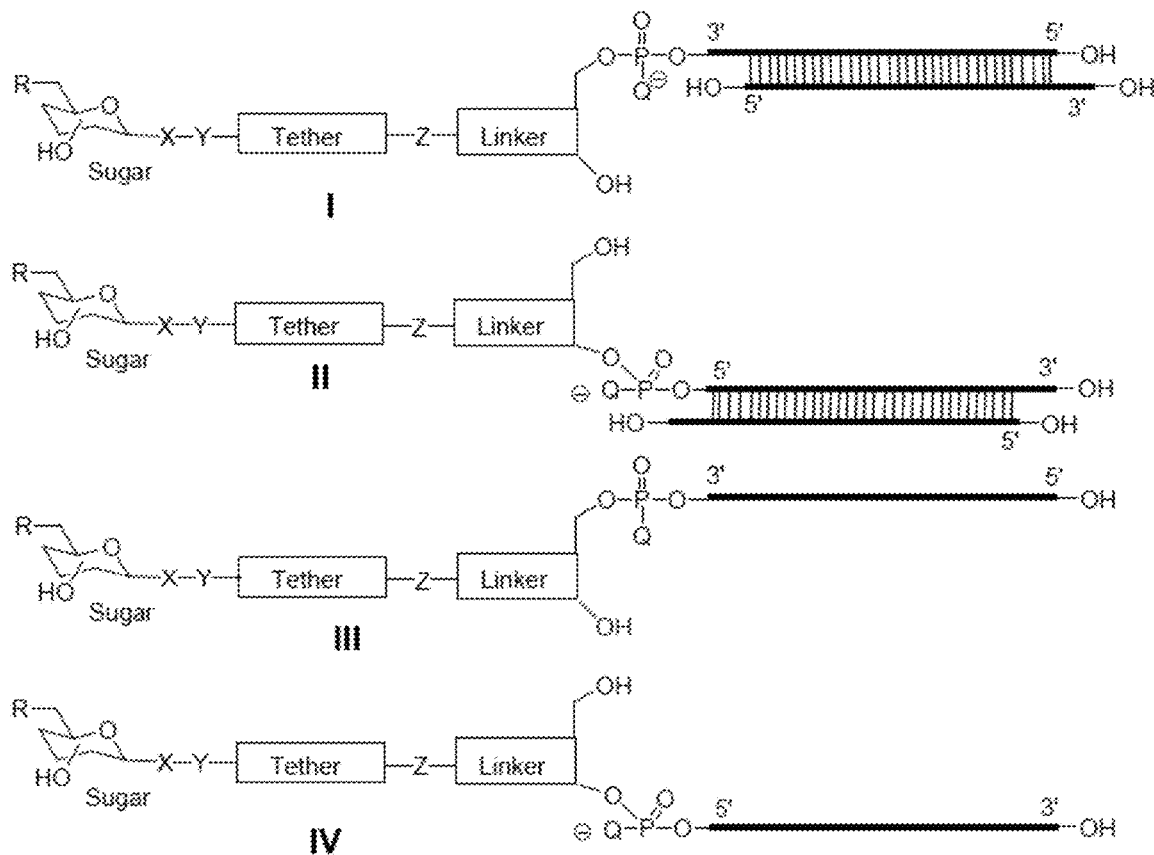
FIG. 1. Conjugation of sugars (monosaccharides) to nucleic acids. Conjugation of Galactose, N-acetylgalactosamine, mannose, glucose, glucosamone, fucose, lactose etc to 3'—(I) and 5'-ends (II) of double stranded nucleic acids and 3'—(III) and 5'-ends (IV) of single stranded nucleic acids. Double stranded nucleic acids can have two 3'-overhangs, one overhang at 3'-end of sense or antisense or with no overhangs; Q is O or S.
Figure 2:
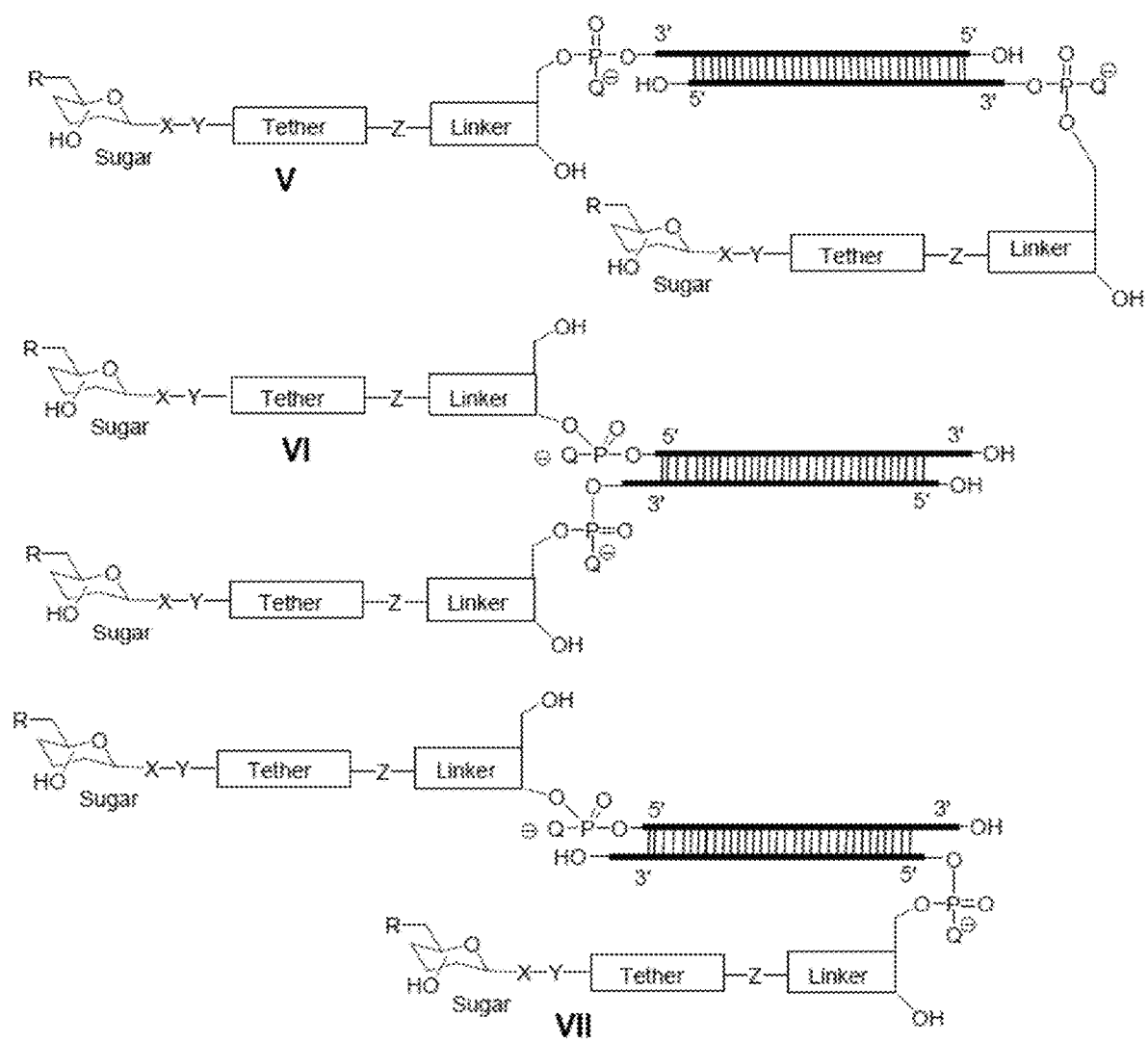
FIG. 2. Conjugation of sugars (monosaccharides) to nucleic acids. Conjugation of Galactose, N-acetylgalactosamine, mannose, glucose, glucosamone, fucose, lactose etc to: (V) 3'-ends of both strands (sense and antisense or guide strands); (VI) 3'-end of one strand (sense or antisense) and 5'-end of second the complementary strand and (VII) 5'-ends of both strands. Double stranded nucleic acids can have two 3'-overhangs, one overhang at 3'-end of sense or antisense or with no overhangs.
Figure 5:
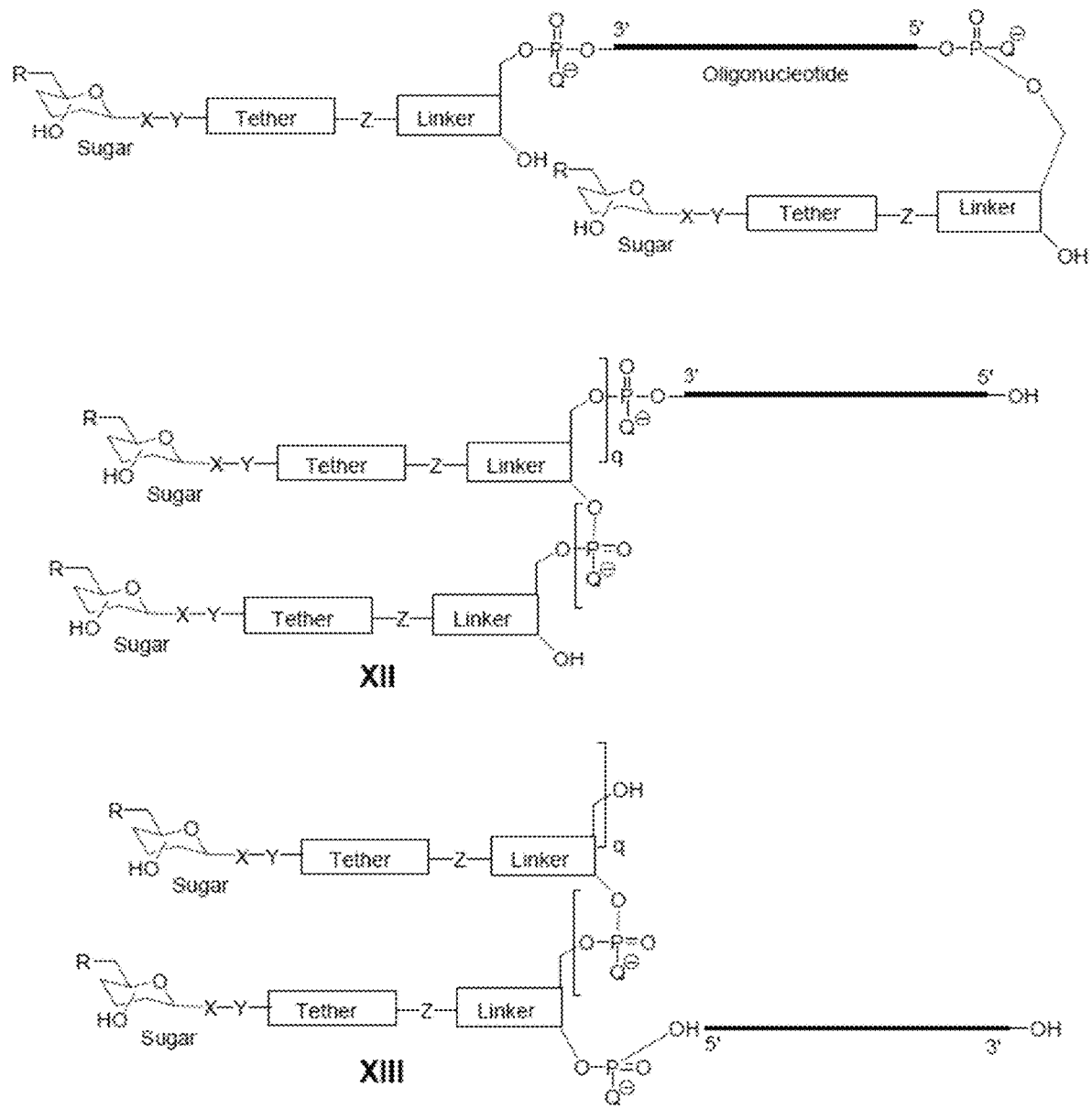
FIG. 5. Conjugation of sugars (monosaccharides) to nucleic acids. Conjugation of Galactose, N-acetylgalactosamine, mannose, glucose, glucosamone, fucose, lactose etc to: 3' and 5'-ends (XI); 3'-end (XII) and 5'-end (XIII) of oligonucleotide; q=0-10.
Figure 6:
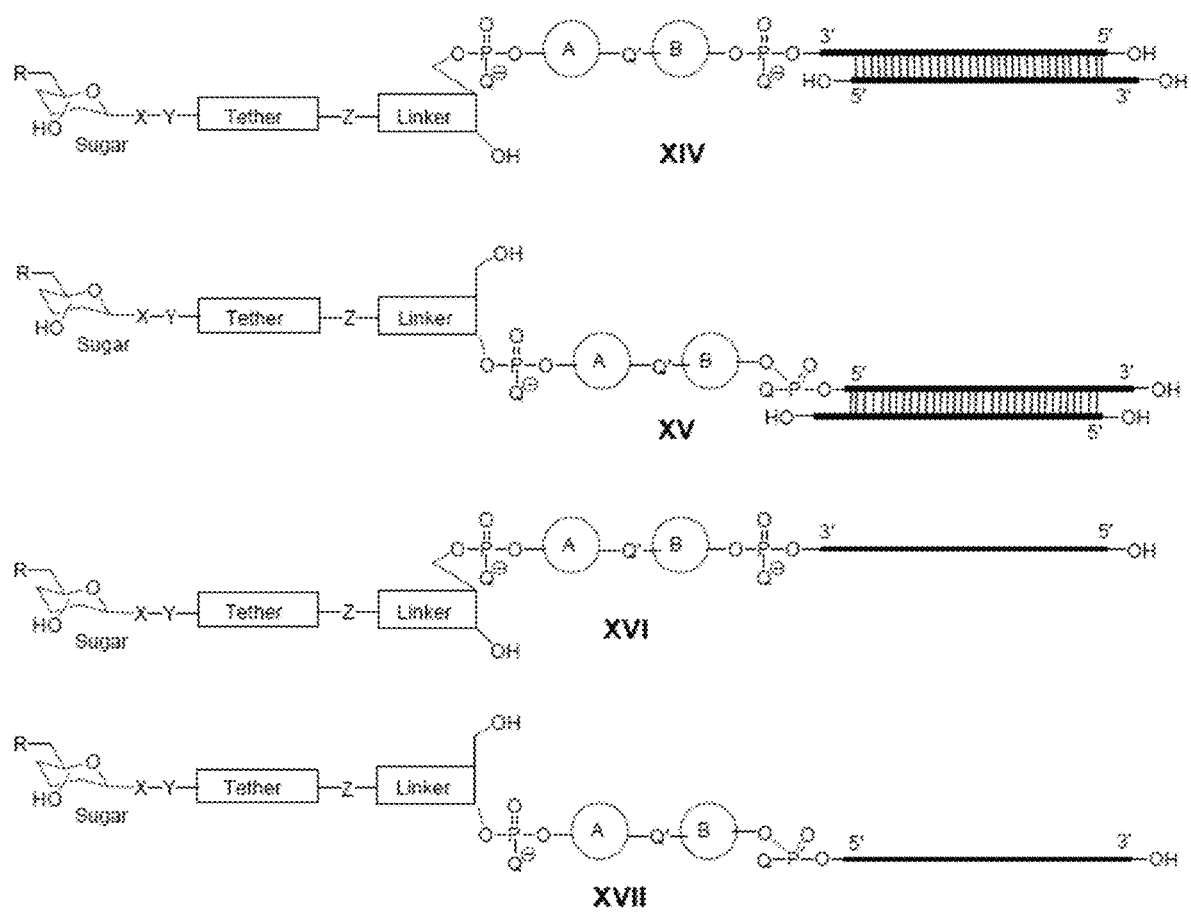
FIG. 6. Conjugation of sugars (monosaccharides) to nucleic acids. Conjugation of Galactose, N-acetylgalactosamine, mannose, glucose, glucosamone, fucose, lactose etc to nucleic acids with additional spacer separation: XIV—3'-end conjugate with alkyl and/or PEG spacer double stranded nucleic acid; XV—5'-end conjugation with alkyl and/or PEG spacer; XVI and XVII—corresponding 3' and 5'-end conjugates of single stranded nucleic acids/oligonucleotides. A, B stands for alkyl or PEG spacer, and combination there of, and Q'=CH$_2$, O, S, S—S, NH or NMe. Double stranded nucleic acids can have two 3'-overhangs, one overhang at 3'-end of sense or antisense or with no overhangs.
Figure 7:
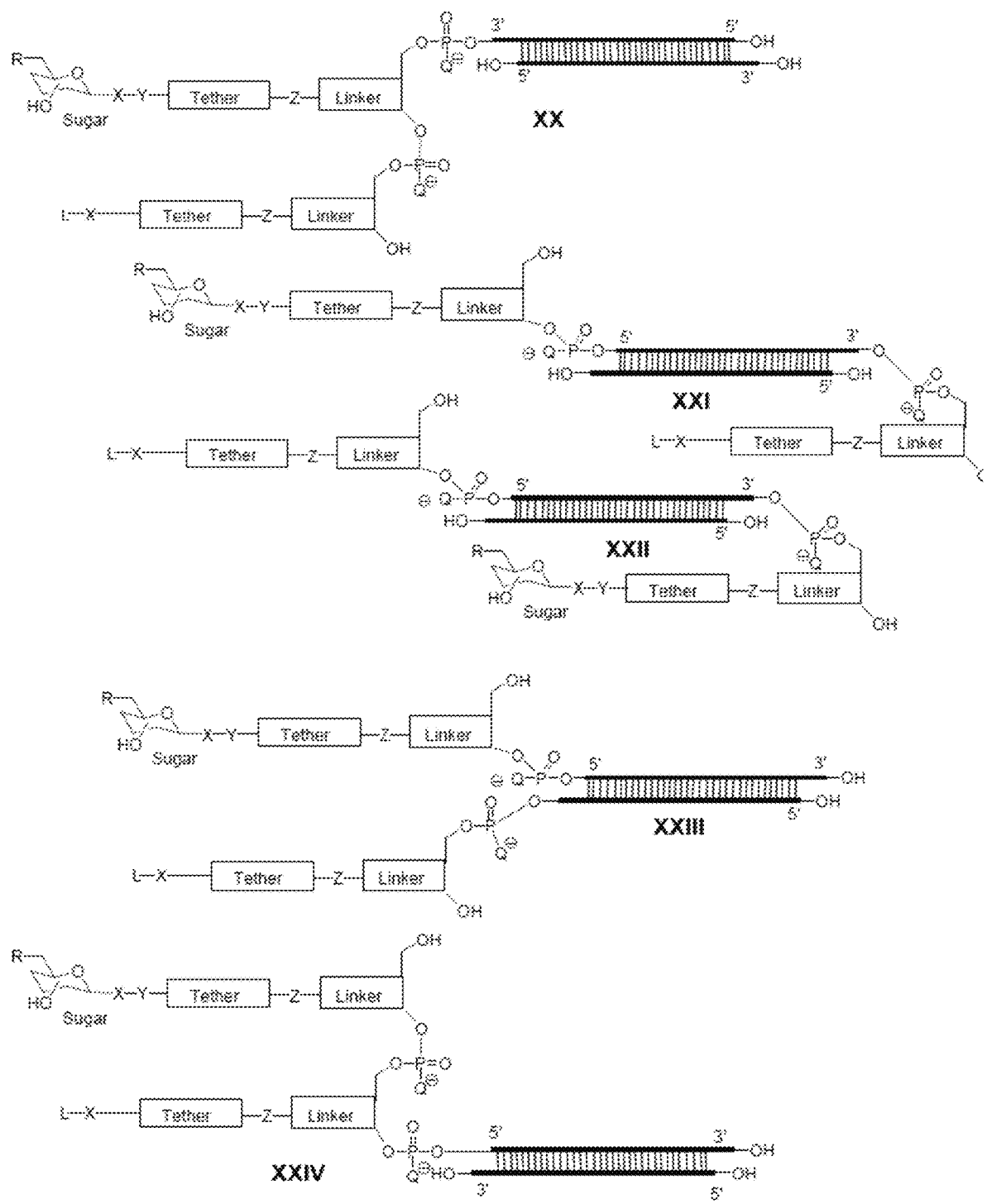
FIG. 7. Hybrid conjugates of sugars (monosaccharides) to nucleic acids. Conjugation of Galactose, N-acetylgalactosamine, mannose, glucose, glucosamone, fucose, lactose etc and a second ligand of choice to double stranded nucleic acids: XX—3'-end serial conjugation; XXI 3'-end ligand and 5'-end pteroic acid analogues on sense or antisense; XXII—5'-end ligand and 3'-end pteroic acid analogues on sense or antisense; XXIII—Pteroic acid analogues on 5'-end of sense or antisense and ligand of choice on 3'-end of antisense or sense or vice versa; XXIV—serial conjugation of ligand of choice and pteroic acid analogues to the 5'-end of sense or antisense strand of double stranded nucleic acids. L is ligand of choice.
Figure 10:
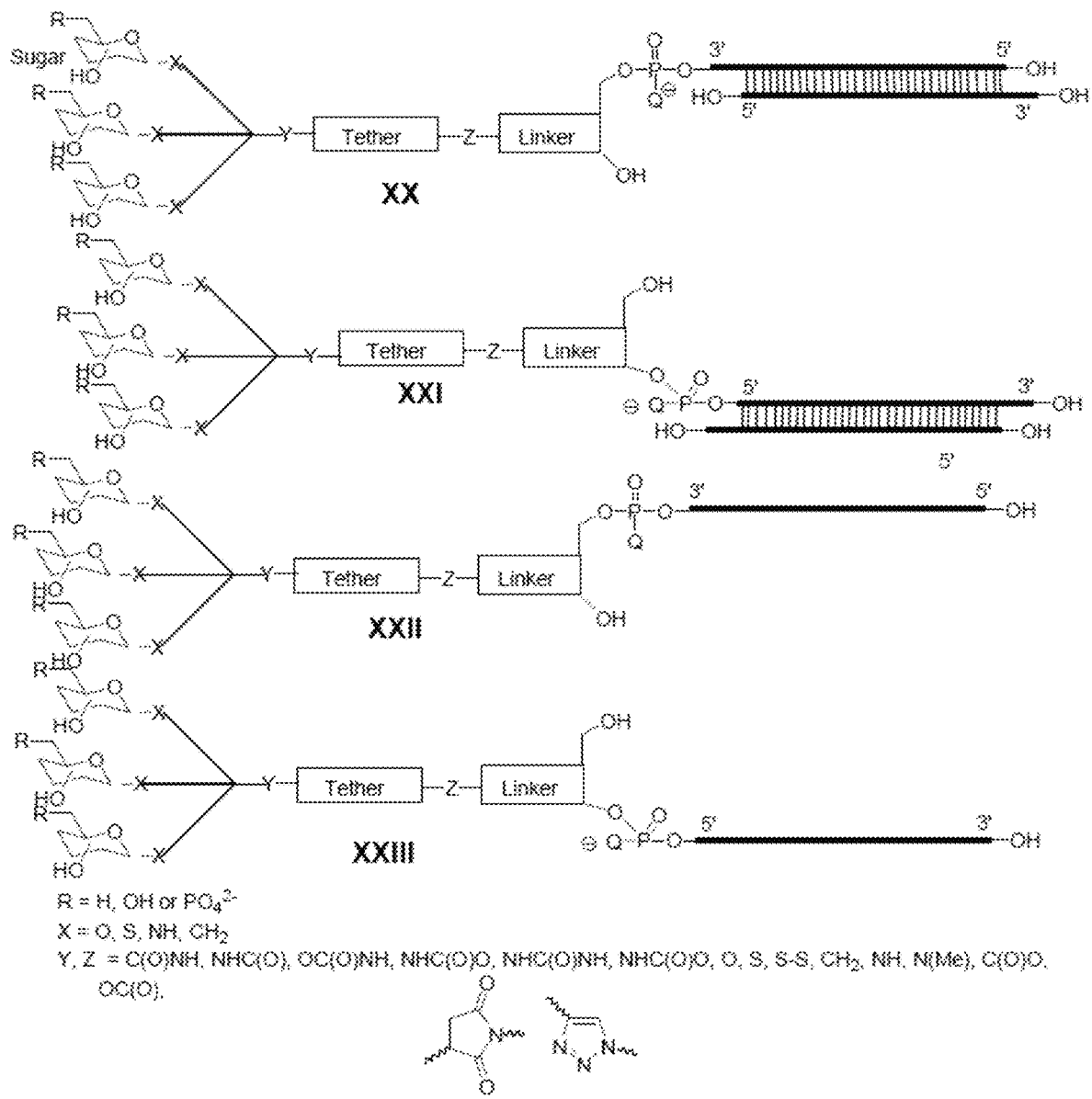
FIG. 10. Conjugation of sugars to nucleic acids. Conjugation of triantenary Galactose, N-acetylgalactosamine, mannose, glucose, glucosamone, fucose, lactose etc to 3'—(XX) and 5'-ends (XXI) of double stranded nucleic acids and 3'—(XXII) and 5'-ends (XXIII) of single stranded nucleic acids. Double stranded nucleic acids can have two 3'-overhangs, one overhang at 3'-end of sense or antisense or with no overhangs; Q is O or S.
Figure 11:
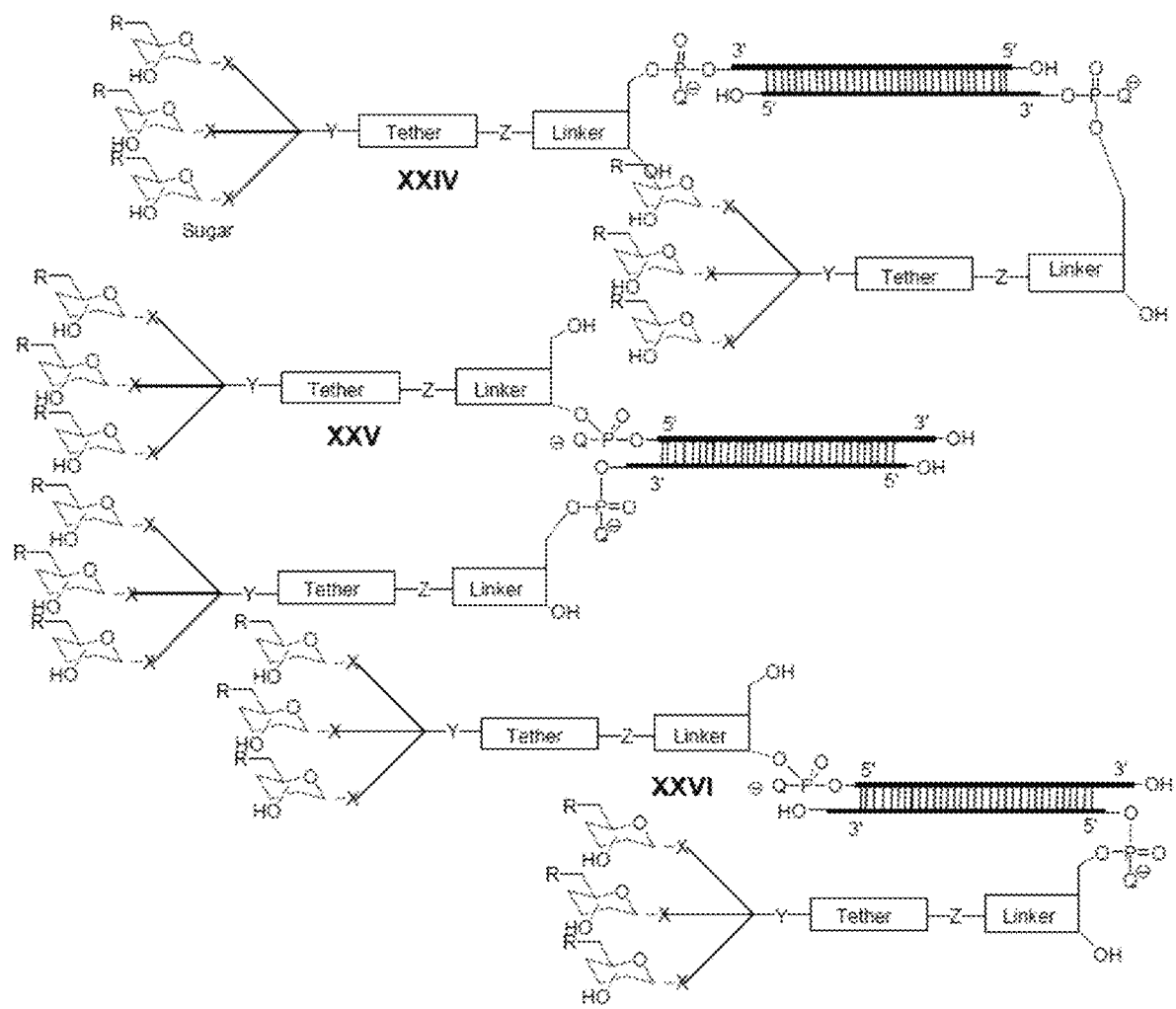
FIG. 11. Conjugation of sugars (monosaccharides) to nucleic acids. Conjugation of triantenary Galactose, N-acetylgalactosamine, mannose, glucose, glucosamone, fucose, lactose etc to: (XXIV) 3'-ends of both strands (sense and antisense or guide strands); (XXV) 3'-end of one strand (sense or antisense) and 5'-end of second the complementary strand and (XXVI) 5'-ends of both strands; For definition of R, X, Y, Z and Q see FIG. 1. Double stranded nucleic acids can have two 3'-overhangs, one overhang at 3'-end of sense or antisense or with no overhangs. Similarly the monoantenary sugar moiety or moieties in FIGS. 3-9 are replaced with triantenary sugar moiety or moieties described in FIGS. 10 and 11.
Figure 13:
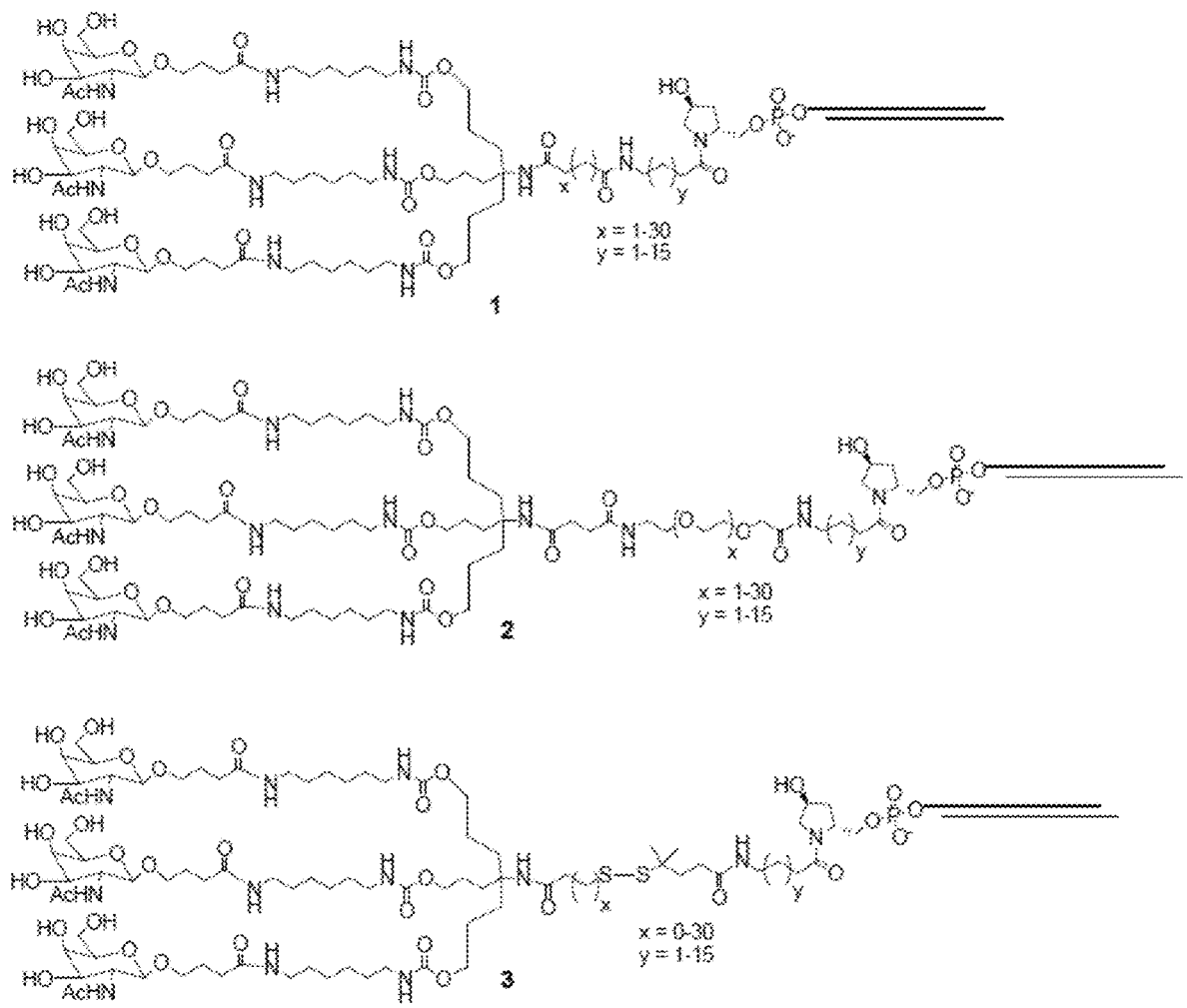
FIG. 13. Triantenary GalNAc double stranded oligonucleotide conjugates with cleavable disulfide linkages.
Figure 14:
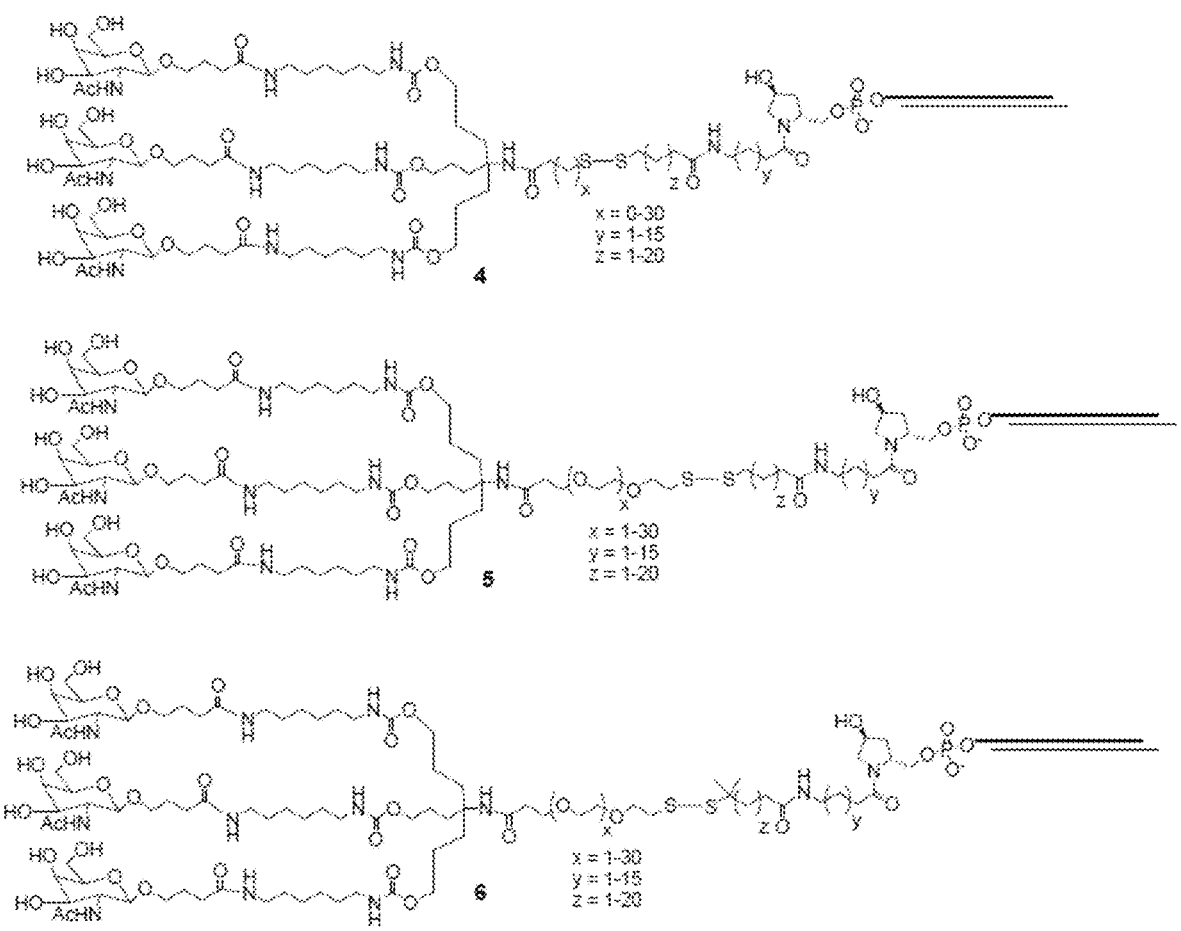
FIG. 14. Triantenary GalNAc double stranded oligonucleotide conjugates with cleavable disulfide linkages.
Figure 34:
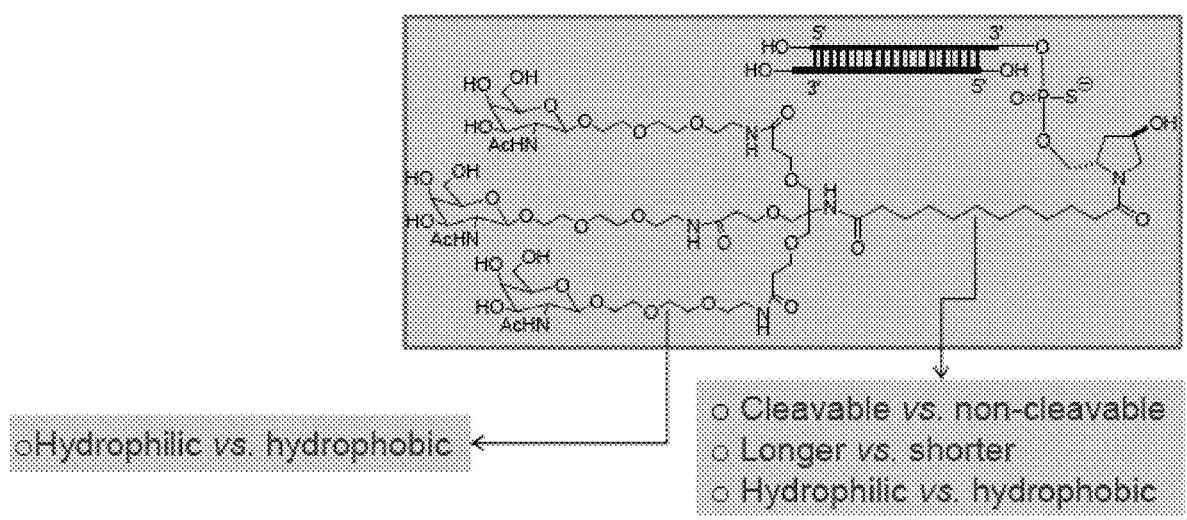
FIG. 34. Schematic view of design consideration for conjugates.
Figure 35:
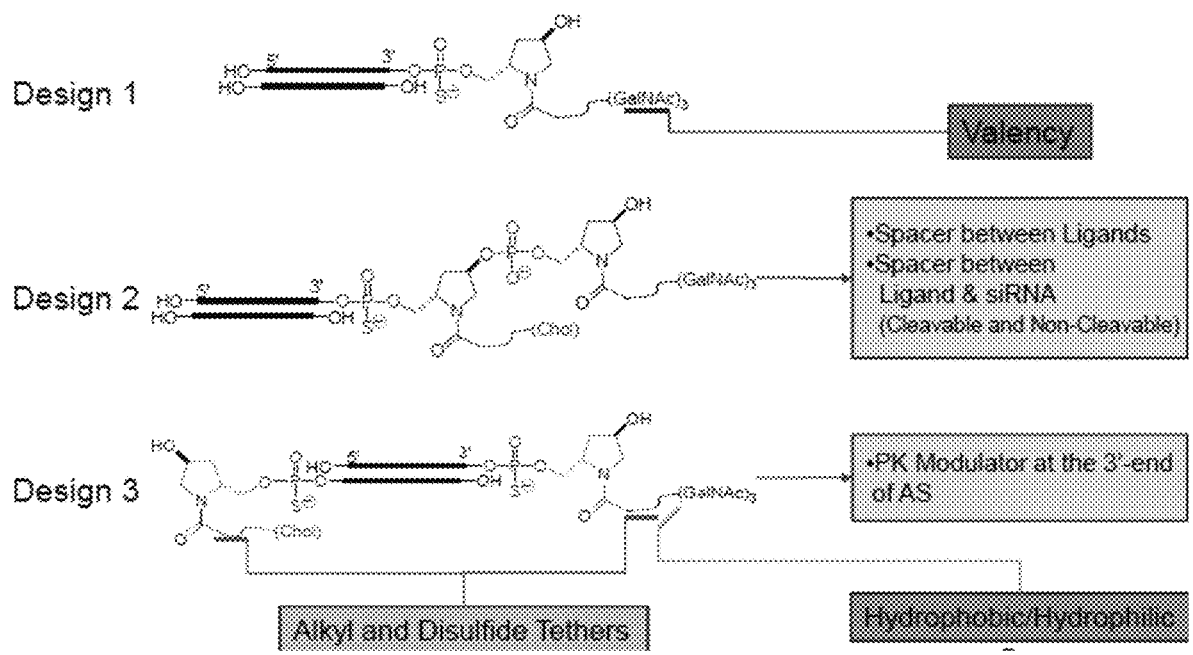
FIG. 35. Schematic view of designs conjugates.
Figure 36:
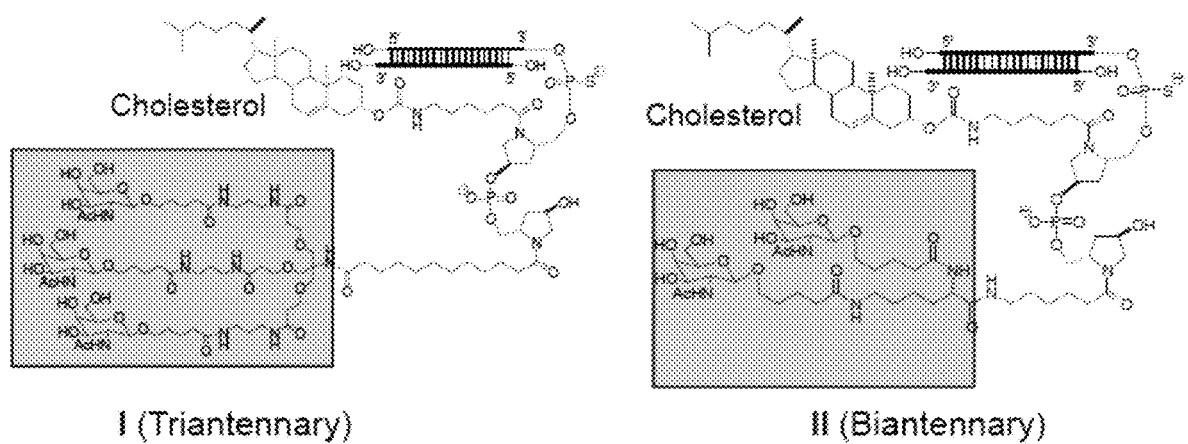
FIG. 36. Biantennary and Triantennary conjugates.
Figure 38A:
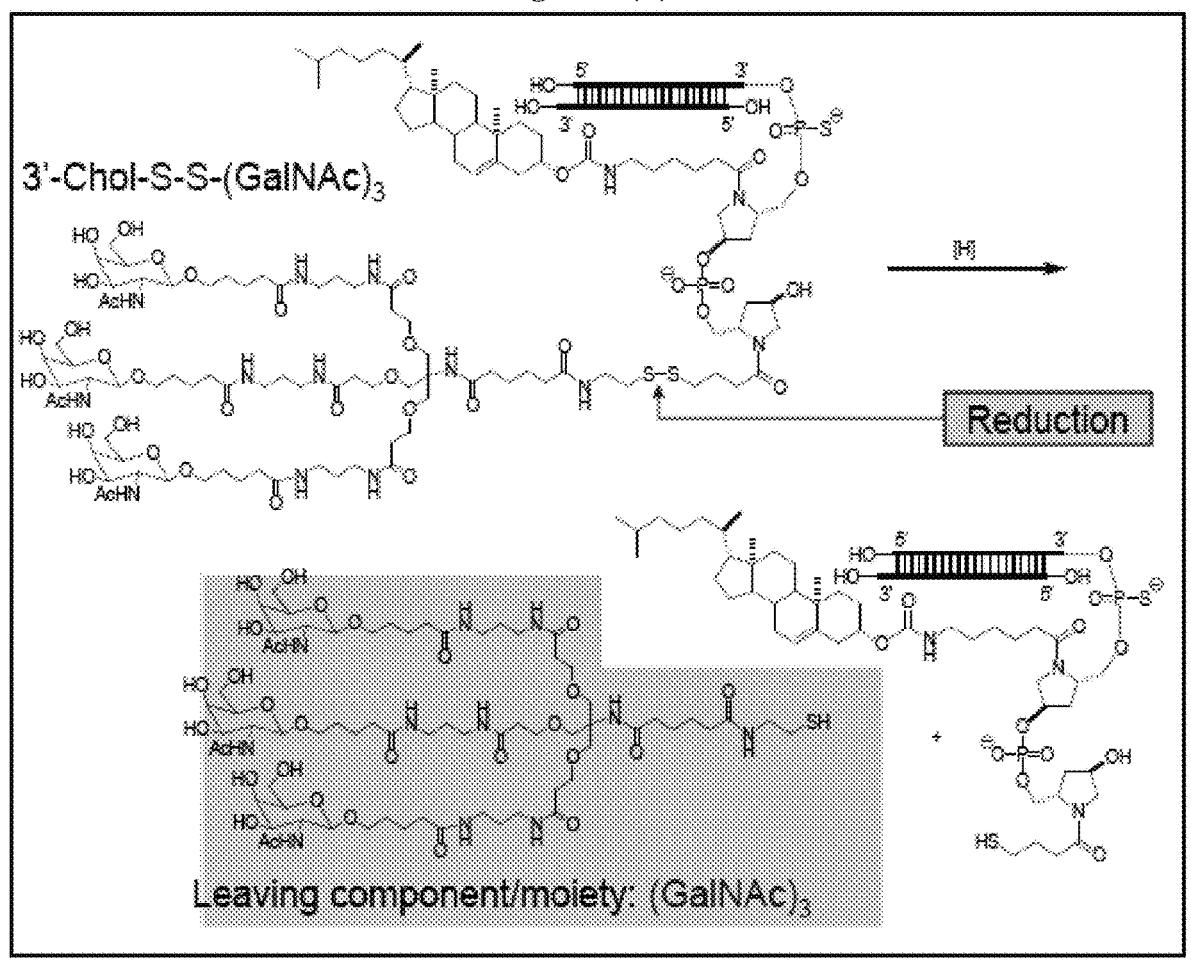
FIGS. 38A-38B. Some exemplary placement of disulfide linkage in conjugates.
Figure 38:
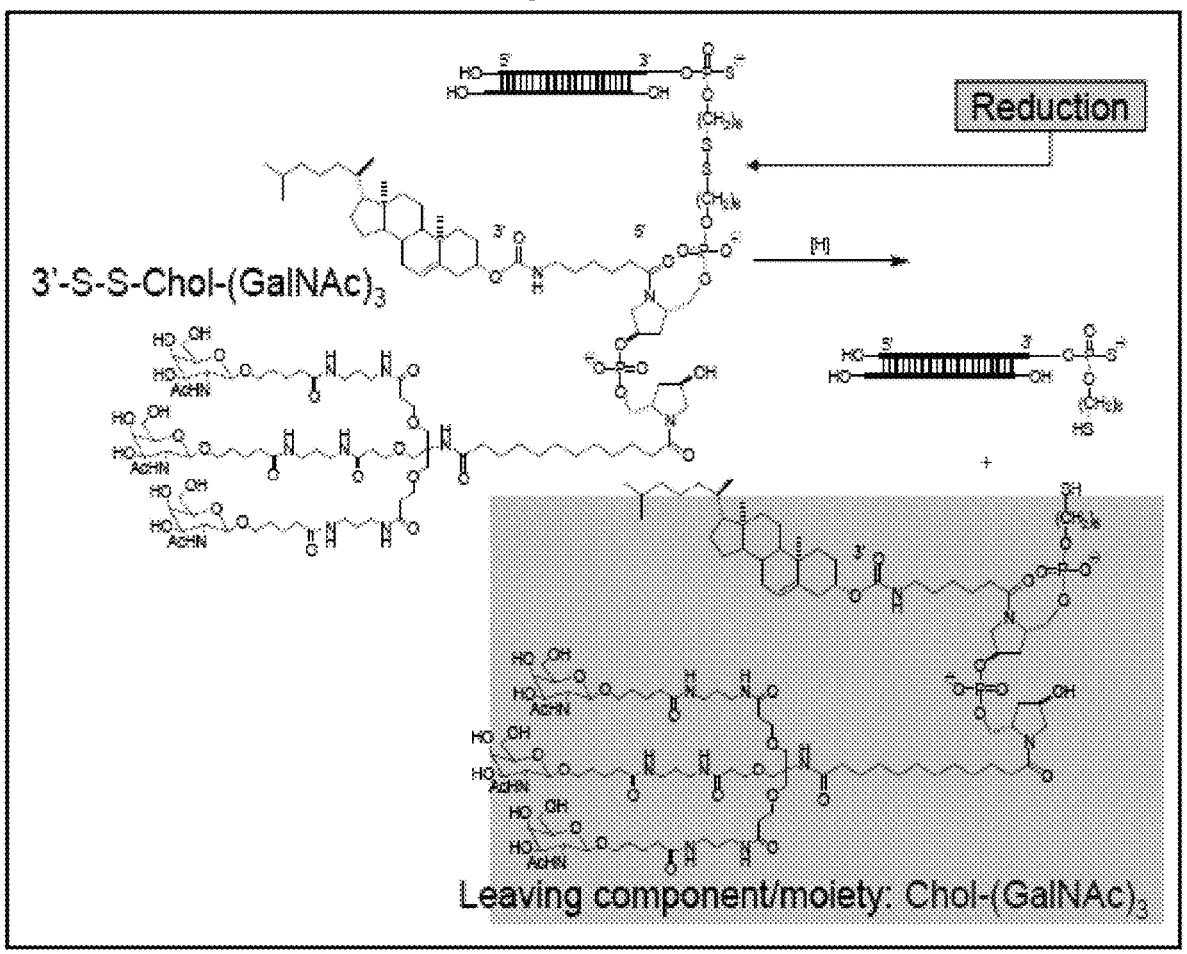

This invention is based on the discovery that conjugation of a carbohydrate moiety to an iRNA agent can optimize one or more properties of the iRNA agent. In many cases, the carbohydrate moiety will be attached to a modified subunit of the iRNA agent. E.g., the ribose sugar of one or more ribonucleotide subunits of an iRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least one "backbone attachment point", preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one aspect, the invention features, a compound having the structure shown in formula (CI)

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, $-P(Z^1)(Z^2)$—O-nucleoside, or $-P(Z^1)(Z^2)$—O-oligonucleotide; wherein $Z^1$ and $Z^2$ are each independently for each occurrence O, S, N(alkyl) or optionally substituted alkyl;

$J_1$ and $J_2$ are independently O, S, $NR^N$, optionally substituted alkyl, OC(O)NH, NHC(O)O, C(O)NH, NHC(O), OC(O), C(O)O, OC(O)O, NHC(O)NH, NHC(S)NH, OC(S)NH, OP(N($R^P$)$_2$)O, or OP(N($R^P$)$_2$); and

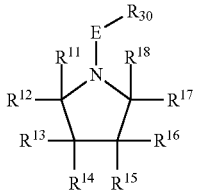

is cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and nd decalin; preferably, the acyclic group is selected from serinol backbone or diethanolamine backbone.

In preferred embodiments, ligand is a carbohydrate e.g. monosaccharide, disaccharide, trisaccharide, tetrasaccharide, polysaccharide.

In one embodiment, the compound is a pyrroline ring system as shown in formula (CII)

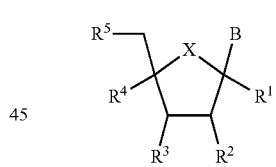

Formula (CII)

wherein E is absent or C(O), C(O)O, C(O)NH, C(S), C(S)NH, SO, $SO_2$, or $SO_2NH$;

$R^{11}$, $R^{12}$, $R^{13}$, $R^{14}$, $R^{15}$, $R^{16}$, $R^{17}$, and $R^{18}$ are each independently for each occurrence H, $-CH_2OR^a$, or $OR^b$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, $-P(Z^1)(Z^2)$—O-nucleoside, $-P(Z^1)(Z^2)$—O-oligonucleotide, $-P(Z^1)$(O-linker-$R^L$)—O-nucleoside, or $-P(Z^1)$(O-linker-$R^L$)—O-oligonucleotide;

$R^{30}$ is independently for each occurrence -linker-$R^L$ or $R^{31}$;

$R^L$ is hydrogen or a ligand;

$R^{31}$ is $-C(O)CH(N(R^{32})_2)(CH_2)_hN(R^{32})_2$;

$R^{32}$ is independently for each occurrence H, $-R^L$, -linker-$R^L$ or $R^{31}$ $Z^1$ is independently for each occurrence O or S;

$Z^2$ is independently for each occurrence O, S, N(alkyl) or optionally substituted alkyl; and h is independently for each occurrence 1-20.

For the pyrroline-based click-carriers, $R^{11}$ is $-CH_2OR^a$ and $R^3$ is $OR^b$; or $R^{11}$ is $-CH_2OR^a$ and $R^9$ is $OR^b$; or $R^{11}$ is $-CH_2OR^a$ and $R^{17}$ is $OR^b$; or $R^{13}$ is $-CH_2OR^a$ and $R^{11}$ is OR; or $R^{13}$ is $-CH_2OR^a$ and $R^{15}$ is $OR^b$; or $R^{13}$ is $-CH_2OR^a$ and $R^{17}$ is $OR^b$. In certain embodiments, $CH_2OR^a$ and $OR^b$ may be geminally substituted. For the 4-hydroxyproline-based carriers, $R^{11}$ is $-CH_2OR^a$ and $R^{17}$ is $OR^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, $CH_2OR^a$ and $OR^b$ may be cis or trans with respect to one another in any of the pairings delineated above Accordingly, all cis trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing $CH_2OR^a$ and $OR^b$ can both have the R configuration; or both have the S configuration; or one center can have the R configuration and the other center can have the S configuration and vice versa).

In one embodiment, $R^{11}$ is $CH_2OR^a$ and $R^9$ is $OR^b$.

In one embodiment, $R^b$ is a solid support.

In one embodiment, carrier of formula (CII) is a phosphoramidite, i.e., one of $R^a$ or $R^b$ is $-P(O-alkyl)N(alkyl)_2$, e.g., $-P(OCH_2CH_2CN)N(i-propyl)_2$. In one embodiment, $R^b$ is $-P(O-alkyl)N(alkyl)_2$.

In embodiment, the compound is a ribose ring system as shown in formula (CIII).

Formula (CIII)

wherein:

X is O, S, $NR^N$ or $CR^P_2$;

B is independently for each occurrence hydrogen, optionally substituted natural or non-natural nucleobase, optionally substituted natural nucleobase conjugated with -linker-$R^L$ or optionally substituted non-natural nucleobase conjugated with -linker-$R^L$;

$R^1$, $R^2$, $R^3$, $R^4$ and $R^5$ are each independently for each occurrence H, $OR^6$, F, $N(R^N)_2$, or -J-linker-$R_L$;

J is absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, OP(N($R^P$)$_2$)O, or OP(N($R^P$)$_2$);

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)($Z^2$)-formula (CIII), —P($Z^1$)(O-linker-$R^L$)—O— nucleoside, —P($Z^1$)(O-linker-$R^L$)—O-oligonucleotide, or —P($Z^1$)(O-linker-$R^L$)—O-formula (CIII);

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

$R^L$ is hydrogen or a ligand;

$Z^1$ and $Z^2$ are each independently for each occurrence O, S N(alkyl) or optionally substituted alkyl; and provided that $R^L$ is present at least once and further provided that $R^L$ is a ligand at least once.

In one embodiment, the carrier of formula (CI) is an acyclic group and is termed an "acyclic carrier". Preferred acyclic carriers can have the structure shown in formula (CIV) or formula (CV) below.

In one embodiment, the compound is an acyclic carrier having the structure shown in formula (CIV).

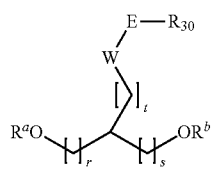

Formula (CIV)

wherein:

W is absent, O, S and N($R^N$), where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, $SO_2$, or $SO_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)(O-linker-$R^L$)—O-nucleoside, or —P($Z^1$)(O-linker-$R^L$)—O-oligonucleotide;

$R^{30}$ is independently for each occurrence -linker-$R^L$ or $R^{31}$ $R^L$ is hydrogen or a ligand;

$R^{31}$ is —C(O)CH(N($R^{32}$)$_2$)(CH$_2$)$_h$N($R^{32}$)$_2$;

$R^{32}$ is independently for each occurrence H, —$R^L$, -linker-$R^L$ or $R^{31}$ $Z^1$ is independently for each occurrence O or S;

$Z^2$ is independently for each occurrence O, S, N(alkyl) or optionally substituted alkyl;

h is independently for each occurrence 1-20; and r, s and t are each independently for each occurrence 0, 1, 2 or 3.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In one embodiment, the compound is an acyclic carrier having the structure shown in formula (CV)

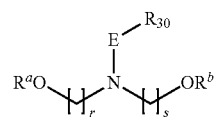

Formula (CV)

wherein E is absent or C(O), C(O)O, C(O)NH, C(S), C(S)NH, SO, $SO_2$, or $SO_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)($Z^2$)-formula (I), —P($Z^1$)(O-linker-$R^L$)—O-nucleoside, or —P($Z^1$)(O-linker-$R^L$)—O-oligonucleotide;

$R^{30}$ is independently for each occurrence -linker-$R^L$ or $R^{31}$ $R^L$ is hydrogen or a ligand;

$R^{31}$ is —C(O)CH(N($R^{32}$)$_2$)(CH$_2$)$_h$N($R^{32}$)$_2$;

$R^{32}$ is independently for each occurrence H, —$R^L$, -linker-$R^L$ or $R^{31}$ $Z^1$ is independently for each occurrence O or S;

$Z^2$ is independently for each occurrence O, S, N(alkyl) or optionally substituted alkyl; and h is independently for each occurrence 1-20; and r and s are each independently for each occurrence 0, 1, 2 or 3. In addition to the cyclic carriers described herein, RRMS can include cyclic and acyclic carriers described in copending and co-owned U.S. application Ser. No. 10/916,185 filed Aug. 10, 2004, U.S. application Ser. No. 10/946,873 filed Sep. 21, 2004, and U.S. application Ser. No. 10/985,426, filed Nov. 9, 2004, U.S. application Ser. No. 10/833,934, filed Aug. 3, 2007 U.S. application Ser. No. 11/115,989 filed Apr. 27, 2005, and U.S. application Ser. No. 11/119,533, filed Apr. 29, 2005, contents of each are hereby incorporated by reference for all purposes.

Accordingly, in one aspect, the invention features, a monomer having the structure shown in formula (I)

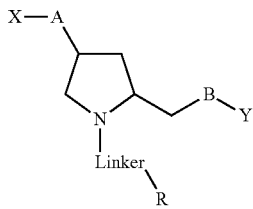

wherein:

A and B are each independently for each occurrence O, N(R$^N$) or S;

R$^N$ is independently for each occurrence H or C$_1$-C$_6$ alkyl;

X and Y are each independently for each occurrence H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, a nucleotide, a nucleoside, —P(Z')(Z") O-Linker-OP(Z''')(Z''')O-oligonucleotide, an oligonucleotide, —P(Z')(Z")-formula (I), —P(Z')(Z")— or -Linker-R;

R is L$^G$ or has the structure shown below:

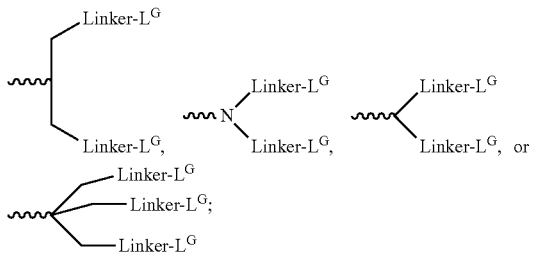

L$^G$ is independently for each occurrence a ligand, e.g., carbohydrate, e.g. monosaccharide, disaccharide, trisaccharide, tetrasaccharide, polysaccharide; and Z', Z", Z''' and Z'''' are each independently for each occurrence O or S.

The term "linker" means an organic moiety that connects two parts of a compound. Linkers typically comprise a direct bond or an atom such as oxygen or sulfur, a unit such as NR$^8$, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylhererocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkynyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R$^8$), C(O), substituted or unsubstituted aryl, substituted or unsubstituted heteroaryl, substituted or unsubstituted heterocyclic; where R$^8$ is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

In one embodiment, the linker is —[(P-Q"-R)$_q$—X—(P'-Q'''-R')$_{q'}$]$_{q''}$-T-, wherein:

P, R, T, P', R' and T are each independently for each occurrence absent, CO, NH, O, S, OC(O), NHC(O), CH$_2$, CH$_2$NH, CH$_2$O; NHCH(R$^a$)C(O), —C(O)—CH(R$^a$)—NH—, CH=N—O,

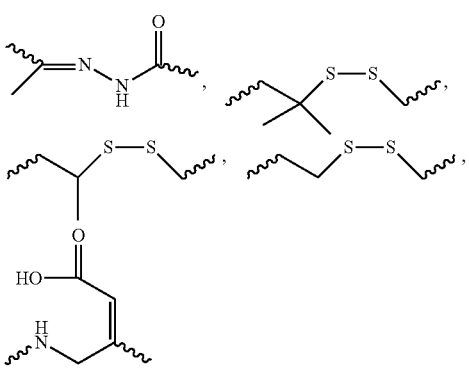

or heterocyclyl;

Q" and Q''' are each independently for each occurrence absent, —(CH$_2$)$_n$—, —C(R$^1$)(R$^2$)(CH$_2$)$_n$—, —(CH$_2$)$_n$C(R$^1$)(R$^2$)—, —(CH$_2$CH$_2$O)$_m$CH$_2$CH$_2$—, or —(CH$_2$CH$_2$O)$_m$CH$_2$CH$_2$NH—;

X is absent or a cleavable linking group;

R$^a$ is H or an amino acid side chain;

R$^1$ and R$^2$ are each independently for each occurrence H, CH$_3$, OH, SH or N(R$^N$)$_2$;

R$^N$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(Q)-C, —O—C, —S—C, —SS—C, —C(O)N(Q)-C, —OC(O)N (Q)-C, —N(Q)C(O)—C, or —N(Q)C(O)O—C; wherein Q is independently for each occurrence H or optionally substituted alkyl. In other embodiment, the branchpoint is glycerol or glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O) (ORk)-O—, —O—P(O)(ORk)-S—, —S—P(O)(ORk)-S—, —O—P(S)(ORk)-S—, —S—P(S)(ORk)-O—, —O—P(O) (Rk)-O—, —O—P(S)(Rk)-O—, —S—P(O)(Rk)-O—, —S—P(S)(Rk)-O—, —S—P(O)(Rk)-S—, —O—P(S) (Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P (O)(OH)—S—, —O—P(S)(OH)—S—, —S—P(S)(OH)—O—, —O—P(O)(H)—O—, —O—P(S)(H)—O—, —S—P (O)(H)—O—, —S—P(S)(H)—O—, —S—P(O)(H)—S—, —O—P(S)(H)—S—. A preferred embodiment is —O—P (O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C$_5$ and above (preferably C$_5$-C$_8$) sugars; di- and trisaccharides include sugars having two or three monosaccharide units (preferably C$_5$-C$_8$).

The term "monosaccharide" embraces radicals of allose, altrose, arabinose, cladinose, erythrose, erythrulose, fructose, D-fucitol, L-fucitol, fucosamine, fucose, fuculose, galactosamine, D-galactosaninitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C═O replaced by C═S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraninic acid, muramic acid, lactosediamine, acosamine, bacillosamine, daunosamine, desosamine, forosamine, garosamine, kanosarnine, kansosamine, mycarninose, mycosamine, perosamine, pneurnosamine, purpurosamine, rhodosamine. It is understood that the monosaccharide and the like can be further substituted.

The terms "disaccharide", "trisaccharide" and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructooligosaccharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mnycarose, mnycinose, neuraminic acid, nigerose, nojirimycin, noviose, oleandrose, panose, paratose, planteose, primeverose, rafftnose, rhodinose, rutinose, sarmentose, sedohieptulose, sedoheptulosan, solatriose, sophorose, stachyose, streptose, sucrose, α,α-trebalose, trebalosamine, turanose, tyvelose, xylobiose, umbelliferose and the like. Further, it is understood that the "disaccharide", "trisaccharide" and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

In one embodiment, the compound having the structure shown in formula (I'):

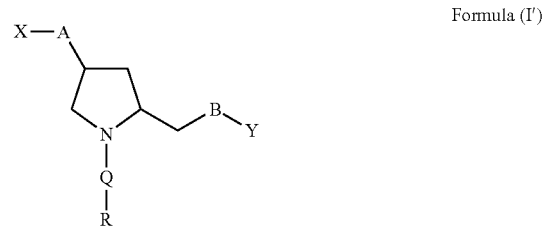

Formula (I')

wherein:

A and B are each independently for each occurrence O, N(R$^N$) or S;

X and Y are each independently for each occurrence H, a protecting group, a phosphate group, a phosphodiester group, an activated phosphate group, an activated phosphite group, a phosphoramidite, a solid support, —P(Z')(Z'')O-nucleoside, —P(Z')(Z'')O-oligonucleotide, a lipid, a PEG, a steroid, a polymer, a nucleotide, a nucleoside, —P(Z')(Z'')O—R$^1$-Q'-R$^2$—OP(Z''')(Z'''')O-oligonucleotide, or an oligonucleotide, —P(Z')(Z'')-formula (I), —P(Z')(Z'')— or -Q-R;

R is L$^1$ or has the structure shown in formula (II)-(V):

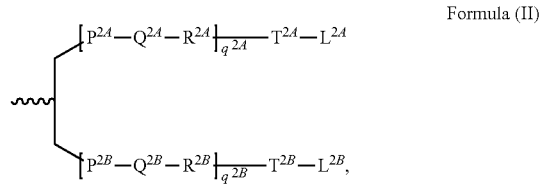

Formula (II)

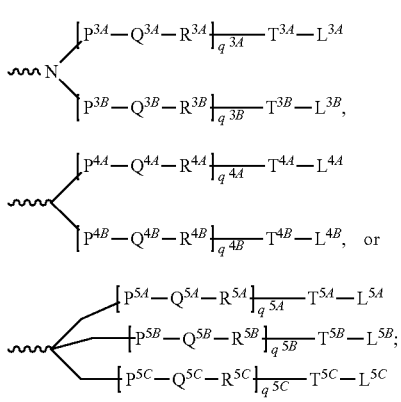

Formula (III), Formula (IV), Formula (V)

$q^{2A}$, $q^{2B}$, $q^{3A}$, $q^{3B}$, $q^{4A}$, $q^{4B}$, $q^{5A}$, $q^{5B}$, and $q^{5C}$ represent independently for each occurrence 0-20 and wherein the repeating unit can be the same or different;

Q and Q' are independently for each occurrence is absent, —(P$^7$-Q$^7$-R$^7$)$_p$-T$^7$- or -T$^7$-Q$^7$-T$^{7'}$-B-T$^{8'}$-Q$^8$-T$^8$;

$P^{2A}$, $P^{2B}$, $P^{3A}$, $P^{3B}$, $P^{4A}$, $P^{4B}$, $P^{5A}$, $P^{5B}$, $P^{5C}$, $P^7$, $T^{2A}$, $T^{2B}$, $T^{3A}$, $T^{3B}$, $T^{4A}$, $T^{4B}$, $T^{4A}$, $T^{5B}$, $T^{5C}$, $T^7$, $T^{7'}$, $T^8$ and $T^{8'}$ are each independently for each occurrence absent, CO, NH, O, S, OC(O), NHC(O), CH$_2$, CH$_2$NH or CH$_2$O;

B is —CH$_2$—N(B$^L$)—CH$_2$—;

B$^L$ is -T$^B$-Q$^B$-T$^{B'}$-R$^x$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene and wherein one or more methylenes can be interrupted or terminated by one or more of O, S, S(O), SO$_2$, N(R$^N$), C(R')=C(R'), C≡C or C(O);

T$^B$ and T$^{B'}$ are each independently for each occurrence absent, CO, NH, O, S, OC(O), OC(O)O, NHC(O), NHC(O)NH, NHC(O)O, CH$_2$, CH$_2$NH or CH$_2$O;

R$^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid;

R$^1$, R$^2$, R$^{2A}$, R$^{2B}$, R$^{3A}$, R$^{3B}$, R$^{4A}$, R$^{4B}$, R$^{5A}$, R$^{5B}$, R$^{5C}$, R$^7$ are each independently for each occurrence absent, NH, O, S, CH$_2$, C(O)O, C(O)NH, NHCH(R$^a$)C(O), —C(O)—CH(R$^a$)—NH—, CO, CH=N—O,

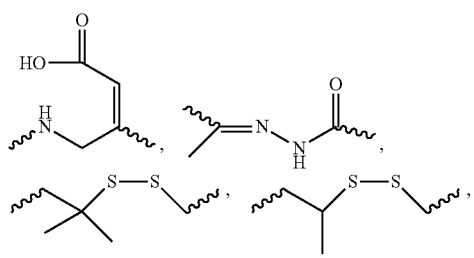

heterocyclyl;

L$^1$, L$^{2A}$, L$^{2B}$, L$^{3A}$, L$^{3B}$, L$^{4A}$, L$^{4B}$, L$^{5A}$, L$^{5B}$ and L$^{5C}$ are each independently for each occurrence a carbohydrate, e.g., monosaccharide, disaccharide, trisaccharide, tetrasaccharide, oligosaccharide and polysaccharide;

R' and R" are each independently H, C$^1$-C$_6$ alkyl, OH, SH, or N(R$^N$)$_2$;

R$^N$ is independently for each occurrence H, methyl, ethyl, propyl, isopropyl, butyl or benzyl;

R$^a$ is H or amino acid side chain;

Z', Z", Z''' and Z"" are each independently for each occurrence O or S;

p represent independently for each occurrence 0-20.

In some embodiments, the formula (I') has the structure

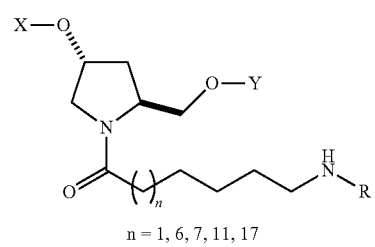

n = 1, 6, 7, 11, 17

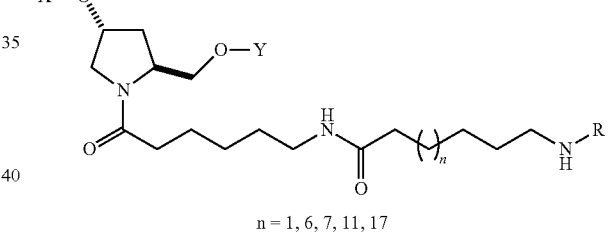

n = 1, 6, 7, 11, 17

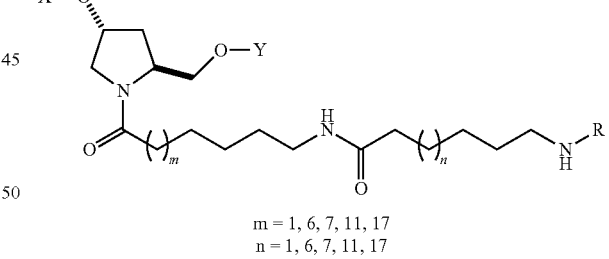

m = 1, 6, 7, 11, 17
n = 1, 6, 7, 11, 17

In some embodiments, the formula (I') has the structure

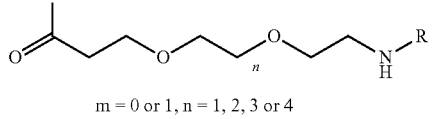

m = 0 or 1, n = 1, 2, 3 or 4

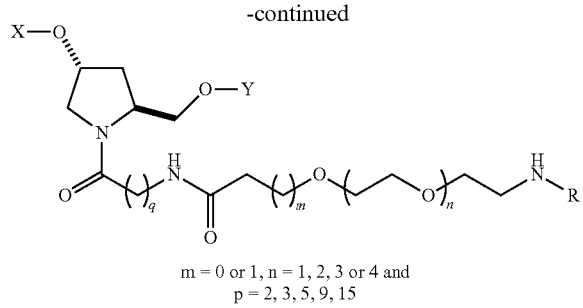

m = 0 or 1, n = 1, 2, 3 or 4 and
p = 2, 3, 5, 9, 15

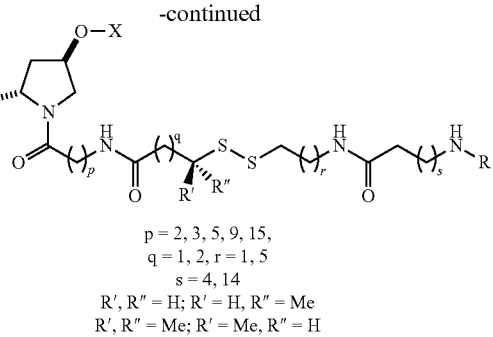

p = 2, 3, 5, 9, 15,
q = 1, 2, r = 1, 5
s = 4, 14
R', R" = H; R' = H, R" = Me
R', R" = Me; R' = Me, R" = H

In some embodiments, the formula (I') has the structure

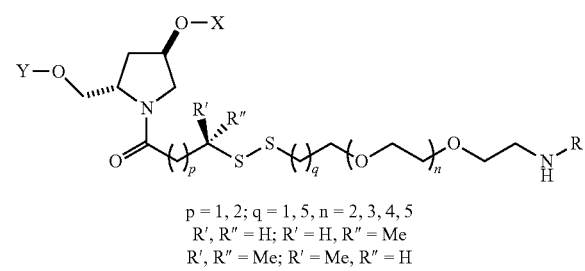

p = 1, 2; q = 1, 5, n = 2, 3, 4, 5
R', R" = H; R' = H, R" = Me
R', R" = Me; R' = Me, R" = H

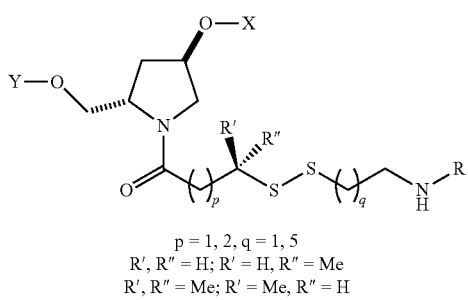

p = 1, 2, q = 1, 5
R', R" = H; R' = H, R" = Me
R', R" = Me; R' = Me, R" = H

In some embodiments, the formula (I') has the structure

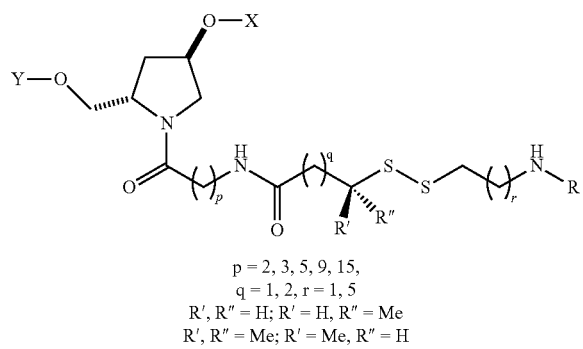

p = 2, 3, 5, 9, 15,
q = 1, 2, r = 1, 5
R', R" = H; R' = H, R" = Me
R', R" = Me; R' = Me, R" = H

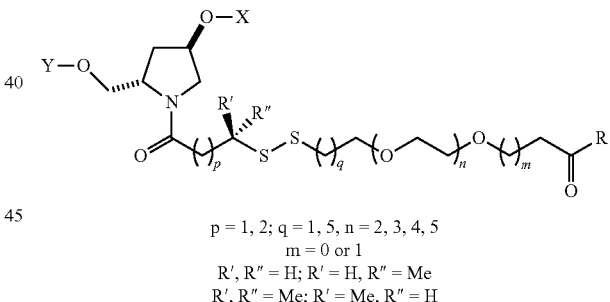

p = 1, 2; q = 1, 5, n = 2, 3, 4, 5
m = 0 or 1
R', R" = H; R' = H, R" = Me
R', R" = Me; R' = Me, R" = H

In some embodiments, the formula (I') has the structure

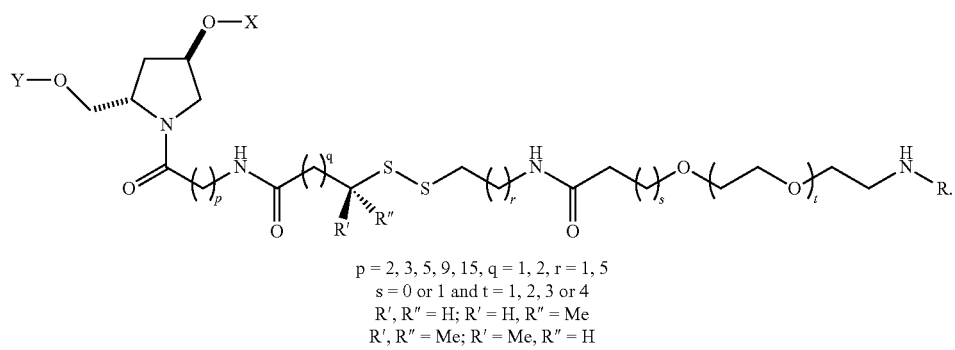

p = 2, 3, 5, 9, 15, q = 1, 2, r = 1, 5
s = 0 or 1 and t = 1, 2, 3 or 4
R', R" = H; R' = H, R" = Me
R', R" = Me; R' = Me, R" = H In some embodiments, R is
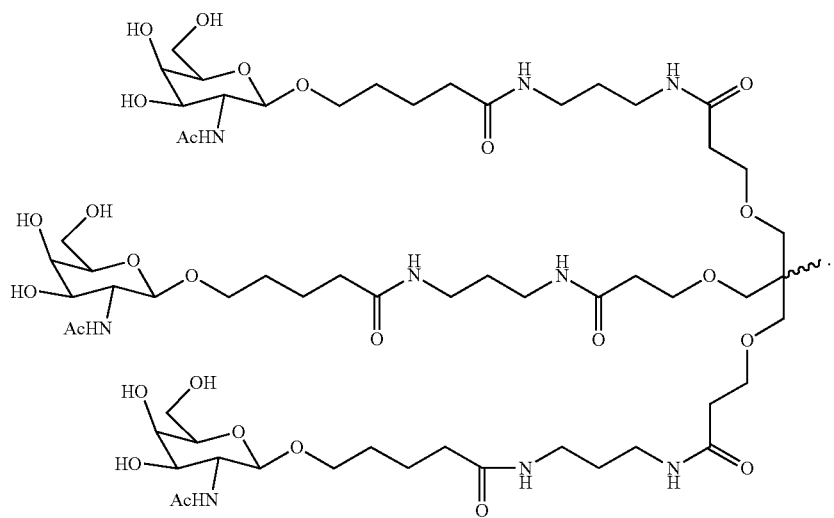 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
In some embodiments, R is
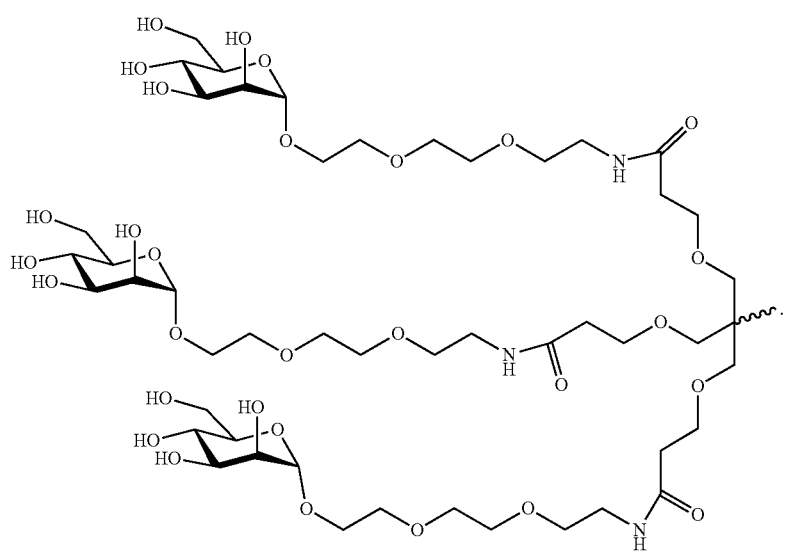
In some embodiments, R is
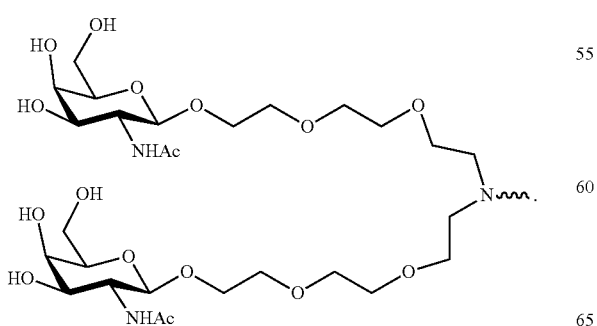

In some embodiments, R is
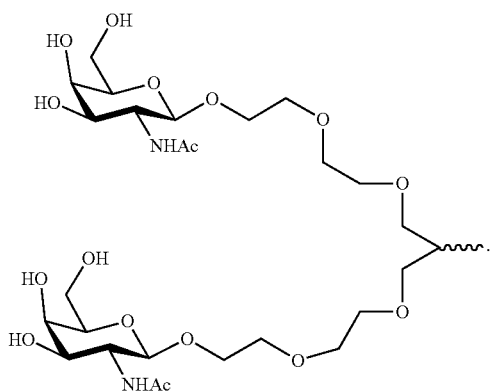
In some embodiments, R is
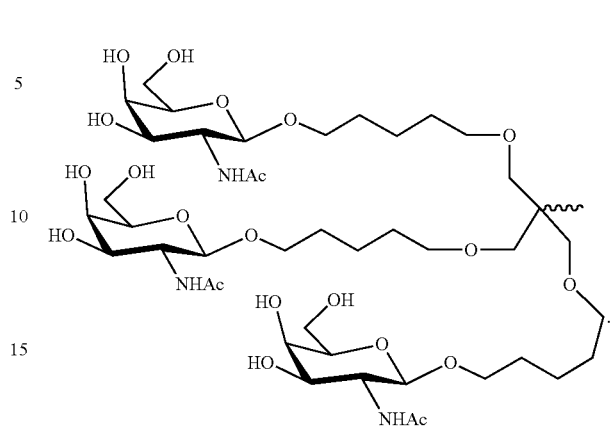
In some embodiments, R is
In some embodiments, R is
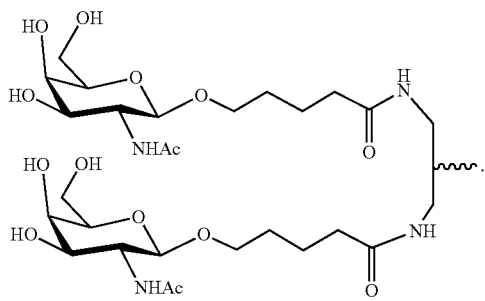
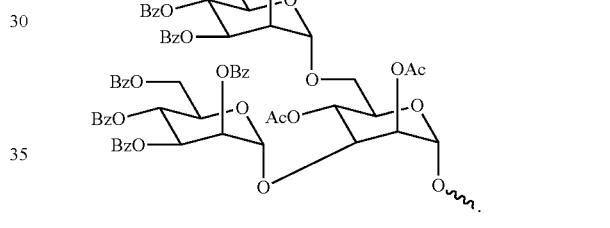
In some embodiments, R is
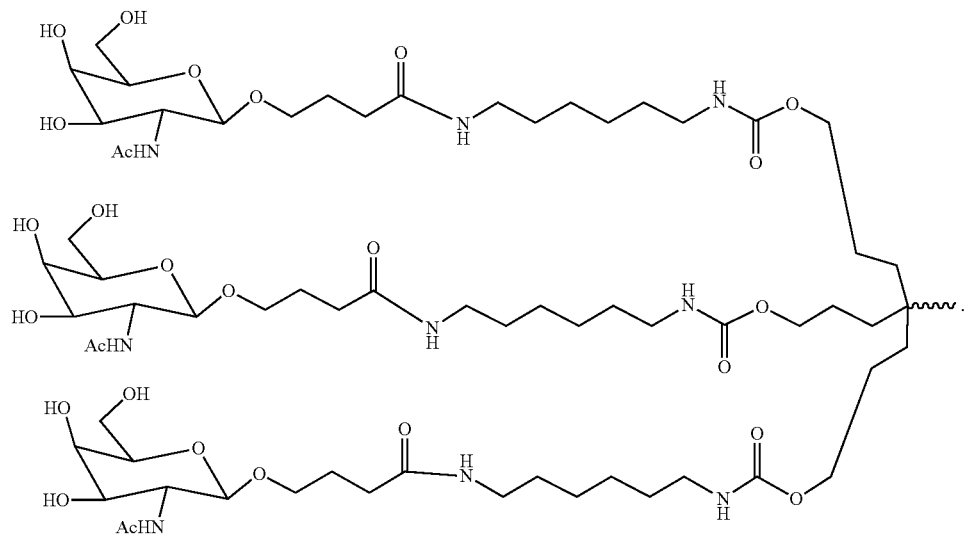

In some embodiments, R is
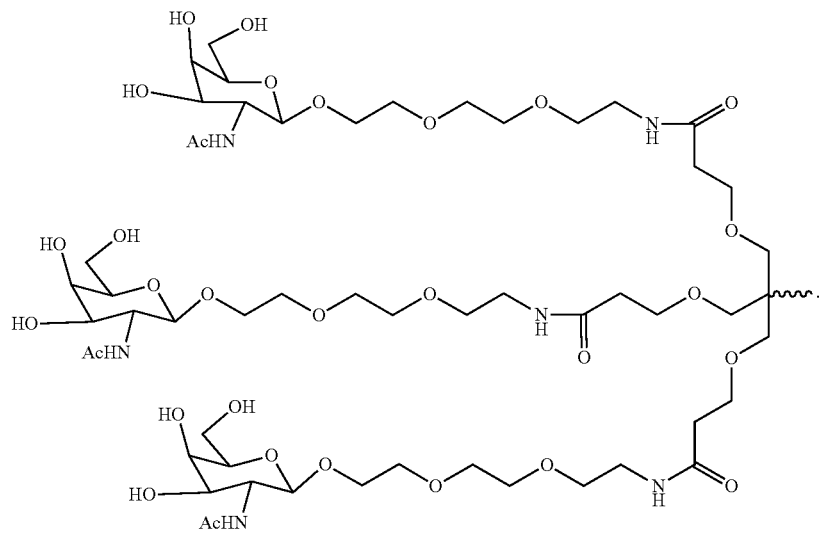 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]
35
In some preferred embodiments, R is
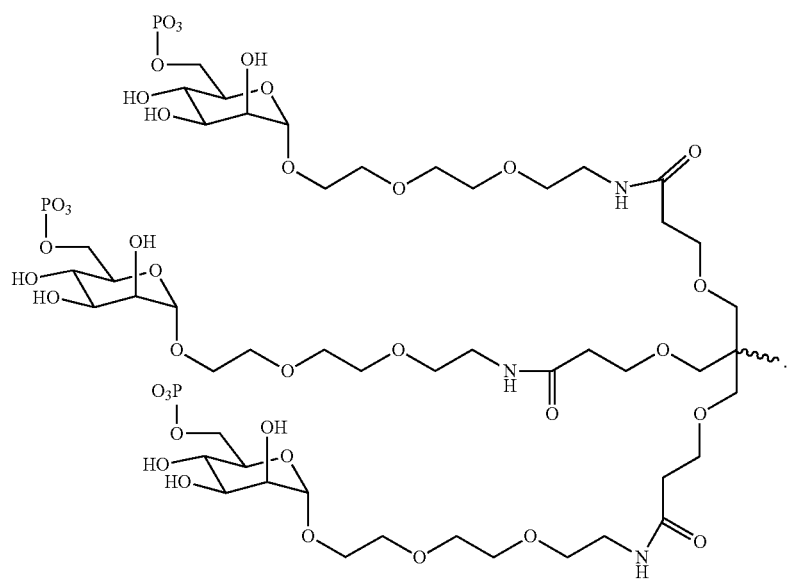

In some preferred embodiments, R is
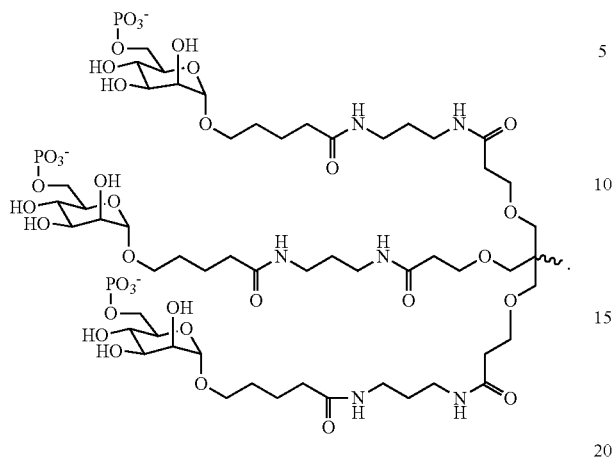
In some preferred embodiments, formula (I) has the structure
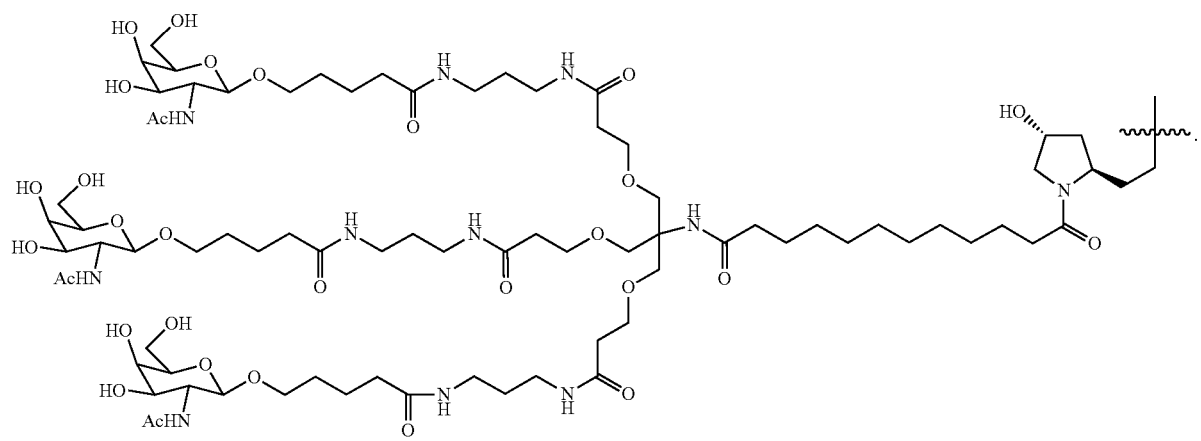 [SMILES: *CC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]
In some embodiments R is
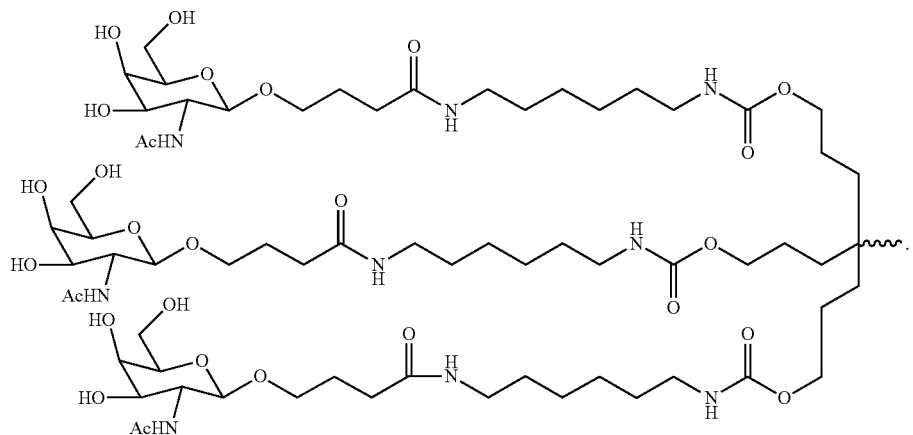 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]

In some embodiments monomer of formula (I) has the structure
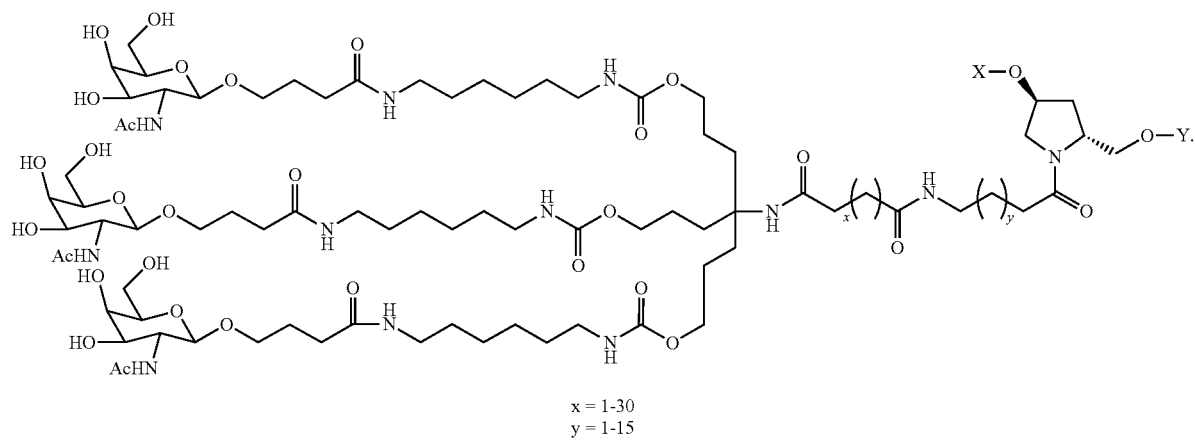
x = 1-30
y = 1-15
In some embodiments monomer of formula (I) has the structure
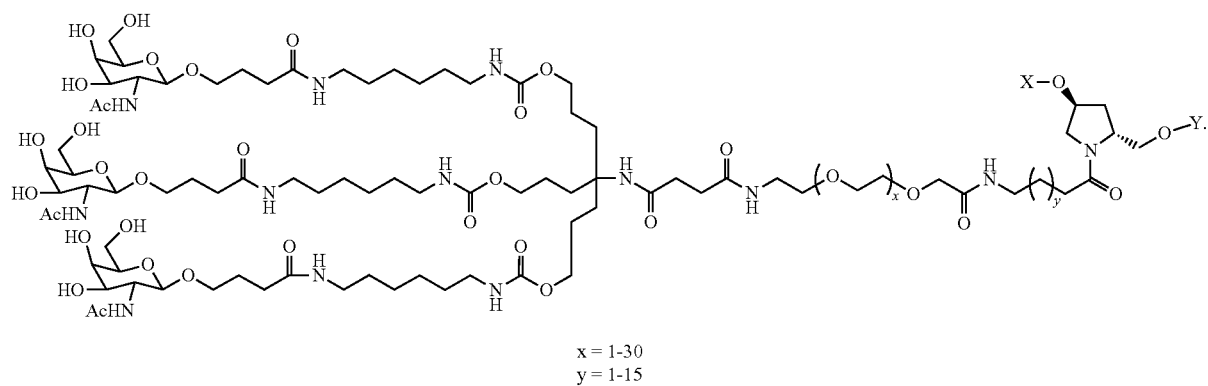
x = 1-30
y = 1-15
In some embodiments monomer of formula (I) has the structure
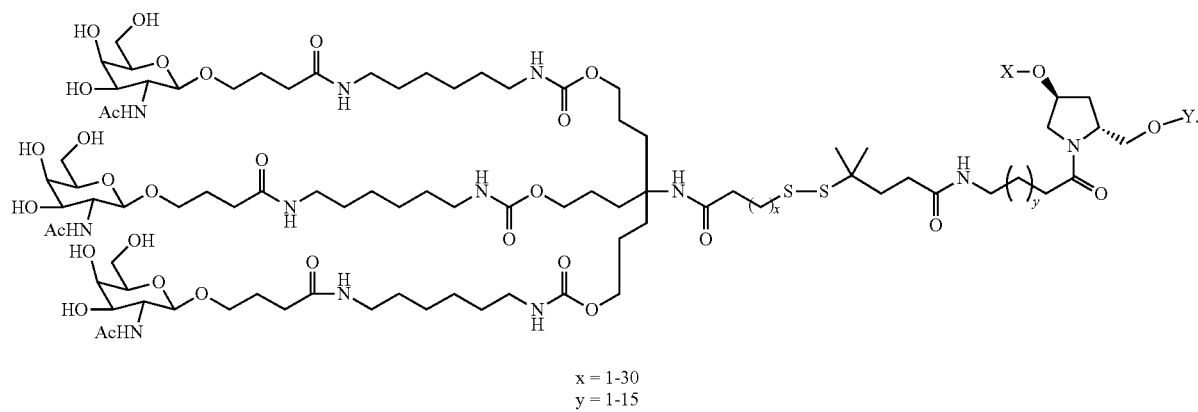
x = 1-30
y = 1-15

In some embodiments monomer of formula (I) has the structure
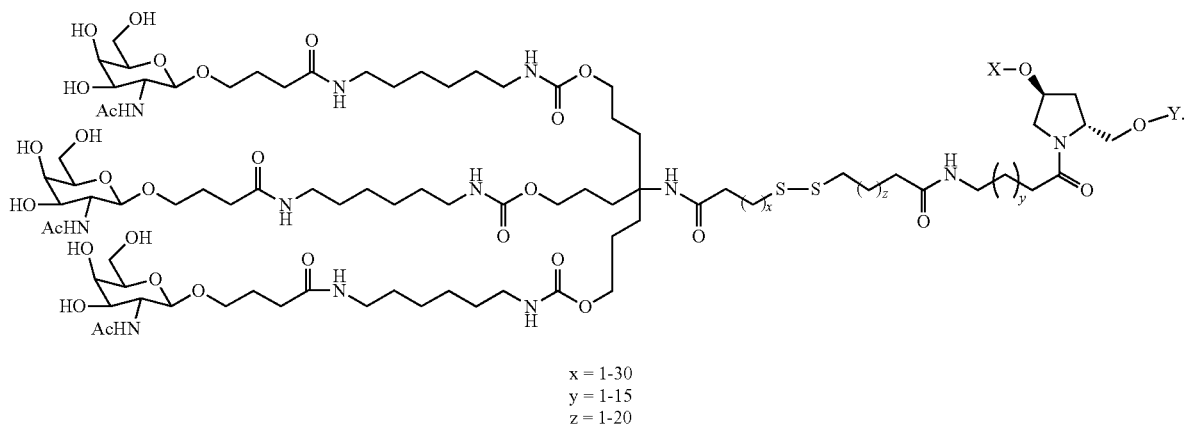
x = 1-30
y = 1-15
z = 1-20
In some embodiments monomer of formula (I) has the structure
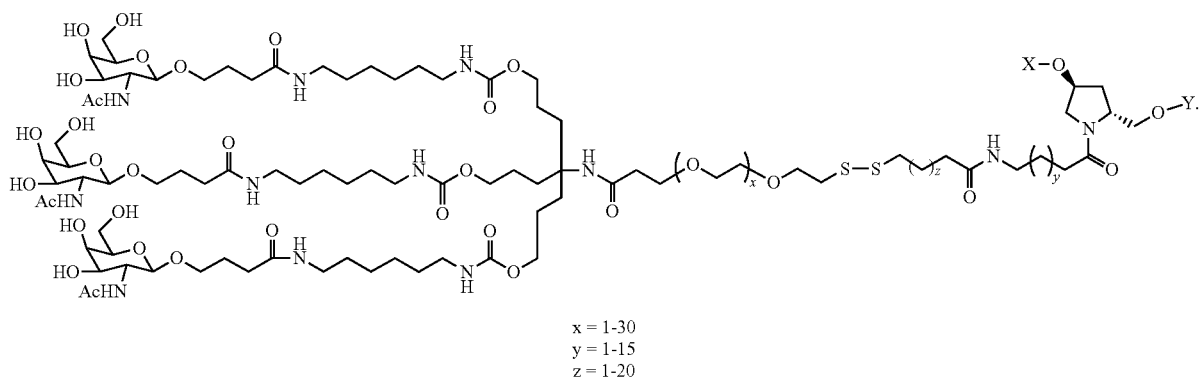
x = 1-30
y = 1-15
z = 1-20
In some embodiments monomer of formula (I) has the structure
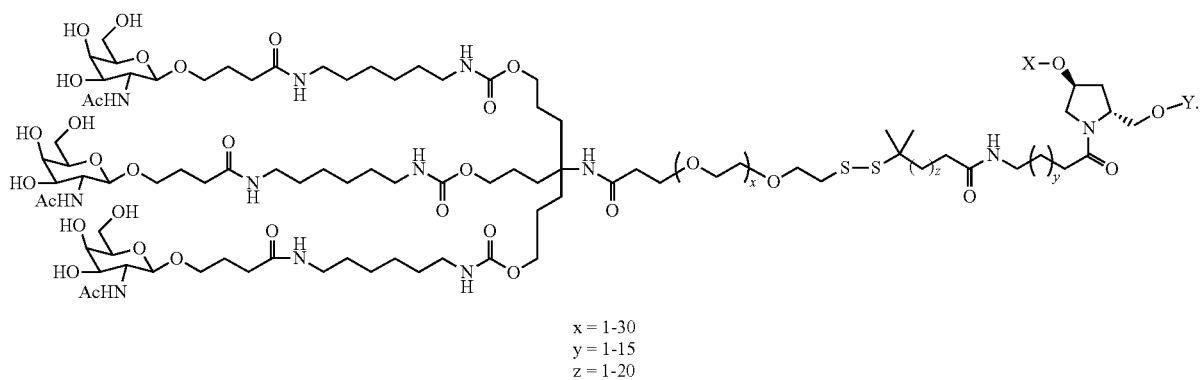
x = 1-30
y = 1-15
z = 1-20

In some embodiments, R is
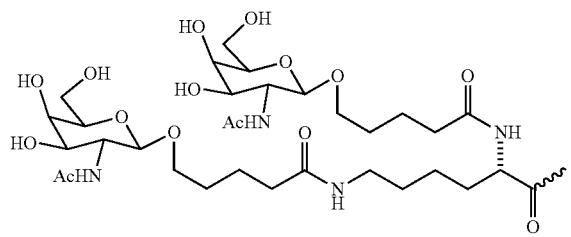
In some embodiments, R is
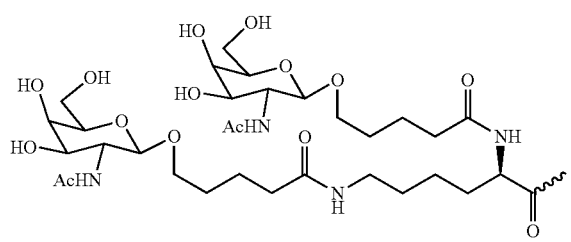
In some embodiments, R is
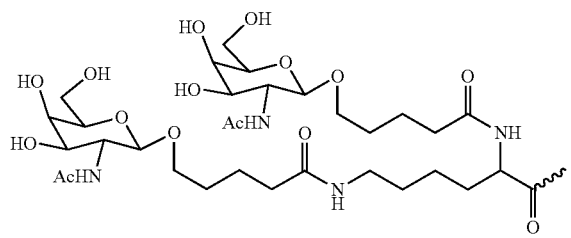
In some embodiments, R is
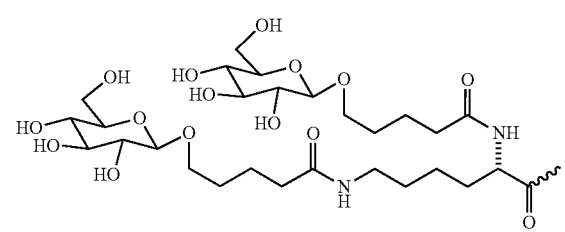
In some embodiments, R is
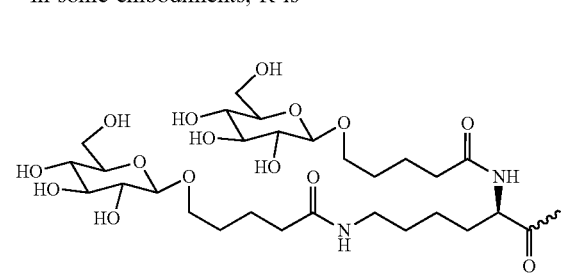
In some embodiments, R is
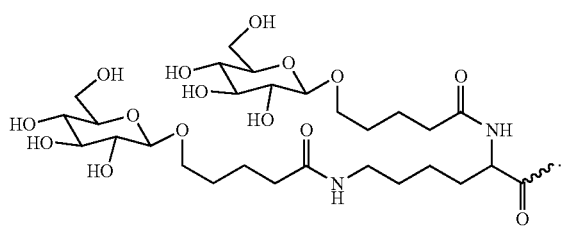
In some embodiments, R is
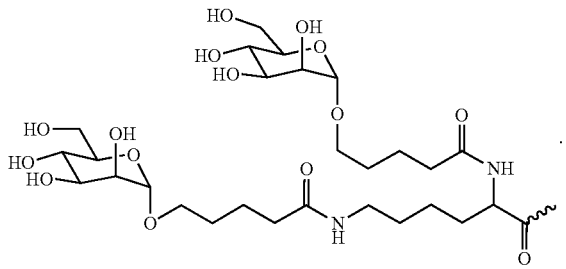
In some embodiments, R is
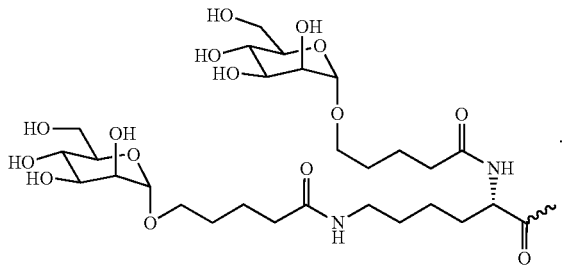
In some embodiments, R is
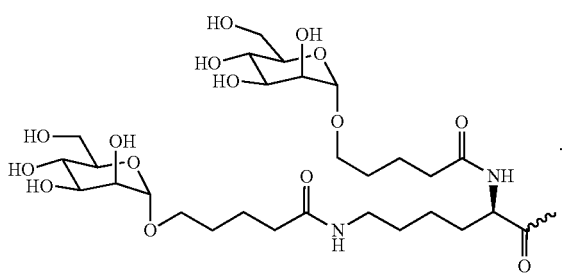

In some preferred embodiments, formula (I) has the structure
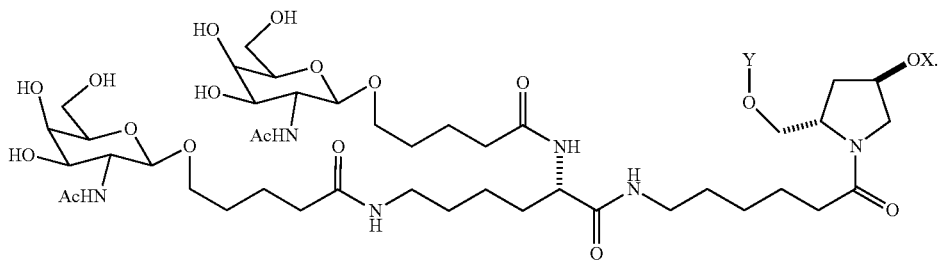
In some preferred embodiments, formula (I) has the structure
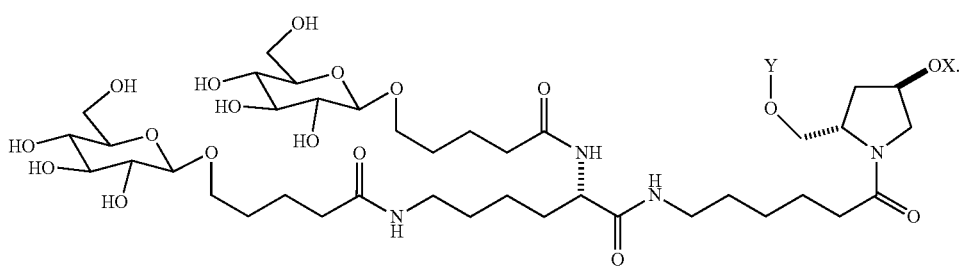
In some preferred embodiments, formula (I) has the structure
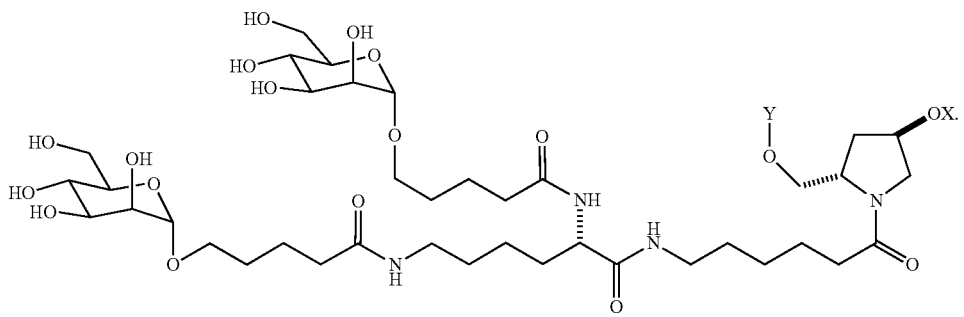
In some preferred embodiments, formula (I) has the structure
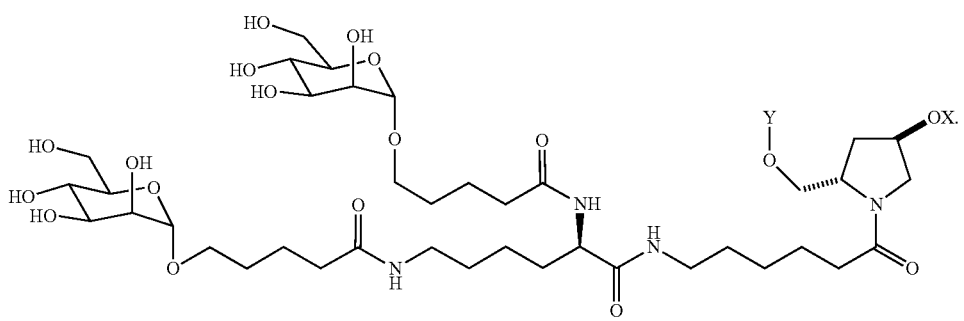

In some preferred embodiments, formula (I) has the structure

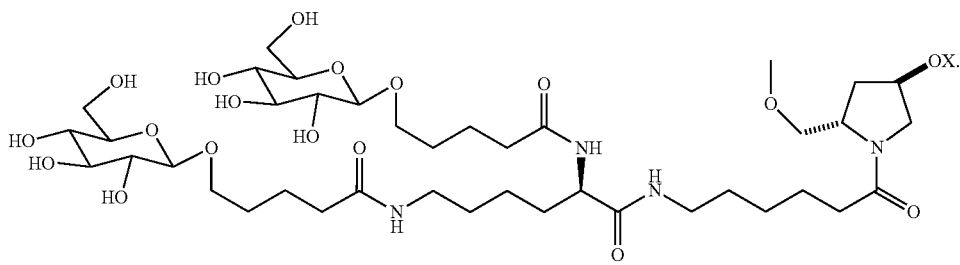

In some preferred embodiments, formula (I) has the structure

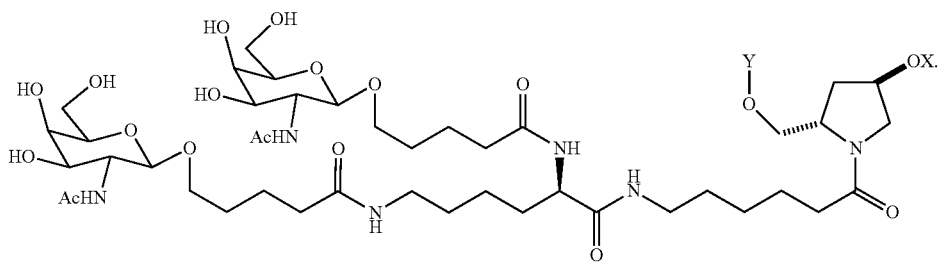

In some preferred embodiments both $L^{2A}$ and $L^{2B}$ are the same.
In some embodiments both $L^{2A}$ and $L^{2B}$ are different
In some preferred embodiments both $L^{3A}$ and $L^{3B}$ are the same.
In some embodiments both $L^{3A}$ and $L^{3B}$ are different.
In some preferred embodiments both $L^{4A}$ and $L^{4B}$ are the same.
In some embodiments both $L^{4A}$ and $L^{4B}$ are different.
In some preferred embodiments all of $L^{5A}$, $L^{5B}$ and $L^{5C}$ are the same.
In some embodiments two of $L^{5A}$, $L^{5B}$ and $L^{5C}$ are the same.
In some embodiments $L^{5A}$ and $L^{5B}$ are the same.
In some embodiments $L^{5A}$ and $L^{5C}$ are the same.
In some embodiments $L^{5B}$ and $L^{5C}$ are the same.
In another aspect, the invention features, an iRNA agent comprising at least one monomer of formula (I).
In some embodiments, the iRNA agent will comprise 1, 2, 3, 4 or 5 monomers of formula (I), more preferably 1, 2 or 3 monomers of formula (I), more preferably 1 or 2 monomers of formula (I), even more preferably only one monomer of formula (I).
In some embodiments, all the monomers of formula (I) are on the same strand of a double stranded iRNA agent.
In some embodiments, the monomers of formula (I) are on the separate strands of a double strand of an iRNA agent.
In some embodiments, all monomers of formula (I) in an iRNA agent are the same.
In some embodiments, the monomers of formula (I) in an iRNA agent are all different.
In some embodiments, only some monomers of formula (I) in an iRNA agent are the same.
In some embodiments, the monomers of formula (I) will be next to each other in the iRNA agent.

In some embodiments, the monomers of formula (I) will not be next to each other in the iRNA agent.

In some embodiments, the monomer of formula (I) will be on the 5'-end, 3'-end, at an internal position, both the 3'- and the 5'-end, both 5'-end and an internal position, both 3'-end and internal position, and at all three positions (5'-end, 3'-end and an internal position) of the iRNA agent.
In some preferred embodiments, $R^x$ is cholesterol.
In some preferred embodiments, $R^x$ is lithocholic.
In some preferred embodiments, $R^x$ is oleyl lithocholic.
In some preferred embodiments, $R^x$ has the structure

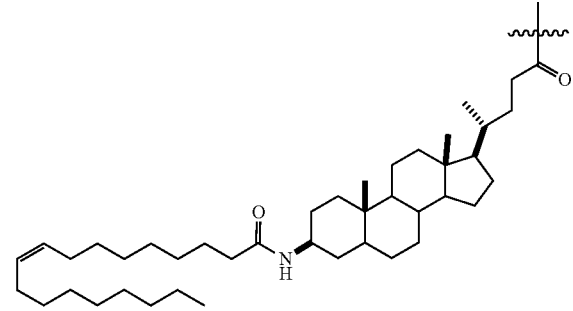 [SMILES: *C(=O)CC[C@@H](C)[C@H]1CCC2C3CCC4C[C@@H](NC(=O)CCCCCCC/C=C\CCCCCCCC)CC[C@]4(C)C3CC[C@@]21C]

In some preferred embodiments, $B^L$ has the structure

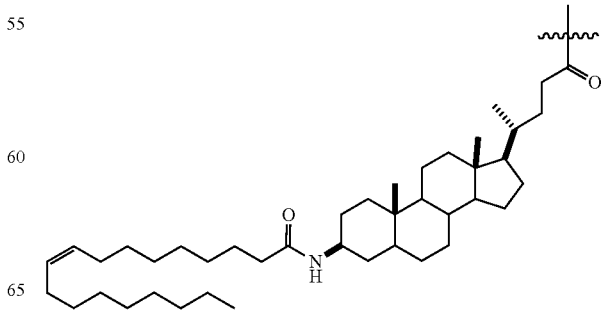

In some preferred embodiments, formula (I) has the structure
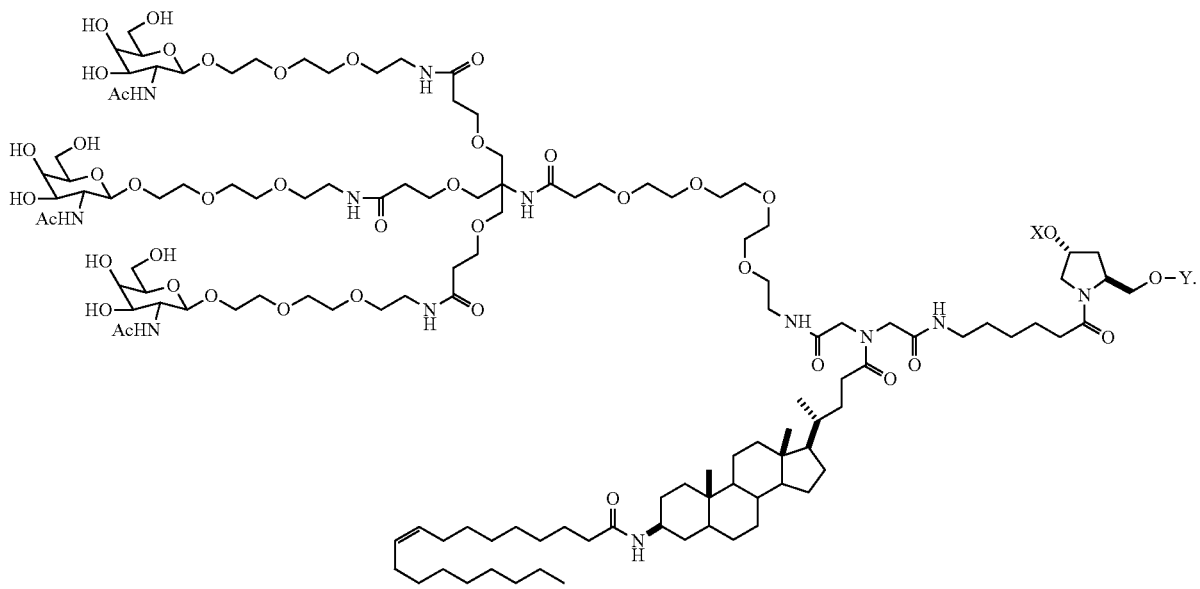
In some preferred embodiments, formula (I) has the structure
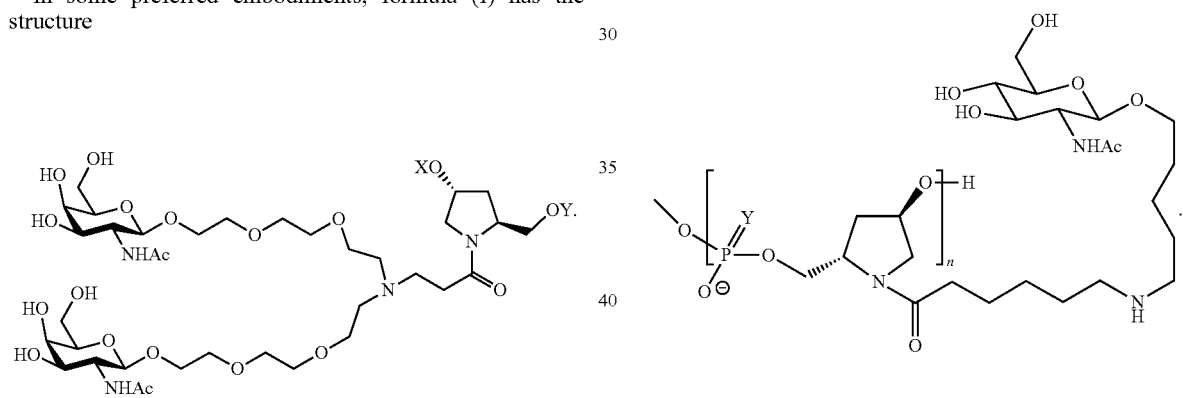
In some preferred embodiments, formula (I) has the structure
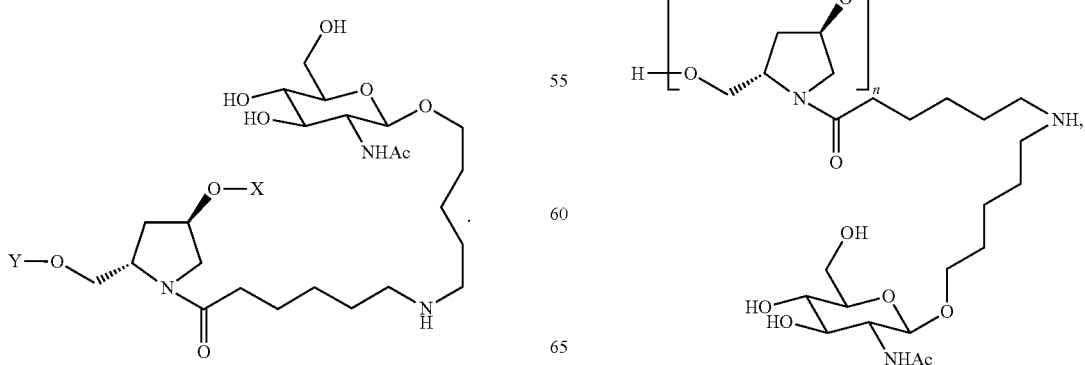
In some preferred embodiments, formula (I) has the structure
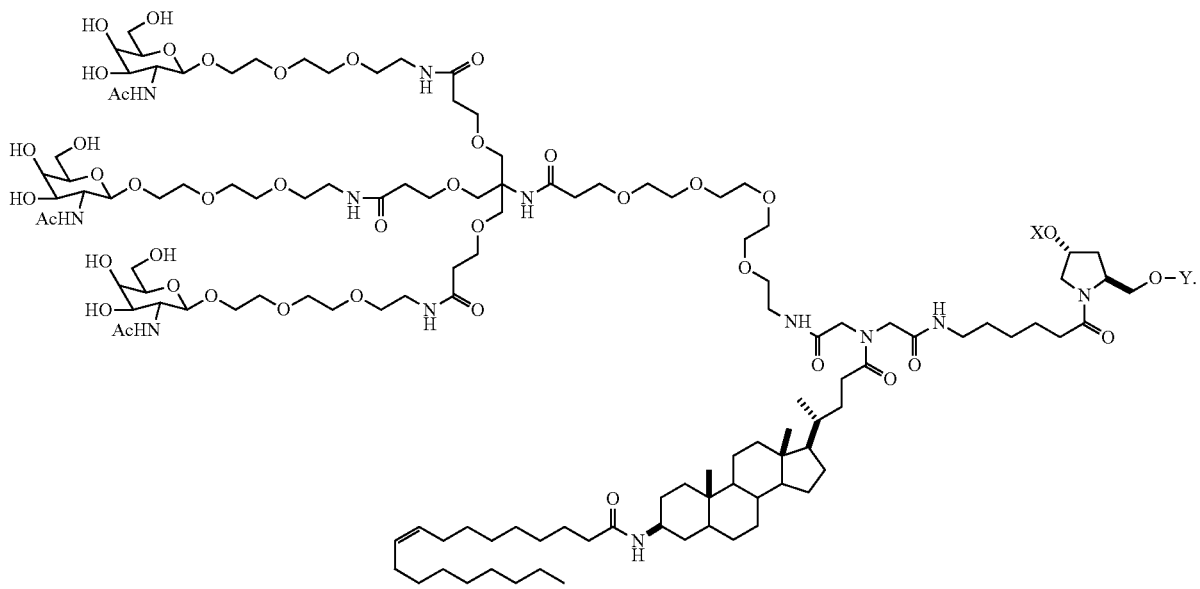
wherein Y is O or S and n is 3-6.
In some preferred embodiments, formula (I) has the structure
wherein Y is O or S and n is 3-6.

In some preferred embodiments, formula (I) has the structure
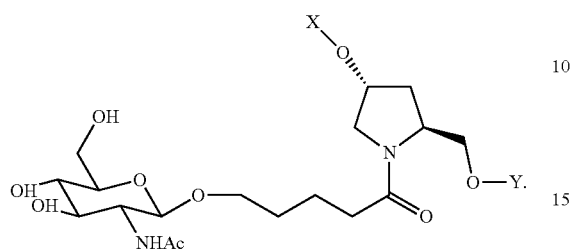
In some preferred embodiments, formula (I) has the structure
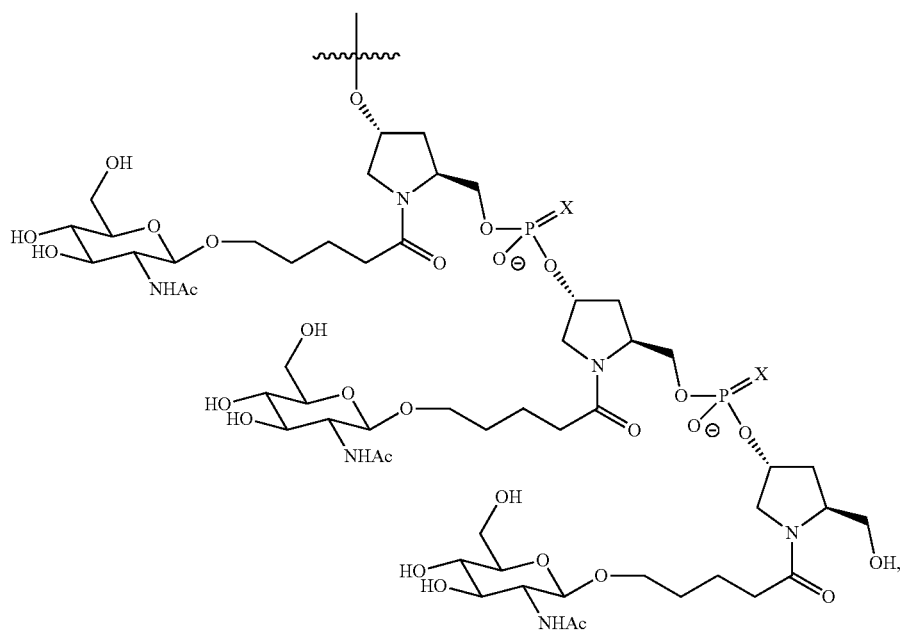
wherein X is O or S.

In some preferred embodiments, formula (I) has the structure
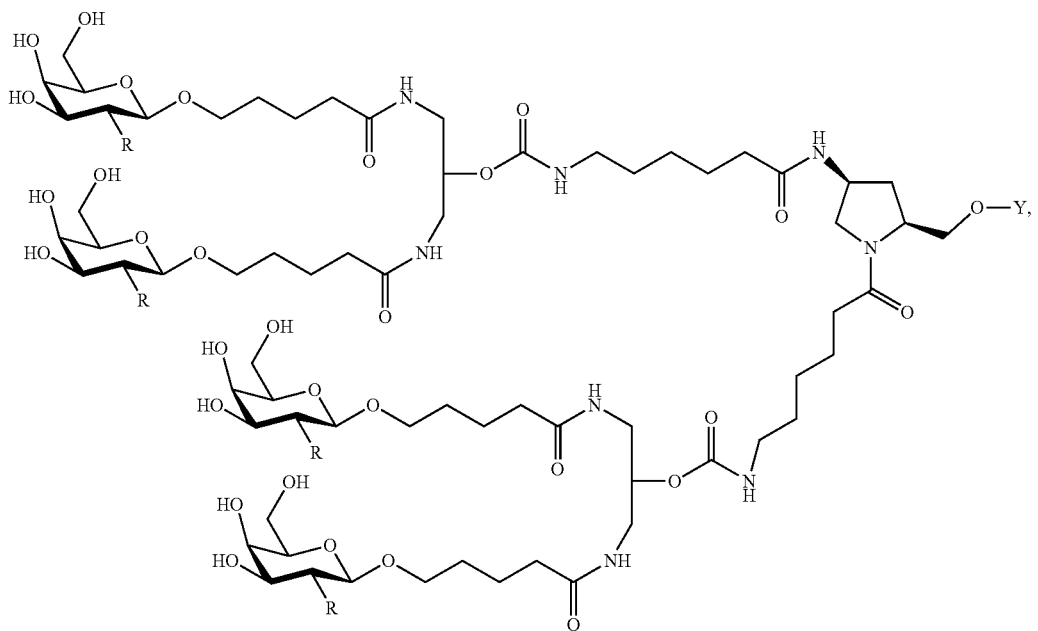
wherein R is OH or NHCOOH.
In some preferred embodiments, formula (I) has the structure
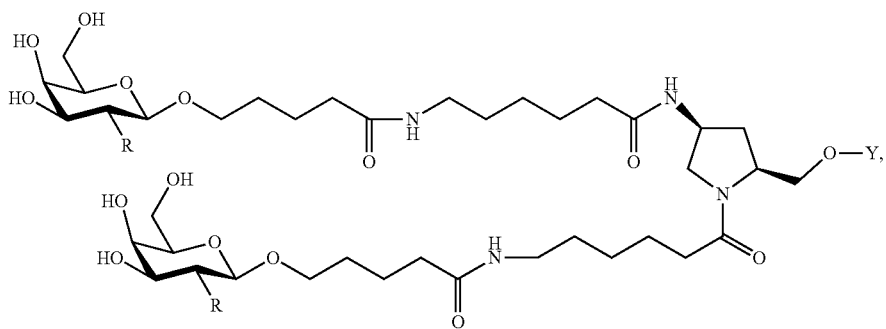
wherein R is OH or NHCOOH.
In some preferred embodiments, monomer of formula (I) is linked to the iRNA agent through a linker of formula (VII)
Formula (VII)
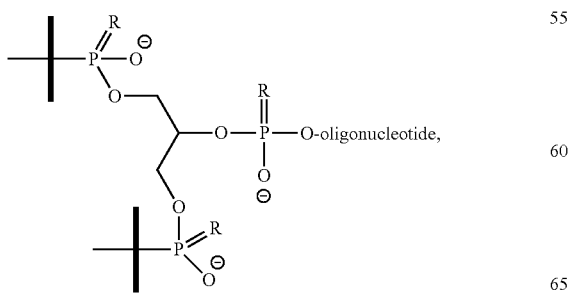
wherein R is O or S.

In some preferred embodiments, formula (I) has the structure
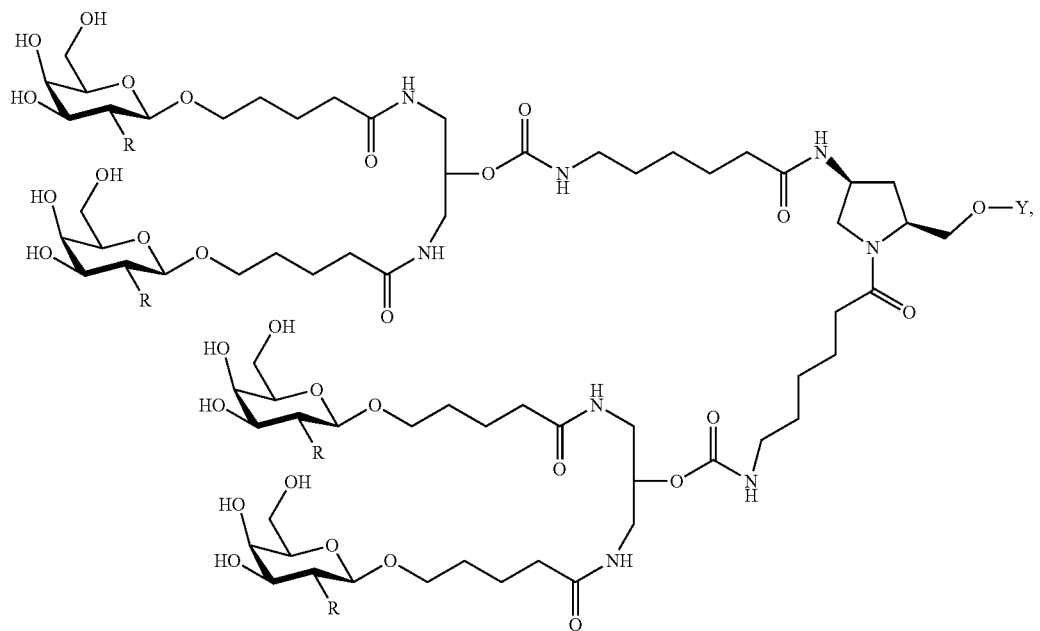
wherein R is OH or NHCOOH.
In some preferred embodiments, formula (I) has the structure
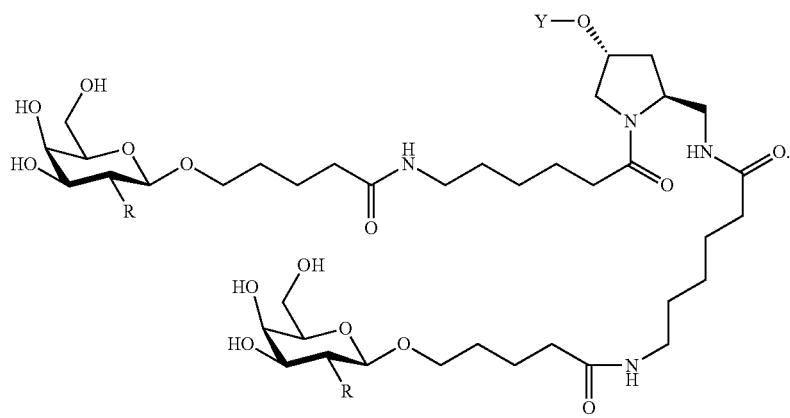
In some preferred embodiments, formula (I) has the structure
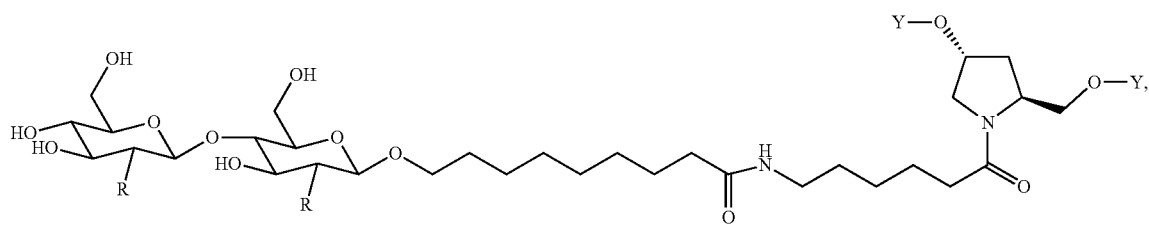
wherein R is OH or NHCOOH.

In some preferred embodiments, formula (I) has the structure
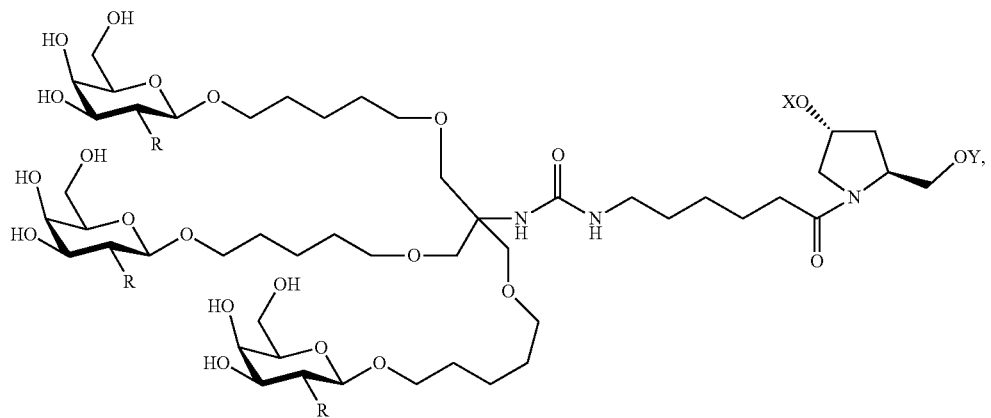
wherein R is OH or NHCOOH.
In some preferred embodiments, formula (I) has the structure
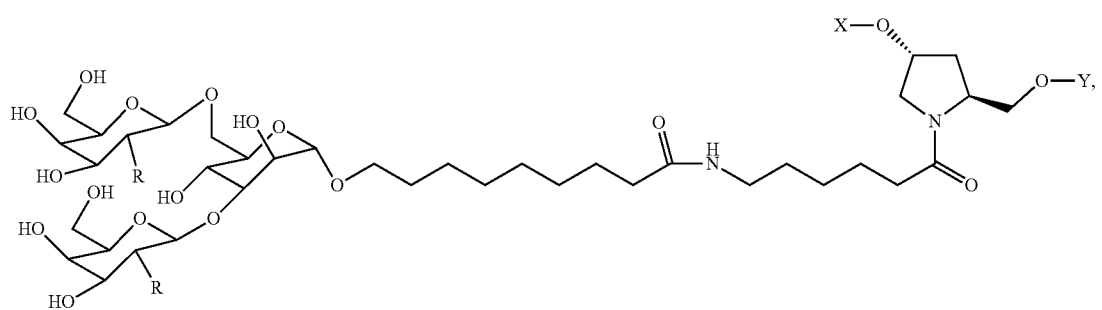
wherein R is OH or NHCOOH.
In some preferred embodiments, formula (I) has the structure
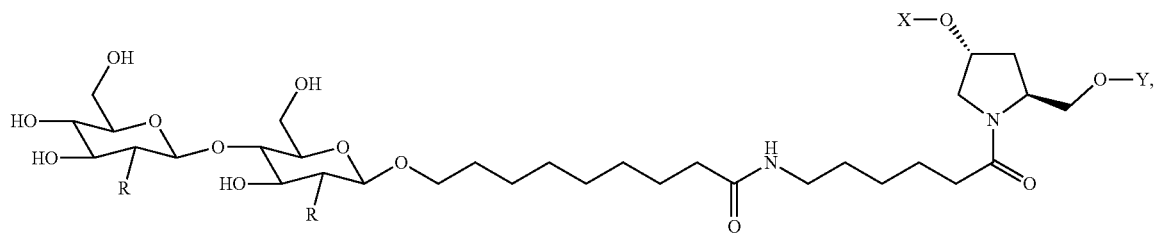
wherein R is OH or NHCOOH.

In some embodiments, the iRNA agent will have a monomer with the structure shown in formula (VI) in addition to monomer of formula (I)

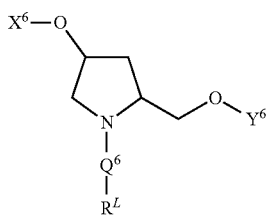

Formula (VI)

wherein $X^6$ and $Y^6$ are each independently H, OH, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O—$R^1$-Q'-$R^2$—OP(Z''')(Z'''')O-oligonucleotide, a nucleotide, or an oligonucleotide, —P(Z')(Z")-formula (I) or —P(Z')(Z")—;

$Q^6$ is absent or —$(P^6-Q^6-R^6)_v$-$T^6$-;

$P^6$ and $T^6$ are each independently for each occurrence absent, CO, NH, O, S, OC(O), NHC(O), $CH_2$, $CH_2NH$ or $CH_2O$;

$Q^6$ is independently for each occurrence absent, substituted alkylene wherein one or more methylenes can be interpreted or terminated by one or more of O, S, S(O), $SO_2$, N($R^N$), C(R')=C(R'), C≡C or C(O);

$R^6$ is independently for each occurrence absent, NH, O, S, $CH_2$, C(O)O, C(O)NH, NHCH($R^a$)C(O), —C(O)—CH($R^a$)—NH—, CO, CH=N—O

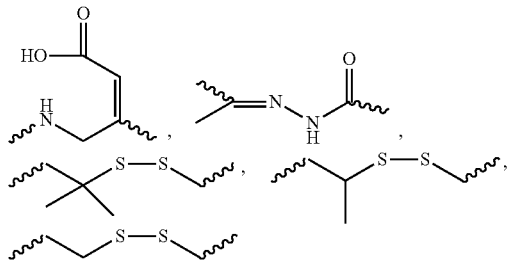

or heterocyclyl;

R' and R" are each independently H, $C_1$-$C_6$ alkyl OH, SH, N($R^N$)$_2$;

$R^N$ is independently for each occurrence methyl, ethyl, propyl, isopropyl, butyl or benzyl;

$R^a$ is H or amino acid side chain;

Z', Z", Z''' and Z'''' are each independently for each occurrence O or S;

v represent independently for each occurrence 0-20;

$R^L$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid.

In some embodiments, one or more, e.g., 1, 2, 3, 4 or 5, monomers of formula (VI) in addition to one or more, e.g. 1, 2, 3, 4, or 5, monomers of formula (I) are present in the iRNA agent.

In some preferred embodiments only 1 monomer of formula (I) and 1 monomer of formula (VI) are present in the iRNA agent.

In some embodiments, $R^L$ is cholesterol.

In some embodiments, $R^L$ is lithocholic.

In some embodiments, $R^L$ is oleyl lithocholic.

In some embodiments, monomer of formula (I) is covalently linked with the monomer of formula (VI).

In some preferred embodiments, monomer of formula (I) is linked with the monomer of formula (VI) through a phosphate linkage, e.g. a phosphodiester linkage, a phosphorothioate linkage, a phosphorodithioate linkage.

In some preferred embodiments, monomer of formula (I) is linked to the iRNA agent through the monomer of formula (VI).

In some embodiments, monomer of formula (I) intervenes between the iRNA agent and the monomer of formula (VI).

In some embodiments, monomer of formula (I) and monomer of formula (II) are directly linked to each other.

In some embodiments, monomer of formula (I) and monomer of formula (II) are not directly linked to each other.

In some embodiments, monomer of formula (I) and monomer of formula (VI) are on separate strands of a double stranded iRNA agent.

In some embodiments, monomer of formula (I) and monomer of formula (VI) are on opposite terminal ends of the iRNA agent.

In some embodiments, monomer of formula (I) and monomer of formula (VI) are on the same terminal end of the iRNA agent.

In some embodiments, one of monomer of formula (I) or monomer of formula (VI) is at an internal position while the other is at a terminal position of an iRNA agent.

In some embodiments, monomer of formula (I) and monomer of formula (VI) are both at an internal position of the iRNA agent.

In some preferred embodiments, monomer of formula (VI) has the structure

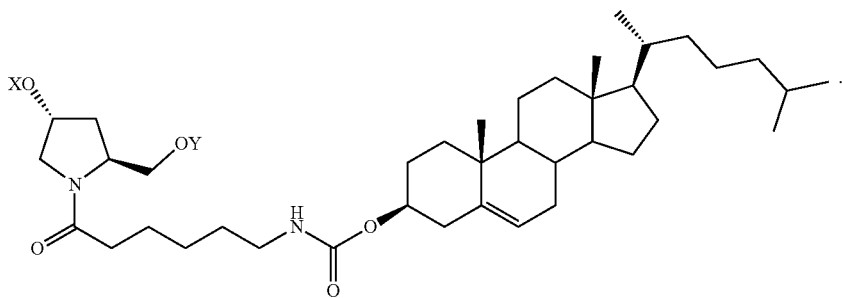
In some embodiments, the iRNA agent of the invention is selected from the group consisting of:
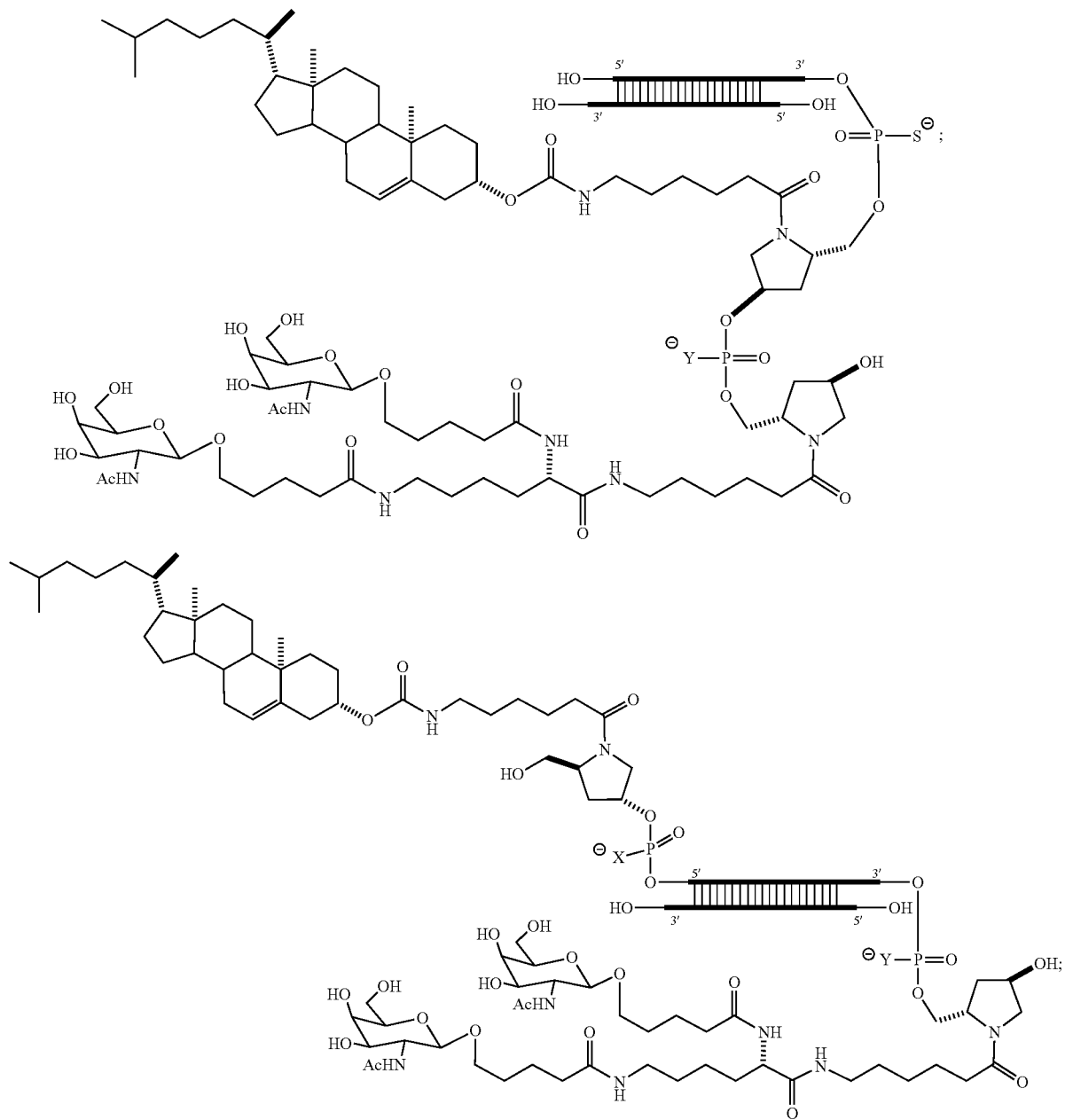

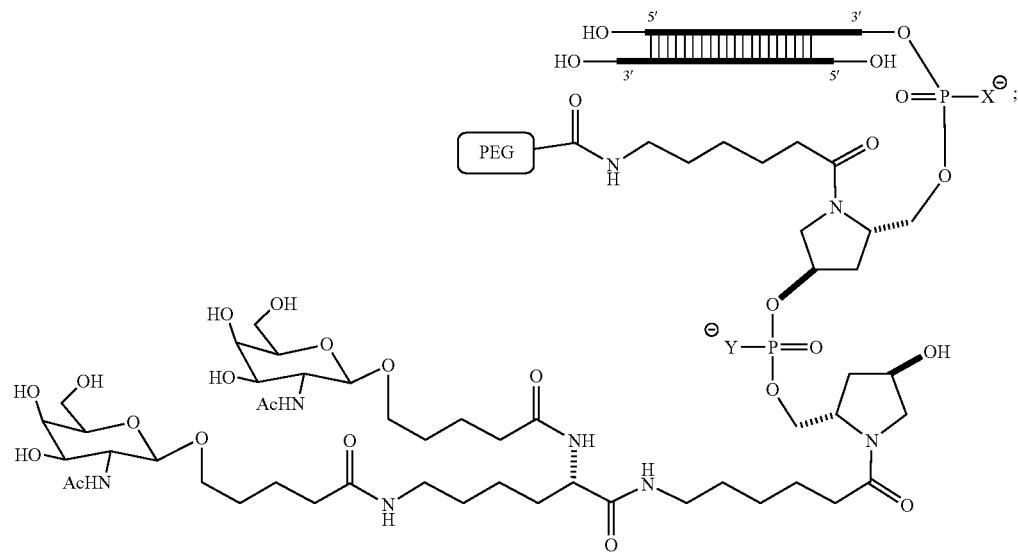
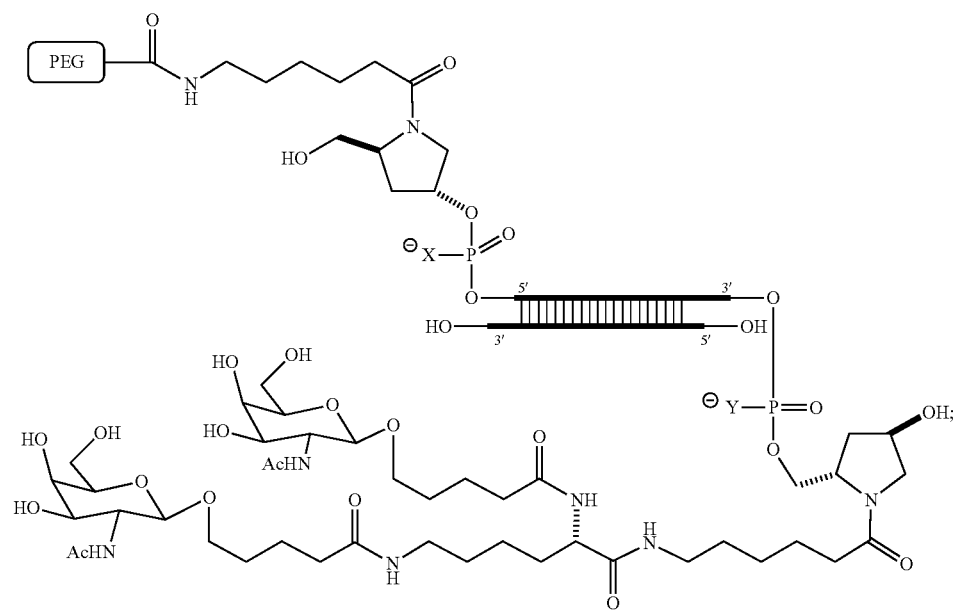

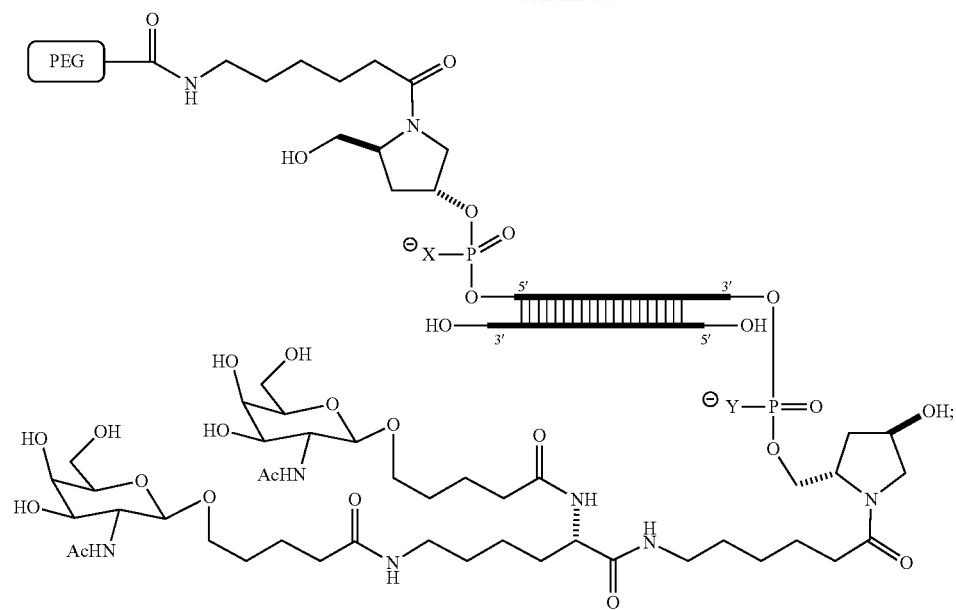
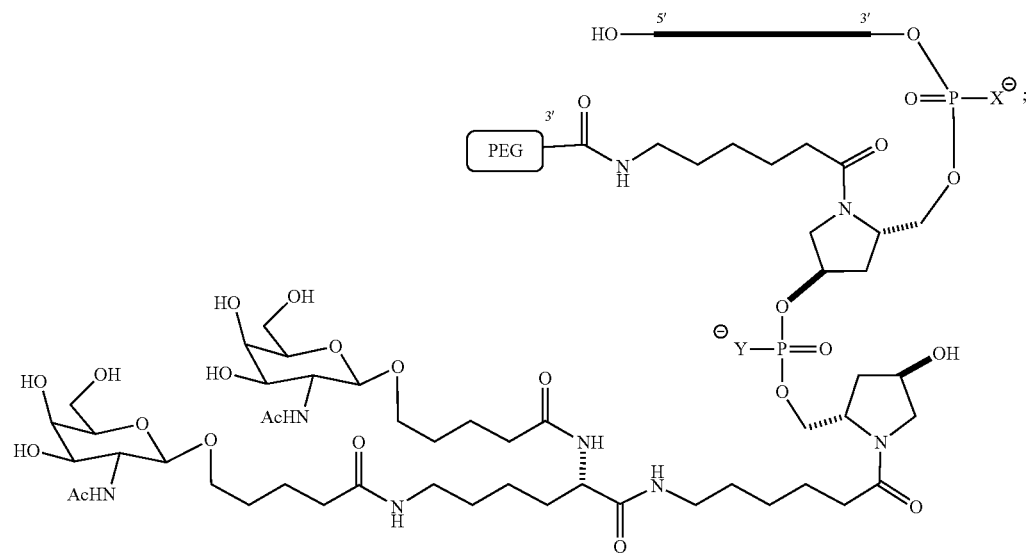

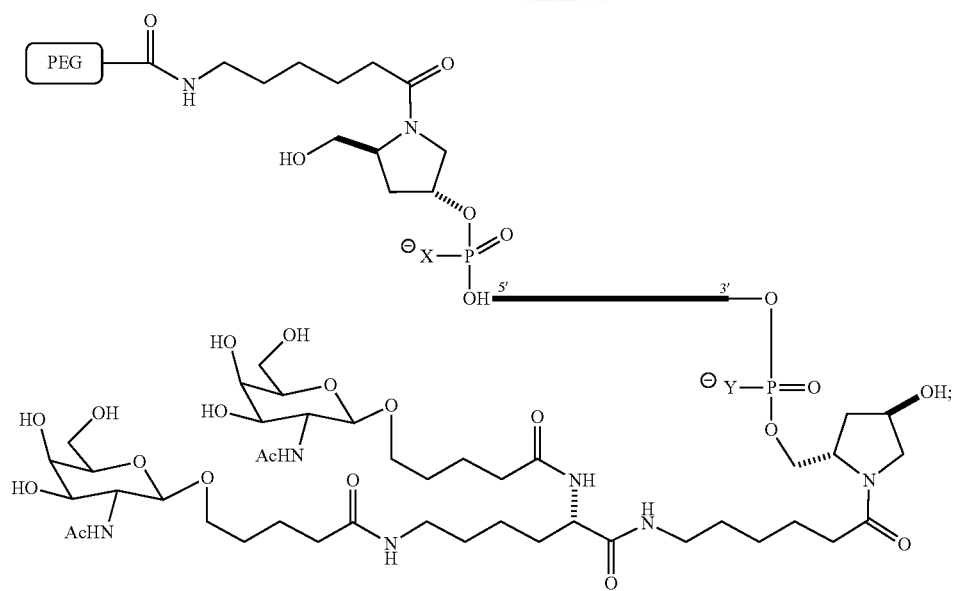
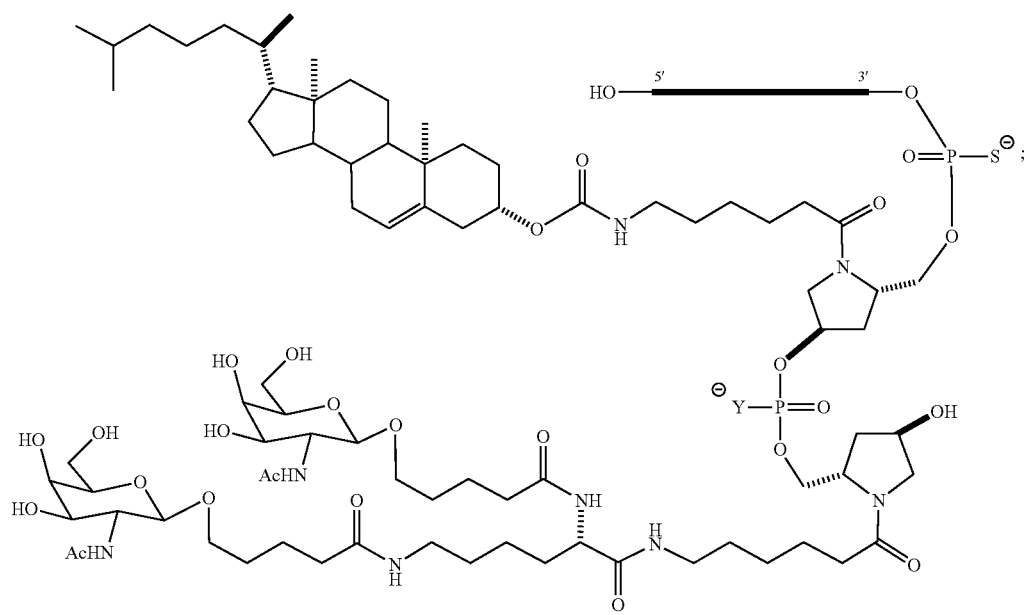

-continued
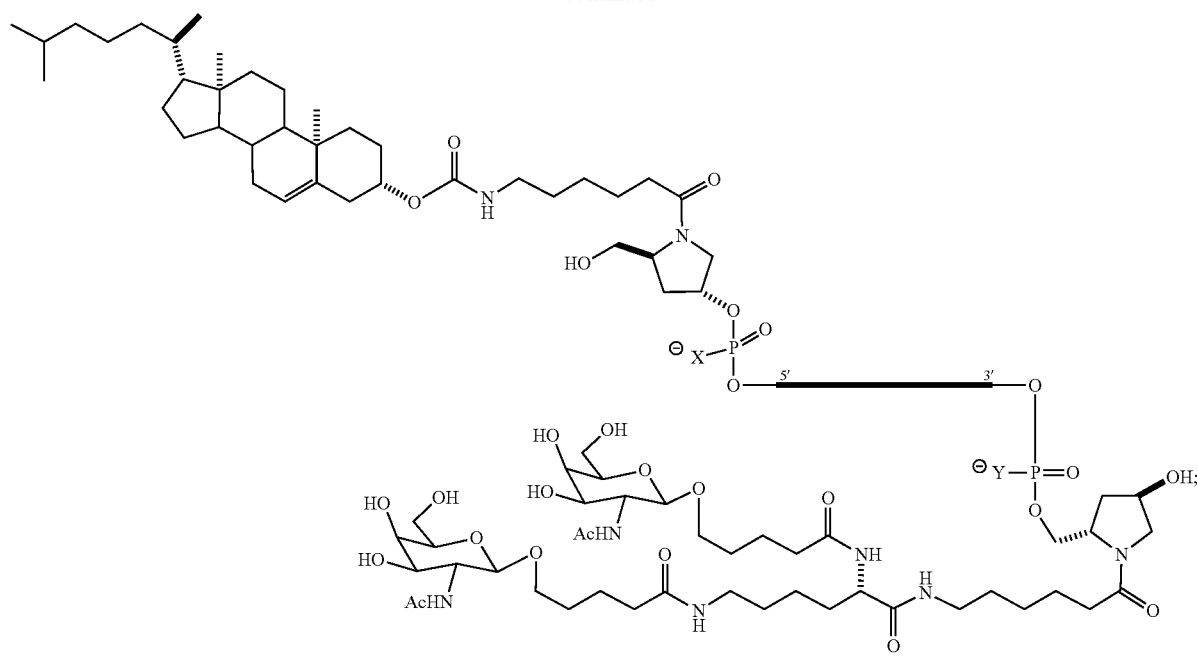
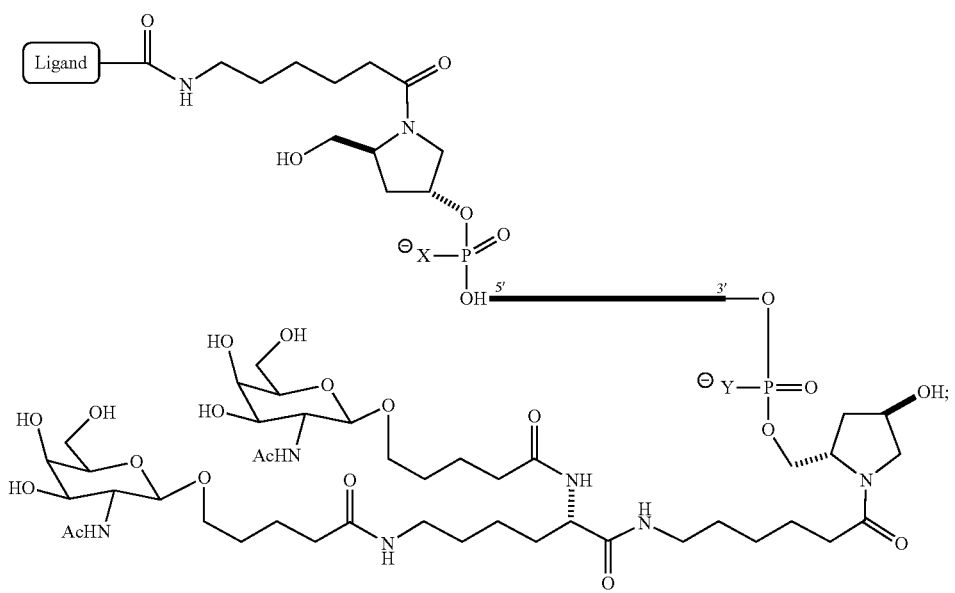

-continued
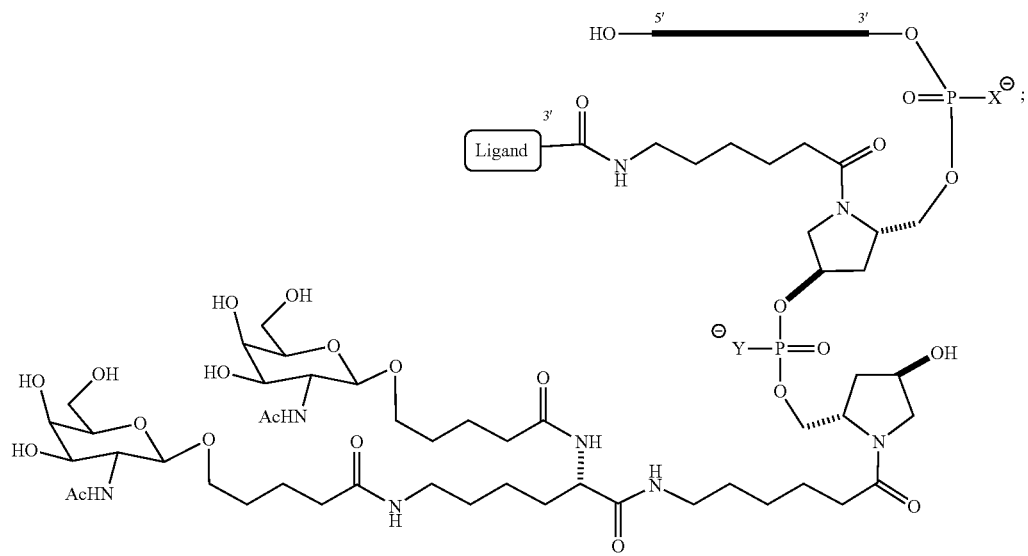
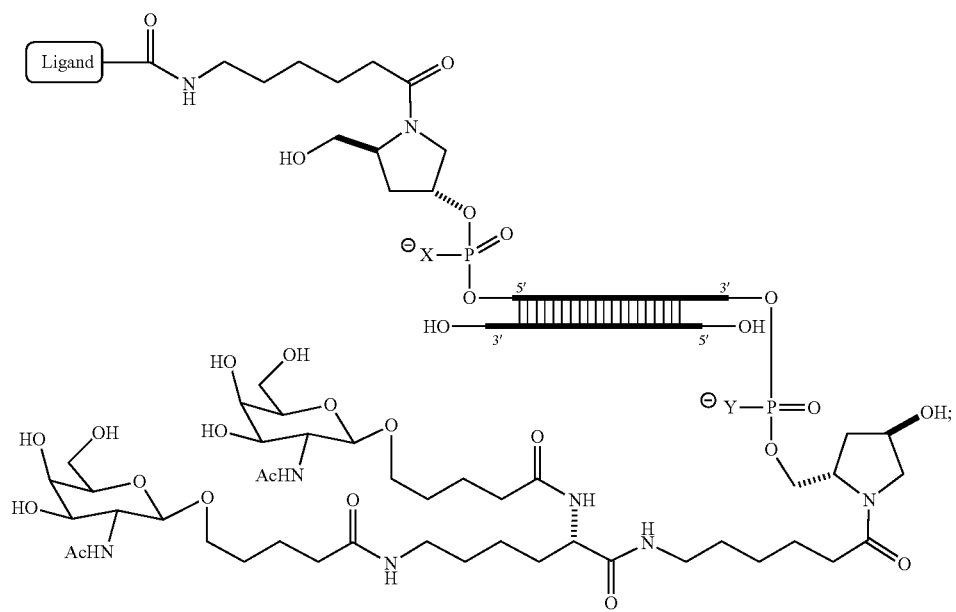

-continued

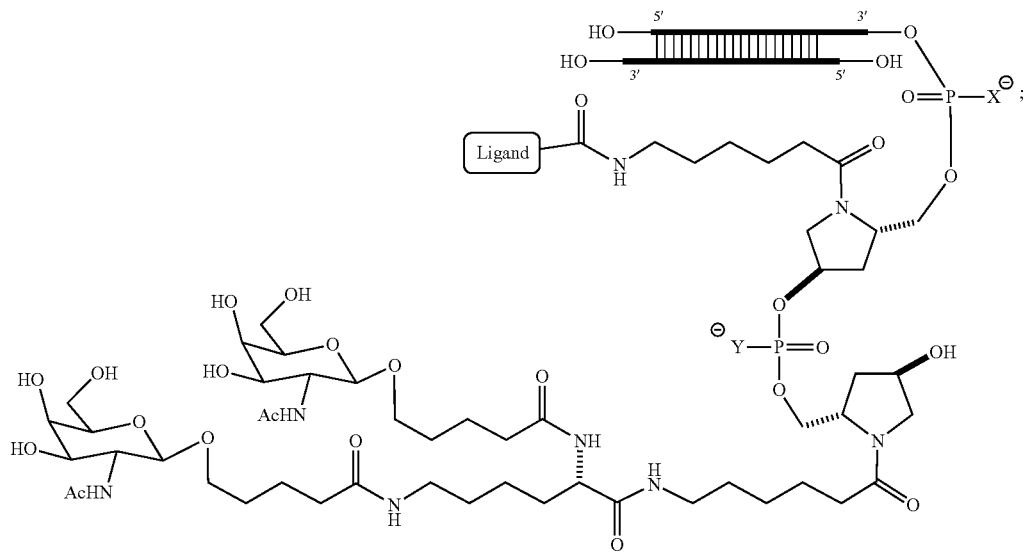

wherein the ligand is a PK modulator: X=O or S; Y=O or S; PEG stands for ω-OH, ω-amino, ω-methoxy, ω-SH, ω-propargyl, ω-azido and ω-ligand PEGS with MW between 200 and 100,000.

Endosomolytic Components

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. *Chem. Biol.* 11, 713-723). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. *Polymers Adv. Technol.* 13, 992-999; Kakudo, Chaki, T., S. et al. (2004). Transferrin-Modified Liposomes Equipped with a pH-Sensitive Fusogenic Peptide: An Artificial Viral-like Delivery System. *Biochemistry* 436, 5618-5628; Yessine, M. A. and Leroux, J. C. (2004). Membrane-destabilizing polyanions: interaction with lipid bilayers and endosomal escape of biomacromolecules. *Adv. Drug Deliv. Rev.* 56, 999-1021; Oliveira, S., van Rooy, I. et al. (2007). Fusogenic peptides enhance endosomal escape improving siRNA-induced silencing of oncogenes. *Int. J. Pharm.* 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs. *Biochim. Biophys. Acta* 1559, 56-68).

In certain embodiments, the endosomolytic components of the present invention may be polyanionic peptides or peptidomimetics which show pH-dependent membrane activity and/or fusogenicity. A peptidomimetic may be a small protein-like chain designed to mimic a peptide. A peptidomimetic may arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Libraries of compounds may be screened for their differential membrane activity at endosomal pH versus neutral pH using a hemolysis assay. Promising candidates isolated by this method may be used as components of the modular compositions of the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GALA peptide (Subbarao et al., Biochemistry, 1987, 26: 2964-2972), the EALA peptide (SEQ ID NO: 1) (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of endosomolytic components include $H_2N$-

(AALEALAEALEALAEALEALAEAAAAGGC)-CO$_2$H (SEQ ID NO: 2); H$_2$N-(AALAEALAEALAEALAEALAEALAAAAGGC)-CO$_2$H (SEQ ID NO: 3); and H$_2$N-(ALEALAEALEALAEA)-CONH$_2$ (SEQ ID NO: 4).

In certain embodiments, more than one endosomolytic component may be incorporated into the iRNA agent of the invention. In some embodiments, this will entail incorporating more than one of the same endosomolytic component into the iRNA agent in addition to the monomers of formula (I). In other embodiments, this will entail incorporating two or more different endosomolytic components into iRNA agent in addition to the monomers of formula (I).

These endosomolytic components may mediate endosomal escape by, for example, changing conformation at endosomal pH. In certain embodiments, the endosomolytic components may exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4). Fusogenic activity is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

In addition to the hemolysis assay described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an iRNA agent described herein is constructed using one or more test or putative fusogenic agents. The iRNA agent can be labeled for easy visulization. The ability of the endosomolytic component to promote endosomal escape, once the iRNA agent is taken up by the cell, can be evaluated, e.g., by preparation of an endosome preparation, or by microscopy techniques, which enable visualization of the labeled iRNA agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition.

A two-step assay can also be performed, wherein a first assay evaluates the ability of a test compound alone to respond to changes in pH, and a second assay evaluates the ability of a modular composition that includes the test compound to respond to changes in pH.

Peptides

Peptides suitable for use with the present invention can be a natural peptide, e.g. tat or antennopedia peptide, a synthetic peptide or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to the oligonucleotide can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 1, for example).

TABLE 1

Exemplary Cell Permeation Peptides

| Cell Permeation Peptide | SEQ ID NO: | Amino acid Sequence | Reference |
|---|---|---|---|
| Penetratin | 5 | RQIKIWFQNRRMKWKK | Derossi et al., J. Biol. Chem. 269: 10444, 1994 |
| Tat fragment (48-60) | 6 | GRKKRRQRRRPPQC | Vives et al., J. Biol. Chem., 272: 16010, 1997 |
| Signal Sequence-based peptide | 7 | GALFLGWLGAAGSTMGAWSQPKKKRKV | Chaloin et al., Biochem. Biophys. Res. Commun., 243: 601, 1998 |
| PVEC | 8 | LLIILRRRIRKQAHAHSK | Elmquist et al., Exp. Cell Res., 269: 237, 2001 |
| Transportan | 9 | GWTLNSAGYLLKINLKALAALAKKIL | Pooga et al., FASEB J., 12: 67, 1998 |
| Amphiphilic model peptide | 10 | KLALKLALKALKAALKLA | Oehlke et al., Mol. Ther., 2: 339, 2000 |

TABLE 1-continued

Exemplary Cell Permeation Peptides

| Cell Permeation Peptide | SEQ ID NO: | Amino acid Sequence | Reference |
|---|---|---|---|
| Arg$_9$ | 11 | RRRRRRRRR | Mitchell et al., J. Pept. Res., 56: 318, 2000 |
| Bacterial cell wall permeating | 12 | KFFKFFKFFK | |
| LL-37 | 13 | LLGDFFRKSKEKIGKEFKRIVQ RIKDFLRNLVPRTES | |
| Cecropin P1 | 14 | SWLSKTAKKLENSAKKRISEG IAIAIQGGPR | |
| α-defensin | 15 | ACYCRIPACIAGERRYGTCIY QGRLWAFCC | |
| b-defensin | 16 | DHYNCVSSGGQCLYSACPIFT KIQGTCYRGKAKCCK | |
| Bactenecin | 17 | RKCRIVVIRVCR | |
| PR-39 | 18 | RRRPRPPYLPRPRPPPFFPPRLP PRIPPGFPPRFPPRFPGKR-NH2 | |
| Indolicidin | 19 | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ TD NO: 20). A RFGF analogue (e.g., amino acid sequence AALLPVL-LAAP (SEQ TD NO: 21)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ TD NO: 6)) and the Drosophila Antennapedia protein (RQIKIWFQNRRMVKWKK (SEQ TD NO: 5)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to the lipid is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting tumors of a variety of other tissues, including the lung, kidney, spleen, or liver (Aoki et al., Cancer Gene Therapy 8:783-787, 2001). Preferably, the RGD peptide will facilitate targeting of the lipid particle to the kidney. The RGD peptide can be linear or cyclic, and can be modified, e.g., glycosylated or methylated to facilitate targeting to specific tissues. For example, a glycosylated RGD peptide can target a tumor cell expressing $α_vβ_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_vθ_3$ integrin. Thus, one could use RGD peptides, cyclic peptides containing RGD, RGD peptides that include D-amino acids, as well as synthetic RGD mimics. In addition to RGD, one can use other moieties that target the $I_v$-$θ_3$ integrin ligand. Generally, such ligands can be used to control proliferating cells and angiogeneis.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

iRNA Agents

The iRNA agent should include a region of sufficient homology to the target gene, and be of sufficient length in terms of nucleotides, such that the iRNA agent, or a fragment thereof, can mediate downregulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more, or for example, 6, 5, 4, 3, 2, or fewer mismatches (with respect to the target RNA). The mismatches, particularly in the antisense strand, are most tolerated in the terminal regions and if present may be in a terminal region or regions, e.g., within 6, 5, 4, or 3 nucleotides of the 5' and/or 3' termini. The sense strand need only be sufficiently complementary with the antisense strand to maintain the over all double stranded character of the molecule.

As discussed elsewhere herein, and in the material incorporated by reference in its entirety, an iRNA agent will often be modified or include nucleoside surrogates. Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-termini of an iRNA agent, e.g., against exonucleases, or to favor the antisense siRNA agent to enter into RISC are also envisioned. Modifications can include C3 (or C6, C7, C12) amino linkers, thiol linkers, carboxyl linkers, non-nucleotide spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

iRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60, 50, 40, or 30 nucleotide pairs. The siRNA agent, or a cleavage product thereof, can down regulate a target gene, e.g., by inducing RNAi with respect to a target RNA, wherein the target may comprise an endogenous or pathogen target RNA.

Each strand of an siRNA agent can be equal to or less than 30, 25, 24, 23, 22, 21, or 20 nucleotides in length. The strand may be at least 19 nucleotides in length. For example, each strand can be between 21 and 25 nucleotides in length. siRNA agents may have a duplex region of 17, 18, 19, 29, 21, 22, 23, 24, or 25 nucleotide pairs, and one or more overhangs, or one or two 3' overhangs, of 2-3 nucleotides.

In addition to homology to target RNA and the ability to down regulate a target gene, an iRNA agent may have one or more of the following properties:

(1) it may be of the Formula VII, VIII, IX or X set out in the RNA Agent section below;
(2) if single stranded it may have a 5' modification which includes one or more phosphate groups or one or more analogs of a phosphate group;
(3) it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;
(4) it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_3$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. A modified moiety at the 2' sugar position may be able to enter into H bonding which is more characteristic of the OH moiety of a ribonucleotide than the H moiety of a deoxyribonucleotide. Certain iRNA agents will: exhibit a $C_3$-endo pucker in all, or at least 50, 75, 80, 85, 90, or 95% of its sugars; exhibit a $C_3$-endo pucker in a sufficient amount of its sugars that it can give rise to a the RNA-characteristic A-family-type helix; will have no more than 20, 10, 5, 4, 3, 2, or 1 sugar which is not a $C_3$-endo pucker structure. Regardless of the nature of the modification, and even though the RNA agent can contain deoxynucleotides or modified deoxynucleotides, particularly in overhang or other single strand regions, it is certain DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents may be antisense with regard to the target molecule. In certain embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)2(O)P-5'—CH2-), 5'-alkyletherphosphonates (R=alkylether=methoxymethyl (MeOCH2-), ethoxymethyl, etc., e.g., RP(OH)(O)—O-5'-). (These modifications can also be used with the antisense strand of a double stranded iRNA.)

A single strand iRNA agent may be sufficiently long that it can enter the RISC and participate in RISC mediated cleavage of a target mRNA. A single strand iRNA agent is at least 14, and in other embodiments at least 15, 20, 25, 29, 35, 40, or 50 nucleotides in length. In certain embodiments, it is less than 200, 100, or 60 nucleotides in length.

Hairpin iRNA agents will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region, in some embodiments at the 3', and in certain embodiments on the antisense side of the hairpin. In some embodiments, the overhangs are 2-3 nucleotides in length.

A "double stranded (ds) iRNA agent" as used herein, is an iRNA agent which includes more than one, and in some cases two, strands in which interchain hybridization can form a region of duplex structure.

The antisense strand of a double stranded iRNA agent may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The sense strand of a double stranded iRNA agent may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded iRNA agent may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the ds iRNA agent is sufficiently large that it can be cleaved by an endogenous molecule, e.g., by Dicer, to produce smaller ds iRNA agents, e.g., siRNAs agents It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active siRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional siRNA 5'-end. Antisense strand modifications include 5' phosphorylation as well as any of the other 5' modifications discussed herein, particularly the 5' modifications discussed above in the section on single stranded iRNA molecules.

The sense and antisense strands may be chosen such that the ds iRNA agent includes a single strand or unpaired region at one or both ends of the molecule. Thus, a ds iRNA agent may contain sense and antisense strands, paired to contain an overhang, e.g., one or two 5' or 3' overhangs, or a 3' overhang of 2-3 nucleotides. Many embodiments will have a 3' overhang. Certain siRNA agents will have single-stranded overhangs, in some embodiments 3' overhangs, of 1 or 2 or 3 nucleotides in length at each end. The overhangs can be the result of one strand being longer than the other, or the result of two strands of the same length being staggered. 5' ends may be phosphorylated.

In some embodiments, the length for the duplexed region is between 15 and 30, or 18, 19, 20, 21, 22, and 23 nucleotides in length, e.g., in the siRNA agent range discussed above. siRNA agents can resemble in length and structure the natural Dicer processed products from long dsiRNAs. Embodiments in which the two strands of the siRNA agent are linked, e.g., covalently linked are also included. Hairpin, or other single strand structures which provide the required double stranded region, and a 3' overhang are also within the invention.

The isolated iRNA agents described herein, including ds iRNA agents and siRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, an iRNA agent is "sufficiently complementary" to a target RNA, e.g., a target mRNA, such that the iRNA agent silences production of protein encoded by the target mRNA. In another embodiment, the iRNA agent is "exactly complementary" to a target RNA, e.g., the target RNA and the iRNA agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

RNA agents discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has often referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA refers to a molecule in which one or more of the components of the nucleic acid, namely sugars, bases, and phosphate moieties, are different from that which occur in nature, for example, different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a double stranded iRNA agent, e.g., a partially double stranded iRNA agent, is envisioned. Thus, it is understood that that double stranded structures (e.g., where two separate molecules are contacted to form the double stranded region or where the double stranded region is formed by intramolecular pairing (e.g., a hairpin structure)) made of the single stranded structures described below are within the invention. Lengths are described elsewhere herein.

As nucleic acids are polymers of subunits, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many cases it will not. By way of example, a modification may only occur at a 3' or 5' terminal position, may only occur in a terminal regions, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

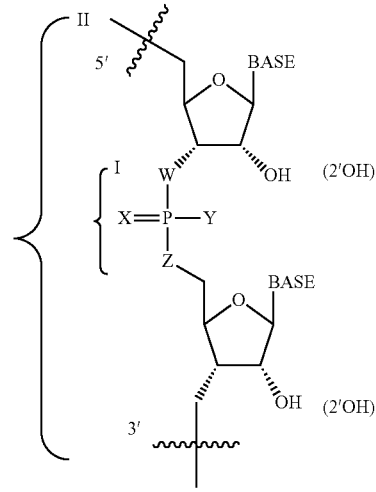

FORMULA (VII)

The scaffold presented above in Formula VII represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula VII represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e., Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is possible.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is possible.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-OCH3, 2'-O-allyl, 2'—C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNA's can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g., nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. In certain embodiments, PNA surrogates may be used.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in certain embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');
5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)₂(O)P-5'—CH₂—), 5'-alkyletherphosphonates (R=alkylether=methoxymethyl (MeOCH2-), ethoxymethyl, etc., e.g., RP(OH)(O)—O-5'-).

Terminal modifications can also be useful for increasing resistance to degradation.

Terminal modifications can also be useful for monitoring distribution, and in such cases the groups to be added may include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N⁴-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are not used for promoting stability, but they can be useful for other reasons, e.g., some, e.g., 2,6-diaminopurine and 2 amino purine, are fluorescent. Modified bases can reduce target specificity. This may be taken into consideration in the design of iRNA agents.

Candidate modifications can be evaluated as described below.

Evaluation of Candidate RNAs

One can evaluate a candidate RNA agent, e.g., a modified RNA, for a selected property by exposing the agent or modified molecule and a control molecule to the appropriate conditions and evaluating for the presence of the selected property. For example, resistance to a degradent can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dsiRNA agents.

In an alternative functional assay, a candidate dsiRNA agent homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dsiRNA agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

RNA Structure References

The disclosure of all publications, patents, and published patent applications listed herein are hereby incorporated by reference.

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7, 651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. *Nucleic Acids Res.* 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Base References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Additional RNA Agents

Certain RNA agents have the following structure (Formula VIII):

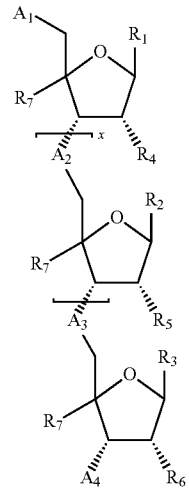

FORMULA VIII wherein:

$R^1$, $R^2$, and $R^3$ are independently H, (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases;

$R^4$, $R^5$, and $R^6$ are independently $OR^8$, $O(CH_2CH_2O)_m CH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2NHR^9$; $NHC(O)R^8$; cyano; mercapto, $SR^8$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—$CH_2$—] covalently bound bridge between the sugar 2' and 4' carbons;

$A^1$ is:

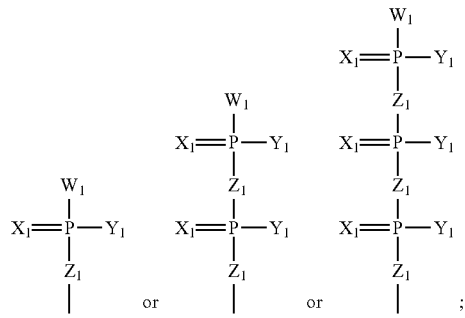

H; OH, $OCH_3$, $W^1$; an abasic nucleotide; or absent;

(in some embodiments, A1, especially with regard to anti-sense strands, is chosen from 5'-monophosphate (($HO)_2(O)P$—O-5'), 5'-diphosphate (($HO)_2(O)P$—O—P(HO)(O)—O-5'), 5'-triphosphate (($HO)_2(O)P$—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—O—(HO)(O)P—O—P(HO)(O)—O-5'), 5'-monothiophosphate (phosphorothioate; $(HO)_2(S)P$—O-5'), 5'-monodithiophosphate (phosphorodithioate; (HO)(HS)(S)P—O-5'), 5'-phosphorothiolate (($HO)_2(O)P$—S—5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates (($HO)_2(O)P$—NH-5', (HO)(NH_2)(O)P—O-5'), 5'-alkylphosphonates (R=alkyl=methyl, ethyl, isopropyl, propyl, etc., e.g., $R^P(OH)(O)$—O-5'-, ($OH)_2(O)P$-5'—$CH_2$—), 5'-alkyletherphosphonates (R=alkylether=methoxymethyl ($MeOCH_2$—), ethoxymethyl, etc., e.g., RP(OH)(O)—O-5'-));

$A^2$ is:

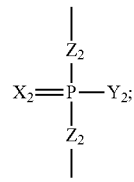

$A^3$ is:

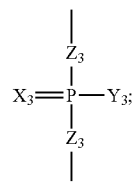

$A^4$ is:

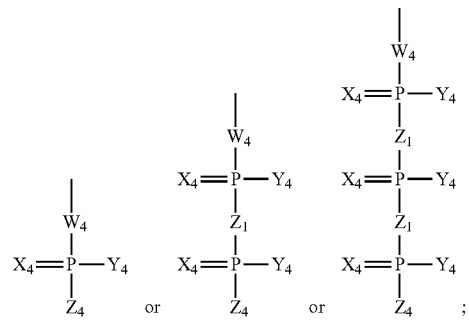

H; $Z^4$; an inverted nucleotide; an abasic nucleotide; or absent;

$W^1$ is OH, $(CH_2)_nR^{10}$, $(CH_2)_nNHR^{10}$, $(CH_2)_n$ $OR^{10}$, $(CH_2)_n$ $SR^{10}$; $O(CH_2)_nR^{10}$; $O(CH_2)_nOR^{10}$, $O(CH_2)_nNR^{10}$, $O(CH_2)_nSR^{10}$; $O(CH_2)_nSS(CH_2)_nOR^{10}$, $O(CH_2)_nC(O)OR^{10}$, $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}$ $O(CH_2CH_2O)_mCH_2CH_2OR^{10}$; $O(CH_2CH_2O)_m$ $CH_2CH_2NHR^{10}$, $NH(CH_2CH_2NH)_mCH_2CH_2NHR^{10}$; Q-$R^{10}$, O-Q-$R^{10}$ N-Q-$R^{10}$, S-Q-$R^{10}$ or —O—;

$W^4$ is O, $CH_2$, NH, or S;

$X^1$, $X^2$, $X^3$, and $X^4$ are each independently O or S;

$Y^1$, $Y^2$, $Y^3$, and $Y^4$ are each independently OH, O⁻, $OR^8$, S, Se, $BH_3^-$, H, $NHR^9$, $N(R^9)_2$ alkyl, cycloalkyl, aralkyl, aryl, or heteroaryl, each of which may be optionally substituted;

$Z^1$, $Z^2$, and $Z^3$ are each independently O, $CH_2$, NH, or S;

$Z^4$ is OH, $(CH_2)_nR^{10}$, $(CH_2)_nNHR^{10}$, $(CH_2)_n$ $OR^{10}$, $(CH_2)_n$ $SR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}$ $O(CH_2CH_2O)_mCH_2CH_2OR^{10}$, $O(CH_2CH_2O)_mCH_2CH_2NHR^{10}$, $NH(CH_2CH_2NH)_mCH_2CH_2NHR^{10}$; Q-$R^{10}$, O-Q-$R^{10}$ N-Q-$R^{10}$, S-Q-$R^{10}$;

x is 5-100, chosen to comply with a length for an RNA agent described herein;

$R^7$ is H; or is together combined with $R^4$, $R^5$, or $R^6$ to form an [—O—CH$_2$—] covalently bound bridge between the sugar 2' and 4' carbons;

$R^8$ is alkyl, cycloalkyl, aryl, aralkyl, heterocyclyl, heteroaryl, amino acid, or sugar;

$R^9$ is NH$_2$, alkylamino, dialkylamino, heterocyclyl, arylamino, diaryl amino, heteroaryl amino, diheteroaryl amino, or amino acid;

$R^{10}$ is H; fluorophore (pyrene, TAMRA, fluorescein, Cy3 or Cy5 dyes); sulfur, silicon, boron or ester protecting group; intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipohilic carriers (cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino; alkyl, cycloalkyl, aryl, aralkyl, heteroaryl; radiolabelled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an RNA agent;

m is 0-1,000,000;

n is 0-20.

Q is a spacer selected from the group consisting of abasic sugar, amide, carboxy, oxyamine, oxyimine, thioether, disulfide, thiourea, sulfonamide, or morpholino, biotin or fluorescein reagents.

Certain RNA agents in which the entire phosphate group has been replaced have the following structure (Formula IX):

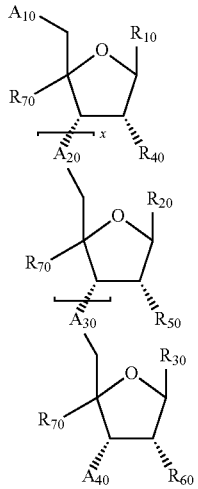

FORMULA IX wherein:

$A^{10}$-$A^{40}$ is L-G-L; $A^{10}$ and/or $A^{40}$ may be absent, wherein L is a linker, wherein one or both L may be present or absent and is selected from the group consisting of CH$_2$(CH$_2$)$_g$; N(CH$_2$)$_g$; O(CH$_2$)$_g$; S(CH$_2$)$_g$;

G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino;

$R^{10}$, $R^{20}$, and $R^{30}$ are independently H, (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases;

$R^{40}$, $R^{50}$, and $R^{60}$ are independently OR$^8$, O(CH$_2$CH$_2$O)$_m$CH$_2$CH$_2$OR$^8$; O(CH$_2$)$_n$R$^9$; O(CH$_2$)$_n$OR$^9$, H; halo; NH$_2$; NHR$^8$; N(R$^8$)$_2$; NH(CH$_2$CH$_2$NH)$_m$CH$_2$CH$_2$R$^9$; NHC(O)R$^8$; cyano; mercapto, SR$^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—CH$_2$—] covalently bound bridge between the sugar 2' and 4' carbons;

x is 5-100 or chosen to comply with a length for an RNA agent described herein;

$R^{70}$ is H; or is together combined with $R^{40}$, $R^{50}$, or $R^{60}$ to form an [—O—CH$_2$—] covalently bound bridge between the sugar 2' and 4' carbons;

$R^8$ is alkyl, cycloalkyl, aryl, aralkyl, heterocyclyl, heteroaryl, amino acid, or sugar;

$R^9$ is NH$_2$, alkylamino, dialkylamino, heterocyclyl, arylamino, diaryl amino, heteroaryl amino, diheteroaryl amino, or amino acid;

m is 0-1,000,000;

n is 0-20;

g is 0-2.

Certain nucleoside surrogates have the following structure (Formula X):

SLR$^{100}$-(M-SLR$^{200}$)$_x$-M-SLR$^{300}$

FORMULA X wherein:

S is a nucleoside surrogate selected from the group consisting of mophilino, cyclobutyl, pyrrolidine and peptide nucleic acid;

L is a linker and is selected from the group consisting of $CH_2(CH_2)_g$; $N(CH_2)_g$; $O(CH_2)_g$; $S(CH_2)_g$; $—C(O)(CH_2)_n—$ or may be absent;

M is an amide bond; sulfonamide; sulfinate; phosphate group; modified phosphate group as described herein; or may be absent;

$R^{100}$, $R^{200}$, and $R^{300}$ are independently H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1, 2, 4,-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases;

x is 5-100, or chosen to comply with a length for an RNA agent described herein;

g is 0-2.

Definitions

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituted" refers to the replacement of one or more hydrogen radicals in a given structure with the radical of a specified substituent including, but not limited to:

halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Palindromes

The iRNA agents of the invention can target more than one RNA region. For example, an iRNA agent can include a first and second sequence that are sufficiently complementary to each other to hybridize. The first sequence can be complementary to a first target RNA region and the second sequence can be complementary to a second target RNA region. The first and second sequences of the iRNA agent can be on different RNA strands, and the mismatch between the first and second sequences can be less than 50%, 40%, 30%, 20%, 10%, 5%, or 1%. The first and second sequences of the iRNA agent are on the same RNA strand, and in a related embodiment more than 50%, 60%, 70%, 80%, 90%, 95%, or 1% of the iRNA agent can be in bimolecular form. The first and second sequences of the iRNA agent can be fully complementary to each other.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The compositions of the invention can include mixtures of iRNA agent molecules. For example, one iRNA agent can contain a first sequence and a second sequence sufficiently complementary to each other to hybridize, and in addition the first sequence is complementary to a first target RNA region and the second sequence is complementary to a second target RNA region. The mixture can also include at least one additional iRNA agent variety that includes a third sequence and a fourth sequence sufficiently complementary to each other to hybridize, and where the third sequence is complementary to a third target RNA region and the fourth sequence is complementary to a fourth target RNA region. In addition, the first or second sequence can be sufficiently complementary to the third or fourth sequence to be capable of hybridizing to each other. The first and second sequences can be on the same or different RNA strands, and the third and fourth sequences can be on the same or different RNA strands.

The target RNA regions can be variant sequences of a viral or human RNA, and in certain embodiments, at least two of the target RNA regions can be on variant transcripts of an oncogene or tumor suppressor gene. The target RNA regions can correspond to genetic hot-spots.

Methods of making an iRNA agent composition can include obtaining or providing information about a region of an RNA of a target gene (e.g., a viral or human gene, or an oncogene or tumor suppressor, e.g., p53), where the region has high variability or mutational frequency (e.g., in humans). In addition, information about a plurality of RNA targets within the region can be obtained or provided, where each RNA target corresponds to a different variant or mutant of the gene (e.g., a region including the codon encoding p53 248Q and/or p53 249S). The iRNA agent can be constructed such that a first sequence is complementary to a first of the plurality of variant RNA targets (e.g., encoding 249Q) and a second sequence is complementary to a second of the plurality of variant RNA targets (e.g., encoding 249S), and the first and second sequences can be sufficiently complementary to hybridize.

Sequence analysis, e.g., to identify common mutants in the target gene, can be used to identify a region of the target gene that has high variability or mutational frequency. A region of the target gene having high variability or muta-tional frequency can be identified by obtaining or providing genotype information about the target gene from a population.

Expression of a target gene can be modulated, e.g., downregulated or silenced, by providing an iRNA agent that has a first sequence and a second sequence sufficiently complementary to each other to hybridize. In addition, the first sequence can be complementary to a first target RNA region and the second sequence can be complementary to a second target RNA region.

An iRNA agent can include a first sequence complementary to a first variant RNA target region and a second sequence complementary to a second variant RNA target region. The first and second variant RNA target regions can correspond to first and second variants or mutants of a target gene, e.g., viral gene, tumor suppressor or oncogene. The first and second variant target RNA regions can include allelic variants, mutations (e.g., point mutations), or polymorphisms of the target gene. The first and second variant RNA target regions can correspond to genetic hot-spots.

A plurality of iRNA agents (e.g., a panel or bank) can be provided.

Other Embodiments

In yet another embodiment, iRNAs agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a iRNA agent and one that produces a transcript that includes the bottom strand of a iRNA agent. When the templates are transcribed, the iRNA agent is produced, and processed into siRNA agent fragments that mediate gene silencing.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein, in its entirety.

Decoy Oligonucleotides

Because transcription factors can recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

Antisense Oligonucleotides

Antisense oligonucleotides are single strands of DNA or RNA that are at least partially complementary to a chosen sequence. In the case of antisense RNA, they prevent translation of complementary RNA strands by binding to it. Antisense DNA can also be used to target a specific, complementary (coding or non-coding) RNA. If binding takes place, the DNA/RNA hybrid can be degraded by the enzyme RNase H. Examples of the utilization of antisense oligonucleotides may be found in Dias et al., Mol. Cancer Ther., 2002, 1: 347-355, which is expressly incorporated by reference herein, in its entirety.

Aptamers

Aptamers are nucleic acid molecules that bind a specific target molecule or molecules. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

Increasing Cellular Uptake of dsiRNAs

A method of the invention that includes administering an iRNA agent and a drug that affects the uptake of the iRNA agent into the cell. The drug can be administered before, after, or at the same time that the iRNA agent is administered. The drug can be covalently linked to the iRNA agent. The drug can be, for example, a lipopolysaccharid, an activator of p38 MAP kinase, or an activator of NF-κB. The drug can have a transient effect on the cell.

The drug can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The drug can also increase the uptake of the iRNA agent into the cell by activating an inflammatory response, for example. Exemplary drug's that would have such an effect include tumor necrosis factor alpha (TNFalpha), interleukin-1 beta, or gamma interferon.

iRNA Conjugates

An iRNA agent can be coupled, e.g., covalently coupled, to a second agent. For example, an iRNA agent used to treat a particular disorder can be coupled to a second therapeutic agent, e.g., an agent other than the iRNA agent. The second therapeutic agent can be one which is directed to the treatment of the same disorder. For example, in the case of an iRNA used to treat a disorder characterized by unwanted cell proliferation, e.g., cancer, the iRNA agent can be coupled to a second agent which has an anti-cancer effect. For example, it can be coupled to an agent which stimulates the immune system, e.g., a CpG motif, or more generally an agent that activates a toll-like receptor and/or increases the production of gamma interferon.

iRNA Production

An iRNA can be produced, e.g., in bulk, by a variety of methods. Exemplary methods include: organic synthesis and RNA cleavage, e.g., in vitro cleavage.

Organic Synthesis

An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed, e.g., after release from the solid support and deprotection.

Organic synthesis can be used to produce a discrete iRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsiRNA Cleavage iRNAs can also be made by cleaving a larger ds iRNA. The cleavage can be mediated in vitro or in vivo. For example, to produce iRNAs by cleavage in vitro, the following method can be used:

In vitro transcription. dsiRNA is produced by transcribing a nucleic acid (DNA) segment in both directions. For example, the HiScribe™ RNAi transcription kit (New England Biolabs) provides a vector and a method for producing a dsiRNA for a nucleic acid segment that is cloned into the vector at a position flanked on either side by a T7 promoter. Separate templates are generated for T7 transcription of the two complementary strands for the dsiRNA. The templates are transcribed in vitro by addition of T7 RNA polymerase and dsiRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsiRNA is cleaved in vitro into iRNAs, for example, using a Dicer or comparable RNAse III-based activity. For example, the dsiRNA can be incubated in an in vitro extract from *Drosophila* or using purified components, e.g., a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293(5532):1146-50.

dsiRNA cleavage generally produces a plurality of iRNA species, each being a particular 21 to 23 nt fragment of a source dsiRNA molecule. For example, iRNAs that include sequences complementary to overlapping regions and adjacent regions of a source dsiRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Formulation

The iRNA agents described herein can be formulated for administration to a subject.

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration (see, below).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least 3, 5, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA). For example, a iRNA composition for the treatment of a viral disease, e.g., HIV, might include a known antiviral agent (e.g., a protease inhibitor or reverse transcriptase inhibitor). In another example, a iRNA composition for the treatment of a cancer might further comprise a chemotherapeutic agent.

Exemplary formulations are discussed below:

Liposomes

For ease of exposition the formulations, compositions and methods in this section are discussed largely with regard to unmodified iRNA agents. It may be understood, however, that these formulations, compositions and methods can be practiced with other iRNA agents, e.g., modified iRNA s agents, and such practice is within the invention. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a iRNA can be prepared by a variety of methods.

In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA preparation is then added to the micelles that include the lipid component. The cationic groups on the lipid interact with the iRNA and condense around the iRNA to form a liposome. After condensation, the detergent is removed, e.g., by dialysis, to yield a liposomal preparation of iRNA.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979;

Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA preparations into liposomes.

Liposomes that are pH-sensitive or negatively-charged, entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNAs to macrophages.

Further advantages of liposomes include: liposomes obtained from natural phospholipids are biocompatible and biodegradable; liposomes can incorporate a wide range of water and lipid soluble drugs; liposomes can protect encapsulated iRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA, into the skin. In some implementations, liposomes are used for delivering iRNA to epidermal cells and also to enhance the penetration of iRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2, 405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA can be delivered, for example, subcutaneously by infection in order to deliver iRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Surfactants

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. Surfactants find wide application in formulations such as emulsions (including microemulsions) and liposomes (see above). iRNA (or a precursor, e.g., a larger dsiRNA which can be processed into a iRNA, or a DNA which encodes a iRNA or precursor) compositions can include a surfactant. In one embodiment, the iRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and other Membranous Formulations

For ease of exposition the micelles and other formulations, compositions and methods in this section are discussed largely with regard to unmodified iRNA agents. It may be understood, however, that these micelles and other formulations, compositions and methods can be practiced with other iRNA agents, e.g., modified iRNA agents, and such practice is within the invention. The iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the iRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the iRNA composition and at least the alkali metal alkyl sulphate. The first micellar composition is then mixed with at least three micelle forming compounds to form a mixed micellar composition. In another method, the micellar composition is prepared by mixing the iRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles

For ease of exposition the particles, formulations, compositions and methods in this section are discussed largely with regard to unmodified iRNA agents. It may be understood, however, that these particles, formulations, compositions and methods can be practiced with other iRNA agents, e.g., modified iRNA agents, and such practice is within the invention. In another embodiment, an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques. See below for further description.

Sustained-Release Formulations. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) described herein can be formulated for controlled, e.g., slow release. Controlled release can be achieved by disposing the iRNA within a structure or substance which impedes its release. E.g., iRNA can be disposed within a porous matrix or in an erodable matrix, either of which allow release of the iRNA over a period of time.

Polymeric particles, e.g., polymeric in microparticles can be used as a sustained-release reservoir of iRNA that is taken up by cells only released from the microparticle through biodegradation. The polymeric particles in this embodiment should therefore be large enough to preclude phagocytosis (e.g., larger than 10 µm or larger than 20 µm). Such particles can be produced by the same methods to make smaller particles, but with less vigorous mixing of the first and second emulsions. That is to say, a lower homogenization speed, vortex mixing speed, or sonication setting can be used to obtain particles having a diameter around 100 µm rather than 10 µm. The time of mixing also can be altered.

Larger microparticles can be formulated as a suspension, a powder, or an implantable solid, to be delivered by intramuscular, subcutaneous, intradermal, intravenous, or intraperitoneal injection; via inhalation (intranasal or intrapulmonary); orally; or by implantation. These particles are useful for delivery of any iRNA when slow release over a relatively long term is desired. The rate of degradation, and consequently of release, varies with the polymeric formulation.

Microparticles may include pores, voids, hollows, defects or other interstitial spaces that allow the fluid suspension medium to freely permeate or perfuse the particulate boundary. For example, the perforated microstructures can be used to form hollow, porous spray dried microspheres.

Polymeric particles containing iRNA (e.g., a siRNA) can be made using a double emulsion technique, for instance. First, the polymer is dissolved in an organic solvent. A polymer may be polylactic-co-glycolic acid (PLGA), with a lactic/glycolic acid weight ratio of 65:35, 50:50, or 75:25. Next, a sample of nucleic acid suspended in aqueous solution is added to the polymer solution and the two solutions are mixed to form a first emulsion. The solutions can be mixed by vortexing or shaking, and in the mixture can be sonicated. Any method by which the nucleic acid receives the least amount of damage in the form of nicking, shearing, or degradation, while still allowing the formation of an appropriate emulsion is possible. For example, acceptable results can be obtained with a Vibra-cell model VC-250 sonicator with a ⅛" microtip probe, at setting #3.

Spray Drying

An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof)) can be prepared by spray drying. Spray dried iRNA can be administered to a subject or be subjected to further formulation. A pharmaceutical composition of iRNA can be prepared by spray drying a homogeneous aqueous mixture that includes a iRNA under conditions sufficient to provide a dispersible powdered composition, e.g., a pharmaceutical composition. The material for spray drying can also include one or more of: a pharmaceutically acceptable excipient, or a dispersibility-enhancing amount of a physiologically acceptable, water-soluble protein. The spray-dried product can be a dispersible powder that includes the iRNA.

Spray drying is a process that converts a liquid or slurry material to a dried particulate form. Spray drying can be used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996.

Spray drying can include atomizing a solution, emulsion, or suspension to form a fine mist of droplets and drying the droplets. The mist can be projected into a drying chamber (e.g., a vessel, tank, tubing, or coil) where it contacts a drying gas. The mist can include solid or liquid pore forming agents. The solvent and pore forming agents evaporate from the droplets into the drying gas to solidify the droplets, simultaneously forming pores throughout the solid. The solid (typically in a powder, particulate form) then is separated from the drying gas and collected.

Spray drying includes bringing together a highly dispersed liquid, and a sufficient volume of air (e.g., hot air) to produce evaporation and drying of the liquid droplets. The preparation to be spray dried can be any solution, course suspension, slurry, colloidal dispersion, or paste that may be atomized using the selected spray drying apparatus. Typically, the feed is sprayed into a current of warm filtered air that evaporates the solvent and conveys the dried product to a collector. The spent air is then exhausted with the solvent. Several different types of apparatus may be used to provide the desired product. For example, commercial spray dryers manufactured by Buchi Ltd. or Niro Corp. can effectively produce particles of desired size.

Spray-dried powdered particles can be approximately spherical in shape, nearly uniform in size and frequently hollow. There may be some degree of irregularity in shape depending upon the incorporated medicament and the spray drying conditions. In many instances the dispersion stability of spray-dried microspheres appears to be more effective if an inflating agent (or blowing agent) is used in their production. Certain embodiments may comprise an emulsion with an inflating agent as the disperse or continuous phase (the other phase being aqueous in nature). An inflating agent may be dispersed with a surfactant solution, using, for instance, a commercially available microfluidizer at a pressure of about 5000 to 15,000 psi. This process forms an emulsion, which may be stabilized by an incorporated surfactant, typically comprising submicron droplets of water immiscible blowing agent dispersed in an aqueous continuous phase. The formation of such dispersions using this and other techniques are common and well known to those in the art. The blowing agent may be a fluorinated compound (e.g., perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable blowing agents include chloroform, freons, and hydrocarbons. Nitrogen gas and carbon dioxide are also contemplated as a suitable blowing agent.

Although the perforated microstructures may be formed using a blowing agent as described above, it will be appreciated that, in some instances, no blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties (e.g., high crystallinity, elevated melting temperature, surface activity, etc.) that make it particularly suitable for use in such techniques.

The perforated microstructures may optionally be associated with, or comprise, one or more surfactants. Moreover, miscible surfactants may optionally be combined with the suspension medium liquid phase. It will be appreciated by those skilled in the art that the use of surfactants may further increase dispersion stability, simplify formulation procedures or increase bioavailability upon administration. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

Surfactants suitable for use include any compound or composition that aids in the formation and maintenance of the stabilized respiratory dispersions by forming a layer at the interface between the structural matrix and the suspension medium. The surfactant may comprise a single compound or any combination of compounds, such as in the case of co-surfactants. Particularly certain surfactants are substantially insoluble in the propellant, nonfluorinated, and selected from the group consisting of saturated and unsaturated lipids, nonionic detergents, nonionic block copolymers, ionic surfactants, and combinations of such agents. It may be emphasized that, in addition to the aforementioned surfactants, suitable (i.e., biocompatible) fluorinated surfactants are compatible with the teachings herein and may be used to provide the desired stabilized preparations.

Lipids, including phospholipids, from both natural and synthetic sources may be used in varying concentrations to form a structural matrix. Generally, compatible lipids comprise those that have a gel to liquid crystal phase transition greater than about 40° C. In certain embodiments, the incorporated lipids are relatively long chain (i.e., $C_6$-$C_{22}$) saturated lipids and may comprise phospholipids. Exemplary phospholipids useful in the disclosed stabilized preparations comprise egg phosphatidylcholine, dilauroylphosphatidylcholine, dioleylphosphatidylcholine, dipalmitoylphosphatidyl-choline, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as, polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (Spans™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.). Certain block copolymers include diblock and triblock copolymers of polyoxyethylene and polyoxypropylene, including poloxamer 188 (Pluronic® F68), poloxamer 407 (Pluronic® F-127), and poloxamer 338. Ionic surfactants such as sodium sulfosuccinate, and fatty acid soaps may also be utilized. In certain embodiments, the microstructures may comprise oleic acid or its alkali salt.

In addition to the aforementioned surfactants, cationic surfactants or lipids may be used, especially in the case of delivery of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). Examples of suitable cationic lipids include: DOTMA, N-[-(2,3-dioleyloxy)propyl]-N,N,N-trimethylammonium-chloride; DOTAP, 1,2-dioleyloxy-3-(trimethylammonio)propane; and DOTB, 1,2-dioleyl-3-(4'-trimethylammonio)butanoyl-sn-glycerol. Polycationic amino acids such as polylysine, and polyarginine are also contemplated.

For the spraying process, such spraying methods as rotary atomization, pressure atomization and two-fluid atomization can be used. Examples of the devices used in these processes include "Parubisu [phonetic rendering] Mini-Spray GA-32" and "Parubisu Spray Drier DL-41", manufactured by Yamato Chemical Co., or "Spray Drier CL-8," "Spray Drier L-8," "Spray Drier FL-12," "Spray Drier FL-16" or "Spray Drier FL-20," manufactured by Okawara Kakoki Co., can be used for the method of spraying using rotary-disk atomizer.

While no particular restrictions are placed on the gas used to dry the sprayed material, it is recommended to use air, nitrogen gas or an inert gas. The temperature of the inlet of the gas used to dry the sprayed materials such that it does not cause heat deactivation of the sprayed material. The range of temperatures may vary between about 50° C. to about 200° C., for example, between about 50° C. and 100° C. The temperature of the outlet gas used to dry the sprayed material, may vary between about 0° C. and about 150° C., for example, between 0° C. and 90° C., and for example between 0° C. and 60° C.

The spray drying is done under conditions that result in substantially amorphous powder of homogeneous constitution having a particle size that is respirable, a low moisture content and flow characteristics that allow for ready aerosolization. In some cases, the particle size of the resulting powder is such that more than about 98% of the mass is in particles having a diameter of about 10 μm or less with about 90% of the mass being in particles having a diameter less than 5 μm. Alternatively, about 95% of the mass will have particles with a diameter of less than 10 μm with about 80% of the mass of the particles having a diameter of less than 5 μm.

The dispersible pharmaceutical-based dry powders that include the iRNA preparation may optionally be combined with pharmaceutical carriers or excipients which are suitable for respiratory and pulmonary administration. Such carriers may serve simply as bulking agents when it is desired to reduce the iRNA concentration in the powder which is being delivered to a patient, but may also serve to enhance the stability of the iRNA compositions and to improve the dispersibility of the powder within a powder dispersion device in order to provide more efficient and reproducible delivery of the iRNA and to improve handling characteristics of the iRNA such as flowability and consistency to facilitate manufacturing and powder filling.

Such carrier materials may be combined with the drug prior to spray drying, i.e., by adding the carrier material to the purified bulk solution. In that way, the carrier particles will be formed simultaneously with the drug particles to produce a homogeneous powder. Alternatively, the carriers may be separately prepared in a dry powder form and combined with the dry powder drug by blending. The powder carriers will usually be crystalline (to avoid water absorption), but might in some cases be amorphous or mixtures of crystalline and amorphous. The size of the carrier particles may be selected to improve the flowability of the drug powder, typically being in the range from 25 μm to 100 μm. A carrier material may be crystalline lactose having a size in the above-stated range.

Powders prepared by any of the above methods will be collected from the spray dryer in a conventional manner for subsequent use. For use as pharmaceuticals and other purposes, it will frequently be desirable to disrupt any agglomerates which may have formed by screening or other conventional techniques. For pharmaceutical uses, the dry powder formulations will usually be measured into a single dose, and the single dose sealed into a package. Such packages are particularly useful for dispersion in dry powder inhalers, as described in detail below. Alternatively, the powders may be packaged in multiple-dose containers.

Methods for spray drying hydrophobic and other drugs and components are described in U.S. Pat. Nos. 5,000,888; 5,026,550; 4,670,419, 4,540,602; and 4,486,435. Bloch and Speison (1983) Pharm. Acta Helv 58:14-22 teaches spray drying of hydrochlorothiazide and chlorthalidone (lipophilic drugs) and a hydrophilic adjuvant (pentaerythritol) in azeotropic solvents of dioxane-water and 2-ethoxyethanol-water. A number of Japanese Patent application Abstracts relate to spray drying of hydrophilic-hydrophobic product combinations, including JP 806766; JP 7242568; JP 7101884; JP 7101883; JP 71018982; JP 7101881; and JP 4036233. Other foreign patent publications relevant to spray drying hydrophilic-hydrophobic product combinations include FR 2594693; DE 2209477; and WO 88/07870.

Lyophilization

An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparation can be made by lyophilization. Lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of nucleic acids in perforated microstructures without compromising physiological activity. Methods for providing lyophilized particulates are known to those of skill in the art and it would clearly not require undue experimentation to provide dispersion compatible microstructures in accordance with the teachings herein. Accordingly, to the extent that lyophilization processes may be used to provide microstructures having the desired porosity and size, they are conformance with the teachings herein and are expressly contemplated as being within the scope of the instant invention.

Genes

In one aspect, the invention features, a method of treating a subject at risk for or afflicted with a disease that may benefit from the administration of the iRNA agent of the invention. The method comprises administering the iRNA agent of the invention to a subject in need thereof, thereby treating the subject. The iRNA agent that is administered will depend on the disease being treated.

In certain embodiments, the iRNA agent silences a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In some embodiments the iRNA agent silences the PDGF beta gene, and thus can be used to treat a subject having or at risk for a disorder characterized by unwanted PDGF beta expression, e.g., testicular and lung cancers.

In some embodiments the iRNA agent silences the Erb-B gene, and thus can be used to treat a subject having or at risk for a disorder characterized by unwanted Erb-B expression, e.g., breast cancer.

In some embodiments the iRNA agent silences the Src gene, and thus can be used to treat a subject having or at risk for a disorder characterized by unwanted Src expression, e.g., colon cancers.

In some embodiments the iRNA agent silences the CRK gene, and thus can be used to treat a subject having or at risk for a disorder characterized by unwanted CRK expression, e.g., colon and lung cancers.

In some embodiments the iRNA agent silences the GRB2 gene, and thus can be used to treat a subject having or at risk for a disorder characterized by unwanted GRB2 expression, e.g., squamous cell carcinoma.

In another embodiment the iRNA agent silences the RAS gene, and thus can be used to treat a subject having or at risk for a disorder characterized by unwanted RAS expression, e.g., pancreatic, colon and lung cancers, and chronic leukemia.

In another embodiment the iRNA agent silences the MEKK gene, and thus can be used to treat a subject having or at risk for a disorder characterized by unwanted MEKK expression, e.g., squamous cell carcinoma, melanoma or leukemia.

In another embodiment the iRNA agent silences the JNK gene, and thus can be used to treat a subject having or at risk for a disorder characterized by unwanted JNK expression, e.g., pancreatic or breast cancers.

In some embodiments the iRNA agent silences the RAF gene, and thus can be used to treat a subject having or at risk for a disorder characterized by unwanted RAF expression, e.g., lung cancer or leukemia.

In some embodiments the iRNA agent silences the Erk1/2 gene, and thus can be used to treat a subject having or at risk for a disorder characterized by unwanted Erk1/2 expression, e.g., lung cancer.

In another embodiment the iRNA agent silences the PCNA(p21) gene, and thus can be used to treat a subject having or at risk for a disorder characterized by unwanted PCNA expression, e.g., lung cancer.

In some embodiments the iRNA agent silences the MYB gene, and thus can be used to treat a subject having or at risk for a disorder characterized by unwanted MYB expression, e.g., colon cancer or chronic myelogenous leukemia.

In some embodiments the iRNA agent silences the c-MYC gene, and thus can be used to treat a subject having or at risk for a disorder characterized by unwanted c-MYC expression, e.g., Burkitt's lymphoma or neuroblastoma.

In another embodiment the iRNA agent silences the JUN gene, and thus can be used to treat a subject having or at risk for a disorder characterized by unwanted JUN expression, e.g., ovarian, prostate or breast cancers.

In another embodiment the iRNA agent silences the FOS gene, and thus can be used to treat a subject having or at risk for a disorder characterized by unwanted FOS expression, e.g., skin or prostate cancers.

In some embodiments the iRNA agent silences the BCL-2 gene, and thus can be used to treat a subject having or at risk for a disorder characterized by unwanted BCL-2 expression, e.g., lung or prostate cancers or Non-Hodgkin lymphoma.

In some embodiments the iRNA agent silences the Cyclin D gene, and thus can be used to treat a subject having or at risk for a disorder characterized by unwanted Cyclin D expression, e.g., esophageal and colon cancers.

In some embodiments the iRNA agent silences the VEGF gene, and thus can be used to treat a subject having or at risk for a disorder characterized by unwanted VEGF expression, e.g., esophageal and colon cancers.

In some embodiments the iRNA agent silences the EGFR gene, and thus can be used to treat a subject having or at risk for a disorder characterized by unwanted EGFR expression, e.g., breast cancer.

In another embodiment the iRNA agent silences the Cyclin A gene, and thus can be used to treat a subject having or at risk for a disorder characterized by unwanted Cyclin A expression, e.g., lung and cervical cancers.

In another embodiment the iRNA agent silences the Cyclin E gene, and thus can be used to treat a subject having or at risk for a disorder characterized by unwanted Cyclin E expression, e.g., lung and breast cancers.

In another embodiment the iRNA agent silences the WNT-1 gene, and thus can be used to treat a subject having or at risk for a disorder characterized by unwanted WNT-1 expression, e.g., basal cell carcinoma.

In another embodiment the iRNA agent silences the beta-catenin gene, and thus can be used to treat a subject having or at risk for a disorder characterized by unwanted beta-catenin expression, e.g., adenocarcinoma or hepatocellular carcinoma.

In another embodiment the iRNA agent silences the c-MET gene, and thus can be used to treat a subject having or at risk for a disorder characterized by unwanted c-MET expression, e.g., hepatocellular carcinoma.

In another embodiment the iRNA agent silences the PKC gene, and thus can be used to treat a subject having or at risk for a disorder characterized by unwanted PKC expression, e.g., breast cancer.

In some embodiments the iRNA agent silences the NFKB gene, and thus can be used to treat a subject having or at risk for a disorder characterized by unwanted NFKB expression, e.g., breast cancer.

In some embodiments the iRNA agent silences the STAT3 gene, and thus can be used to treat a subject having or at risk for a disorder characterized by unwanted STAT3 expression, e.g., prostate cancer.

In another embodiment the iRNA agent silences the survivin gene, and thus can be used to treat a subject having or at risk for a disorder characterized by unwanted survivin expression, e.g., cervical or pancreatic cancers.

In another embodiment the iRNA agent silences the Her2/Neu gene, and thus can be used to treat a subject having or at risk for a disorder characterized by unwanted Her2/Neu expression, e.g., breast cancer.

In another embodiment the iRNA agent silences the topoisomerase I gene, and thus can be used to treat a subject having or at risk for a disorder characterized by unwanted topoisomerase I expression, e.g., ovarian and colon cancers.

In some embodiments the iRNA agent silences the topoisomerase II alpha gene, and thus can be used to treat a subject having or at risk for a disorder characterized by unwanted topoisomerase II expression, e.g., breast and colon cancers.

In some embodiments the iRNA agent silences mutations in the p73 gene, and thus can be used to treat a subject having or at risk for a disorder characterized by unwanted p73 expression, e.g., colorectal adenocarcinoma.

In some embodiments the iRNA agent silences mutations in the p21(WAF1/CIP1) gene, and thus can be used to treat a subject having or at risk for a disorder characterized by unwanted p21(WAF1/CIP1) expression, e.g., liver cancer.

In some embodiments the iRNA agent silences mutations in the p27(KIP1) gene, and thus can be used to treat a subject having or at risk for a disorder characterized by unwanted p27(KIP1) expression, e.g., liver cancer.

In some embodiments the iRNA agent silences mutations in the PPM1D gene, and thus can be used to treat a subject having or at risk for a disorder characterized by unwanted PPM1D expression, e.g., breast cancer.

In some embodiments the iRNA agent silences mutations in the RAS gene, and thus can be used to treat a subject having or at risk for a disorder characterized by unwanted RAS expression, e.g., breast cancer.

In another embodiment the iRNA agent silences mutations in the caveolin I gene, and thus can be used to treat a subject having or at risk for a disorder characterized by unwanted caveolin I expression, e.g., esophageal squamous cell carcinoma.

In another embodiment the iRNA agent silences mutations in the MIB I gene, and thus can be used to treat a subject having or at risk for a disorder characterized by unwanted MIB I expression, e.g., male breast carcinoma (MBC).

In another embodiment the iRNA agent silences mutations in the MTAI gene, and thus can be used to treat a subject having or at risk for a disorder characterized by unwanted MTAI expression, e.g., ovarian carcinoma.

In another embodiment the iRNA agent silences mutations in the M68 gene, and thus can be used to treat a subject having or at risk for a disorder characterized by unwanted M68 expression, e.g., human adenocarcinomas of the esophagus, stomach, colon, and rectum.

In certain embodiments the iRNA agent silences mutations in tumor suppressor genes, and thus can be used as a method to promote apoptotic activity in combination with chemotherapeutics.

In some embodiments the iRNA agent silences mutations in the p53 tumor suppressor gene, and thus can be used to treat a subject having or at risk for a disorder characterized by unwanted p53 expression, e.g., gall bladder, pancreatic and lung cancers.

In some embodiments the iRNA agent silences mutations in the p53 family member DN-p63, and thus can be used to treat a subject having or at risk for a disorder characterized by unwanted DN-p63 expression, e.g., squamous cell carcinoma In some embodiments the iRNA agent silences mutations in the pRb tumor suppressor gene, and thus can be used to treat a subject having or at risk for a disorder characterized by unwanted pRb expression, e.g., oral squamous cell carcinoma.

In some embodiments the iRNA agent silences mutations in the APC1 tumor suppressor gene, and thus can be used to treat a subject having or at risk for a disorder characterized by unwanted APC1 expression, e.g., colon cancer.

In some embodiments the iRNA agent silences mutations in the BRCA1 tumor suppressor gene, and thus can be used to treat a subject having or at risk for a disorder characterized by unwanted BRCA1 expression, e.g., breast cancer.

In some embodiments the iRNA agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In some embodiments the iRNA agent silences MLL fusion genes, e.g., MLL-AF9, and thus can be used to treat a subject having or at risk for a disorder characterized by unwanted MLL fusion gene expression, e.g., acute leukemias.

In another embodiment the iRNA agent silences the BCR/ABL fusion gene, and thus can be used to treat a subject having or at risk for a disorder characterized by unwanted BCR/ABL fusion gene expression, e.g., acute and chronic leukemias.

In another embodiment the iRNA agent silences the TEL/AML1 fusion gene, and thus can be used to treat a subject having or at risk for a disorder characterized by unwanted TEL/AML1 fusion gene expression, e.g., childhood acute leukemia.

In another embodiment the iRNA agent silences the EWS/FLI1 fusion gene, and thus can be used to treat a subject having or at risk for a disorder characterized by unwanted EWS/FLI1 fusion gene expression, e.g., Ewing Sarcoma.

In another embodiment the iRNA agent silences the TLS/FUS1 fusion gene, and thus can be used to treat a subject having or at risk for a disorder characterized by unwanted TLS/FUS1 fusion gene expression, e.g., Myxoid liposarcoma.

In another embodiment the iRNA agent silences the PAX3/FKHR fusion gene, and thus can be used to treat a subject having or at risk for a disorder characterized by unwanted PAX3/FKHR fusion gene expression, e.g., Myxoid liposarcoma.

In another embodiment the iRNA agent silences the AML1/ETO fusion gene, and thus can be used to treat a subject having or at risk for a disorder characterized by unwanted AML1/ETO fusion gene expression, e.g., acute leukemia.

Diseases

Angiogenesis

In another aspect, the invention features, a method of treating a subject, e.g., a human, at risk for or afflicted with a disease or disorder that may benefit by angiogenesis inhibition, e.g., cancer. The method comprises administering the iRNA agent of the invention to a subject in need thereof, thereby treating the subject. The iRNA agent that is administered will depend on the type of angiogenesis-related gene being treated.

In some embodiments the iRNA agent silences the alpha v-integrin gene, and thus can be used to treat a subject having or at risk for a disorder characterized by unwanted alpha V integrin, e.g., brain tumors or tumors of epithelial origin.

In some embodiments the iRNA agent silences the Flt-1 receptor gene, and thus can be used to treat a subject having or at risk for a disorder characterized by unwanted Flt-1 receptors, eg. cancer and rheumatoid arthritis.

In some embodiments the iRNA agent silences the tubulin gene, and thus can be used to treat a subject having or at risk for a disorder characterized by unwanted tubulin, eg. cancer and retinal neovascularization.

In some embodiments the iRNA agent silences the tubulin gene, and thus can be used to treat a subject having or at risk for a disorder characterized by unwanted tubulin, eg. cancer and retinal neovascularization.

Viral Diseases

In yet another aspect, the invention features a method of treating a subject infected with a virus or at risk for or afflicted with a disorder or disease associated with a viral infection. The method comprises administering an iRNA agent of the invention to a subject in need thereof, thereby treating the subject. The iRNA agent that is administered will depend on the type of viral disease being treated. In some embodiments, the nucleic acid may target a viral gene. In other embodiments, the nucleic acid may target a host gene.

Thus, the invention provides for a method of treating patients infected by the Human Papilloma Virus (HPV) or at risk for or afflicted with a disorder mediated by HPV, e.g, cervical cancer. HPV is linked to 95% of cervical carcinomas and thus an antiviral therapy is an attractive method to treat these cancers and other symptoms of viral infection. In some embodiments, the expression of a HPV gene is reduced. In another embodiment, the HPV gene is one of the group of E2, E6, or E7. In some embodiments the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In some embodiments, the expression of a HIV gene is reduced. In another embodiment, the HIV gene is CCR5, Gag, or Rev. In some embodiments the expression of a human gene that is required for HIV replication is reduced. In another embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In some embodiments, the expression of a HBV gene is reduced. In another embodiment, the targeted HBV gene encodes one of the group of the tail region of the HBV core protein, the pre-cregious (pre-c) region, or the cregious (c) region. In another embodiment, a targeted HBV-RNA sequence is comprised of the poly(A) tail. In certain embodiment the expression of a human gene that is required for HBV replication is reduced.

The invention also provides for a method of treating patients infected by the Hepatitis A Virus (HAV), or at risk for or afflicted with a disorder mediated by HAV. In some embodiments the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In some embodiments, the expression of a HCV gene is reduced. In another embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In some embodiments, the expression of a Hepatitis, D, E, F, G, or H gene is reduced. In another embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In some embodiments, the expression of a RSV gene is reduced. In another embodiment, the targeted HBV gene encodes one of the group of genes N, L, or P. In some embodiments the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In some embodiments, the expression of a HSV gene is reduced. In another embodiment, the targeted HSV gene encodes DNA polymerase or the helicase-primase. In some embodiments the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In some embodiments, the expression of a CMV gene is reduced. In some embodiments the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In some embodiments, the expression of a EBV gene is reduced. In some embodiments the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In some embodiments, the expression of a KSHV gene is reduced. In some embodiments the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In some embodiments, the expression of a JCV gene is reduced. In certain embodiments the expression of a human gene that is required for JCV replication is reduced.

Methods of the invention also provide for treating patients infected by the myxovirus or at risk for or afflicted with a disorder mediated by myxovirus, e.g., influenza. In some embodiments, the expression of a myxovirus gene is reduced. In some embodiments the expression of a human gene that is required for myxovirus replication is reduced.

Methods of the invention also provide for treating patients infected by the rhinovirus or at risk for of afflicted with a disorder mediated by rhinovirus, e.g., the common cold. In some embodiments, the expression of a rhinovirus gene is reduced. In certain embodiments the expression of a human gene that is required for rhinovirus replication is reduced.

Methods of the invention also provide for treating patients infected by the coronavirus or at risk for of afflicted with a disorder mediated by coronavirus, e.g., the common cold. In some embodiments, the expression of a coronavirus gene is reduced. In certain embodiments the expression of a human gene that is required for coronavirus replication is reduced.

Methods of the invention also provide for treating patients infected by the flavivirus West Nile or at risk for or afflicted with a disorder mediated by West Nile Virus. In some embodiments, the expression of a West Nile Virus gene is reduced. In another embodiment, the West Nile Virus gene is one of the group comprising E, NS3, or NS5. In some embodiments the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In some embodiments, the expression of a St. Louis Encephalitis gene is reduced. In some embodiments the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In some embodiments, the expression of a Tick-borne encephalitis virus gene is reduced. In some embodiments the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In some embodiments, the expression of a Murray Valley encephalitis virus gene is reduced. In some embodiments the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In some embodiments, the expression of a dengue virus gene is reduced. In some embodiments the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In some embodiments, the expression of a SV40 gene is reduced. In some embodiments the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In some embodiments, the expression of a HTLV gene is reduced. In another embodiment the HTLV1 gene is the Tax transcriptional activator. In some embodiments the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In some embodiments, the expression of a Mo-MuLV gene is reduced. In some embodiments the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g., myocarditis. EMCV leads to myocarditis in mice and pigs and is capable of infecting human myocardial cells. This virus is therefore a concern for patients undergoing xenotransplantation. In some embodiments, the expression of a EMCV gene is reduced. In some embodiments the expression of a human gene that is required for EMCV replication is reduced.

The invention also includes a method for treating patients infected by the measles virus (MV) or at risk for or afflicted with a disorder mediated by MV, e.g., measles. In some embodiments, the expression of a MV gene is reduced. In some embodiments the expression of a human gene that is required for MV replication is reduced.

The invention also includes a method for treating patients infected by the Vericella zoster virus (VZV) or at risk for or afflicted with a disorder mediated by VZV, e.g., chicken pox or shingles (also called zoster). In some embodiments, the expression of a VZV gene is reduced. In some embodiments the expression of a human gene that is required for VZV replication is reduced.

The invention also includes a method for treating patients infected by an adenovirus or at risk for or afflicted with a disorder mediated by an adenovirus, e.g., respiratory tract infection. In some embodiments, the expression of an adenovirus gene is reduced. In some embodiments the expression of a human gene that is required for adenovirus replication is reduced.

The invention includes a method for treating patients infected by a yellow fever virus (YFV) or at risk for or afflicted with a disorder mediated by a YFV, e.g., respiratory tract infection. In some embodiments, the expression of a YFV gene is reduced. In another embodiment, the gene may be one of a group that includes the E, NS2A, or NS3 genes. In some embodiments the expression of a human gene that is required for YFV replication is reduced.

Methods of the invention also provide for treating patients infected by the poliovirus or at risk for or afflicted with a disorder mediated by poliovirus, e.g., polio. In some embodiments, the expression of a poliovirus gene is reduced. In some embodiments the expression of a human gene that is required for poliovirus replication is reduced.

Methods of the invention also provide for treating patients infected by a poxvirus or at risk for or afflicted with a disorder mediated by a poxvirus, e.g., smallpox. In some embodiments, the expression of a poxvirus gene is reduced. In some embodiments the expression of a human gene that is required for poxvirus replication is reduced.

Other Pathogens

In another, aspect the invention features methods of treating a subject infected with a pathogen, e.g., a bacterial, amoebic, parasitic, or fungal pathogen. The method comprises administering an iRNA of the invention to a subject in need thereof, thereby treating the subject. The iRNA agent that is administered will depend on the type of pathogen being treated. In some embodiments, the iRNA agent may target a pathogen gene. In other embodiments, the nucleic acid may target a host gene.

The target gene can be one involved in growth, cell wall synthesis, protein synthesis, transcription, energy metabolism, e.g., the Krebs cycle, or toxin production.

Thus, the present invention provides for a method of treating patients infected by a plasmodium that causes malaria. In some embodiments, the expression of a plasmodium gene is reduced. In another embodiment, the gene is apical membrane antigen 1 (AMA1). In some embodiments the expression of a human gene that is required for plasmodium replication is reduced.

The invention also includes methods for treating patients infected by the *Mycobacterium ulcerans*, or a disease or disorder associated with this pathogen, e.g., Buruli ulcers. In some embodiments, the expression of a *Mycobacterium ulcerans* gene is reduced. In some embodiments the expression of a human gene that is required for *Mycobacterium ulcerans* replication is reduced.

The invention also includes methods for treating patients infected by the *Mycobacterium tuberculosis*, or a disease or disorder associated with this pathogen, e.g., tuberculosis. In some embodiments, the expression of a *Mycobacterium tuberculosis* gene is reduced. In some embodiments the expression of a human gene that is required for *Mycobacterium tuberculosis* replication is reduced.

The invention also includes methods for treating patients infected by the *Mycobacterium leprae*, or a disease or disorder associated with this pathogen, e.g., leprosy. In some embodiments, the expression of a *Mycobacterium leprae* gene is reduced. In some embodiments the expression of a human gene that is required for *Mycobacterium leprae* replication is reduced.

The invention also includes methods for treating patients infected by the bacteria *Staphylococcus aureus*, or a disease or disorder associated with this pathogen, e.g., infections of the skin and muscous membranes. In some embodiments, the expression of a *Staphylococcus aureus* gene is reduced. In some embodiments the expression of a human gene that is required for *Staphylococcus aureus* replication is reduced.

The invention also includes methods for treating patients infected by the bacteria *Streptococcus pneumoniae*, or a disease or disorder associated with this pathogen, e.g., pneumonia or childhood lower respiratory tract infection. In some embodiments, the expression of a *Streptococcus pneumoniae* gene is reduced. In some embodiments the expression of a human gene that is required for *Streptococcus pneumoniae* replication is reduced.

The invention also includes methods for treating patients infected by the bacteria *Streptococcus pyogenes*, or a disease or disorder associated with this pathogen, e.g., Strep throat or Scarlet fever. In some embodiments, the expression of a *Streptococcus pyogenes* gene is reduced. In some embodiments the expression of a human gene that is required for *Streptococcus pyogenes* replication is reduced.

The invention also includes methods for treating patients infected by the bacteria *Chlamydia pneumoniae*, or a disease or disorder associated with this pathogen, e.g., pneumonia or childhood lower respiratory tract infection. In some embodiments, the expression of a *Chlamydia pneumoniae* gene is reduced. In some embodiments the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g., pneumonia or childhood lower respiratory tract infection. In some embodiments, the expression of a *Mycoplasma pneumoniae* gene is reduced. In some embodiments the expression of a human gene that is required for *Mycoplasma pneumoniae* replication is reduced.

Immune Disorders

In one aspect, the invention features, a method of treating a subject, e.g., a human, at risk for or afflicted with a disease or disorder characterized by an unwanted immune response, e.g., an inflammatory disease or disorder, or an autoimmune disease or disorder. The method comprises administering an iRNA agent of the invention to a subject in need thereof, thereby treating the subject. The iRNA agent that is administered will depend on the type of immune disorder being treated.

In some embodiments the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis.

In some embodiments the disease or disorder is restenosis, e.g., restenosis associated with surgical intervention e.g., angioplasty, e.g., percutaneous transluminal coronary angioplasty.

In certain embodiments the disease or disorder is Inflammatory Bowel Disease, e.g., Crohn Disease or Ulcerative Colitis.

In certain embodiments the disease or disorder is inflammation associated with an infection or injury.

In certain embodiments the disease or disorder is asthma, lupus, multiple sclerosis, diabetes, e.g., type II diabetes, arthritis, e.g., rheumatoid or psoriatic.

In certain other embodiments the iRNA agent silences an integrin or co-ligand thereof, e.g., VLA4, VCAM, ICAM.

In certain other embodiments the iRNA agent silences a selectin or co-ligand thereof, e.g., P-selectin, E-selectin (ELAM), I-selectin, P-selectin glycoprotein-1 (PSGL-1).

In certain other embodiments the iRNA agent silences a component of the complement system, e.g., C3, C5, C3aR, C5aR, C3 convertase, C5 convertase.

In certain other embodiments the iRNA agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, CCR3.

In other embodiments the iRNA agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, I-309.

Pain

In one aspect, the invention features, a method of treating a subject, e.g., a human, at risk for or afflicted with acute pain or chronic pain. The method comprises administering an iRNA agent of the invention to a subject in need thereof, thereby treating the subject. The iRNA agent that is administered will depend on the type of pain being treated.

In certain other embodiments the iRNA agent silences a component of an ion channel.

In certain other embodiments the iRNA agent silences a neurotransmitter receptor or ligand.

In one aspect, the invention features, a method of treating a subject, e.g., a human, at risk for or afflicted with a neurological disease or disorder. The method includes:

providing an iRNA agent which iRNA is homologous to and can silence, e.g., by cleavage, a gene which mediates a neurological disease or disorder;

administering the to a subject, thereby treating the subject.

Neurological Disorders

In certain embodiments the disease or disorder is a neurological disorder, including Alzheimer's Disease or Parkinson Disease. The method comprises administering an iRNA agent of the invention to a subject in need thereof, thereby treating the subject. The iRNA agent that is administered will depend on the type of neurological disorder being treated.

In certain other embodiments the iRNA agent silences an amyloid-family gene, e.g., APP; a presenilin gene, e.g., PSEN1 and PSEN2, or I-synuclein.

In some embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In certain other embodiments the iRNA agent silences HD, DRPLA, SCA1, SCA2, MJD1, CACNL1A4, SCA7, SCA8.

Loss of Heterozygosity

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with an iRNA agent of the invention. The iRNA agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH.

One of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, the invention features, a method of treating a disorder characterized by LOH, e.g., cancer. The method comprises optionally, determining the genotype of the allele of a gene in the region of LOH and determining the genotype of both alleles of the gene in a normal cell; providing an iRNA agent which preferentially cleaves or silences the allele found in the LOH cells; and administering the iRNA to the subject, thereby treating the disorder.

The invention also includes a iRNA agent disclosed herein, e.g, an iRNA agent which can preferentially silence, e.g., cleave, one allele of a polymorphic gene.

In another aspect, the invention provides a method of cleaving or silencing more than one gene with an iRNA agent. In these embodiments the iRNA agent is selected so that it has sufficient homology to a sequence found in more than one gene. For example, the sequence AAGCTGGCCCTGGACATGGAGAT (SEQ ID NO: 22) is conserved between mouse lamin B1, lamin B2, keratin complex 2-gene 1 and lamin A/C. Thus an iRNA agent targeted to this sequence would effectively silence the entire collection of genes.

The invention also includes an iRNA agent disclosed herein, which can silence more than one gene.

Routes of Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. A composition that includes a iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes may be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

Topical Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. In some embodiments, an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface.

As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 µm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. A composition that includes an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can be administered to a subject by pulmonary delivery. Pulmonary delivery compositions can be delivered by inhalation by the patient of a dispersion so that the composition, for example, iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are may be used. One of the benefits of using an atomizer or inhaler is that the potential for contamination is minimized because the devices are self contained. Dry powder dispersion devices, for example, deliver drugs that may be readily formulated as dry powders. A iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." For example, the average particle size is less than about 10 µm in diameter with a relatively uniform spheroidal shape distribution. In some embodiments, the diameter is less than about 7.5 µm and in some embodiments less than about 5.0 µm. Usually the particle size distribution is between about 0.1 µm and about 5 µm in diameter, sometimes about 0.3 µm to about 5 µm.

The term "dry" means that the composition has a moisture content below about 10% by weight (% w) water, usually below about 5% w and in some cases less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A group of carbohydrates may includes lactose, threhalose, raffinose maltodextrins, and mannitol. Suitable polypeptides include aspartame. Amino acids include alanine and glycine, with glycine being used in some embodiments.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate may be used in some embodiments.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Devices

For ease of exposition the devices, formulations, compositions and methods in this section are discussed largely with regard to unmodified iRNA agents. It may be understood, however, that these devices, formulations, compositions and methods can be practiced with other iRNA agents, e.g., modified iRNA agents, and such practice is within the invention. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can be disposed on or in a device, e.g., a device which implanted or otherwise placed in a subject. Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a iRNA, e.g., a device can release insulin.

Other devices include artificial joints, e.g., hip joints, and other orthopedic implants.

In one embodiment, unit doses or measured doses of a composition that includes iRNA are dispensed by an implanted device. The device can include a sensor that monitors a parameter within a subject. For example, the device can include pump, e.g., and, optionally, associated electronics.

Tissue, e.g., cells or organs can be treated with An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) ex vivo and then administered or implanted in a subject.

The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation.

Introduction of treated tissue, whether autologous or transplant, can be combined with other therapies.

In some implementations, the iRNA treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). Exemplary devices include condoms, diaphragms, IUD (implantable uterine devices, sponges, vaginal sheaths, and birth control devices. In one embodiment, the iRNA is chosen to inactive sperm or egg. In another embodiment, the iRNA is chosen to be complementary to a viral or pathogen RNA, e.g., an RNA of an STD. In some instances, the iRNA composition can include a spermicide.

Dosage

In one aspect, the invention features a method of administering an iRNA agent, e.g., a double-stranded iRNA agent, or siRNA agent, to a subject (e.g., a human subject). The method includes administering a unit dose of the iRNA agent, e.g., a siRNA agent, e.g., double stranded siRNA agent that (a) the double-stranded part is 19-25 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous or intramuscular), an inhaled dose, or a topical application. In some embodiments dosages may be less than 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than an iRNA agent, e.g., other than a double-stranded iRNA agent, or siRNA agent. In another embodiment, the subject has atherosclerosis and the effective dose of an iRNA agent, e.g., a double-stranded iRNA agent, or siRNA agent, is administered in combination with, e.g., after surgical intervention, e.g., angioplasty.

In one embodiment, a subject is administered an initial dose and one or more maintenance doses of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are, for example, administered no more than once every 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

In some cases, a patient is treated with a iRNA agent in conjunction with other therapeutic modalities. For example, a patient being treated for a viral disease, e.g., an HIV associated disease (e.g., AIDS), may be administered a iRNA agent specific for a target gene essential to the virus in conjunction with a known antiviral agent (e.g., a protease inhibitor or reverse transcriptase inhibitor). In another example, a patient being treated for cancer may be administered a iRNA agent specific for a target essential for tumor cell proliferation in conjunction with a chemotherapy.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g., nasal, buccal, pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can include a single treatment or, for example, can include a series of treatments. It will also be appreciated that the effective dosage of a iRNA agent such as a siRNA agent used for treatment may increase or decrease over the course of a particular treatment. Changes in dosage may result and become apparent from the results of diagnostic assays as described herein. For example, the subject can be monitored after administering a iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA. The transgenic animal can be deficient for the corresponding endogenous RNA. In another embodiment, the composition for testing includes a iRNA agent that is complementary, at least in an internal region, to a sequence that is conserved between the target RNA in the animal model and the target RNA in a human.

The inventors have discovered that iRNA agents described herein can be administered to mammals, particularly large mammals such as nonhuman primates or humans in a number of ways.

In one embodiment, the administration of the iRNA agent, e.g., a double-stranded iRNA agent, or siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of iRNA agents described herein.

Accordingly, an iRNA agent, e.g., a double-stranded iRNA agent, or siRNA agent, (e.g., a precursor, e.g., a larger iRNA agent which can be processed into a siRNA agent, or a DNA which encodes a an iRNA agent, e.g., a double-stranded iRNA agent, or siRNA agent, or precursor thereof) described herein, e.g., a therapeutically effective amount of a iRNA agent described herein, e.g., a iRNA agent having a double stranded region of less than 40, and, for example, less than 30 nucleotides and having one or two 1-3 nucleotide single strand 3' overhangs can be administered rectally, e.g., introduced through the rectum into the lower or upper colon. This approach is particularly useful in the treatment of, inflammatory disorders, disorders characterized by unwanted cell proliferation, e.g., polyps, or colon cancer.

The medication can be delivered to a site in the colon by introducing a dispensing device, e.g., a flexible, camera-guided device similar to that used for inspection of the colon or removal of polyps, which includes means for delivery of the medication.

The rectal administration of the iRNA agent is by means of an enema. The iRNA agent of the enema can be dissolved in a saline or buffered solution. The rectal administration can also by means of a suppository, which can include other ingredients, e.g., an excipient, e.g., cocoa butter or hydropropylmethylcellulose.

Any of the iRNA agents described herein can be administered orally, e.g., in the form of tablets, capsules, gel capsules, lozenges, troches or liquid syrups. Further, the composition can be applied topically to a surface of the oral cavity.

Any of the iRNA agents described herein can be administered buccally. For example, the medication can be sprayed into the buccal cavity or applied directly, e.g., in a liquid, solid, or gel form to a surface in the buccal cavity. This administration is particularly desirable for the treatment of inflammations of the buccal cavity, e.g., the gums or tongue, e.g., in one embodiment, the buccal administration is by spraying into the cavity, e.g., without inhalation, from a dispenser, e.g., a metered dose spray dispenser that dispenses the pharmaceutical composition and a propellant.

Any of the iRNA agents described herein can be administered to ocular tissue. For example, the medications can be applied to the surface of the eye or nearby tissue, e.g., the inside of the eyelid. They can be applied topically, e.g., by spraying, in drops, as an eyewash, or an ointment. Administration can be provided by the subject or by another person, e.g., a health care provider. The medication can be provided in measured doses or in a dispenser which delivers a metered dose. The medication can also be administered to the interior of the eye, and can be introduced by a needle or other delivery device which can introduce it to a selected area or structure. Ocular treatment is particularly desirable for treating inflammation of the eye or nearby tissue.

Any of the iRNA agents described herein can be administered directly to the skin. For example, the medication can be applied topically or delivered in a layer of the skin, e.g., by the use of a microneedle or a battery of microneedles which penetrate into the skin, but, for example, not into the underlying muscle tissue. Administration of the iRNA agent composition can be topical. Topical applications can, for example, deliver the composition to the dermis or epidermis of a subject. Topical administration can be in the form of transdermal patches, ointments, lotions, creams, gels, drops, suppositories, sprays, liquids or powders. A composition for topical administration can be formulated as a liposome, micelle, emulsion, or other lipophilic molecular assembly. The transdermal administration can be applied with at least one penetration enhancer, such as iontophoresis, phonophoresis, and sonophoresis.

Any of the iRNA agents described herein can be administered to the pulmonary system. Pulmonary administration can be achieved by inhalation or by the introduction of a delivery device into the pulmonary system, e.g., by introducing a delivery device which can dispense the medication. Certain embodiments may use a method of pulmonary delivery by inhalation. The medication can be provided in a dispenser which delivers the medication, e.g., wet or dry, in a form sufficiently small such that it can be inhaled. The device can deliver a metered dose of medication. The subject, or another person, can administer the medication.

Pulmonary delivery is effective not only for disorders which directly affect pulmonary tissue, but also for disorders which affect other tissue.

iRNA agents can be formulated as a liquid or nonliquid, e.g., a powder, crystal, or aerosol for pulmonary delivery.

Any of the iRNA agents described herein can be administered nasally. Nasal administration can be achieved by introduction of a delivery device into the nose, e.g., by introducing a delivery device which can dispense the medication. Methods of nasal delivery include spray, aerosol, liquid, e.g., by drops, or by topical administration to a surface of the nasal cavity. The medication can be provided in a dispenser with delivery of the medication, e.g., wet or dry, in a form sufficiently small such that it can be inhaled. The device can deliver a metered dose of medication. The subject, or another person, can administer the medication.

Nasal delivery is effective not only for disorders which directly affect nasal tissue, but also for disorders which affect other tissue iRNA agents can be formulated as a liquid or nonliquid, e.g., a powder, crystal, or for nasal delivery.

An iRNA agent can be packaged in a viral natural capsid or in a chemically or enzymatically produced artificial capsid or structure derived therefrom.

The dosage of a pharmaceutical composition including a iRNA agent can be administered in order to alleviate the symptoms of a disease state, e.g., cancer or a cardiovascular disease. A subject can be treated with the pharmaceutical composition by any of the methods mentioned above.

Gene expression in a subject can be modulated by administering a pharmaceutical composition including an iRNA agent.

A subject can be treated by administering a defined amount of an iRNA agent, e.g., a double-stranded iRNA agent, or siRNA agent, (e.g., a precursor, e.g., a larger iRNA agent which can be processed into a siRNA agent) composition that is in a powdered form, e.g., a collection of microparticles, such as crystalline particles. The composition can include a plurality of iRNA agents, e.g., specific for one or more different endogenous target RNAs. The method can include other features described herein.

A subject can be treated by administering a defined amount of an iRNA agent composition that is prepared by a method that includes spray-drying, i.e., atomizing a liquid solution, emulsion, or suspension, immediately exposing the droplets to a drying gas, and collecting the resulting porous powder particles. The composition can include a plurality of iRNA agents, e.g., specific for one or more different endogenous target RNAs. The method can include other features described herein.

The iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), can be provided in a powdered, crystallized or other finely divided form, with or without a carrier, e.g., a micro- or nano-particle suitable for inhalation or other pulmonary delivery. This can include providing an aerosol preparation, e.g., an aerosolized spray-dried composition. The aerosol composition can be provided in and/or dispensed by a metered dose delivery device.

The subject can be treated for a condition treatable by inhalation, e.g., by aerosolizing a spray-dried iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) composition and inhaling the aerosolized composition. The iRNA agent can be an siRNA. The composition can include a plurality of iRNA agents, e.g., specific for one or more different endogenous target RNAs. The method can include other features described herein.

A subject can be treated by, for example, administering a composition including an effective/defined amount of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), wherein the composition is prepared by a method that includes spray-drying, lyophilization, vacuum drying, evaporation, fluid bed drying, or a combination of these techniques.

In another aspect, the invention features a method that includes: evaluating a parameter related to the abundance of a transcript in a cell of a subject; comparing the evaluated parameter to a reference value; and if the evaluated parameter has a preselected relationship to the reference value (e.g., it is greater), administering a iRNA agent (or a precursor, e.g., a larger iRNA agent which can be processed into a siRNA agent, or a DNA which encodes a iRNA agent or precursor thereof) to the subject. In one embodiment, the iRNA agent includes a sequence that is complementary to the evaluated transcript. For example, the parameter can be a direct measure of transcript levels, a measure of a protein level, a disease or disorder symptom or characterization (e.g., rate of cell proliferation and/or tumor mass, viral load).

In another aspect, the invention features a method that includes: administering a first amount of a composition that comprises an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) to a subject, wherein the iRNA agent includes a strand substantially complementary to a target nucleic acid; evaluating an activity associated with a protein encoded by the target nucleic acid; wherein the evaluation is used to determine if a second amount may be administered. In some embodiments the method includes administering a second amount of the composition, wherein the timing of administration or dosage of the second amount is a function of the evaluating. The method can include other features described herein.

In another aspect, the invention features a method of administering a source of a double-stranded iRNA agent (ds iRNA agent) to a subject. The method includes administering or implanting a source of a ds iRNA agent, e.g., a siRNA agent, that (a) includes a double-stranded region that is 19-25 nucleotides long, for example, 21-23 nucleotides, (b) is complementary to a target RNA (e.g., an endogenous RNA or a pathogen RNA), and, optionally, (c) includes at least one 3' overhang 1-5 nt long. In one embodiment, the source releases ds iRNA agent over time, e.g., the source is a controlled or a slow release source, e.g., a microparticle that gradually releases the ds iRNA agent. In another embodiment, the source is a pump, e.g., a pump that includes a sensor or a pump that can release one or more unit doses.

In one aspect, the invention features a pharmaceutical composition that includes an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) including a nucleotide sequence complementary to a target RNA, e.g., substantially and/or exactly complementary. The target RNA can be a transcript of an endogenous human gene. In one embodiment, the iRNA agent (a) is 19-25 nucleotides long, for example, 21-23 nucleotides, (b) is complementary to an endogenous target RNA, and, optionally, (c) includes at least one 3' overhang 1-5 nt long. In one embodiment, the pharmaceutical composition can be an emulsion, microemulsion, cream, jelly, or liposome.

In one example the pharmaceutical composition includes an iRNA agent mixed with a topical delivery agent. The topical delivery agent can be a plurality of microscopic vesicles. The microscopic vesicles can be liposomes. In some embodiments the liposomes are cationic liposomes.

In another aspect, the pharmaceutical composition includes an iRNA agent, e.g., a double-stranded iRNA agent, or siRNA agent (e.g., a precursor, e.g., a larger iRNA agent which can be processed into a siRNA agent, or a DNA which encodes an iRNA agent, e.g., a double-stranded iRNA agent, or siRNA agent, or precursor thereof) admixed with a topical penetration enhancer. In one embodiment, the topical penetration enhancer is a fatty acid. The fatty acid can be arachidonic acid, oleic acid, lauric acid, caprylic acid, capric acid, myristic acid, palmitic acid, stearic acid, linoleic acid, linolenic acid, dicaprate, tricaprate, monolein, dilaurin, glyceryl 1-monocaprate, 1-dodecylazacycloheptan-2-one, an acylcarnitine, an acylcholine, or a $C_{1-10}$ alkyl ester, monoglyceride, diglyceride or pharmaceutically acceptable salt thereof.

In another embodiment, the topical penetration enhancer is a bile salt. The bile salt can be cholic acid, dehydrocholic acid, deoxycholic acid, glucholic acid, glycholic acid, glycodeoxycholic acid, taurocholic acid, taurodeoxycholic acid, chenodeoxycholic acid, ursodeoxycholic acid, sodium tauro-24,25-dihydro-fusidate, sodium glycodihydrofusidate, polyoxyethylene-9-lauryl ether or a pharmaceutically acceptable salt thereof.

In another embodiment, the penetration enhancer is a chelating agent. The chelating agent can be EDTA, citric acid, a salicyclate, a N-acyl derivative of collagen, laureth-9, an N-amino acyl derivative of a beta-diketone or a mixture thereof.

In another embodiment, the penetration enhancer is a surfactant, e.g., an ionic or nonionic surfactant. The surfactant can be sodium lauryl sulfate, polyoxyethylene-9-lauryl ether, polyoxyethylene-20-cetyl ether, a perfluorchemical emulsion or mixture thereof.

In another embodiment, the penetration enhancer can be selected from a group consisting of unsaturated cyclic ureas, 1-alkyl-alkones, 1-alkenylazacyclo-alakanones, steroidal anti-inflammatory agents and mixtures thereof. In yet another embodiment the penetration enhancer can be a glycol, a pyrrol, an azone, or a terpenes.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a form suitable for oral delivery. In one embodiment, oral delivery can be used to deliver an iRNA agent composition to a cell or a region of the gastro-intestinal tract, e.g., small intestine, colon (e.g., to treat a colon cancer), and so forth. The oral delivery form can be tablets, capsules or gel capsules. In one embodiment, the iRNA agent of the pharmaceutical composition modulates expression of a cellular adhesion protein, modulates a rate of cellular proliferation, or has biological activity against eukaryotic pathogens or retroviruses. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methylcellulose phthalate or cellulose acetate phthalate.

In another embodiment, the oral dosage form of the pharmaceutical composition includes a penetration enhancer. The penetration enhancer can be a bile salt or a fatty acid. The bile salt can be ursodeoxycholic acid, chenodeoxycholic acid, and salts thereof. The fatty acid can be capric acid, lauric acid, and salts thereof.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an iRNA agent and a delivery vehicle. In one embodiment, the iRNA agent is (a) is 19-25 nucleotides long, for example, 21-23 nucleotides, (b) is complementary to an endogenous target RNA, and, optionally, (c) includes at least one 3' overhang 1-5 nucleotides long.

In one embodiment, the delivery vehicle can deliver an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) to a cell by a topical route of administration. The delivery vehicle can be microscopic vesicles. In one example the microscopic vesicles are liposomes. In some embodiments the liposomes are cationic liposomes. In another example the microscopic vesicles are micelles. In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in an injectable dosage form. In one embodiment, the injectable dosage form of the pharmaceutical composition includes sterile aqueous solutions or dispersions and sterile powders. In some embodiments the sterile solution can include a diluent such as water; saline solution; fixed oils, polyethylene glycols, glycerin, or propylene glycol.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in oral dosage form. In one embodiment, the oral dosage form is selected from the group consisting of tablets, capsules and gel capsules. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methyl cellulose phthalate or cellulose acetate phthalate. In one embodiment, the oral dosage form of the pharmaceutical composition includes a penetration enhancer, e.g., a penetration enhancer described herein.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a rectal dosage form. In one embodiment, the rectal dosage form is an enema. In another embodiment, the rectal dosage form is a suppository.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a vaginal dosage form. In one embodiment, the vaginal dosage form is a suppository. In another embodiment, the vaginal dosage form is a foam, cream, or gel.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a pulmonary or nasal dosage form. In one embodiment, the iRNA agent is incorporated into a particle, e.g., a macroparticle, e.g., a microsphere. The particle can be produced by spray drying, lyophilization, evaporation, fluid bed drying, vacuum drying, or a combination thereof. The microsphere can be formulated as a suspension, a powder, or an implantable solid.

In one aspect, the invention features a spray-dried iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) composition suitable for inhalation by a subject, including: (a) a therapeutically effective amount of a iRNA agent suitable for treating a condition in the subject by inhalation; (b) a pharmaceutically acceptable excipient selected from the group consisting of carbohydrates and amino acids; and (c) optionally, a dispersibility-enhancing amount of a physiologically-acceptable, water-soluble polypeptide.

In one embodiment, the excipient is a carbohydrate. The carbohydrate can be selected from the group consisting of monosaccharides, disaccharides, trisaccharides, and polysaccharides. In some embodiments the carbohydrate is a monosaccharide selected from the group consisting of dextrose, galactose, mannitol, D-mannose, sorbitol, and sorbose. In another embodiment the carbohydrate is a disaccharide selected from the group consisting of lactose, maltose, sucrose, and trehalose.

In another embodiment, the excipient is an amino acid. In one embodiment, the amino acid is a hydrophobic amino acid. In some embodiments the hydrophobic amino acid is selected from the group consisting of alanine, isoleucine, leucine, methionine, phenylalanine, proline, tryptophan, and valine. In yet another embodiment the amino acid is a polar amino acid. In some embodiments the amino acid is selected from the group consisting of arginine, histidine, lysine, cysteine, glycine, glutamine, serine, threonine, tyrosine, aspartic acid and glutamic acid.

In one embodiment, the dispersibility-enhancing polypeptide is selected from the group consisting of human serum albumin, α-lactalbumin, trypsinogen, and polyalanine.

In one embodiment, the spray-dried iRNA agent composition includes particles having a mass median diameter (MMD) of less than 10 microns. In another embodiment, the spray-dried iRNA agent composition includes particles having a mass median diameter of less than 5 microns. In yet another embodiment the spray-dried iRNA agent composition includes particles having a mass median aerodynamic diameter (MMAD) of less than 5 microns.

In certain other aspects, the invention provides kits that include a suitable container containing a pharmaceutical formulation of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an iRNA agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In another aspect, the invention features a device, e.g., an implantable device, wherein the device can dispense or administer a composition that includes an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), e.g., a iRNA agent that silences an endogenous transcript. In one embodiment, the device is coated with the composition. In another embodiment the iRNA agent is disposed within the device. In another embodiment, the device includes a mechanism to dispense a unit dose of the composition. In other embodiments the device releases the composition continuously, e.g., by diffusion. Exemplary devices include stents, catheters, pumps, artificial organs or organ components (e.g., artificial heart, a heart valve, etc.), and sutures.

As used herein, the term "crystalline" describes a solid having the structure or characteristics of a crystal, i.e., particles of three-dimensional structure in which the plane faces intersect at definite angles and in which there is a regular internal structure. The compositions of the invention may have different crystalline forms. Crystalline forms can be prepared by a variety of methods, including, for example, spray drying.

In one aspect the invention provides a method of modulating the expression of a target gene in a cell, comprising providing to said cell an iRNA agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

The invention is further illustrated by the following examples, which should not be construed as further limiting. The contents of all references, pending patent applications and published patents, cited throughout this application are hereby expressly incorporated by reference.

EXAMPLES

Example 1. Synthesis of Carbohydrate Conjugate Building Blocks 110 and 112

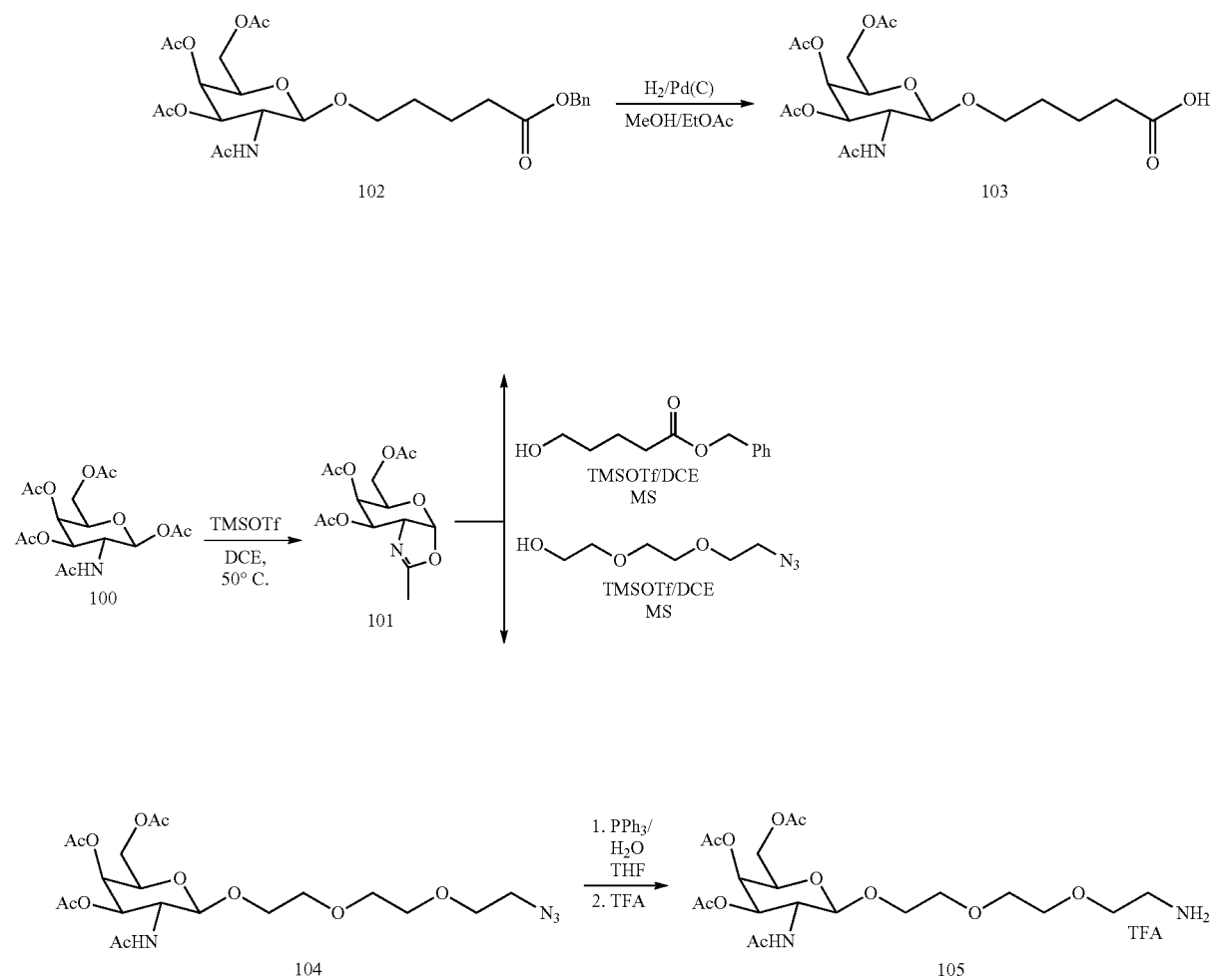

Preparation of 101:

Galactosamine pentaacetate 100 (52.00 g, 133.63 mmol) was taken in dichloroethane (300 mL) at ambient temperature. TMSOTf (44.55 g, 200.44 mmol) was added that and the mixture stirred at 50 C for 90 minutes in a water bath, heating stopped and the mixture stirred overnight at room temperature. It was poured in to an ice cold sodium bicarbonate solution; extracted with dichloromethane, washed with water and dried over sodium sulfate. Solvents were removed the residue dried under high vacuum overnight to get the compound as dark gum (44.50 g, quantitative). It was used for next reaction with out any further purification. H NMR and MALDI confirmed the product formation. MS: Calculated for $C_{14}H_{19}NO_8$, 329.11; Found 352.1 (M+Na).

Preparation of 102:

Compound 101 (43.70 g, 133.56 mmol) and the benzyl ester (41.71 g, 200.34 mmol) were dissolved in dichloroethane (300 mL), molecular sieves (50 g) was added to that and stirred for 30 minutes. TMSOTf (14.50 g, 66.78 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethylacetate/hexanes) to get the required compound as light brown gummy liquid (60.50 g, 86%). 1HNMR, $^{13}$CNMR MS: Calculated for $C_{26}H_{35}NO_{11}$, 537.22; Found 560.21 (M+Na).

Preparation 103:

Compound 102 (60.00 g, 111.68 mmol) was dissolved in a mixture of Methanol/ethylacetate and degassed with argon. Pd/C (6.00 g, 10 wt % Degussa, wet type) was added and hydrogenated under balloon pressure overnight. Filtered through a small pad of celite; washed with methanol and dried under high vacuum overnight to get the product (48.85 g, 98%). 1HNMR, $^{13}$CNMR MS: Calculated for $C_{19}H_{29}NO_{11}$, 447.17; Found 469.9 (M+Na).

Preparation of 104:

Compound 101 (42.30 g, 128.43 mmol) and the azido ethanol (26 g, 192.45 mmol) were dissolved in dichloroethane (300 mL), molecular sieves (50 g) were added to that and stirred for 30 minutes. TMSOTf (14.29 g, 64.21 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethyl acetate/hexanes, followed by 5-10% Methanol/ethylacetate) to get the required compound as light brown gummy liquid (59.23 g, 91.00%). 1HNMR, $^{13}$CNMR MS: Calculated for $C_{20}H_{32}N_4O_{11}$, 504.21; Found 527.1 (M+Na).

Preparation of 105:

Compound 104 (9.33 g, 18.50 mmol) was dissolved in THE (100 mL) to that PPh$_3$ (5.97 g, 22.2 mmol) was added and the mixture stirred for 48 h. TLC checked to see complete disappearance of starting material. Water (1 mL, 55 mmol) and stirred for another 24 h. TFA (2.85 mL, 23.12 mmol) and toluene (40 mL) were added and the solvents were removed under reduced pressure. The residue was co-evaporated with toluene (2×40 mL) two times and dried under high vacuum. It was used for the next reaction in the same day. MS: Calculated for $C_{20}H_{34}N_2O_{11}$, 478.22; Found 500.8 (M+Na).

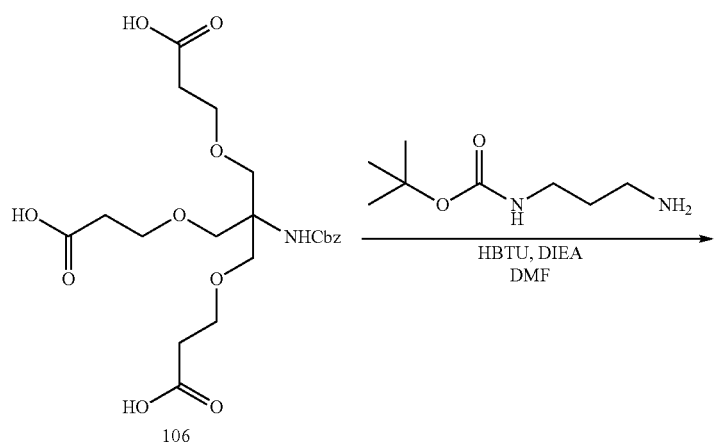

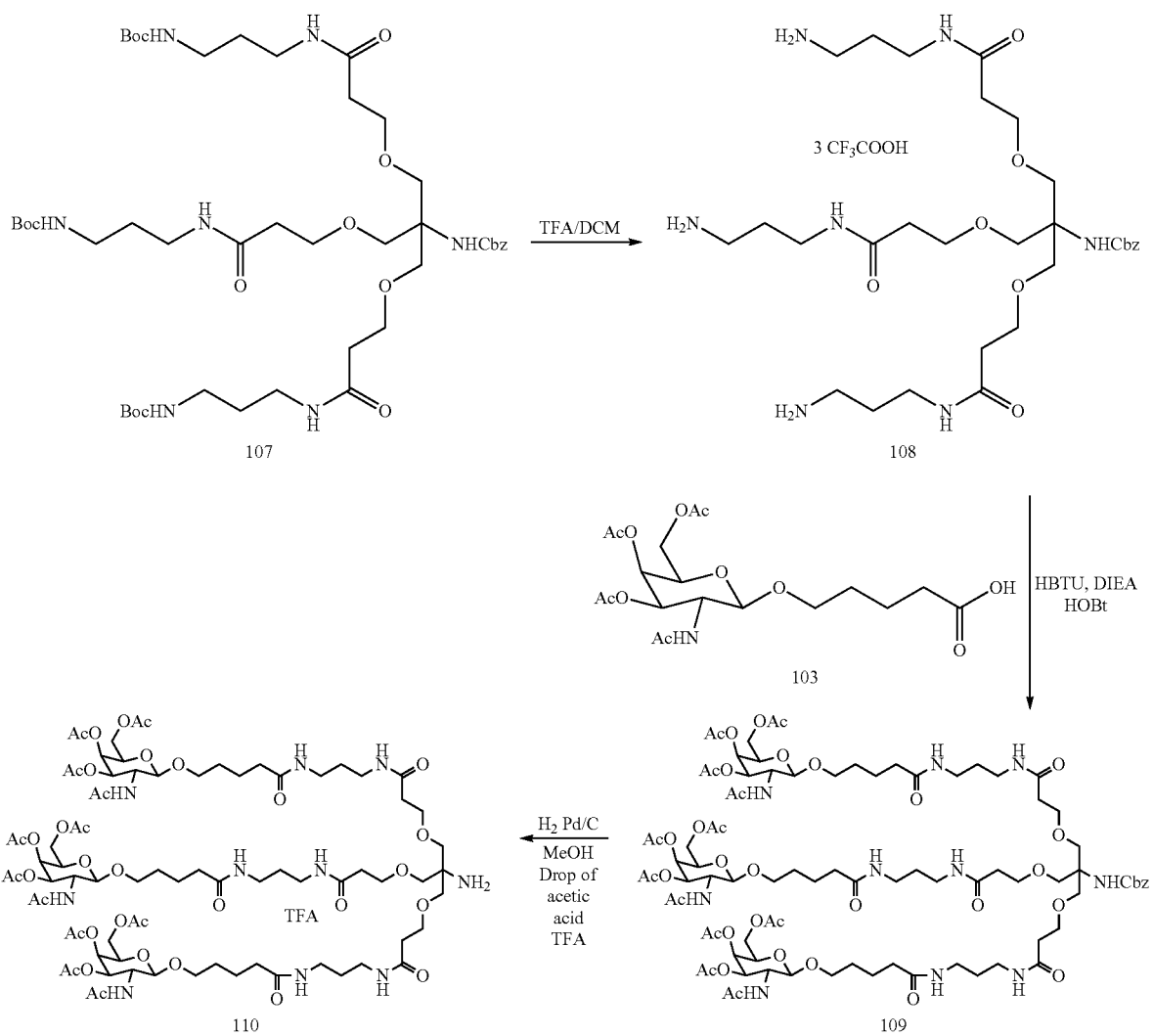

Preparation of 107:

Compound 106 (JOC 2002) (6.94 g, 14.73 mmol) and monoboc propyl amine (10.26 g, 58.89 mmol) were dissolved in DMF (100 mL), to that HBTU (17.26 g, 45.50 mmol) and DIEA (15.36 mL, 88.14 mmol) were added and stirred overnight. Reaction mixture was poured in to ice-water mixture and extracted with dichloromethane, washed with sodium bicarbonate solution, brine and dried over sodium sulfate. Solvents were removed and the residue was purified by chromatography (Ethyl acetate, followed by 2-10% MeOH/DCM) to get the product as white fluffy solid (10.49 g, 76%). MS: Calculated for $C_{45}H_{77}N_7O_{14}$, 939.55; Found 940.53 (M+H).

Preparation of 108:

Compound 107 (2.40 g, 2.56 mmol) was dissolved in dichloromethane (10 mL), to that a mixture of TFA/DCM (1:4, 10 mL) was added and stirred for 30 minutes. Reaction was monitored by mass spectra. 100 mL of toluene was added and removed the solvent under reduced pressure. The residue was co-evaporated two times with toluene (2×100 mL) and dried under high vacuum to get the compound as its TFA salt (white gum, 2.47 g, 99%). It was used for the next reaction with out any further purification. MS: Calculated for $C_{30}H_{53}N_7O_8$, 639.40; Found 640.45 (M+H).

Preparation of 109:

GalNAc acid 103 (4.00 g, 8.99 mmol) was dissolved in DMF (50 mL); HBTU (3.75 g, 9.88 mmol), HOBt (1.34 g, 9.88 mmol) and DIEA (5 mL, 3.2 eq) was added to that and stirred for 3-4 minutes. A solution of 108 (2.47 g, 2.50 mmol) in DMF was added to that and stirred the reaction mixture overnight. TLC was checked, solvents were removed under reduced pressure. The residue was dissolved in dichloromethane, washed with sodium bicarbonate solution (50 mL), water (100 mL) and dried over sodium sulfate. Solvents were removed and the residue was purified by chromatography (ethyl acetate, followed by gradient elution 5-15% MeOH/DCM) to get the product 109 as a white solid (4.20 g, 87%). MS: Calculated for $C_{87}H_{134}N_{10}O_{38}$, 1926.89; Found 1949.5 (M+Na).

Preparation of 110:

GalNAc derivative 109 (7.50 g, 4.18 mmol) was taken in methanol (50 mL) degassed with argon. Pd/C (0.800 g, 10 wt % Degussa type wet) and couple of drops of acetic acid were added; the mixture was hydrogenated under balloon pressure overnight. Reaction mixture was filtered through a small pad of celite, washed with methanol. TFA (0.465 mL, 5.22 mmol) was added and removed the solvent under reduced pressure. The residue was co-evaporated with toluene (2 times) and dried under high vacuum overnight to get the compound as TFA salt (pale yellow solid, 7.30 g, 99%). MS: Calculated for $C_{79}H_{128}N_{10}O_{36}$, 1792.85; Found 1815.9 (M+Na).

was purified by chromatography (ethyl acetate, followed by 3-15% MeOH/DCM) to get the required compound 111 as a white solid (5.80 g, 68%) MS: Calculated for $C_{81}H_{125}N_7O_{41}$, 1851.79; Found 1874.20 (M+Na).

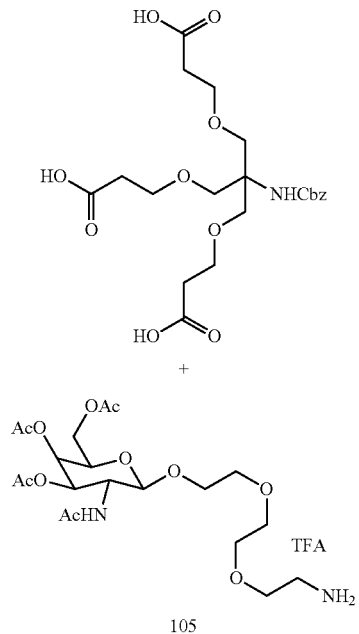

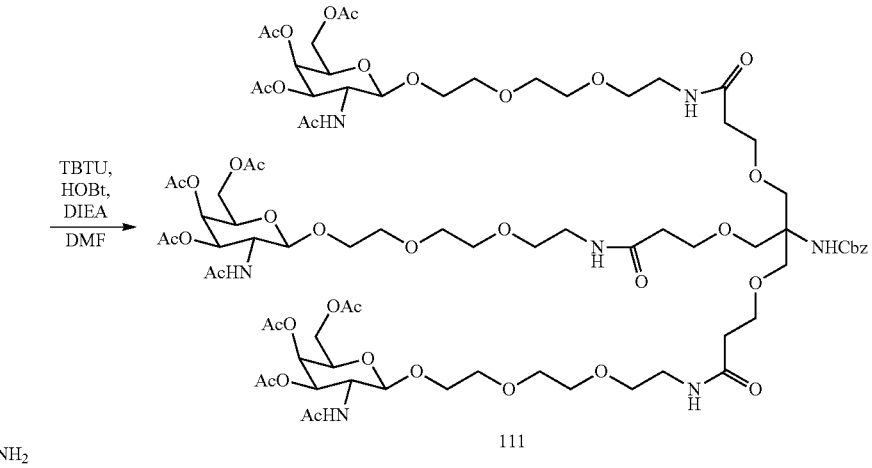

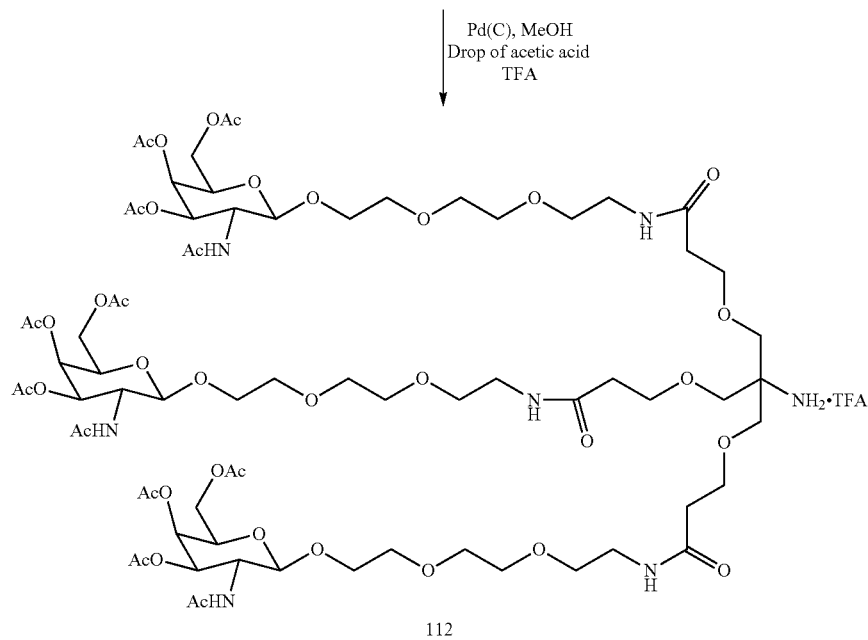

Preparation of 111:

The tricarboxylic acid 106 (2.17 g, 4.625 mmol) and amine (18.50 mmol, crude from previous reaction) was dissolved in DMF (100 mL). To that TBTU (5.34 g, 16.63 mmol), HOBt (2.24 g, 16.59 mmol) and DIEA (5.64 mL, 32.36 mmol) was added and stirred the reaction mixture for 24 h. After stirring 24 hrs an additional amount of DIEA (4 mL) was added continued stirring. After 48 hrs solvents were removed under reduced pressure, the residue was dissolved in dichloromethane, washed with 1M phosphoric acid solution, sodium bicarbonate solution, water and dried over sodium sulfate. Solvents were removed and the residue Preparation of 112:

GalNAc derivative 111 (5.75 g, 3.09 mmol) was taken in methanol (100 mL) degassed with argon. Pd/C (0.600 g, 10 wt % Degussa type wet) and couple of drops of acetic acid were added; the mixture was hydrogenated under balloon pressure for 36 hrs. Reaction mixture was filtered through a small pad of celite, washed with methanol. TFA (0.354 mL, 1.25 eq) and toluene (30 mL) was added and removed the solvent under reduced pressure. The residue was co-evaporated with toluene (2 times) and dried under high vacuum overnight to get the compound as TFA salt (5.70 g, crude).

MS: Calculated for $C_{81}H_{125}N_7O_{41}$, 1717.75; Found 1740.5 (M+Na).
Example 2. Synthesis of Carbohydrate Conjugate 118
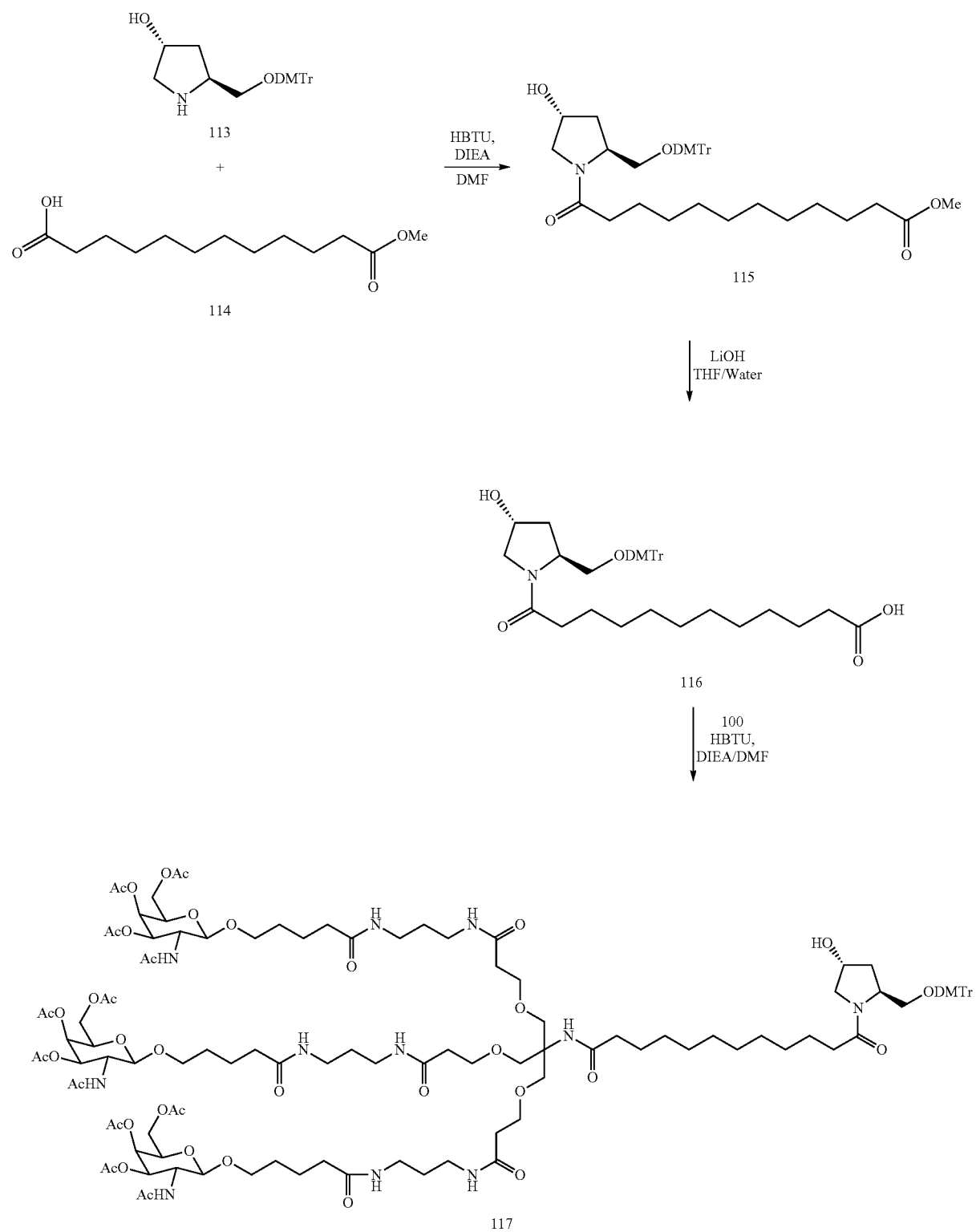

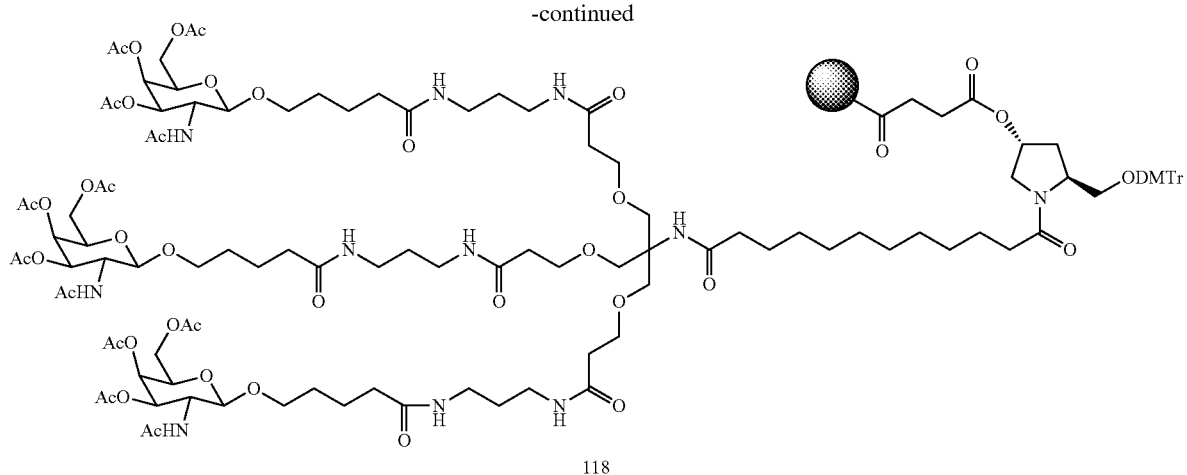

118

Preparation of 115:

Hydroxy proline amine (3.00 g, 7.15 mmol) and Dodecanedioic acid mono methyl ester (1.748 g, 7.15 mmol) were taken together in DMF (50 mL). To that HBTU (3.25 g, 8.56 mmol) and DIEA (3.7 mL, 21.24 mmol) were added and stirred the reaction over night. The reaction mixture was poured in to ice water mixture and extracted with DCM. Washed with bicarbonate solution, water, brine and dried over sodium sulfate. Solvent was removed and the residue was purified by chromatography (eluted with 50% ethyl acetate/hexane, ethyl acetate, followed by 5% MeOH/DCM) to get the required compound 115 as white solid (4.30 g, 93%). MS: Calculated for $C_{39}H_{51}NO_7$, 645.37; Found 646.35 (M+H).

Preparation of 116:

Compound 115 (4.25 g, 6.58 mmol) was dissolved in a mixture of THF/DCM/Water (50 mL, 2:1:1). LiOH (1.90 g, 45.2 mmol) was added and the mixture stirred overnight. TLC checked, acetic acid was added to neutralize the reaction mixture. Solvent was removed and the residue extracted with DCM. TEA (excess) added to the DCM solution and filtered the solution through a small pad of silica gel to get the required product 116 as its TEA salt (4.15 g, 86%). MS: Calculated for $C_{38}H_{49}NO_7$, 631.35; Found 630.34 (M−H).

Preparation of 117:

Compound 116 (1.30 g, 2.06 mmol) and HBTU (0.821 g, 1.05 eq.) were taken together in DMF (30 mL). To that DIEA (1.07 ml, 3 eq) was added and stirred the reaction mixture for 3-4 minutes. A solution of amine 110 (3.00 g, 1.58 mmol) was added followed by 1 eq. DIEA. The reaction mixture stirred overnight at room temperature. Solvents were removed under reduced pressure. The residue dissolved in DCM, washed with bicarbonate and water. DCM layer was dried over sodium sulfate and removed the solvents. The residue was purified by chromatography (eluted first with ethyl acetate, followed by 5-20% MeOH/DCM) to get the product 117 as white solid (3.35 g, 88%). MS: Calculated for $C_{117}H_{175}N_{11}O_{42}$, 2406.19; Found 2429.10 (M+Na).

Preparation of Solid Support 118:

Compound 117 (3.30 g, 1.37 mol), succinic anhydride (0.274 g, 2 eq) and DMAP (0.501 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid (3.81 g) as its TEA salt. MS: Calculated for $C_{121}H_{179}NO_{45}$, 2506.21; Found 2529.20 (M+Na). Succinate (2.20 g, 0.877 mmol) and HBTU (0.334 g, 0.877 mmol) were dissolved in DMF (100 mL). To that DIEA (0.457 mL, 2.62 mmol) was added and swirl the reaction for 3-4 minutes. Polystyrene support (12.30 g) was added to that and shaken the mixture for 24 hrs. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 118 (13.10 g, 50.5 □mol/g loading).

Example 3. Synthesis of Carbohydrate Conjugate 122
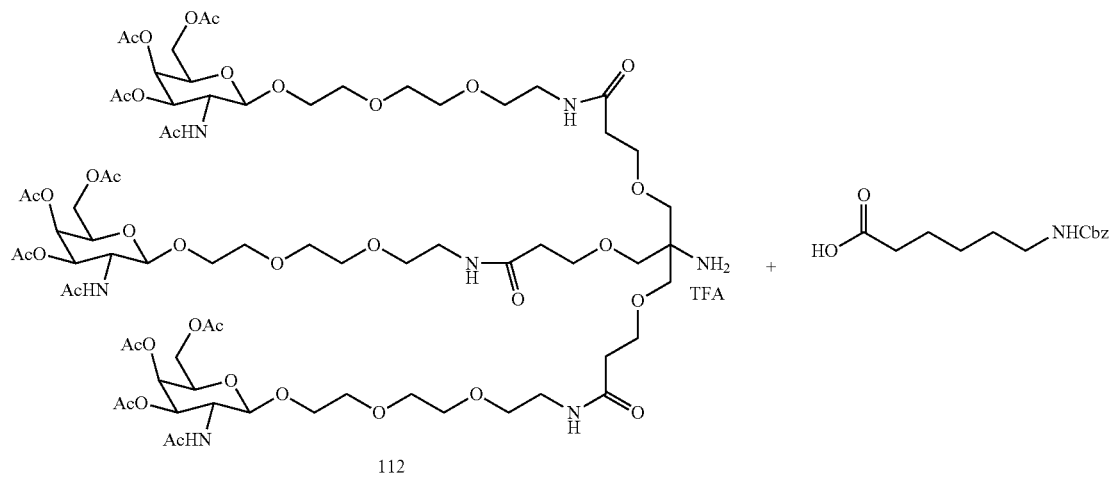
112
HBTU, DIEA DMF
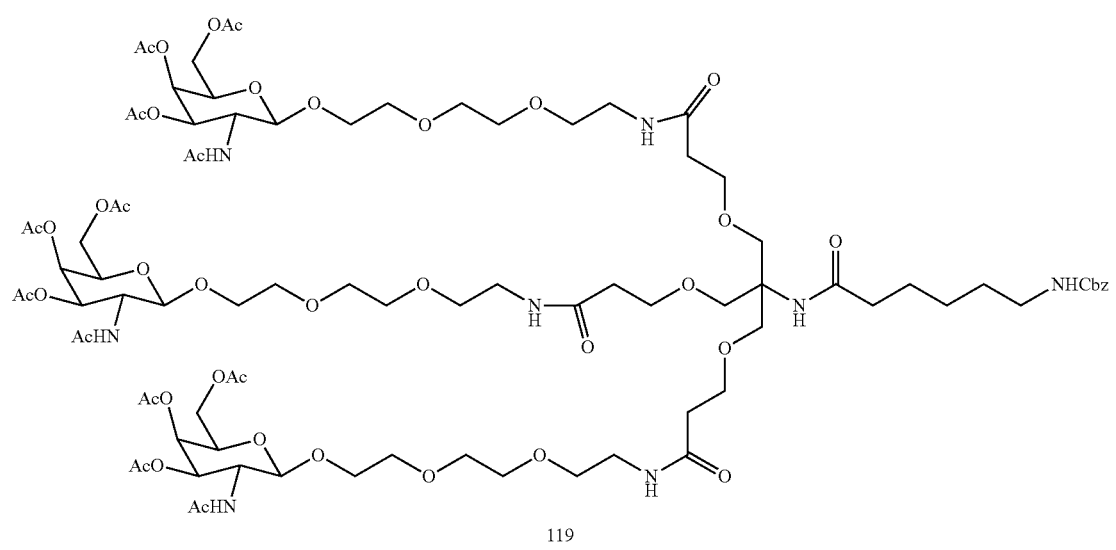
119
1. H₂/Pd(C)/MeOH three drops of AcOH
2. TFA -continued

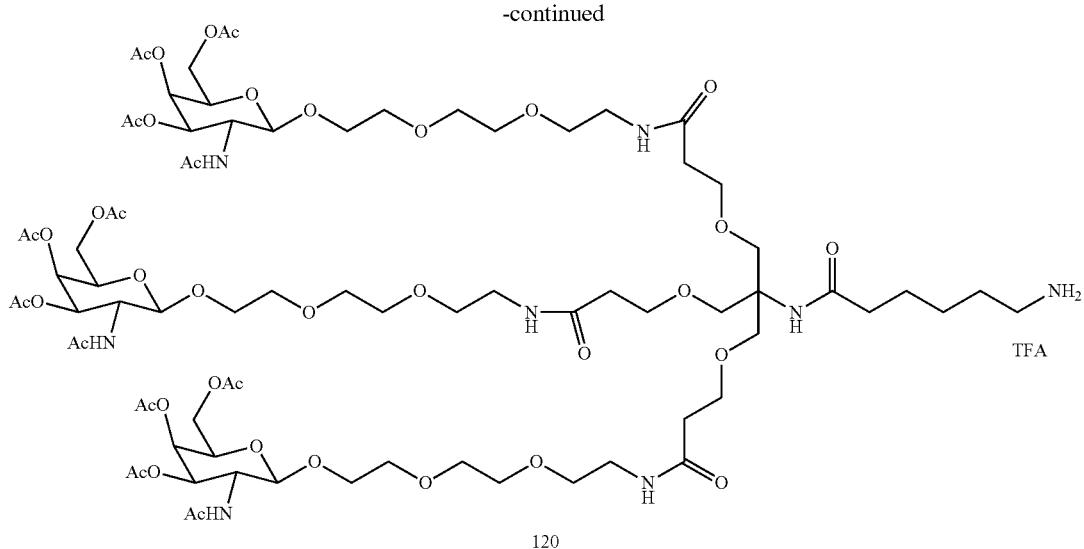

120

Preparation of 119:

Z-amino caproic acid (2.19 g, 8.25 mmol) was dissolved in DMF (50 mL). To that HBTU (3.13 g, 8.25 mmol) and DIEA (7.19 mL, 5.00 eq.) was added and stirred the mixture for few minutes. GalNAc amine 112 (10.10 g, 5.52 mmol) was dissolved in 50 ml of DMF was added to that and stirred for 48 hrs. TLC and MALDI were checked for product formation. Solvents were removed and the residue was dissolved in DCM, washed with $NaHCO_3$ solution and water. Dried over sodium sulfate and removed the solvents under reduced pressure. Residue was purified by chromatography (eluted with ethyl acetate, followed by gradient elution of 5-15% MeOH/DCM) to get the required compound 119 as off white solid (6.20 g, 57%). MS: Calculated for $C_{87}H_{136}N_8O_{42}$, 1964.88; Found 1987.75 (M+Na).

Preparation of 120:

Compound 119 (6.10 g, 3.10 mmol) was dissolved in Methanol (50 mL), to that 1 mL of acetic acid was added. Degassed the reaction mixture, Pd/C (0.700 g, 10 wt % Degussa wet type) was added to that and hydrogenated under balloon pressure for 36 hrs. Reaction mixture was filtered through a small pad of celite, washed with MeOH. To that 1.25 eq of TFA and toluene (50 mL) were added and removed solvents under reduced pressure. The residue was co-evaporated with toluene two times and dried under high vacuum overnight night to get the required compound as an off white solid (6.10 g, quantitative). This compound used as such for the next reaction with out any further purification. MS: Calculated for $C_{79}H_{130}N_8O_{40}$, 1830.84; Found 1853.81 (M+Na).

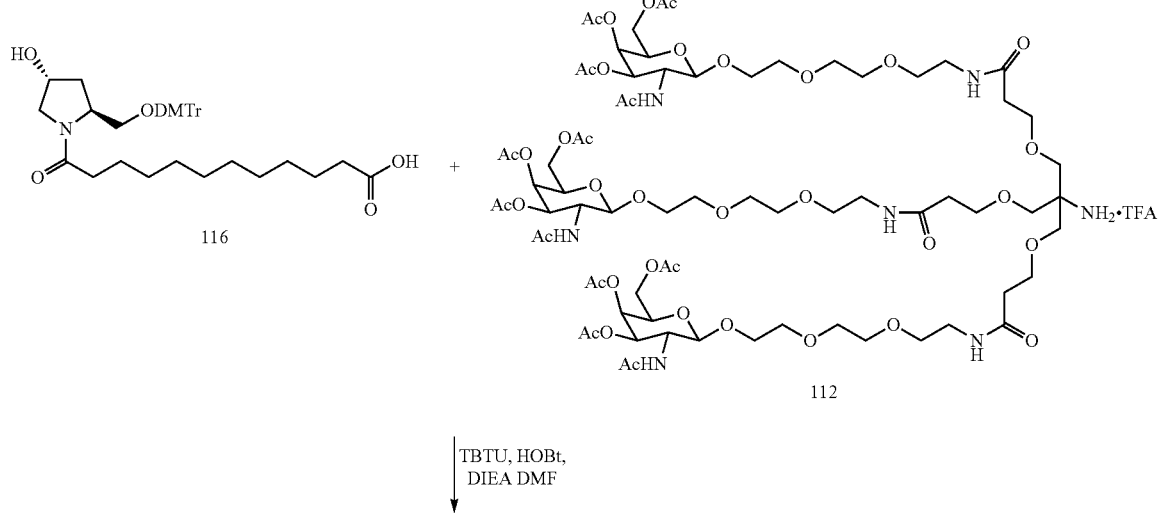

TBTU, HOBt, DIEA DMF

-continued

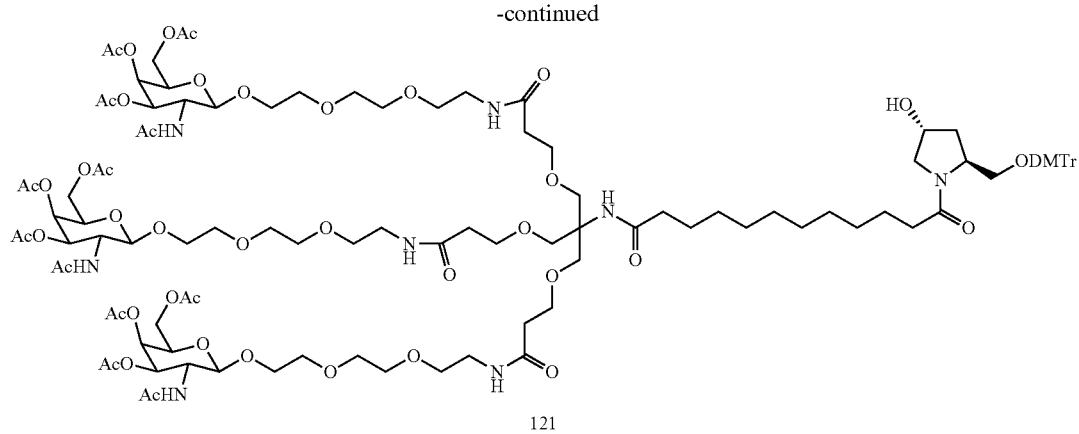

121

1. Succinic anhydride, DMAP, DCM
2. HBTU, DIEA, DMF
   Polystyrene support

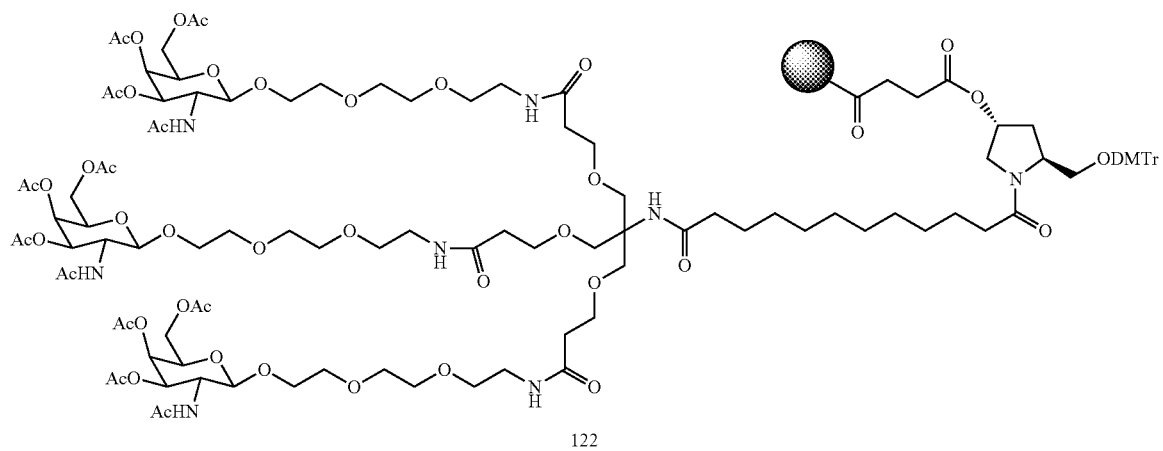

122

Preparation of 121:

Compound 116 (5.06 g, 6.90 mmol), GalNAc amine 112 (10.55 g, 5.756 mmol) TBTU (2.44 g, 1.1 eq.) and HOBt (1.025 g, 1.1 eq) were taken together in DMF (100 mL). To that DIEA (6 mL ml, 34.51 mmol) was added and stirred the reaction mixture for 48 hrs. Reaction was monitored by TCL as well as MALDI. Solvents were removed under reduced pressure. The residue dissolved in DCM, washed with bicarbonate and water. DCM layer was dried over sodium sulfate and removed the solvents. The residue was purified by chromatography (eluted first with ethyl acetate, followed by 3-10% MeOH/DCM) to get the product 121 as off white solid (10.50 g, 79%). MS: Calculated for $C_{111}H_{166}N_8O_{45}$, 2331.09; Found 2354.03 (M+Na).

Preparation of 122:

Compound 121 (2.00 g, 0.857 mmol), succinic anhydride (0.186 g, 2 eq), DMAP (0.314 g, 3 eq.) are taken together in DCM and stir overnight. Solvent is removed and the residue filter through a small pad of silica gel to get the succinate as its TEA salt. Succiniate (2.00 g, 0.857 mmol) and HBTU (0.325 g, 0.857 mmol) are dissolved in DMF (100 mL). To that DIEA (0.450 mL, 2.57 mmol) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 122.

Example 4. Synthesis of Carbohydrate Conjugate 128
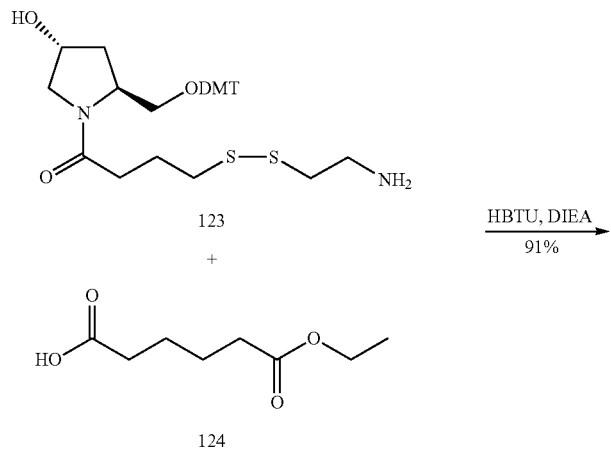
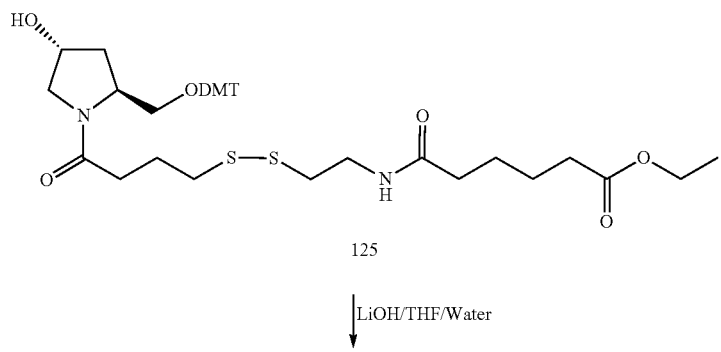
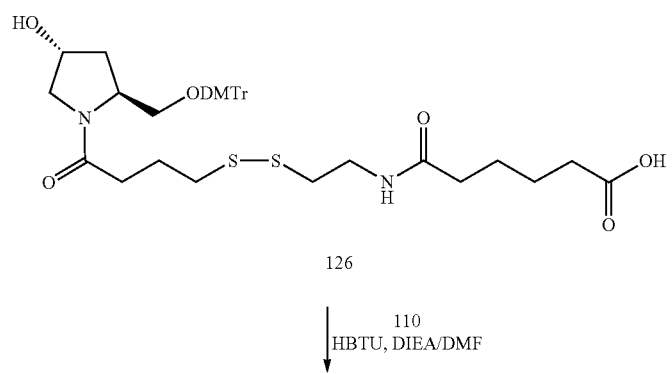

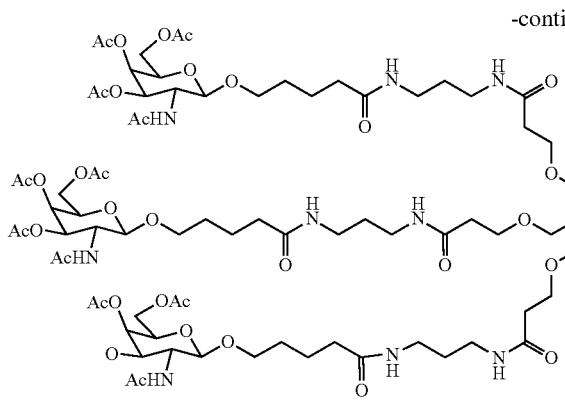

127

1. Succinic anhydride, DMAP/DCM
2. HBTU, DIPEA, DMF
   Solid support

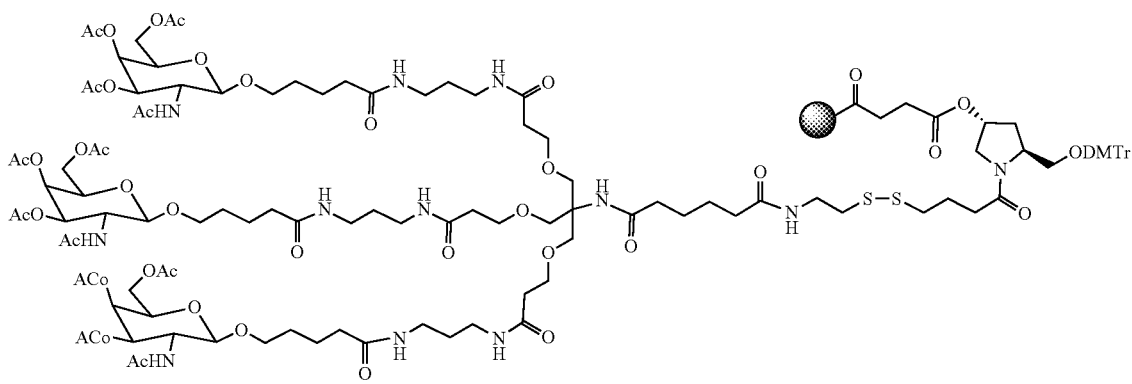

128

Preparation of 125:

Amine 123 (2.75 g, 4.61 mmol) and Mono ethyl hexane dioic acid (0.886 g, 5.09 mmol) were dissolved in DMF (50 mL). To that HBTU (2.09 g, 5.51 mmol) and DIEA (2.88 mL, 16.53 mmol) were added and stirred the reaction mixture overnight. Reaction mixture was poured in to an ice water mixture and extracted with DCM, washed with bicarbonate solution and dried over sodium sulfate. Solvent was removed and the residue was purified by chromatography (eluted with 50% EtOAc/Hexane, EtOAc, followed by 5-10% MeOH/DCM) to get the required product as a fluffy white solid (2.25 g, 65%). MS: Calculated for $C_{40}H_{52}N_2O_8S_2$, 752.32; Found 753.31 (M+Na).

Preparation of 126:

Compound 125 (2.20 g, 2.97 mmol) was dissolved in a mixture of THF/Water (20 mL, 2:1). LiOH (0.187 g, 4.45 mmol) was added and the mixture stirred 4 hrs. Reaction was monitored TLC, after 4 hrs, cooled and citric acid was added to quench the reaction mixture. Solvent was removed and the residue was extracted DCM, washed with water. Dried over sodium sulfate and removed the solvent. The residue was purified by chromatography (EtOAc, 3-20% MeOH/DCM) to get the required product 126 (0.750 g, 35%) as its TEA salt. MS: Calculated for $C_{38}H_{48}N_2O_8S_2$, 724.29; Found 723.28 (M−H).

Preparation of 127:

Compound 126 (1.008 g, 1.390 mmol), 110 (1.904 g, 1.007 mmol) and HBTU (0.400 g, 1.054 mmol) were dissolved in DMF (20 mL). To that DIEA (0.525 mL, 3 eq.) was added and stirred the reaction for 2 days. Reaction mixture was monitored by TLC and MALDI. Solvents were removed and the residue dissolved in DCM, washed with water and bicarbonate solution. DCM layer was dried over sodium sulfate and removed the solvent. It was then purified by chromatography (first ethyl acetate, followed by 3-15% MeOH/DCM) to get the required product as a fluffy off white solid (1.90 g, 76%). MS: Calculated for $C_{117}H_{174}N_{12}O_{43}S_2$, 2499.12; Found 2522.12 (M+Na).

Preparation of solid support 128:

Compound 127 (2.00 g, 0.800 mmol), succinic anhydride (0.160 g, 2 eq), DMAP (0.300 g, 3 eq.) are taken together in DCM and stir overnight. Solvent is removed and the residue filter through a small pad of silica gel to get the succinate as its TEA salt. Compound 127 (2.00 g, 0.769 mmol) and HBTU (0.290 g, 0.769 mmol) are dissolved in DMF (100 mL). To that DIEA (0.500 mL, 3 mmol) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 128.

Example 5. Synthesis of Carbohydrate Conjugate 136

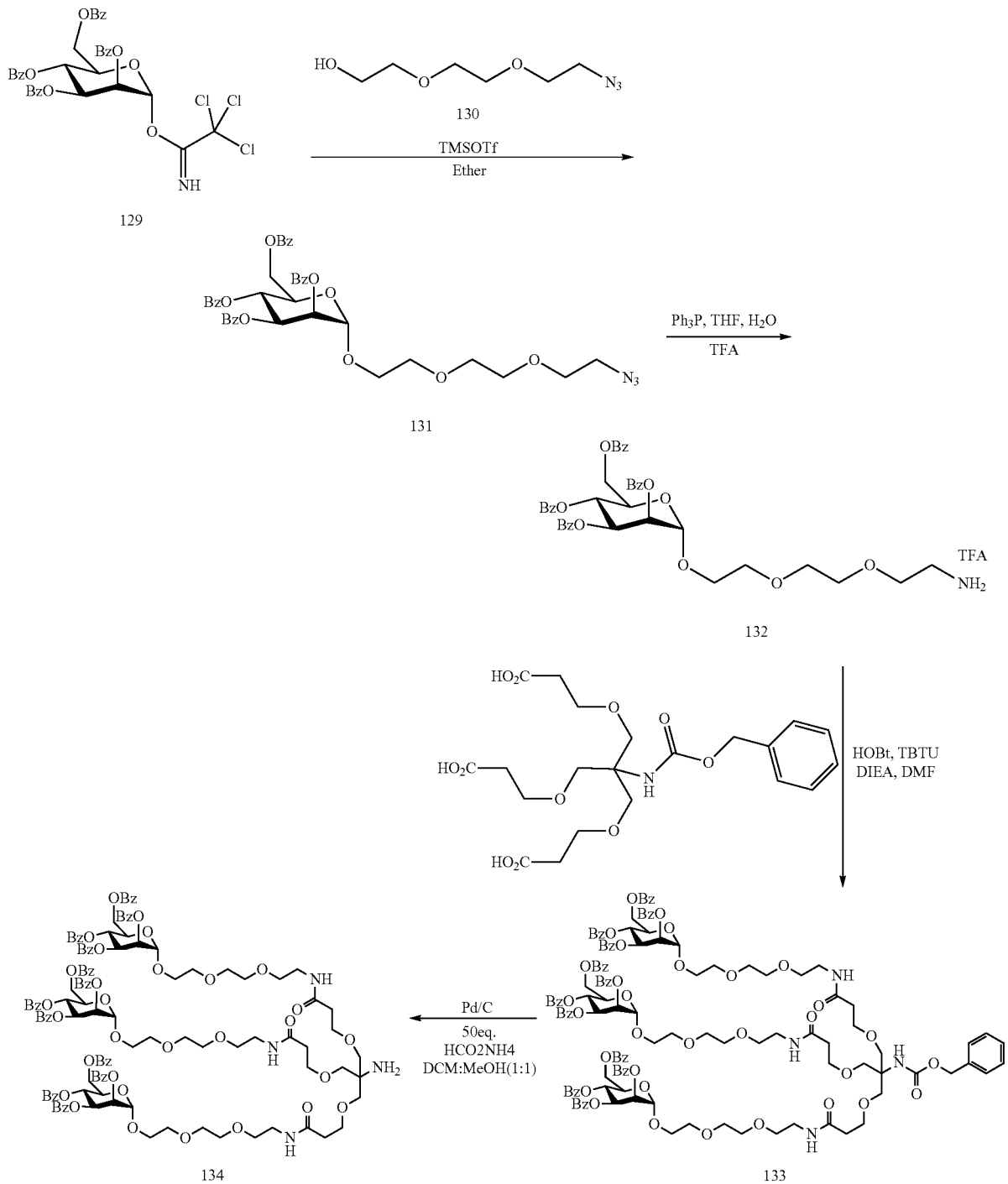

Preparation of 131:

Mannose trichloroacetimidate 129 (15.00 g, 20.24 mmol) and azido alcohol (4.25 g, 1.2 eq) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (20-50% EtOAc/Hexane) to get compound as colorless liquid (8.36 g, 55%). MS: Calculated for $C_{40}H_{39}N_3O_{12}$, 753.25; Found 776.23 ((M+Na)

Preparation of 132:

Compound 131 (8.30 g, 11.01 mmol) was dissolved in anhy. THF (70 mL), to that PPh3 (3.46 g, 1.2 eq) was added and the mixture stirred for two days at ambient temperature. Water (1 mL) was added to that and stirred the mixture for another 24 hrs.

Reaction was monitored by TLC. Trifluro acetic acid (1.06 mL, 1.25 eq) and toluene (50 mL) was added to that. Solvents were removed under reduced pressure and residue was co-evaporated toluene two times and dried under high vacuum. This used as such for the next reaction without further purification. MS: Calculated for $C_{40}H_{41}NO_{12}$, 727.26; Found 750.23 ((M+Na).

Preparation of 133:

Tricarboxylic acid (11.05 g, 23.45 mmol), and amine (68.19 g, 94 mmol, crude from previous reaction) was dissolved in DMF (200 mL). To that TBTU (27.09 g, 84 mmol), HOBt (11.34 g, 84 mmol) and DIEA (28 mL, 160 mmol) was added and stirred the reaction mixture for 24 h. After stirring 24 hrs an additional amount of DIEA (28 mL) was added continued stirring. After 48 hrs solvents were removed under reduced pressure, the residue was dissolved in dichloromethane, washed with 1M phosphoric acid solution, sodium bicarbonate solution, and water and dried over sodium sulfate. Solvents were removed and the residue was purified by chromatography (ethyl acetate, followed by 3-15% MeOH/DCM) to get the required compound 133 as a white solid (41.95 g, 67%) MS: Calculated for $C_{141}H_{146}N_4O_{44}$, 2598.93; Found 2621.89 (M+Na).

Preparation of 134:

Compound 133 (3.05 g, 1.176 mmol) was dissolved in a mixture of DCM/MeOH. To that 50 eq. of ammoniumformate was added followed by 5% Pd/C (1.5 g, 50 wt %) and stirred for 8 hrs at ambient temperature. It was filtered through small pad of celite, washed with MeOH/DCM, solvent was removed and residue dried under high vacuum over night to the compound as a white solid (2.65 g, 92%). MS: Calculated for $C_{133}H_{140}N_4O_{42}$, 2464.89; Found 2487.92 (M+Na).

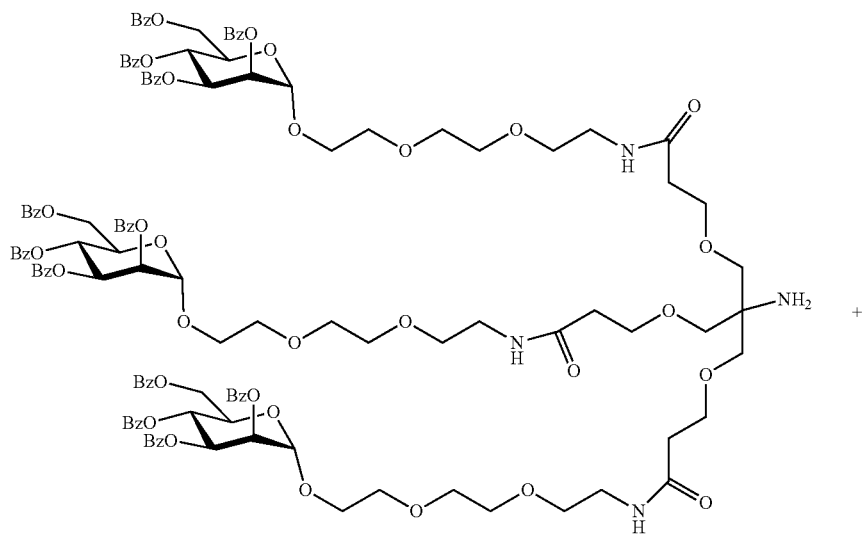

134

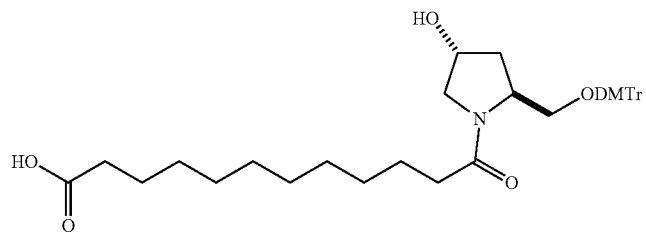

116

~50% | TBTU, HOBt, DIEA
DMF

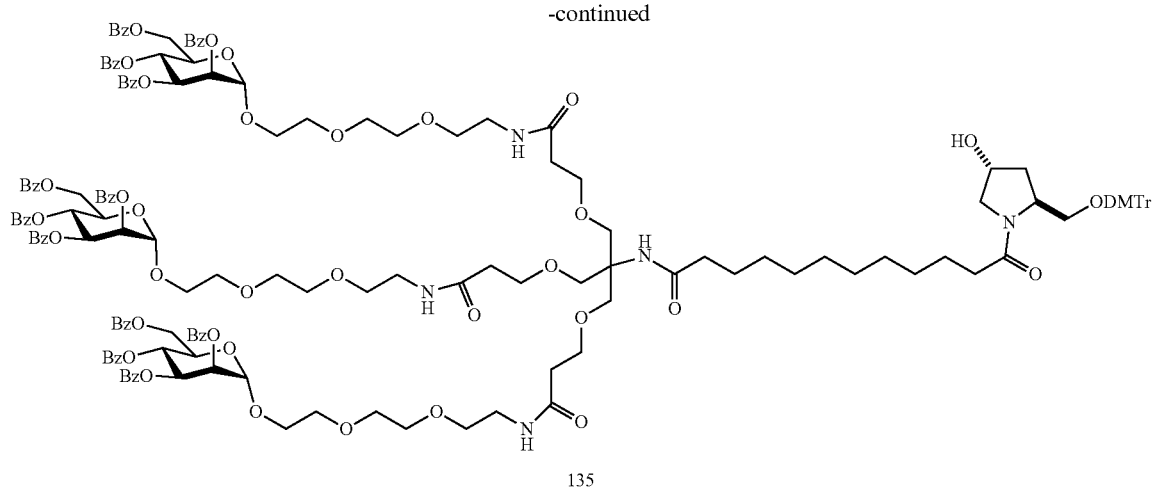

135

1. Succinic anhydride, DMAP, DCM
2. HBTU, DIEA DMF
   Polystyrene support

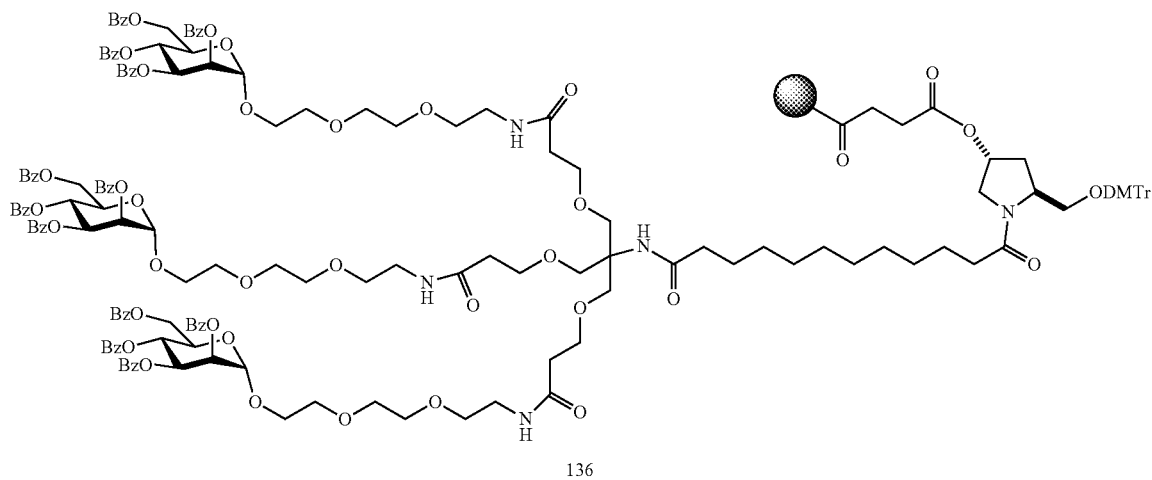

136

Preparation of 135:

Mannose amine (2.076 g, 0.842 mmol), 116 (0.740 g, 1.00 mmol) and TBTU (0.0.353 g, 1.1 eq.) and HOBt (0.149 g, 1.1 eq) were dissolved in DMF (30 mL). To that DIEA (0.0.869 mL, 5 eq.) was added and stirred the reaction for 2 days. Reaction mixture was monitored by TLC and MALDI. Solvents were removed and the residue dissolved in DCM, washed with water and bicarbonate solution. DCM layer was dried over sodium sulfate and removed the solvent. It was then purified by chromatography (first ethyl acetate, followed by 2-4% MeOH/DCM) to get the required product as a fluffy off white solid (1.48 g, 57%). MS: Calculated for $C_{71}H_{187}N_5O_{48}$, 3078.23; Found 3101.25 (M+Na).

Preparation of Solid Support 136:

Compound 117 (2.10 g, 0.681 mmol), succinic anhydride (0.136 g, 2 eq) and DMAP (0.249 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid (1.56 g) as its TEA salt. MS: Calculated for $C_{175}H_{191}N_5O_{51}$, 3178.25; Found 3201.20 (M+Na). Succinate (1.00 g, 0.305 mmol) and HBTU (0.138 g, 1.2 eq.) were dissolved in DMF (100 mL). To that DIEA (0.50 mL, excess) was added and swirl the reaction for 3-4 minutes. Polystyrene support (6.05 g) was added to that and shaken the mixture for 24 hrs. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 136 (6.70 g, 42 µmol/g loading).

Example 6. Synthesis of Carbohydrate Conjugate 143

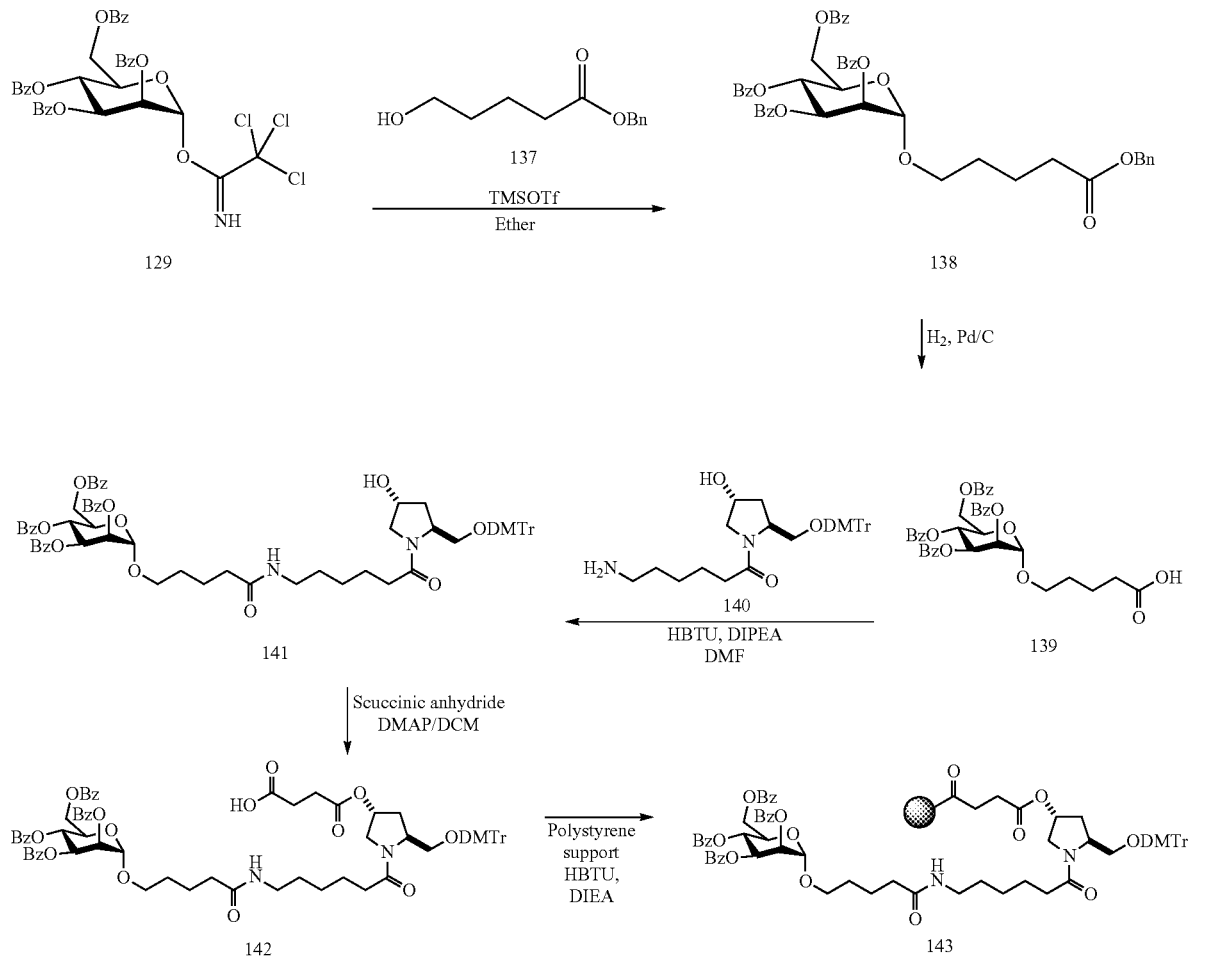

Preparation of 138:

Mannose trichloroacetimidate 129 (15.23 g, 20.55 mmol) and 137 (4.36 g, 1.02 eq.) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (hexane, 15-25% EtOAc/Hexane) to get compound as colorless liquid (14.52 g, 90%). MS: Calculated for $C_{46}H_{42}O_{12}$, 786.27; Found 809.25 ((M+Na).

Preparation of 139:

Mannose benzyl ester (14.30 g, 18.17 mmol) was dissolved in Ethyl acetate (100 mL) to that two drops of acetic acid was added. Degassed, Pd/C (1.50 g, 10 wt % Degussa wet type) was added and hydrogenated under balloon pressure for 24 hrs. Reaction was monitored by TLC and MALDI. It was filtered through a small pad of celite, washed with ethyl acetate. Solvent was removed and the residue dried under high vacuum to get the compound as color less oil (11.20 g, 90%). MS: Calculated for $C_{39}H_{36}O_{12}$, 696.22; Found 719.18 ((M+Na).

Preparation of 141:

Hydroxy Proline amine 140 (3.82 g, 7.18 mmol), 141 (5.00 g, 7.18 mmol) and HBTU (2.65 g, 7.18 mmol) were dissolved in DMF (50 mL). To that DIEA (3.65 mL, 5 eq.) was added and stirred the reaction for 3 hrs. Reaction mixture was monitored by TLC. Solvents were removed and the residue dissolved in DCM, washed with water and bicarbonate solution. DCM layer was dried over sodium sulfate and removed the solvent. It was then purified by chromatography (first ethyl acetate, followed by 5-10% MeOH/EtOAc) to get the required product as a white solid (4.08 g, 46%). MS: Calculated for $C_{71}H_{74}N_2O_{16}$, 1210.50; Found 1233.40 (M+Na).

Preparation of Solid support 143:

Compound 141 (2.00 g, 1.652 mmol), succinic anhydride (0.330 g, 2 eq), DMAP (0.604 g, 3 eq.) are taken together in DCM and stir overnight. Solvent is removed and the residues filter through a small pad of silica gel to get the succinate as its TEA salt 142. Succiniate (2.00 g, 1.526 mmol) and HBTU (0.578 g, 1.526 mmol) are dissolved in DMF (100 mL). To that DIEA (1.32 mL, 5 eq.) is added and swirl the reaction for 3-4 minutes. Polystyrene support (10.00 g) is added to that and shaken the mixture for 24 hrs. Filter through a frit and washed with DCM, 10% MeOH/DCM, DCM and ether, it is capped with acetic anhydride to get the solid support 143.

Example 7. Synthesis of Carbohydrate Conjugate
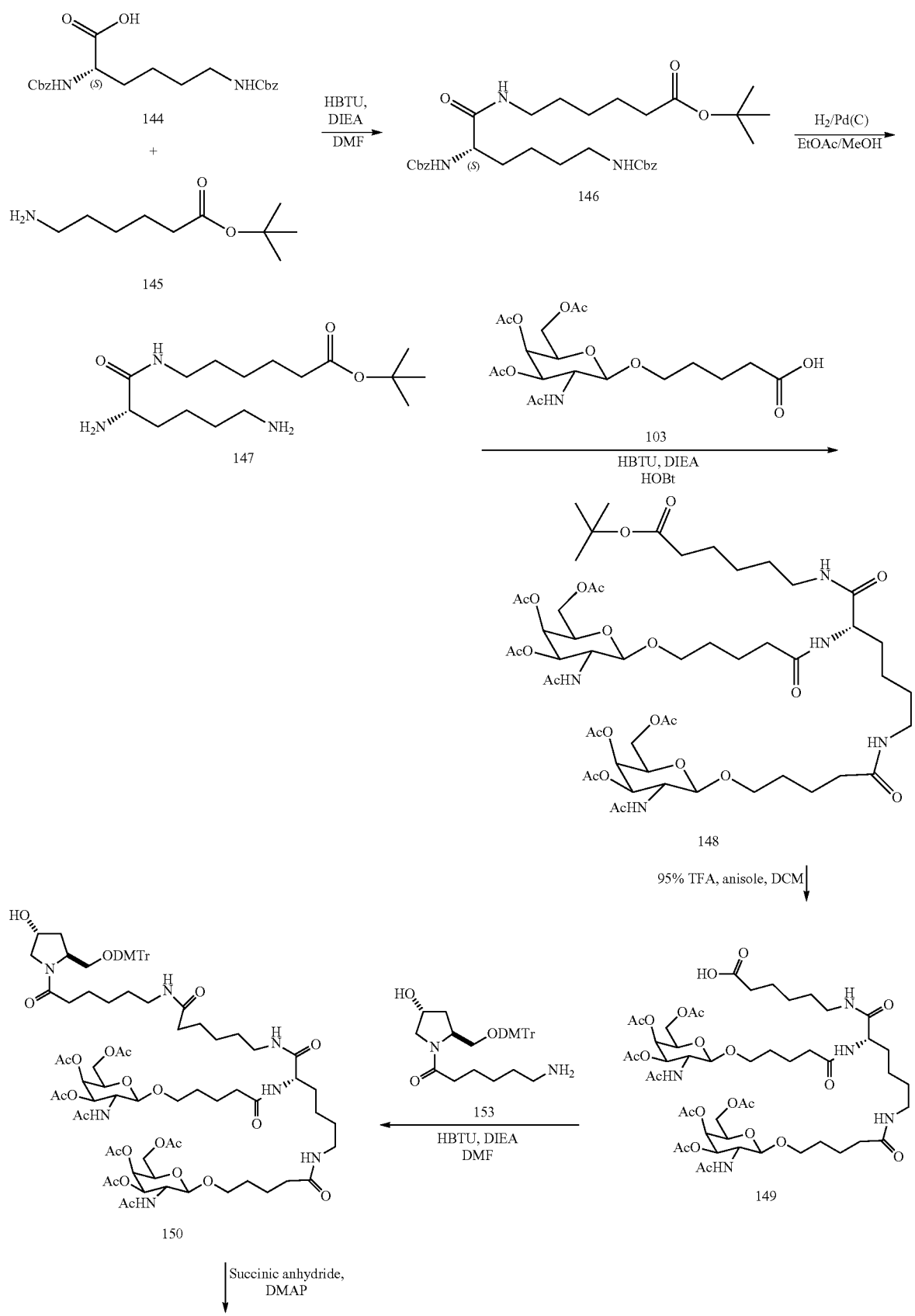

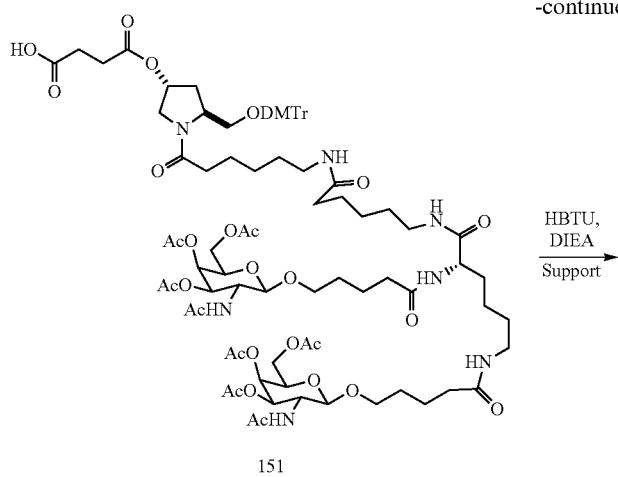

151

HBTU, DIEA
Support
→

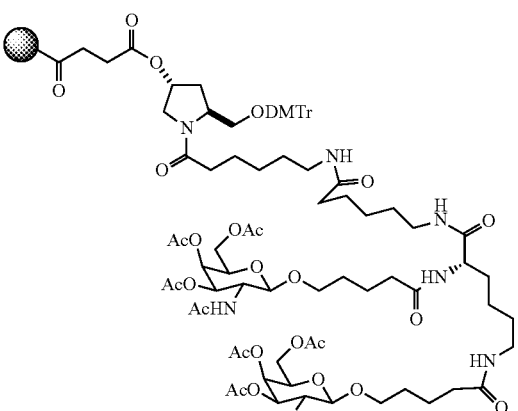

152

Preparation of 146:

Compound 144 (26.55 g, 64.06 mmol) and 145 (10.00 g, 53.43 mmol) were dissolved in DMF (150 mL). To that HBTU (24.12 g, 64 mmol) and DIEA (46 mL, 5 eq) were added and stirred the reaction mixture overnight. TLC checked and the mixture was added to ice cold water and extracted with a mixture of ether and ethyl acetate dried over sodium sulfate. Solvents were removed and the crude product was purified by chromatography (20-50% ethylacetate/Hexane) to get the required product as an off white solid (23.20 g, 74%). MS. MW calc. for $C_{32}H_{45}N_3O_7$: 583.72, Found 584.73 (M+H).

Preparation of 147:

Compound 146 (3.30 g, 5.65 mmol) was dissolved in a mixture of ethyl acetate/MeOH and hydrogenated under balloon pressure using Pd/C (500 mg) as catalyst overnight. Filtered through a small pad of celite and removed the solvent, this product used for the next reaction without further purification. MS. MW calc. for $C_{16}H_{33}N_3O_3$: 315.25, Found 316.26 (M+H).

Preparation of 148:

Compound 147 (5.65 mmol) and GalNAc acid 103 (5.81 g, 12.99 mmol) were dissolved in DMF (80 mL). To that HBTU (4.97 g, 13.10 mmol) and DIEA (7.00 mL, 3 eq) were added and stirred the reaction mixture overnight. Solvents were removed and the residue dissolved in DCM and washed with water and brine, dried over sodium sulfate. Solvents were removed and the crude product was purified by chromatography (EtOAc, followed by 3-10% MeOH/DCM) to get the required product as an off white solid (5.25 g, 79%). MS. MW calc. for $C_{54}H_{87}N_5O_{23}$: 1173.58, Found 1196.60 (M+Na).

Preparation of 149:

Biantineary GalNAc derivative 148 (5.15 g, 4.40 mmol) was dissolved in 15 mL of anhydrous DCM, to that 3 mL of anisole and 30 mL of TFA were added and stirred the reaction mixture for 2 hrs at ambient temperature. TLC checked and toluene was added to the reaction mixture, removed the solvents under reduced pressure. Co-evaporated with toluene two times and the residue dissolved in DCM, washed with water, dried over anhydrous sodium sulfate. Crude product was purified by filtration column (10% MeOH/DCM) to get the required product as pale brown solid (4.40 g, 91%). MS. MW calc. for $C_{50}H_{79}N_5O_{23}$: 1117.52, Found 1140.62 (M+Na).

Preparation of 150:

Biantineary GalNAc acid 149 (4.30 g, 3.84 mmol) and hydroxyl proline amine 153 (2.25 g, 1.1 eq) were dissolved in DMF (50 mL). To that HBTU (1.46 g, 3.84 mmol) and DIEA (3.3 mL) were added and stirred the reaction mixture for 3 hrs. Solvents were removed and the residue dissolved in DCM, washed with water and bicarbonate, dried over sodium sulfate. Solvents were removed and the crude product purified by chromatography (3-10% MeOH/DCM) to get the required product as white solid (3.25 g, 52%). MS. MW calc. for $C_{72}H_{117}N_7O_{27}$: 1631.80, Found 1654.45 (M+Na).

Preparation of 151:

Compound 150 (3.30 g, 2.02 mmol), succinic anhydride (0.404 g, 2 eq), DMAP (0.740 g, 3 eq.) are taken together in DCM (30 mL) and stir overnight. Solvent is removed and the residues filter through a small pad of silica gel to get the succinate as its TEA salt 151. MS. MW calc. for $C_{86}H_{121}N_7O_{30}$: 1731.82, Found 1753.87 (M+Na).

Preparation of Solid Support 152:

Succinate 151 (2.02 mmol) and HBTU (0.842 g, 1.1 eq.) were dissolved in DMF (100 mL). To that DIEA (1.50 mL, excess) was added and swirl the reaction for 3-4 minutes. Polystyrene support (28 g) was added to that and shaken the mixture overnight. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 152 (30.10 g, 30 µmol/g loading).

Example 8. Synthesis of Carbohydrate Conjugate 161
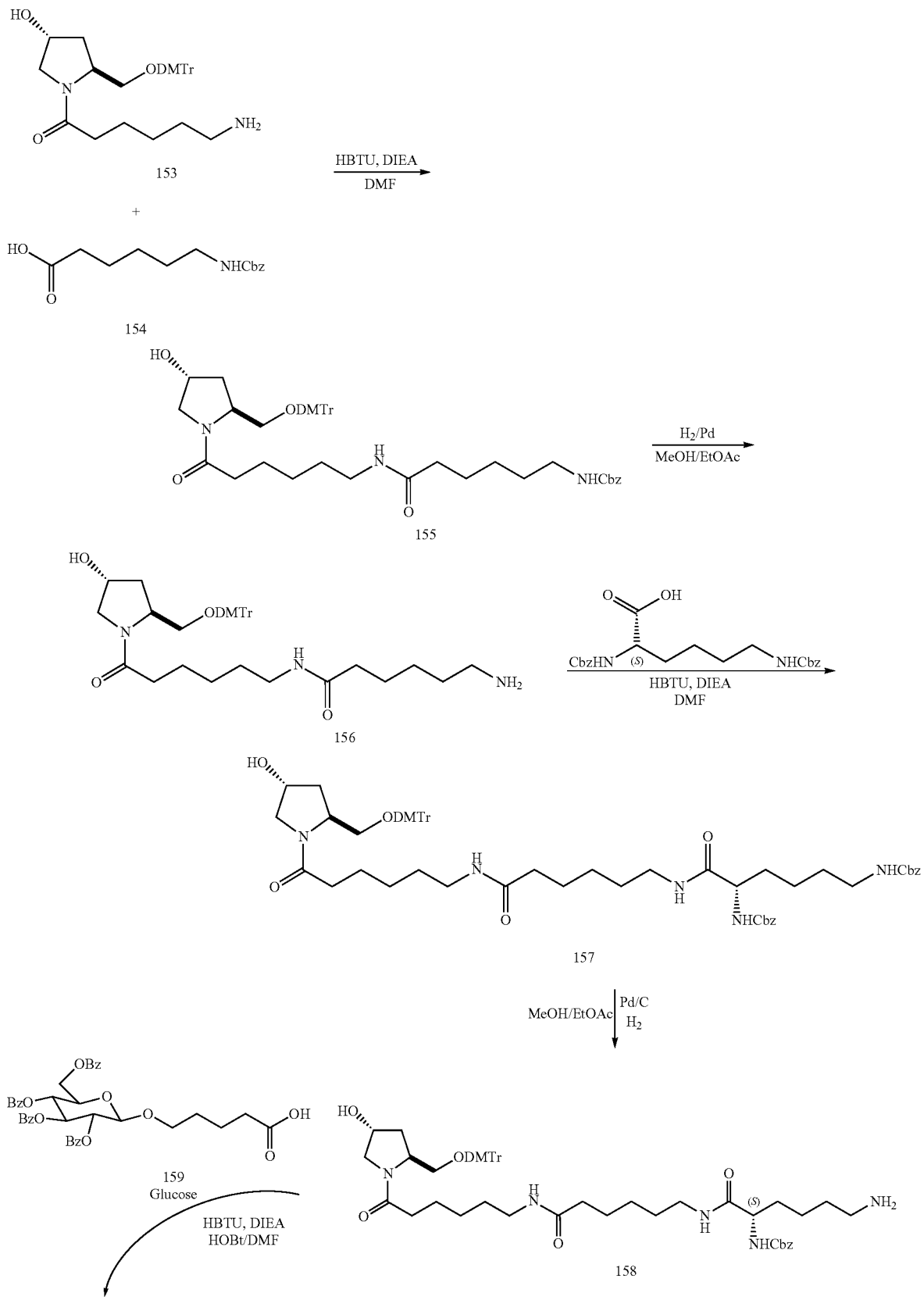

-continued
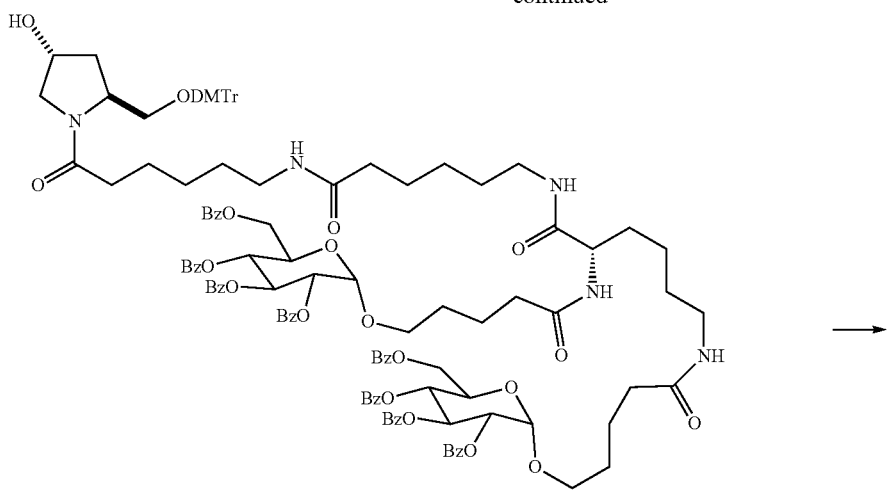
160
1. Succinic anhydride
2. Polymer support, HBTU
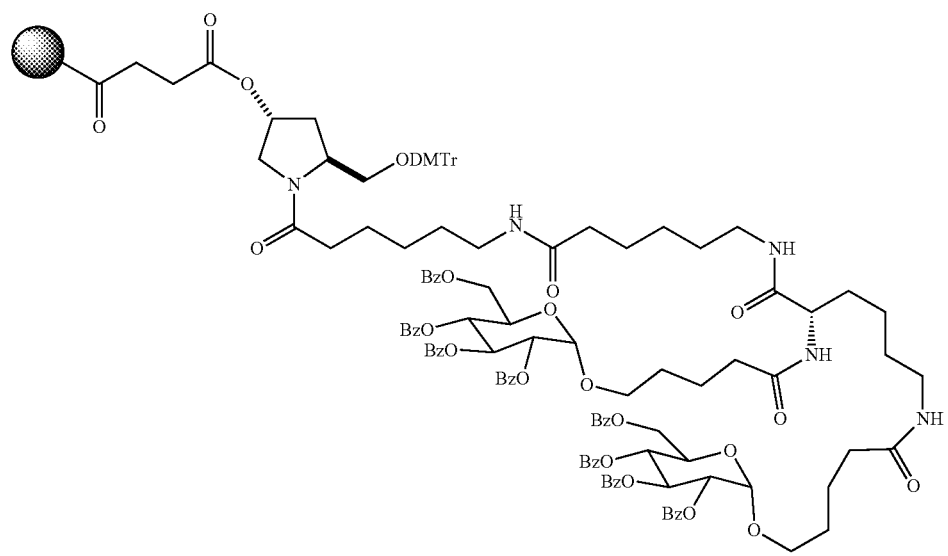
161

Preparation of 155:

Hydroxy proline amine 153 (10.00 g, 18.76 mmol) and 154 (4.98 g, 18.76 mmol) were dissolved in DMF (100 mL). To that HBTU (7.83 g, 20.64 mmol) and DIEA (9.81 mL, 56.29 mmol) were added and stirred the reaction for 2 hrs. TLC checked and the mixture was added to ice cold water and extracted with a mixture of ether and ethyl acetate dried over sodium sulfate. Solvents were removed and the crude product was purified by chromatography (0-15% MeOH/DCM) to get the required product as an off white solid (13.20 g, 90%). MS. MW calc. for $C_{46}H_{57}N_3O_8$: 779.41, Found 780.42 (M+H).

Preparation of 156:

Compound 155 (13.00 g, 16.66 mmol) was dissolved in a mixture of ethyl acetate/MeOH and hydrogenated under balloon pressure using Pd/C (1.50 g) as catalyst overnight in presence of small amount of triethyl amine. Filtered through a small pad of celite and removed the solvent, this product used for the next reaction without further purification (9.93 g, 92%). MS. MW calc. for $C_{38}H_{51}N_3O_6$: 645.38, Found 646.40 (M+H).

Preparation of 157:

Compound 156 (9.90 g, 15.33 mmol) and diCbz lysine (6.36 g, 15.33 mmol) were dissolved in DMF (100 mL). To that HBTU (6.11 g, 15.33 mmol) and DIEA (8 mL, excess) were added and stirred the reaction for 2 hrs. TLC checked and the mixture was added to ice cold water and extracted with a mixture of ether and ethyl acetate dried over sodium sulfate. Solvents were removed and the crude product was purified by chromatography (0-10% MeOH/DCM) to get the required product as an off white solid (13.10 g, 83%). MS. MW calc. for $C_{60}H_{75}N_5O_{11}$: 1041.55, Found 1042.57 (M+H).

Preparation of 158:

Compound 157 (12.90 g, 12.37 mmol) was dissolved in a mixture of ethyl acetate/MeOH and hydrogenated under balloon pressure using Pd/C (1.30 g) as catalyst. TLC checked after 3 hrs filtered through a small pad of celite and removed the solvent, this product used for the next reaction without further purification. MS. MW calc. for $C_{44}H_{63}N_5O_7$: 773.47, Found 774.50 (M+H).

Preparation of 160:

Compound 158 (2.32 g, 3 mmol) and Glucose acid 159 (4.50 g 6.45 mmol) were dissolved in DMF (60 mL). To that HBTU (2.44 g, 6.45 mmol) and DIEA (3.36 mL, 3 eq) were added and stirred the reaction for 2 hrs and poured the reaction mixture to ice cold water and extracted with EtOAc/DCM, dried over sodium sulfate. Solvents were removed and the crude product was purified by chromatography (EtOAc, followed by 0-10% MeOH/DCM) to get the required product as an off white solid (5.40 g, 85%). MS. MW calc. for $C_{122}H_{131}N_5O_{29}$: 2129.89, Found 2152.90 (M+Na).

Preparation of Solid Support 161:

Compound 160 (5.20 g, 2.44 mmol), succinic anhydride (0.488 g, 2 eq) and DMAP (0.894 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid as its TEA salt. MS: MW calc. for $C_{126}H_{135}N_5O_{32}$: 2229.91, Found 2252.50 (M+Na). Succinate (2.44 mmol) and HBTU (0.925 g, 1.2 eq.) were dissolved in DMF (200 mL). To that DIEA (1.27 mL, excess) was added and swirl the reaction for 3-4 minutes. Polystyrene support (24 g) was added to that and shaken the mixture for 24 hrs. Filtered through a frit and washed with DCM, 10% MeOH/DCM, DCM and ether. Solid support dried under vacuum for 2 hrs. It was capped with 25% Ac$_2$O/Py mixture for ½ hr. The same washing and drying procedure repeated to the solid support 161 (27 g, 31 umol/g loading).

Example 9. Synthesis of Carbohydrate Conjugate 165 and 166

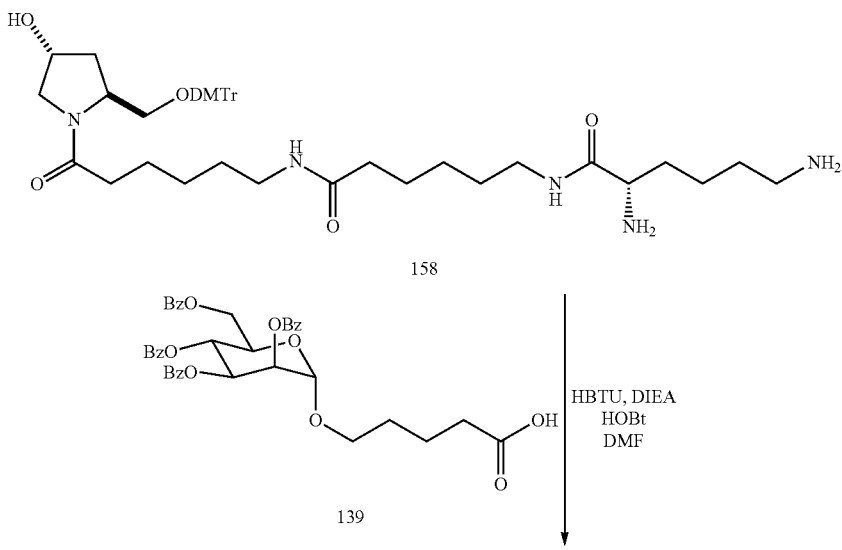

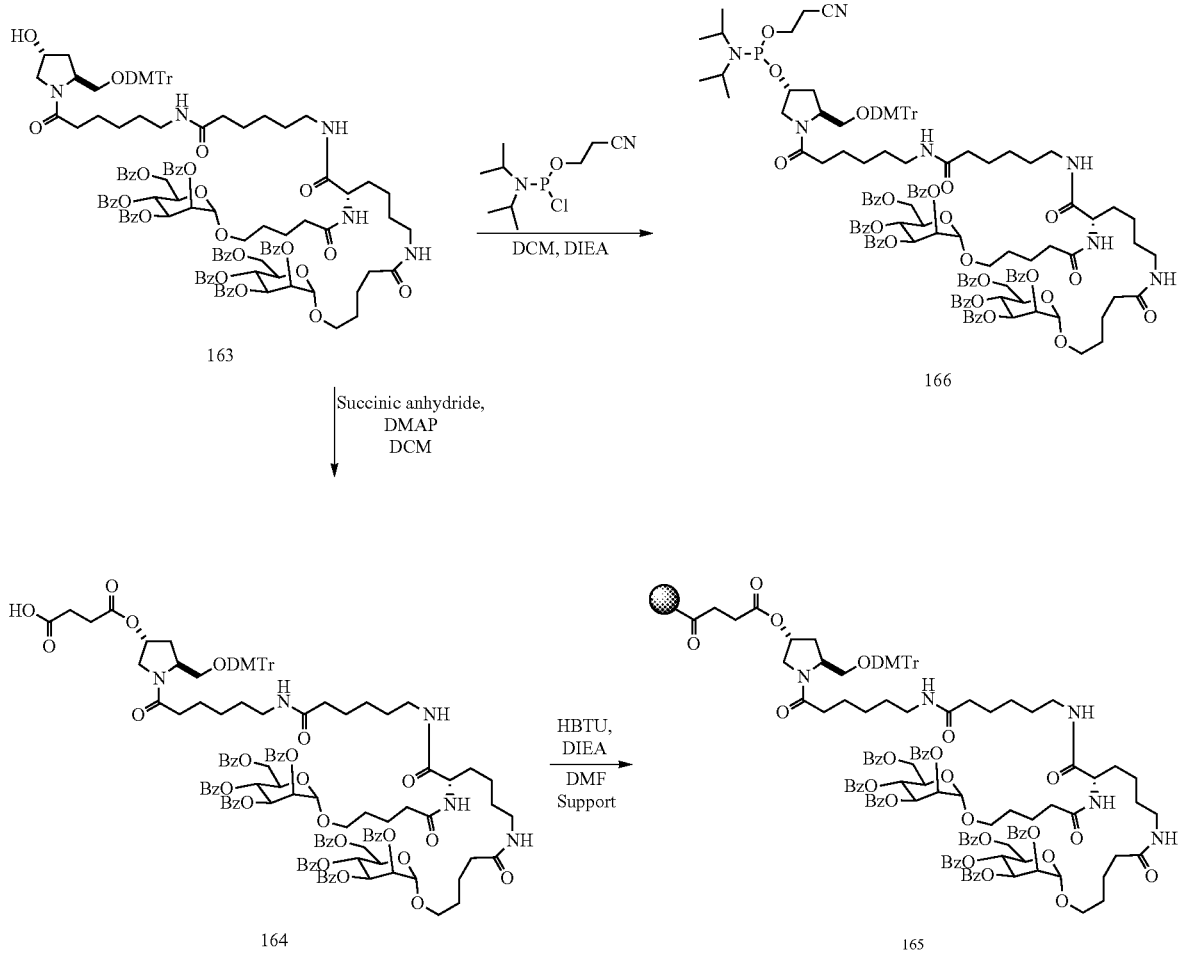

Preparation of 163:

Compound 158 (5.40 g, 6.97 mmol) and mannose acid 139 (9.96 g 14.30 mmol) were dissolved in DMF (100 mL). To that HBTU (5.42 g, 14.30 mmol) and DIEA (7.45 mL, excess) were added and stirred the reaction for 2 hrs and poured the reaction mixture to ice cold water and extracted with EtOAc/DCM, dried over sodium sulfate. Solvents were removed and the crude product was purified by chromatography (EtOAc, followed by 2-10% MeOH/DCM) to get the required product as an off white solid (9.20 g, 62%). MS. MW calc. for $C_{122}H_{131}N_5O_{29}$: 2129.89, Found 2152.65 (M+Na).

Preparation of Solid Support 165:

Compound 163 (3.20 g, 1.408 mmol), succinic anhydride (0.2835 g, 2 eq) and DMAP (0.516 g, 3 eq.) were dissolved the DCM and stirred overnight. Reaction mixture was diluted with DCM, washed with water and cold dilute citric acid solution. DCM layer was dried over sodium sulfate and removed the solvent. The residue as filtered through a small pad of silica gel to the succinate as an off white solid as its TEA salt. MS: MW calc. for $C_{126}H_{135}N_5O_{32}$: 2229.91, Found 2252.90 (M+Na). Succinate (1.408 mmol) and HBTU (0.640 g, 1.2 eq.) were dissolved in DMF (200 mL). To that DIEA (1.22 mL, excess) was added and swirl the reaction for 3-4 minutes. Polystyrene support (20 g) was added to that and shaken the mixture for 24 hrs. Filtered through a frit and washed with DCM, 10% MeOH/DCM, DCM and ether. Solid support dried under vacuum for 2 hrs. It was capped with 25% $Ac_2O$/Py mixture for ½ hr. The same washing and drying procedure repeated to the solid support 161 (23.2 g, 54.7 umol/g loading).

Preparation of 166:

Compound 163 (4.01 g, 1.88 mmol) was dissolved in DCM (50 mL) and DIEA (0.65 mL, 3.75 mmol) was added. Amidite reagent (0.629 mL, 2.822 mmol) was added to this mixture and stirred the reaction mixture for 15 minutes. TLC checked and transferred the reaction mixture to a separatory funnel, washed with water and sodium bicarbonate solution. Dried over anhydrous sodium sulfate and removed the solvent. The crude product was purified by chromatography (30-80% Acetone/DCM) to get the product (4.20 g, 96%). $^{31}P$ NMR (CDCl$_3$, 400 MHz) δ=148.19, 147.79, 147.33. MS. MW calc. for $C_{131}H_{148}N_7O_{30}P$: 2330.00, Found 2353.20 (M+Na).

Example 10. Synthesis of Carbohydrate Conjugate Building Blocks

Synthesis of 171, 172, 173 and 174.

Building blocks 171 and 172 are synthesized using a procedure similar to that for synthesis of 103. Building blocks 173 and 174 are synthesized using a procedure similar to that for synthesis of 105.

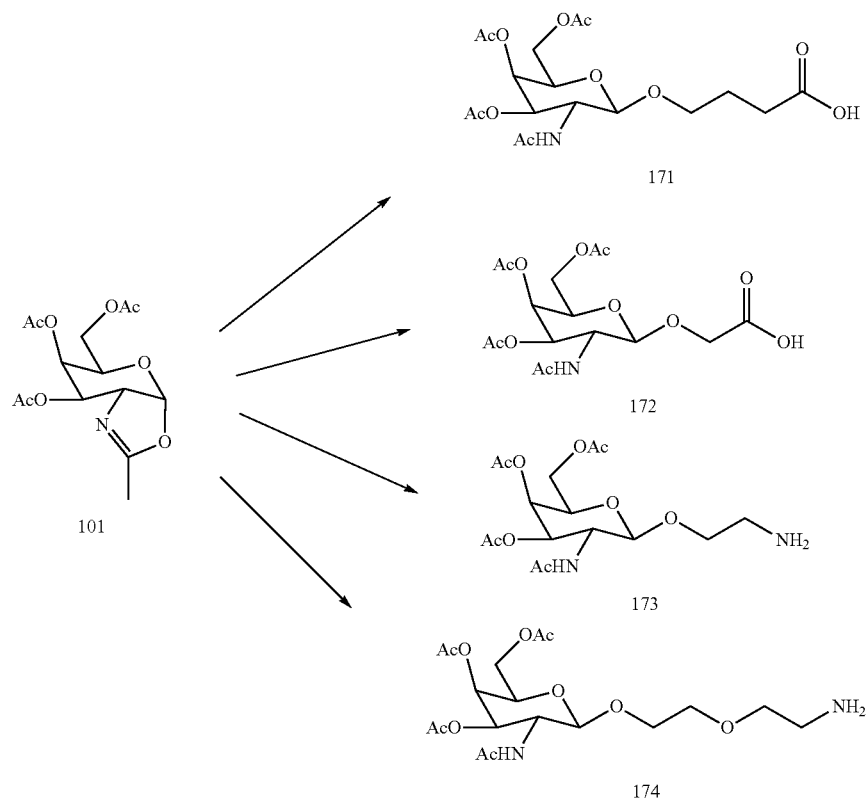 [SMILES: CC(=O)NC1C(OCCCC(=O)O)OC(COC(C)=O)C(OC(C)=O)C1OC(C)=O ; CC(=O)OCC1OC2OC(C)=NC2C(OC(C)=O)C1OC(C)=O ; CC(=O)NC1C(OCCN)OC(COC(C)=O)C(OC(C)=O)C1OC(C)=O ; CC(=O)NC1C(OCC(=O)O)OC(COC(C)=O)C(OC(C)=O)C1OC(C)=O ; CC(=O)NC1C(OCCOCCN)OC(COC(C)=O)C(OC(C)=O)C1OC(C)=O]
Synthesis of 180.
Building block 180 is synthesized using a procedure similar to that for synthesis of 110.
Scheme 2
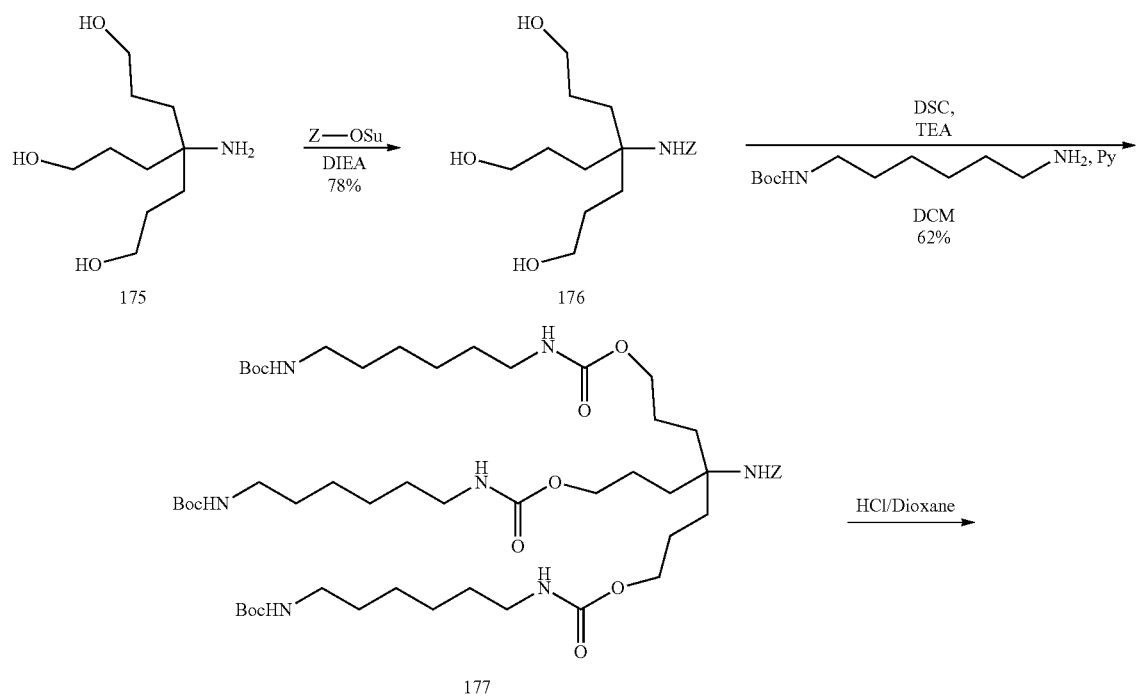

-continued
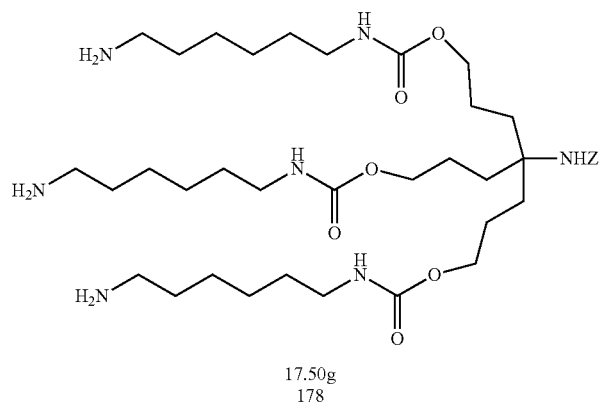
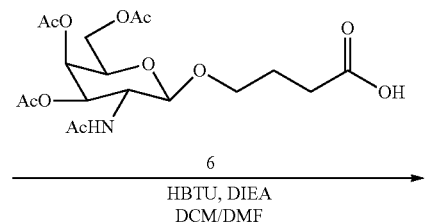
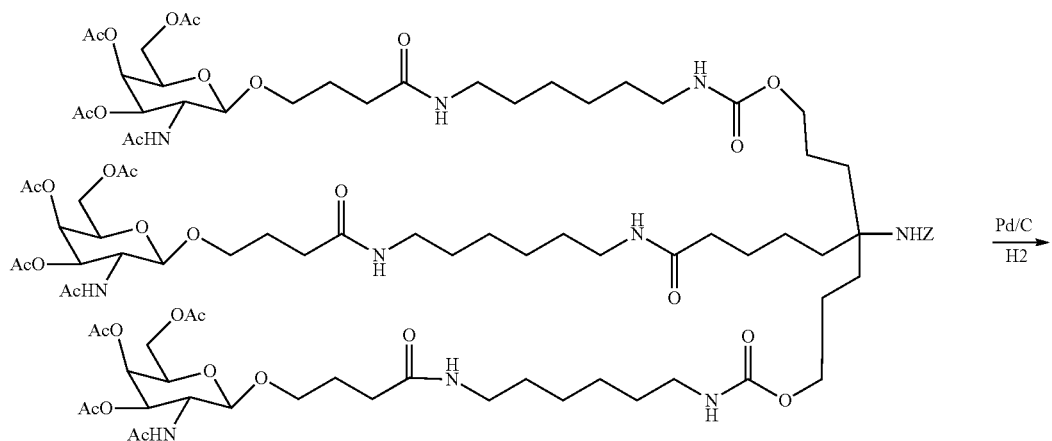
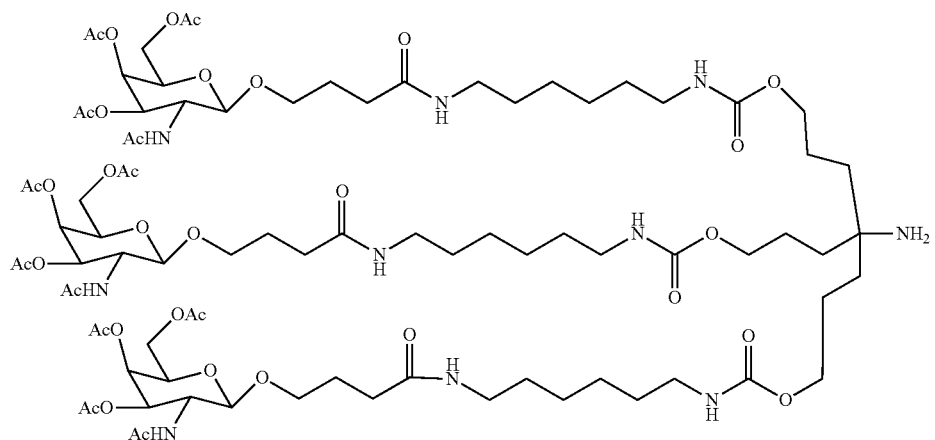

Synthesis of Building Block 188.
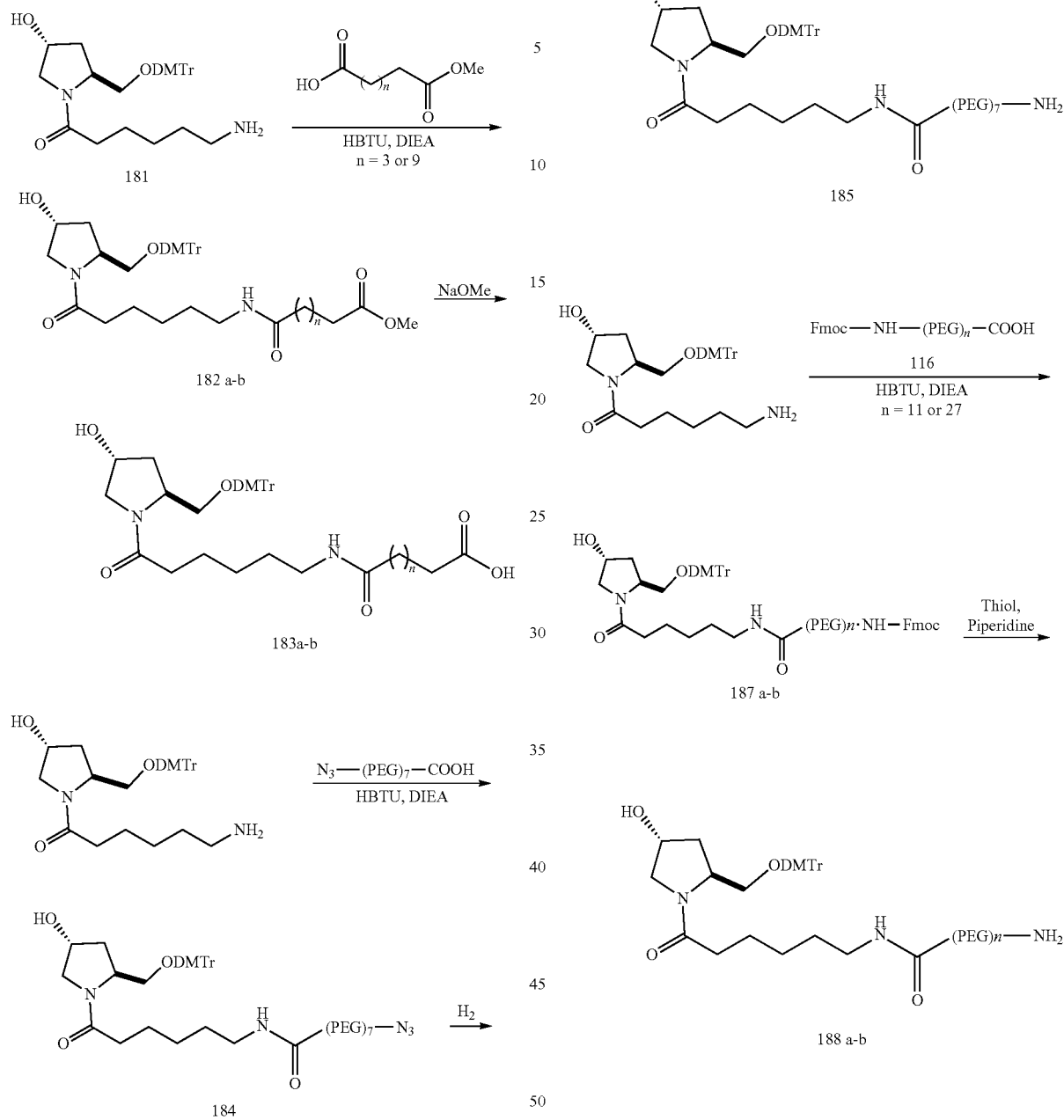
Example 11. Synthesis of Carbohydrate Conjugates
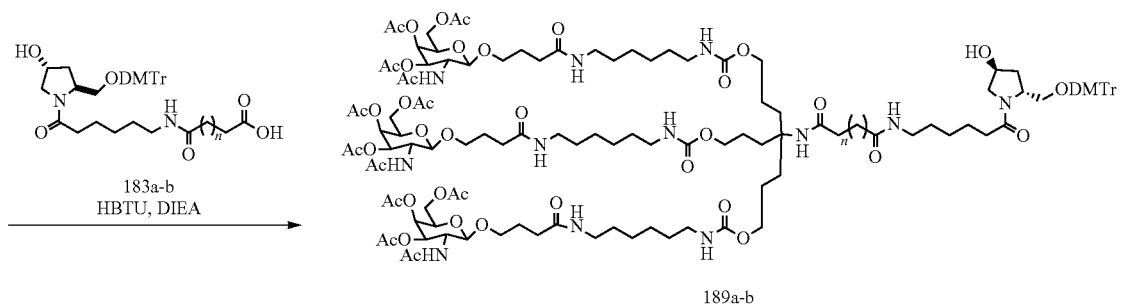
Scheme 4

-continued
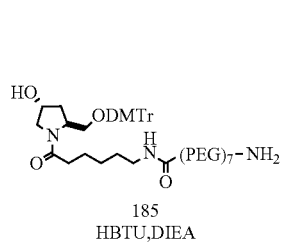 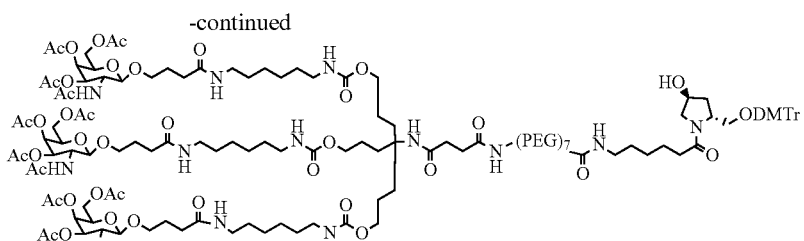
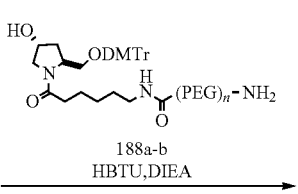 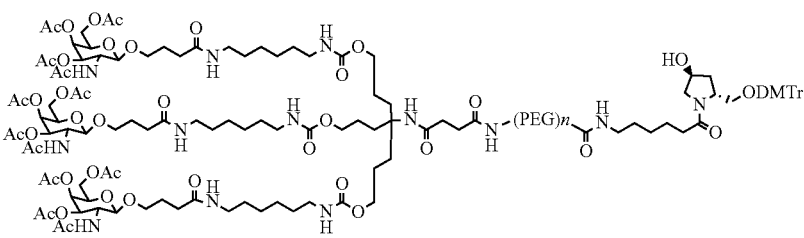
The building block 180 is coupled with amines 183, 185 and 188 to provide carbohydrate conjugates 189, 190 and 191 respectively.
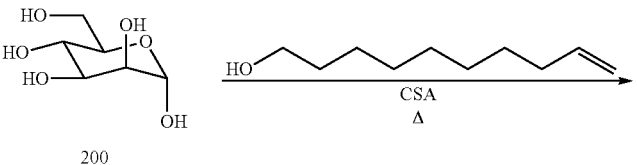
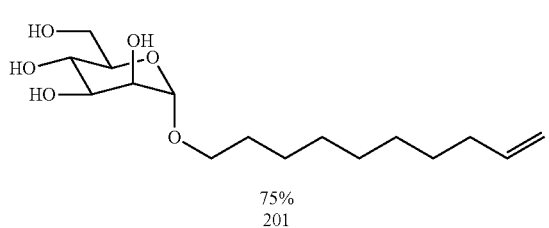 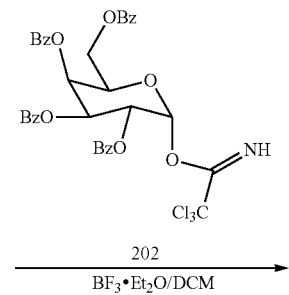
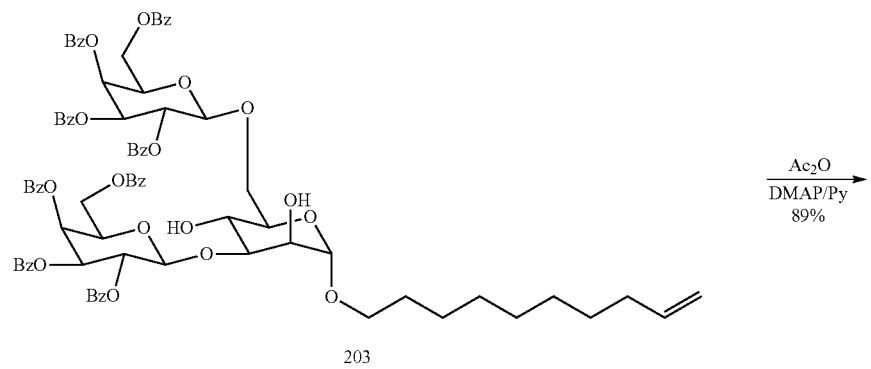

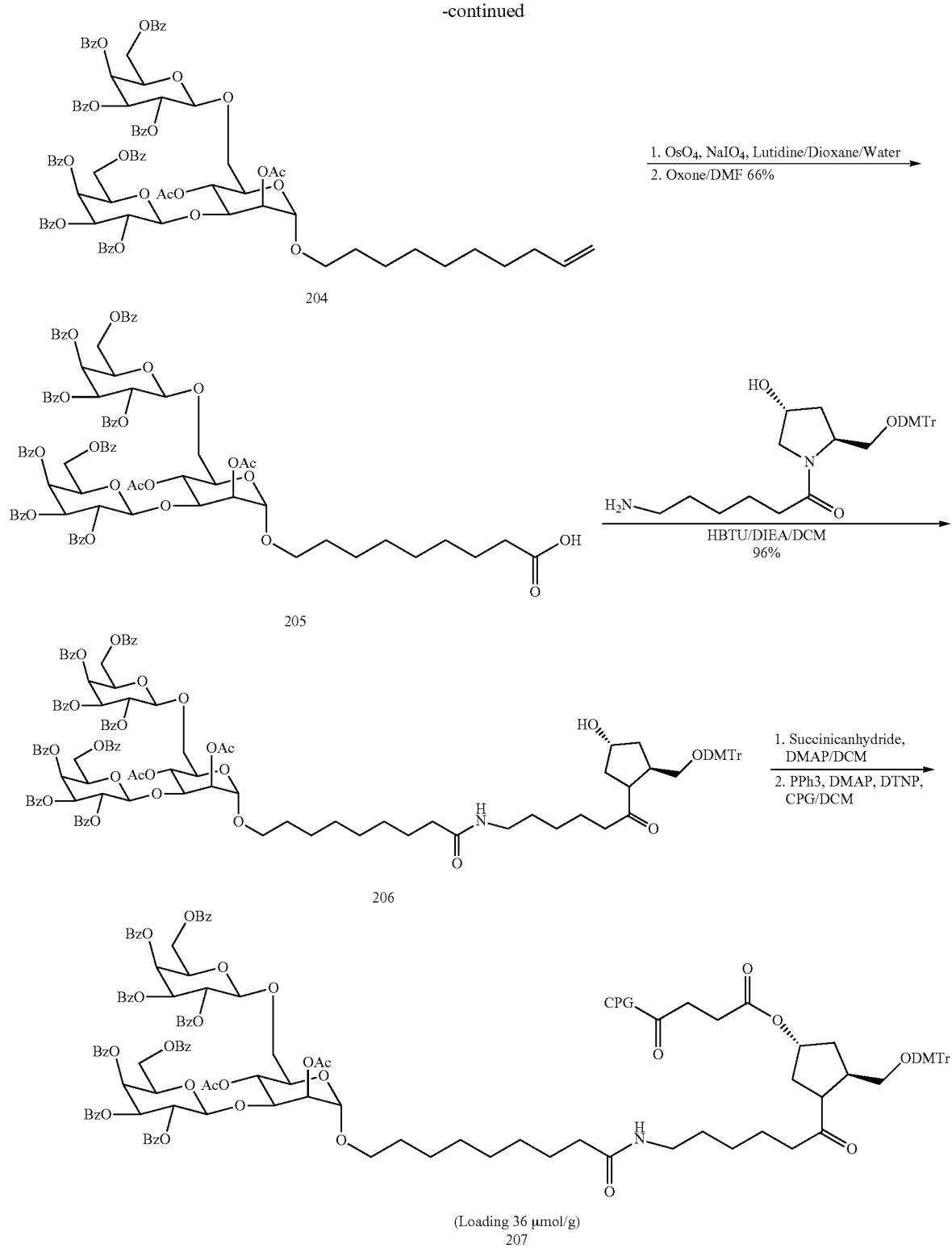

Preparation of 201:

Mannose (10.00 g, 55.53 mmol) and Decinol (100 g, solvent) and CSA (500 mg) were stirred at 110° C. in an oil bath for overnight. The color of the decinol turned to dark brown overnight. Bulk of the decinol was distilled out under reduced pressure. The residue was dissolved in DCM and neutralized with TEA. Extracted the solution with water and dried over sodium sulfate. Solvent was removed and the residue was purified by filtration through a small pad of silica gel, first ethyl acetate followed by 10-15% MeOH/DCM to get the product (7.52 g, 42%). $^1$H NMR (CDCl$_3$, 400 MHz) δ=5.90-5.75 (m, 1H), 5.02-4.85 (m, 2H), 4.00-

3.30 (m, 7H), 2.10-1.94 (m, 2H), 1.60-1.49 (m, 2H), 1.41-1.20 (m, 12H).

Preparation of 203:

Compound 201 (0.172 g, 0.541 mmol) was dissolved in anhydrous DCM (10 mL) under argon. MS was added to that and cooled the reaction in an ice bath. $BF_3.Et_2O$ (10 µl) was added to the reaction mixture with stirring. Galactose trichloroacetimidate 202 (1.00 g. 1.35 mmol) in 5 mL of DCM was added drop wise over a period of 15 minutes. Reaction was monitored by TLC, once the acceptor was finished the reaction was quenched with TEA and diluted with DCM, filtered off MS and dried. The residue was purified by chromatography (gradient elution 10-40% EtOAc/Hexane) to the compound as a white fluffy solid (0.550 g, 69%). $^1$H NMR (CDCl$_3$, 400 MHz) δ=7.95-7.20 (m, 40H), 5.90-5.50 (m, 7H), 5.35 (d, J=8.05 Hz, 1H), 5.17 (d, J=8.06 Hz, 1H), 4.98-4.81 (m, 3H), 4.65-4.09 (m, 9H), 3.81-3.42 (m, 5H), 3.20 (bs, 1H), 2.79 (bs, 1H), 2.01-1.88 (m, 2H), 1.30-0.92 (m, 12H). $^{13}$C NMR (CDCl$_3$, 100 MHz) δ=166.28, 166.20, 165.88, 165.76, 165.66, 165.64, 165.40, 139.34, 134.04, 133.82, 133.71, 133.66, 133.42, 133.30, 130.21, 129.99, 129.86, 129.70, 129.59, 129.28, 129.03, 129.00, 128.94, 128.77, 128.73, 128.63, 128.61, 128.54, 128.47, 128.44, 114.37, 102.74, 102.68, 98.81, 85.27, 72.43, 71.96, 71.37, 71.31, 71.01, 70.30, 70.26, 70.05, 68.31, 68.23, 67.41, 66.11, 62.63, 62.08, 33.96, 29.65, 29.58, 29.53, 29.58, 29.08, 26.20. MS. Molecular weight calculated for $C_{84}H_{82}O_{24}$, Cal. 1474.52, Found 1497.60 (M+Na).

Preparation of 204:

Compound 203 (0.104 g, 0.07 mmol) was dissolved in a mixture of DCM/Py (10 mL, 1:1). Ac$_2$O (0.5 mL, excess) and DMAP (0.050 g) and stirred the reaction overnight. The reaction was quenched with MeOH, solvents were removed and residue was purified by chromatography (gradient elution 10-30% EtOAc/Hexane) to the compound was white fluffy solid (0.108 g, 99%). $^1$H NMR (CDCl$_3$, 400 MHz) δ=8.10-7.20 (m, 40H), 5.99 (dd, J=3.1, 7.8 Hz, 2H), 5.88-5.75 (m, 2H), 5.70 (dd, J=7.82, 10.43 Hz, 1H), 5.65-5.47 (m, 2H), 5.10-4.07 (m, 13H), 3.90-3.80 (m, 1H), 3.69-3.61 (m, 1H), 3.36-3.28 (m, 1H), 2.98-2.81 (m, 1H), 2.08 (s, 3H), 2.10-2.01 (m, 4H), 1.35 (s, 3H), 1.42-1.20 (m, 12H). $^{13}$C NMR (CDCl$_3$, 100 MHz) δ=170.12, 170.08, 166.16, 165.67, 165.64, 165.48, 165.46, 164.78, 139.29, 133.80, 133.70, 133.70, 133.54, 133.44, 133.41, 133.35, 130.13, 130.02, 129.92, 129.69, 129.58, 129.49, 129.40, 129.15, 129.10, 128.88, 128.83, 128.79, 128.73, 128.66, 128.47, 128.40, 114.35, 102.32, 99.58, 96.64, 74.51, 72.11, 71.91, 71.46, 71.21, 69.78, 69.72, 69.51, 69.28, 68.19, 68.03, 67.82, 67.12, 61.97, 61.83, 33.94, 29.63, 29.61, 29.55, 29.49, 29.27, 29.20, 29.05, 26.11, 21.06, 20.02. MS: Molecular weight calculated for $C_{88}H_{86}O_{26}$, Cal. 1558.54, Found 1581.8 (M+Na).

Preparation of 205:

Compound 205 (1.36 g, 0.873 mmol) was dissolved in a mixture of Dioxane:Water (40 mL, 3:1). To the reaction mixture lutidine (0.203 mL, 2 eq), followed by OsO$_4$ solution (1 mL. 0.05M solution in $^t$Butanol) were added. Sodium periodate (0.774 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (20 mL) to that Oxone (0.590 g, 1.05 eq) and stirred at ambient temperature for 3 h. Once the starting material was consumed, 2 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound as a white solid (1.08 g 79%). $^1$H NMR (DMSO-d$_6$, 400 MHz) δ=11.96 (s, 1H), 8.00-7.23 (m, 40H), 5.85 (d, J=3.41 Hz, 1H), 5.82 (d, J=3.17 Hz, 1H), 5.79-5.63 (m, 2H), 5.56 (dd, J=8.00, 10.01 Hz, 1H), 5.41 (dd, J=8.00, 10.01 Hz, 1H), 5.25 (d, J=7.8 Hz, 1H), 5.15 (d, J=7.8 Hz, 1H), 4.90-4.35 (m, 7H), 4.10-3.55 (m, 4H), 3.30-3.20 (m, 1H), 2.96-2.87 (m, 1H), 2.18-2.10 (m, 2H), 1.96 (s, 3H), 2.01-1.95 (m, 1H), 1.51-1.39 (m, 2H), 1.27 (s, 3H), 1.20-1.01 (m, 12H). $^{13}$C NMR (CDCl$_3$, 100 MHz) δ=178.68, 178.48, 170.26, 170.16, 166.25, 165.78, 165.73, 165.70, 165.54, 165.53, 164.83, 133.85, 133.75, 133.60, 133.49, 130.18, 130.08, 128.85, 129.61, 129.52, 129.44, 129.20, 129.13, 128.91, 128.89, 128.81. 128.78, 128.71, 128.51, 128.45, 102.34, 99.67, 96.65, 74.60, 72.17, 71.94, 71.49, 71.21, 69.82, 69.79, 69.59, 69. 37, 68.22, 68.11, 67.81, 67.20, 64.55, 61.99, 61.85, 60.59, 44.06, 33.96, 30.79, 29.39, 29.31, 29.24, 29.20, 29.17, 29.08, 26.08, 24.85, 24.79, 22.20, 21.24, 21.11, 20.07.

MS: Molecular weight calculated for $C_{87}H_{84}O_{28}$, Cal. 1576.51, Found 1599.50 (M+Na).

Preparation of 206:

Compound 205 (0.850 g, 0.539 mmol), hydroxyl proline amine (0.300 g, 0.563 mmol) and HBTU (0.265 g, 0.698 mmol) were dissolved in DMF under argon. DIEA (0.281 mL, 3 eq.) was added to that and stirred for 3 hrs at ambient temperature. The reaction was monitored by TLC; once the starting material was consumed the mixture was poured in to an ice water mixture; extracted with ethyl acetate washed with water, brine and dried over sodium sulfate. Solvents was removed and the residue was purified by chromatography (first ethyl acetate followed by a gradient elution 3-10% MeOH/DCM) to get the product as a pale yellow solid (1.09 g, 96%). $^1$H NMR (CDCl$_3$, 400 MHz) δ=8.00-7.10 (m, 53H), 6.90-6.80 (m, 4H), 5.85 (d, J=3.41 Hz, 1H), 5.82 (d, J=3.17 Hz, 1H), 5.79-5.63 (m, 2H), 5.56 (dd, J=8.00, 10.01 Hz, 1H), 5.41 (dd, J=8.00, 10.01 Hz, 1H), 5.25 (d, J=7.8 Hz, 1H), 5.15 (d, J=7.8 Hz, 1H), 4.97 (d, J=4.15 Hz, 1H), 4.90-4.80 (m, 3H), 4.70-4.30 (m, 7H), 4.20-4.00 (m, 2H), 3.95-3.85 (m, 2H), 3.70 (s, 6H), 3.69-3.50 (m, 1H), 3.30-3.20 (m, 2H), 2.96-2.87 (m, 1H), 2.18-2.10 (m, 2H), 1.96 (s, 3H), 2.01-1.95 (m, 1H), 1.51-1.39 (m, 2H), 1.27 (s, 3H), 1.20-1.01 (m, 20H). $^{13}$C NMR (CDCl$_3$, 100 MHz) δ=171.87, 170.85, 169.46, 169.04, 165.25, 165.21, 165.09, 164.95, 164.48, 164.53, 162.29, 158.09, 157.97, 145.08, 135.87, 135.73, 134.04, 133.74, 133.56, 129.60, 129.18, 129.06, 128.91, 128.84, 128.81, 128.75, 128.67, 128.63, 128.52, 128.41, 127.77, 127.58, 113.19, 113.09, 102.30, 99.60, 96.60, 85.10, 75.68, 71.48, 70.02, 69.81, 68.99, 68.58, 66.55, 61.86, 6=54.96, 45.74, 38.27, 36.32, 35.76, 35.46, 34.15, 30.74, 28.69, 26.20, 25.34, 26.20, 25.34, 24.15, 20.48, 19.54. MS: Molecular weight calculated for $C_{119}H_{122}N_2O_{32}$, Cal. 2090.80, Found 2013.90 (M+Na).

Preparation of Long Alkyl Chain CPG 207:

Hydroxy derivative 206 (0.550 g, 0.263 mmol) was dissolved in DCM (10 mL) to that Succinic anhydride (0.078 g, 3 eq) and DMAP (0.128 g, 4 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate. PPh$_3$ (0.90 g, 1.3 eq.), DMAP (0.048 g, 1.5 eq.) and the succinate from the previous step were dissolved in a mixture of acetonitrile and DCM (6 mL). A solution of DTNP (0.086 g, 1.05 eq.) in DCM (1 mL)

was added to the above solution. The mixture was slowly shaken for 3-4 minutes. Long chain alkyl amine-CPG (lcaa CPG, 1.40 g, 133 µmol/g) was added to the mixture and gently shaken for 2 h. The CPG was filtered, successively washed with DCM, mixture of MeOH/DCM (1:9) and DCM until filtrate remained colorless and dried. The dried CPG was transferred into another flask treated with Ac₂O in pyridine (25%) in the presence of TEA (1 mL) for 15 min. under gentle shaking. Finally the CPG was filtered, washed with DCM, DCM:MeOH (9:1), followed by DCM and ether. The CPG 207 was dried under vacuum overnight and the loading was measured as reported (1.48 g, loading 36 µmol/g).

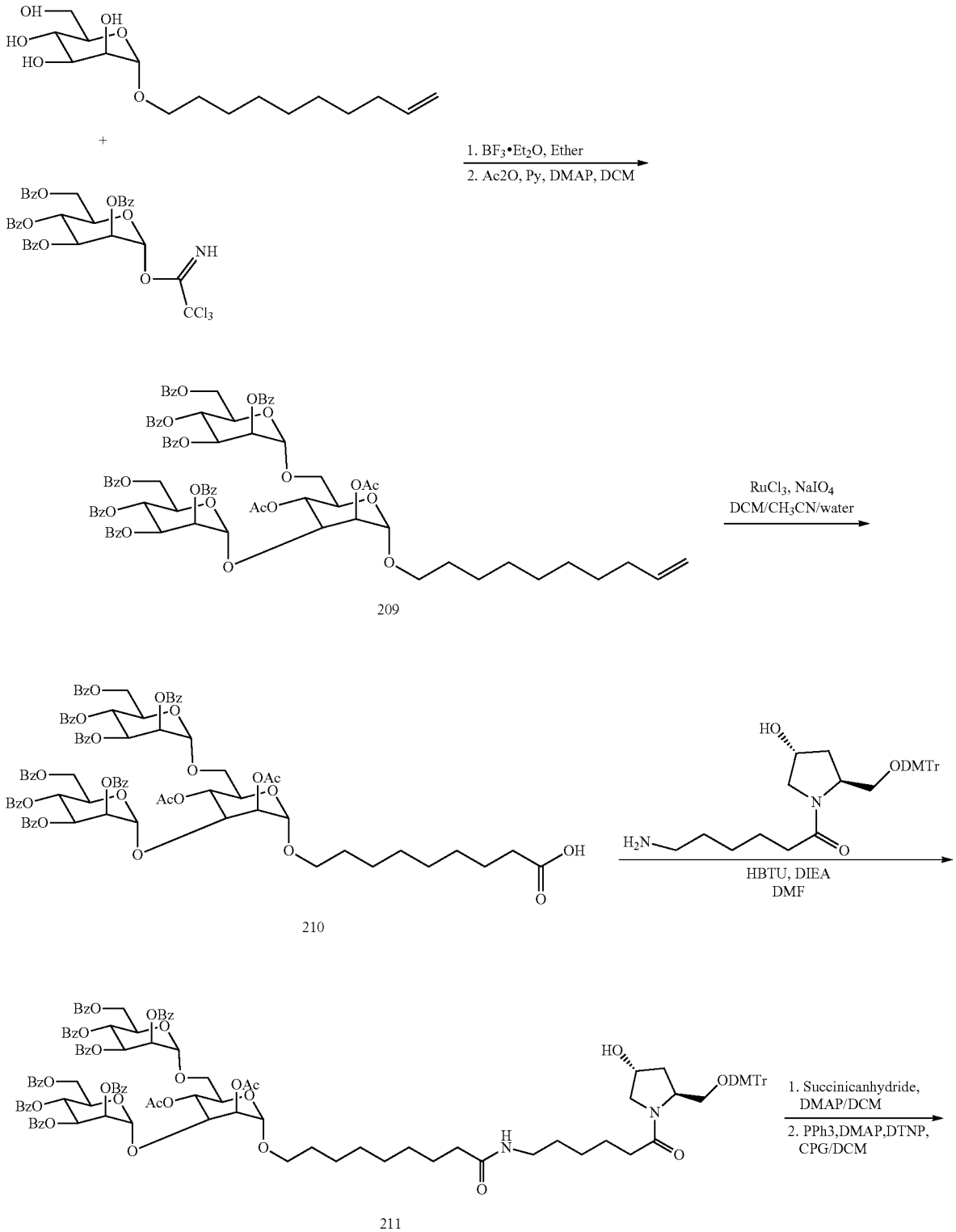

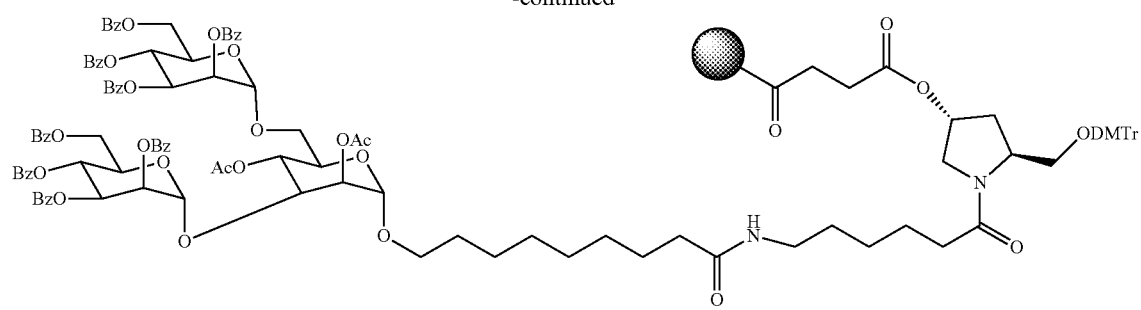
212
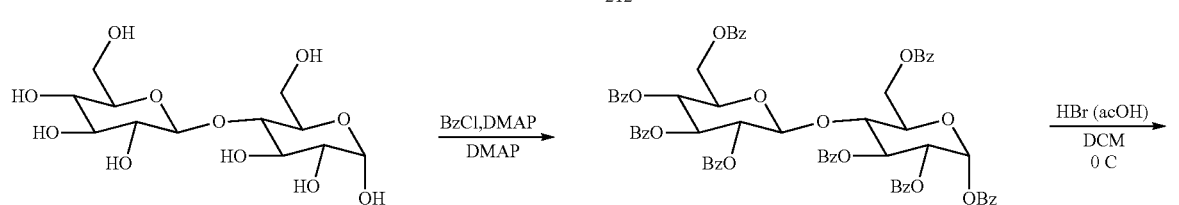
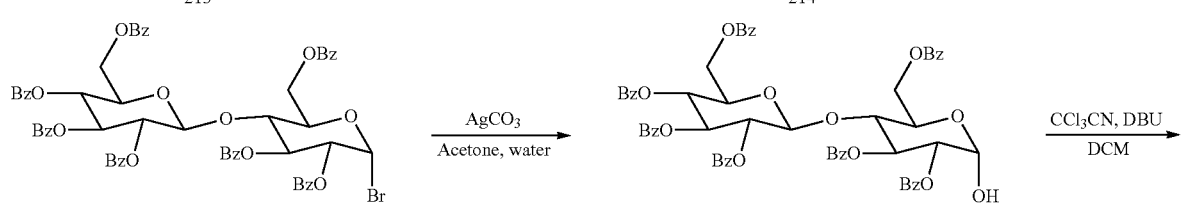
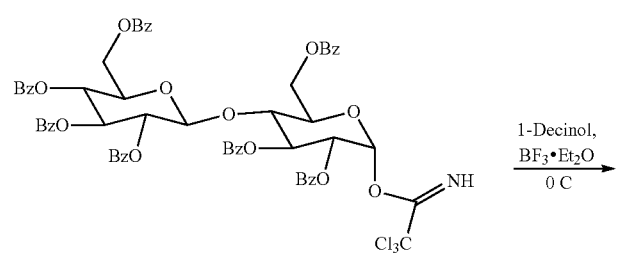
217
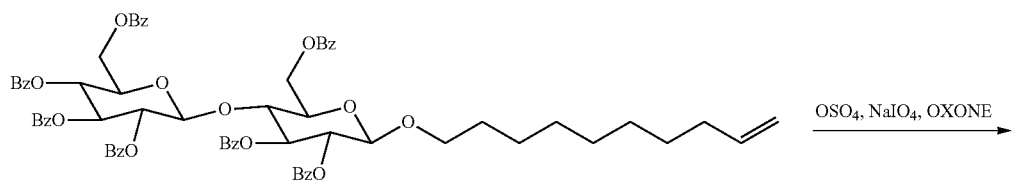
218
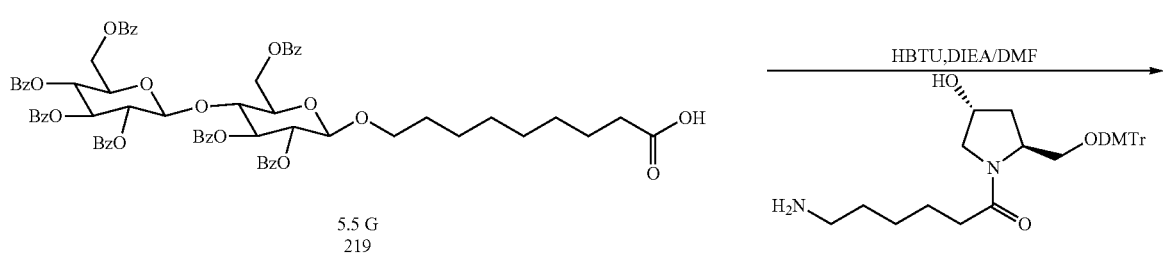
5.5 G
219

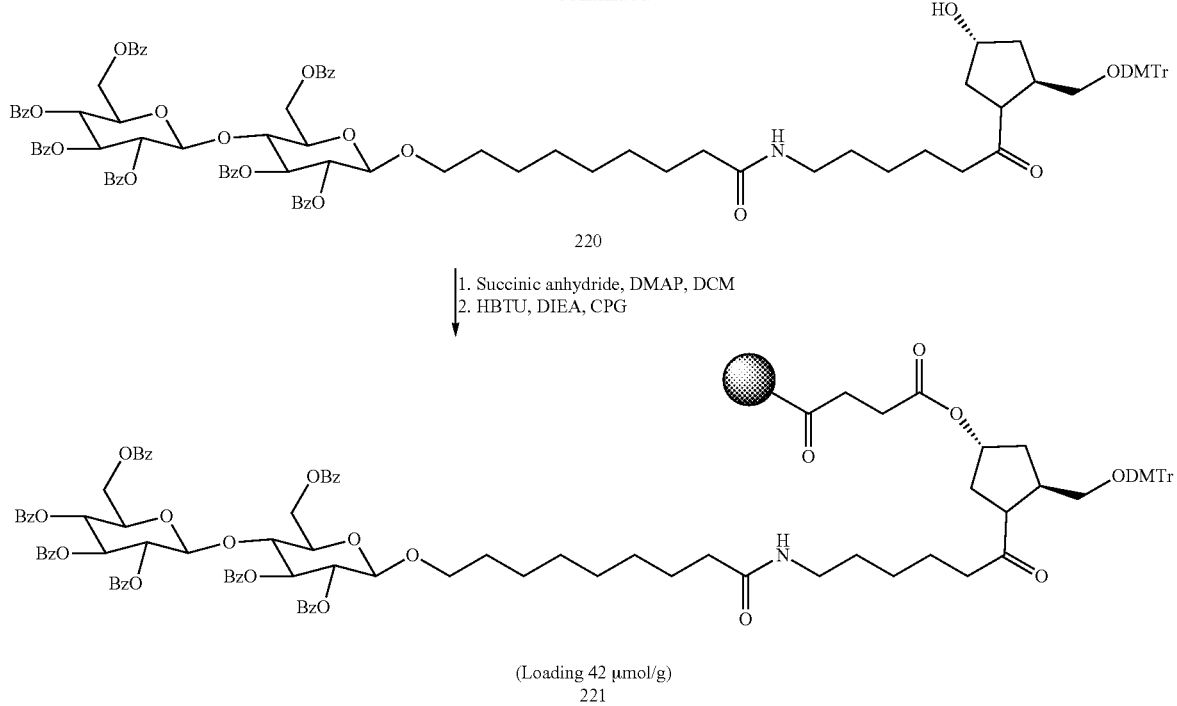

Compound 217 was synthesized according to the reported procedure (Martin, C.; Karen, P.; Laurence, V. Chem. Pharm. Bull. 2004, 52, 965-971.)

Preparation of 218:

1-Decinol (0.300 g, 1.92 mmol) and trichloroacetimidate 217 (2.33 g, 1.2 eq) was dissolved in anhydrous DCM (10 mL) under argon. MS was added to that and cooled the reaction in an ice bath. $BF_3.Et_2O$ (30 μl) was added to the reaction mixture with stirring. Reaction was monitored by TLC, once the donor reacted the reaction was quenched with TEA and diluted with DCM, filtered off MS and dried. The residue was purified by chromatography (gradient elution 10-40% EtOAc/Hexane) to the compound as a white fluffy solid (2.01 g, 86%). $^1$H NMR (CDCl$_3$, 400 MHz) δ=7.80-8.12 (m, 10H), 7.60-7.78 (m, 4H), 7.18-7.60 (m, 21H), 6.20-6.05 (m, 2H), 5.60-5.91 (m, 5H), 5.10-5.43 (m, 3H), 3.80-5.02 (m, 7H), 3.40-3.56 (m, 1H), 1.95-2.10 (m, 4H), 1.00-1.60 (m, 11H). $^{13}$C NMR (CDCl$_3$, 100 MHz) δ=169.89, 166.51, 166.40, 166.35, 166.32, 166.24, 166.10, 166.03, 165.99, 165.96, 165.86, 165.61, 165.46, 166.38, 165.34, 165.27, 165.23, 163.68, 139.36, 133.71, 133.67, 133.56, 133.40, 133.27, 133.21, 130.12, 130.05, 129.98, 129.95, 129.92, 129.88, 129.80, 129.77, 129.73, 129.68, 129.62, 129.55, 129.50, 129.47, 129.41, 129.40, 129.29, 129.14, 129.11, 129.03, 128.96, 128.87, 128.84, 128.83, 128.78, 128.76, 128.63, 128.56, 128.54, 128.48, 128.37, 128.26, 114.33, 114.26, 100.92, 100.84, 97.04, 96.52, 75.36, 75.17, 74.84, 73.37, 72.95, 72.90, 72.81, 72.57, 72.507, 71.94, 71.58, 71.05, 70.37, 70.27, 70.19, 70.06, 69.86, 69.24, 69.19, 69.02, 63.71, 63.56, 63.20, 62.93, 62.69, 33.96, 33.91, 32.93, 29.60, 29.53, 29.50, 29.46, 29.42, 29.33, 29.30, 29.22, 29.14, 29.06, 29.00. MS. Molecular weight calculated for $C_{71}H_{68}O_{18}$, Cal. 1208.44, Found 1231.4 (M+Na).

Preparation of 219:

Compound 218 (7.26 g, 6 mmol) was dissolved in a mixture of Dioxane:Water (100 mL, 3:1). To the reaction mixture lutidine (0.7 mL, 2 eq), followed by OsO$_4$ solution (5 mL. 0.05M solution in $^t$Butanol) were added. Sodium periodate (5.11 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (60 mL) to that Oxone (3.86 g, 1.05 eq) and stirred at ambient temperature for 3 h. Once the starting material was consumed, 10 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound 219 as a white solid (5.50 g 75%). $^1$H NMR (DMSO-d$_6$, 400 MHz) δ=12.00 (bs, 1H), 8.42-7.10 (m, 35H), 6.10-4.5 (m, 13H), 4.20-3.30 (m, 3H), 2.20-2.03 (m, 3H), 1.50-0.8 (11H). $^{13}$C NMR (DMSO-d$_6$, 100 MHz) δ=174.55, 174.51, 169.13, 165.59, 165.52, 165.39, 165.27, 165.24, 165.14, 164.99, 164.88, 164.75, 164.70, 164.66, 164.60, 164.54, 164.50, 162.92, 165.59, 165.51, 165.39, 165.27, 165.24, 165.14, 164.99, 164.88, 164.75, 164.70, 164.60, 164.54, 164.50, 133.80, 133.71, 133.58, 133.42, 133.29, 133.15, 129.88, 129.42, 129.36, 129.29, 129.23, 129.20, 129.12, 129.07, 129.05, 129.03, 128.91, 128.88, 128.72, 128.59, 128.48, 128.38, 99.96, 99.29, 99.22, 95.96, 95.64, 95.22, 93.10, 75.61, 74.86, 74.57, 74.37, 74.15, 73.59, 73.14, 72.58, 71.46, 71.15, 70.48, 70.31, 70.09, 69.97, 69.00, 68.87, 68.22, 67.81, 63.65, 62.49, 60.73, 59.76, 43.01, 33.68, 33.62, 32.54, 28.84, 28.82, 28.61, 28.55, 28.47, 28.40, 25.47, 25.21, 24.52, 24.43, 20.45. MS. Molecular weight calculated for $C_{70}H_{66}O_{20}$, Cal. 1226.41, Found 1249.4 (M+Na).

Preparation of 220:

Compound 219 (1.65 g, 1.37 mmol), hydroxyl proline amine (0.945 g, 1.3 eq) and HBTU (0.623 g, 1.64 mmol)

were dissolved in DMF under argon. DIEA (0.71 mL, 3 eq.) was added to that and stirred for 3 hrs at ambient temperature. The reaction was monitored by TLC; once the starting material was consumed the mixture was poured in to an ice water mixture; extracted with ethyl acetate washed with water, brine and dried over sodium sulfate. Solvents was removed and the residue was purified by chromatography (first ethyl acetate followed by a gradient elution 3-10% MeOH/EtOAc) to get the product 220 as a pale yellow solid (1.55 g, 65%). $^1$H NMR (DMSO-d$_6$, 400 MHz) δ=8.20-7.32 (m, 35H), 7.32-7.10 (m, 9H), 6.90-6.82 (m, 4H), 6.00-5.63 (m, 4H), 5.41-5.37 (m, 1H), 5.20-5.03 (m, 2H), 4.98 (d, J=4.15 Hz, 1H), 4.90 (d, J=4.15 Hz, 1H), 4.88-4.05 (m, 9H), 3.70 (s, 6H), 3.65-2.93 (m, 10H), 2.20-0.80 (m, 22H). $^{13}$C high vacuum to get the succinate. The succinate from the above step and HBTU (0.392 g, 1.2 eq) were dissolved in DMF (30 mL). DIEA (0.450 mL) was added to that and the mixture stirred for 5 minutes under argon. Long chain alkyl amine-CPG (lcaa CPG, 5.30 g, 133 μmol/g) was added to the mixture and gently shaken for 2 h. The CPG was filtered, successively washed with DMF, a mixture of DCM/MeOH, DCM and dried. The dried CPG was transferred into another flask treated with Ac$_2$O in pyridine (25%) in the presence of TEA (1 mL) for 15 min. under gentle shaking. Finally the CPG was filtered, washed with DCM, DCM:MeOH (9:1), followed by DCM and ether. The CPG 221 was dried under vacuum overnight and the loading was measured as reported (5.62 g, loading: 42 μmol/g).

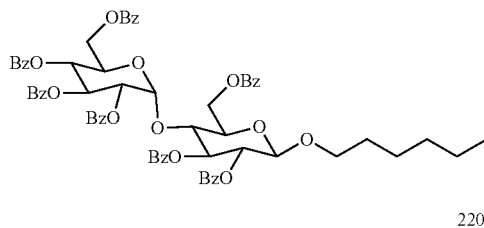

220

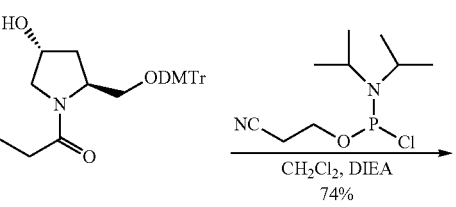

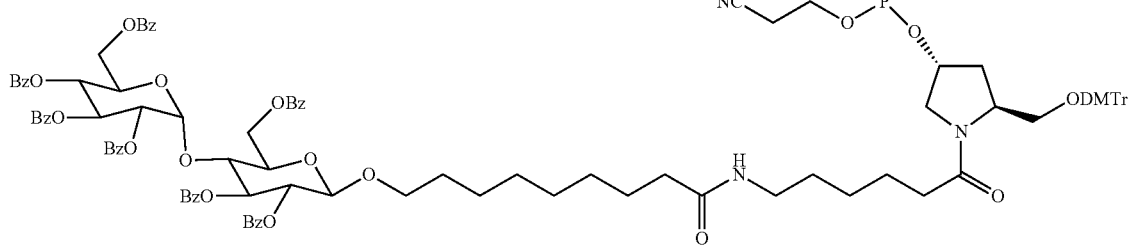

222

NMR (DMSO-d$_6$, 100 MHz) δ=171.81, 170.94, 170.90, 170.84, 165.56, 165.53, 165.49, 165.19, 165.12, 164.87, 164.72, 164.63, 164.58, 164.46, 158.09, 158.03, 157.96, 145.08, 144.74, 135.87, 135.73, 135.48, 135.42, 133.80, 133.57, 133.42, 133.29, 129.60, 129.55, 129.26, 129.20, 129.04, 129.00, 128.87, 128.74, 128.69, 128.59, 128.36, 128.34, 128.27, 128.02, 127.86, 127.77, 127.57, 126.74, 126.56, 113.19, 113.09, 99.26, 95.94, 85.77, 85.10, 74.83, 73.58, 72.55, 71.43, 70.44, 70.07, 69.01, 68.87, 68.58, 68.19, 67.45, 65.19, 63.29, 63.48, 63.33, 62.47, 59.75, 55.59, 54.99, 54.96, 53.44, 44.56, 38.21, 36.30, 35.76, 35.41, 34.15, 32.52, 30.74, 30.15, 29.09, 28.84, 28.66, 28.56, 28.52, 26.18, 25.27, 25.22, 24.54, 24.14. 21.22, 20.75, 20.71, 18.59, 14.07, 13.54 MS. Molecular weight calculated for C$_{102}$H$_{104}$N$_2$O$_{24}$, Cal. 1740.70, Found 1263.7 (M+Na).

Preparation of Long Alkyl Chain CPG 221:

Hydroxy derivative 220 (1.50 g, 0.862 mmol) was dissolved in DCM (20 mL) to that Succinic anhydride (0.174 g, 2 eq) and DMAP (0.316 g, 3 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under Hydroxy derivative 220 (0.200 g, 0.115 mmol) was dissolved in anhy. DCM (5 mL) to that DIEA (0.80 mL) and chloroamidite reagent (0.068 mL) was added and stirred overnight. The reaction was monitored by TLC, solvents were removed under reduced pressure and charged directly charged to a silica gel column (neutralized with TEA). First eluted with 2:1 (EtOAc/Hexane) followed by EtOAc to get the product (0.150 g, 67%). $^1$H NMR (CDCl$_3$, 400 MHz) δ=7.10-8.12 (m, 48H), 6.85-6.75 (m, 4H) 6.10 (t, J=10.19 Hz, 1H), 5.80-5.60 (m, 3H), 5.33-5.20 (m, 2H), 5.00-4.06 (m, 12H), 3.77 (s, 6H), 3.90-3.05 (m, 16H), 2.80-1.01 (27H). $^{31}$P(CDCl$_3$, 161 MHz) δ=145.83, 145.41, 144.95 MS. Molecular weight calculated for C$_{111}$H$_{121}$N$_4$O$_{25}$, Cal. 1940.81, Found 1963.80 (M+Na).

Example 12. RNA Synthesis and Duplex Annealing

1. Oligonucleotide Synthesis:

All oligonucleotides were synthesized on an AKTAoligopilot synthesizer or an ABI 394 synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2- cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis unless otherwise specified. The 2'-F phosphoramidites, 5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite were purchased from (Promega). All phosphoramidites were used at a concentration of 0.2M in acetonitrile ($CH_3CN$) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used.

Ligand conjugated strands were synthesized using solid support containing the corresponding ligand. For example, the introduction of carbohydrate moiety/ligand (for e.g., GalNAc) at the 3'-end of a sequence was achieved by starting the synthesis with the corresponding carbohydrate solid support. Similarly a cholesterol moiety at the 3'-end was introduced by starting the synthesis on the cholesterol support. In general, the ligand moiety was tethered to trans-4-hydroxyprolinol via a tether of choice as described in the previous examples to obtain a hydroxyprolinol-ligand moiety. The hydroxyprolinol-ligand moiety was then coupled to a solid support via a succinate linker or was converted to phosphoramidite via standard phosphitylation conditions to obtain the desired carbohydrate conjugate building blocks. See Examples 1-11 for details. Fluorophore labeled siRNAs were synthesized from the corresponding phosphoramidite or solid support, purchased from Biosearch Technologies. The oleyl lithocholic $(GalNAc)_3$ polymer support made in house at a loading of 38.6 μmol/gram. The Mannose $(Man)_3$ polymer support was also made in house at a loading of 42.0 μmol/gram.

Conjugation of the ligand of choice at desired position, for example at the 5'-end of the sequence, was achieved by coupling of the corresponding phosphoramidite to the growing chain under standard phosphoramidite coupling conditions unless otherwise specified. An extended 15 min coupling of 0.1M solution of phosphoramidite in anhydrous $CH_3CN$ in the presence of 5-(ethylthio)-1H-tetrazole activator to a solid bound oligonucleotide. Oxidation of the internucleotide phosphite to the phosphate was carried out using standard iodine-water as reported (1) or by treatment with tert-butyl hydroperoxide/acetonitrile/water (10:87:3) with 10 min oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent The cholesterol phosphoramidite was synthesized in house, and used at a concentration of 0.1 M in dichloromethane. Coupling time for the cholesterol phosphoramidite was 16 minutes.

Syntheses of 3'—Cholesterol-3'—Carbohydrate containing oligonucleotides was accomplished by coupling of the cholesterol phosphoramidite to the desired carbohydrate bearing solid support followed by coupling of the nucleoside phosphoramdites. PEGylated Oligonucleotides with or without a second ligand was obtained by post-synthetic conjugation of the corresponding PEG-NHS ester to amino-linked sequence. The amino linker was introduced at desired position in a sequence by using a corresponding trans-4-hydroxyprolinol based amino linker or commercially available amino linkers. For example, syntheses of 3'-PEG-3'-GalNAc containing oligonucleotides was accomplished by coupling of trans-4-hydroxyprolinol-amino linker phosphoramidite to the desired GalNAc bearing solid support followed by coupling of the nucleoside phosphoramdites. The oligonucleotide thus obtained was subjected to post-synthetic conjugation with PEG-NHS ester between pH 7.5 and 9 in sodium bicarbonate buffer depends on the nature of the sequence.

2. Deprotection-I (Nucleobase Deprotection)

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia:ethanol (3:1)] for 6.5 h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 ml by roto-vap. The mixture was then frozen on dry ice and dried under vacuum on a speed vac.

3. Deprotection-II (Removal of 2' TBDMS Group)

The dried residue was resuspended in 26 ml of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction was then quenched with 50 ml of 20 mM sodium acetate and pH adjusted to 6.5, and stored in freezer until purification.

4. Analysis

The oligoncuelotides were analyzed by high-performance liquid chromatography (HPLC) prior to purification and selection of buffer and column depends on nature of the sequence and or conjugated ligand.

5. PEGylation of Sugar Conjugated Oligonucleotides

Oligonucleotide containing functionalized with an amino linker was treated with PEG-NHS ester of desired molecular weight in sodium bicarbonate buffer between pH 7.5 and 9.0. The progress of the reaction was monitored by HPLC. After completion of the reaction the PEGylated oligonucleotide was purified by HPLC and analyzed by MS.

5. HPLC Purification

The ligand conjugated oligonucleotides were purified reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotides were diluted in water to 150 μl and then pipetted in special vials for CGE and LC/MS analysis. Compounds were finally analyzed by LC-ESMS and CGE.

6. siRNA Preparation

For the preparation of siRNA, equimolar amounts of sense and antisense strand were heated in 1×PBS at 95° C. for 5 min and slowly cooled to room temperature. Integrity of the duplex was confirmed by HPLC analysis.

TABLE 2

GalNAc Conjugated duplexes

| Target | Duplex ID | SEQ ID No. | S/AS | Sequence 5'-3' |
|---|---|---|---|---|
| PCSK9 | AD-3672 | 23 | A-30693 | GccuGGAGuuuAuucGGAAdTdTsL96 |
|  |  | 24 | A-18242 | PUUCCGAAUAAACUCCAGGCdTsdT |
| PCSK9 | AD-3673 | 25 | A-30693 | GccuGGAGuuuAuucGGAAdTdTsL96 |
|  |  | 26 | A-30696 | PuUfcCfgAfaUfaAfaCfuCfcAfgGfcdTdTsL10 |
| PCSK9 | AD-3674 | 27 | A-30694 | GccuGGAGuuuAuucGGAAdTdTsQ11L96 |
|  |  | 28 | A-18242 | PUUCCGAAUAAACUCCAGGCdTsdT |
| PCSK9 | AD-3718 | 29 | A-30983 | GccuGGAGuuuAuucGGAAdTdTsL101 |
|  |  | 30 | A-18242 | PUUCCGAAUAAACUCCAGGCdTsdT |
| PCSK9 | AD-3627 | 31 | A-30824 | GccuGGAGuuuAuucGGAAdTdTL96 |
|  |  | 32 | A-18242 | PUUCCGAAUAAACUCCAGGCdTsdT |
| PCSK9 | AD-3628 | 33 | A-30824 | GccuGGAGuuuAuucGGAAdTdTL96 |
|  |  | 34 | A-30682 | PuUfcCfgAfaUfaAfaCfuCfcAfgGfcdTdTL43 |
| PCSK9 | AD-3629 | 35 | A-16865 | GccuGGAGuuuAuucGGAAdTsdT |
|  |  | 36 | A-18242 | PUUCCGAAUAAACUCCAGGCdTsdT |
| PCSK9 | AD-3671 | 37 | A-16865 | GccuGGAGuuuAuucGGAAdTsdT |
|  |  | 38 | A-30693 | GccuGGAGuuuAuucGGAAdTdTsL96 |
| apoB | AD-6490 | 39 | A-5296 | 5'-GGAAUCuuAuAuuuGAUCcAsA |
|  |  | 40 | A-5475 | uuGGAUcAAAuAuAAGAuUCcscsU |
| apoB | AD-5544 | 41 | A-5474 | GGAAUCuuAuAuuuGAUCcAAsL10 |
|  |  | 42 | A-5475 | uuGGAUcAAAuAuAAGAuUCcscsU |
| apoB | AD-3697 | 43 | A-30863 | GGAAUCuuAuAuuuGAUCcAAsL96 |
|  |  | 44 | A-5475 | uuGGAUcAAAuAuAAGAuUCcscsU |
| apoB | AD-3698 | 45 | A-30864 | GGAAUCuuAuAuuuGAUCcAAsQ11L96 |
|  |  | 46 | A-5475 | uuGGAUcAAAuAuAAGAuUCcscsU |
| apoB | AD-3699 | 47 | A-30863 | GGAAUCuuAuAuuuGAUCcAAsL96 |
|  |  | 48 | A-30865 | uuGGAUcAAAuAuAAGAuUCccsUsL10 |
| apoB | AD-3717 | 49 | A-30982 | GGAAUCuuAuAuuuGAUCcAAsL101 |
|  |  | 50 | A-5475 | uuGGAUcAAAuAuAAGAuUCcscsU |
| apoB | AD-18117 | 51 | A-5474 | GGAAUCuuAuAuuuGAUCcAAsL10 |
|  |  | 52 | A-31849 | Q38uuGGAUcAAAuAuAAGAuUCcscsU |
| apoB | AD-18118 | 53 | A-30863 | GGAAUCuuAuAuuuGAUCcAAsL96 |
|  |  | 54 | A-31849 | Q38uuGGAUcAAAuAuAAGAuUCcscsU |
| apoB | AD-18119 | 55 | A-30864 | GGAAUCuuAuAuuuGAUCcAAsQ11L96 |
|  |  | 56 | A-31849 | Q38uuGGAUcAAAuAuAAGAuUCcscsU |
| apoB | Ad-18648 | 57 | A-31644 | GGAAUCuuAuAuuuGAUCcAAsQ11L90 |
|  |  | 58 | A-5475 | uuGGAUcAAAuAuAAGAuUCcscsU |
| apoB | AD-18649 | 59 | A-31649 | GGAAUCuuAuAuuuGAUCcAAsQ51Q11L96 |
|  |  | 60 | A-5475 | uuGGAUcAAAuAuAAGAuUCcscsU |
| apoB | AD-18650 | 61 | A-32147 | GGAAUCuuAuAuuuGAUCcAAsQ11L80 |
|  |  | 62 | A-5475 | uuGGAUcAAAuAuAAGAuUCcscsU |
| apoB | AD-18651 | 63 | A-32148 | Q11-GGAAUCuuAuAuuuGAUCcAAsL96 |
|  |  | 64 | A-5475 | uuGGAUcAAAuAuAAGAuUCcscsU |
| apoB | AD-18652 | 65 | A-32801 | GGAAUCuuAuAuuuGAUCcAAsQ11L110 |
|  |  | 66 | A-5475 | uuGGAUcAAAuAuAAGAuUCcscsU |
| apoB |  | 67 | A-34132 | GGAAUCuuAuAuuuGAUCcAAsQ8L110 |
|  |  | 68 | A-5475 | uuGGAUcAAAuAuAAGAuUCcscsU |
| apoB |  | 69 | A-34133 | GGAAUCuuAuAuuuGAUCcAAsQ90L110 |
|  |  | 70 | A-5475 | uuGGAUcAAAuAuAAGAuUCcscsU |
| apoB |  | 71 | A-34134 | Q8GGAAUCuuAuAuuuGAUCcAAsL110 |
|  |  | 72 | A-5475 | uuGGAUcAAAuAuAAGAuUCcscsU |

TABLE 2-continued

GalNAc Conjugated duplexes

| Target | Duplex ID | SEQ ID No. | S/AS | Sequence 5'-3' |
|---|---|---|---|---|
| apoB |  | 73 | A-34135 | Q90GGAAUCuuAuAuuuGAUCcAAsL110 |
|  |  | 74 | A-5475 | uuGGAUcAAAuAuAAGAuUCcscsU |
| apoB | AD-19031 | 75 | A-33593 | GGAAUCuuAuAuuuGAUCcAAsQ11L117 |
|  |  | 76 | A-5475 | uuGGAUcAAAuAuAAGAuUCcscsU |
| apoB |  | 77 | A-34176 | GGAAUCuuAuAuuuGAUCcAAsL117 |
|  |  | 78 | A-5475 | uuGGAUcAAAuAuAAGAuUCcscsU |
| apoB |  | 79 | A-32800 | GGAAUCuuAuAuuuGAUCcAAsL110 |
|  |  | 80 | A-5475 | uuGGAUcAAAuAuAAGAuUCcscsU |
| apoB |  | 81 | A-34156 | GGAAUCuuAuAuuuGAUCcAAsL82 |
|  |  | 82 | A-5475 | uuGGAUcAAAuAuAAGAuUCcscsU |
| apoB |  | 83 | A-34157 | GGAAUCuuAuAuuuGAUCcAAsL83 |
|  |  | 84 | A-5475 | uuGGAUcAAAuAuAAGAuUCcscsU |
| FVII | AD-18572 | 85 | A-31843 | GGAUfCfAUfCfUfCfAAGUfCfUfUfACfdTdTsL96 |
|  |  | 86 | A-31848 | Q11GUfAAGACfUfUfGAGAUfGAUfCfCfdTsdT |
| FVII | AD-18567 | 87 | A-31844 | GGAUfCfAUfCfUfCfAAGUfCfUfUfACfdTdTsQ51Q11L96 |
|  |  | 88 | A-4724 | GUfAAGACfUfUfGAGAUfGAUfCfCfdTsdT |
| FVII | AD-18568 | 89 | A-31845 | GGAUfCfAUfCfUfCfAAGUfCfUfUfACfdTdTsQ11L90 |
|  |  | 90 | A-4724 | GUfAAGACfUfUfGAGAUfGAUfCfCfdTsdT |
| FVII | AD-18569 | 91 | A-31846 | GGAUfCfAUfCfUfCfAAGUfCfUfUfACfdTdTsQ11L80 |
|  |  | 92 | A-4724 | GUfAAGACfUfUfGAGAUfGAUfCfCfdTsdT |
| FVII | AD-18570 | 93 | A-31847 | Q11GGAUfCfAUfCfUfCfAAGUfCfUfUfACfdTdTsL96 |
|  |  | 94 | A-4724 | GUfAAGACfUfUfGAGAUfGAUfCfCfdTsdT |
| FVII | AD-18571 | 95 | A-32817 | GGAUfCfAUfCfUfCfAAGUfCfUfUfACfdTdTsQ11L110 |
|  |  | 96 | A-4724 | GUfAAGACfUfUfGAGAUfGAUfCfCfdTsdT |
| FVII |  | 97 | A-35052 | GGAUCAUCUCAAGUCUUACdTsdTsL10 |
|  |  | 98 | A-4724 | GUfAAGACfUfUfGAGAUfGAUfCfCfdTsdT |
| FVII |  | 99 | A-33571 | GGAUfCfAUfCfUfCfAAGUfCfUfUfACfdTdTsL116 |
|  |  | 100 | A-4724 | GUfAAGACfUfUfGAGAUfGAUfCfCfdTsdT |
| FVII |  | 101 | A-33572 | GGAUfCfAUfCfUfCfAAGUfCfUfUfACfdTdTsQ92L96 |
|  |  | 102 | A-4724 | GUfAAGACfUfUfGAGAUfGAUfCfCfdTsdT |
| FVII |  | 103 | A-4639 | GGAUCAUCUCAAGUCUUACdTdT |
|  |  | 104 | A-4640 | GUAAGACUUGAGAUGAUCCdTdT |
| FVII |  | 105 | A-34128 | GGAUfCfAUfCfUfCfAAGUfCfUfUfACfdTdTsQ8L110 |
|  |  | 106 | A-4724 | GUfAAGACfUfUfGAGAUfGAUfCfCfdTsdT |
| FVII |  | 107 | A-34129 | GGAUfCfAUfCfUfCfAAGUfCfUfUfACfdTdTsQ90L110 |
|  |  | 108 | A-4724 | GUfAAGACfUfUfGAGAUfGAUfCfCfdTsdT |
| FVII |  | 109 | A-34130 | Q8GGAUfCfAUfCfUfCfAAGUfCfUfUfACfdTdTsL110 |
|  |  | 110 | A-4724 | GUfAAGACfUfUfGAGAUfGAUfCfCfdTsdT |
| FVII |  | 111 | A-34131 | Q90GGAUfCfAUfCfUfCfAAGUfCfUfUfACfdTdTsL110 |
|  |  | 112 | A-4724 | GUfAAGACfUfUfGAGAUfGAUfCfCfdTsdT |
| FVII | AD-19032 | 113 | A-33573 | GGAUfCfAUfCfUfCfAAGUfCfUfUfACfdTdTsQ11L117 |
|  |  | 114 | A-4724 | GUfAAGACfUfUfGAGAUfGAUfCfCfdTsdT |
| FVII | AD-19033 | 115 | A-33570 | GGAUfCfAUfCfUfCfAAGUfCfUfUfACfdTdTsQ91L96 |
|  |  | 116 | A-4724 | GUfAAGACfUfUfGAGAUfGAUfCfCfdTsdT |

TABLE 2-continued

GalNAc Conjugated duplexes

| Target | Duplex ID | SEQ ID No. | S/AS | Sequence 5'-3' |
|---|---|---|---|---|
| FVII | AD-18047 | 117 | A-31841 | GGAUfCfAUfCfUfCfAAGUfCfUfUfACfdTdTsQ11L96 |
|  |  | 118 | A-4724 | GUfAAGACfUfUfGAGAUfGAUfCfCfdTsdT |

Note:
S is PS linkge, lowercase is 2'-O-methyl nucleotide, Nf is 2'-fluoro nucleotide, P is a phosphate group, L10 is N-(cholesterylcarboxamidocaproyl)-4-hydroxyprolinol (Hyp-C6-Chol), L43 is Quasar 570 CPG (BG5-5063, Biosearch Tech), L80 is N-[tris(GalNAc-alkyl)-amidohexanoyl-carboxamidoethyl-dithio-butyryl]-4-hydroxyprolinol(Hyp-S-S-(GalNAc-alkyl)3), L82 is PEG 5K CarboxymethylNHS, L83 is PEG 20K CarboxymethylNHS, L96 is N-[tris(GalNAc-alkyl)-amidodecanoyl]-4-hydroxyprolinol (Hyp-(GalNAc-alkyl)3), L110 is N-[N'N"-(bis(GalNAc-alkyl)-lysine)-aminocapryl]-4-hydroxyprolinol (Hyp-Lys-(GalNAc-alkyl)2), L101 is Hyp-(GalNAc-TEG)3-LCO, L116 is N-(lithocholylcarboxamidocaproyl)-4-hydroxyprolinol (Hyp-C6-lithocholic acid), Q8 is N-(aminocaproyl)prolinol-4-phosphate, Q11 is N-(cholesterylcarboxamidocaproyl)prolinol-4-phosphate, Q38 is Quasar 570 phosphate (BNS-5063, Biosearch Tech), Q90 is N-(PEG(20K) pentylcarboxamidocaproyl)-4-hydroxyprolinol, Q91 is N-(myristylcarboxamidocaproyl)-4-hydrodroxyprolinol (Hyp-C6-C14). Q92 is N-(lithocholylcarboxamidocaproyl)-4-hydroxyprolinol (Hyp-C6-lithocholic acid), Q51 is6-hydroxyhexyldithiohexylphosphate (Thiol-Modifier C6 S-S Glen Res. 10-1936) and L117 is N-[N',N"-(bis(glucose-alkyl)-lysine)-aminocapryl]-4-hydroxyprolinol (Hyp-Lys-(Gluc-alky 1)2).

TABLE 3

Conjugated single strands

| Alnylam No | SEQ ID No | Project | sequence | calc. MW | obs. MW |
|---|---|---|---|---|---|
| ALSQ-3465 | 119 | ApoB | GUCAUCACACUGAAUACCAAUsL36 | 7512.0 | 7574.3 |
| ALSQ-3466 | 120 | ApoB | Q11GUCAUCACACUGAAUACCAAUsL36 | 8216.0 | 8279.2 |
| ALSQ-3467 | 121 | ApoB | GUCAUCACACUGAAUACCAAUQ11sL36 | 8216.0 | 8279.2 |
| ALSQ-3613 | 122 | Eg5 | oCoUGAAGAoCoCoUGAAGAoCAAoUdTdTsL49 | 7587.2 | 7586.1 |
| ALSQ-3617 | 123 | Eg5 | oCoUGAAGAoCoCoUGAAGAoCAAoUdTdTsQ38Q49 | 8360.0 | 8358.9 |
| ALSQ-3618 | 124 | Luc | CUUACGCUGAGUACUUCGAdTdTsL49 | 7395.8 | 7394.9 |
| ALSQ-3619 | 125 | Luc | Q38CUUACGCUGAGUACUUCGAdTdTsL49 | 8016.0 | 8014.4 |
| ALSQ-31013 | 126 |  | 5' cuGGcuGAAuuucAGAGcAdTdT-(Man)3 3' |  |  |

Note:
oN is 2'-O-methyl ucleotide, lowercase is 2'-F nucleotide, s is PS linkage, L36 is galactose moiety derived from support 207, L49 is maltose moiety derived from support 221, Q11 is cholesterol-hydroxyprolinol moiety, Q38 is maltose moiety derived from phosphoramidite 222, (MAN)₃ is a trivalent mannose conjugate at 3'-end

Example 13: Animal Testing in Mice

Bolus dosing of formulated siRNAs in C57/BL6 mice (5/group, 8-10 weeks old, Charles River Laboratories, MA) was performed by low volume tail vein injection using a 27G needle. For AD-3629, AD-3671, AD-3672, AD-3673 and AD-3674 dosing was carried out on three consecutive days at 100 mg/kg. Mice were kept under an infrared lamp for approximately 3 min prior to dosing to ease injection. 48 hour post last dose mice were sacrificed by $CO_2$-asphyxiation. 0.2 ml blood was collected by retro-orbital bleeding and the liver was harvested and frozen in liquid nitrogen. Serum, livers and ileums were stored at −80° C. Total serum cholesterol in mouse serum was measured using the Wako Cholesterol E enzymatic colorimetric method (Wako Chemicals USA, Inc., Richmond, Va., USA) according to manufacturer's instructions. Measurements were taken on a VERSA Max Tunable microplate reader (Molecular Devices, Sunnyvale, Calif.) using SoftMax Pro software. Message levels of the target gene ApoB were measured via bDNA analysis as below.

bDNA Analysis:

Frozen livers and ileums were grinded using 6850 Freezer/Mill Cryogenic Grinder (SPEX CentriPrep, Inc) and powders stored at −80° C. until analysis. PCSK9 mRNA levels were detected using the branched-DNA technology based QuantiGene Reagent System (Panomics, Fremont, Calif., USA) according to the protocol. 10-20 mg of frozen liver powders was lysed in 600 ul of 0.3 ug/ml Proteinase K (Epicentre, #MPRK092) in Tissue and Cell Lysis Solution (Epicentre, #MTC096H) at 65° C. for overnight. Then 10 ul of the lysates were added to 90 ul of Lysis Working Reagent (1 volume of stock Lysis Mixture in two volumes of water) and incubated at 55° C. overnight on Panomics capture plates with probe sets specific to mouse PCSK9 and mouse GAPDH (Panomics, USA). Capture plates then were processed for signal amplification and detection according to the protocol and chemiluminescence was read as relative light units (RLUs) on a microplate luminometer Victor2-Light (Perkin Elmer). The ratio of PCSK9 mRNA to GAPDH mRNA in liver and ileum lysates was averaged over each treatment group and compared to a control group treated with PBS Results:

As shown in Table 6, as compared to the PBS control, treatment with compounds AD-3673, and AD-3674 resulted in significant (~50%) and (~76%) lowering of PCSK9 transcript levels in mouse liver and ileum (as indicated by a smaller PCSK9 to GAPDH transcript ratio when normalized to a PBS control group), indicating that the conjugated siRNA molecules were active in vivo. As shown in Table 4, the silencing activity translated in lowering of total cholesterol by 32 and 46% respectively in those animals.

−80° C. until analysis. ApopB and GAPDH mRNA levels were detected using the branched-DNA technology based QuantiGene Reagent System (Panomics, Fremont, Calif., USA) according to the protocol. 10-20 mg of frozen liver powders was lysed in 1000 ul of 0.3 ug/ml Proteinase K (Epicentre, #MPRK092) in Tissue and Cell Lysis Solution (Epicentre, #MTC096H) at 65° C. for 40 minutes. Then 10 ul of the lysates were added to 90 ul of Lysis Working Reagent (1 volume of stock Lysis Mixture in two volumes of water) and incubated at 55° C. overnight on Panomics capture plates with probe sets specific to mouse ApoB and mouse GAPDH (Panomics, USA). Capture plates then were processed for signal amplification and detection according to

TABLE 4

Efficacy of GalNAc PCSK9 conjugates in mice.
Efficacy of GalNAc PCSK9 conjugates in mice C57BL6 N = 6/group
3 × 100 mg/kg , Sac 1 day post last injection
All data normalized to PBS control

|  | Sense strand | Antisense strand | Liver PCSK9/ GAPDH | SD | Ileum PCSK9/ GAPDH | SD | Serum Cholesterol | SD |
| --- | --- | --- | --- | --- | --- | --- | --- | --- |
| PBS |  |  | 1.00 | 0.22 | 1.00 | 0.20 | 1.00 | 0.07 |
| AD-3629 | A-16865 | A-18242 | 0.73 | 0.14 | 1.09 | 0.24 | 0.89 | 0.05 |
| AD-3671 | A-16865 | A-30696 | 0.90 | 0.24 | 1.08 | 0.29 | 0.70 | 0.06 |
| AD-3672 | A-30693 | A-18242 | 0.86 | 0.22 | 0.95 | 0.13 | 0.91 | 0.08 |
| AD-3673 | A-30693 | A-30696 | 0.50 | 0.07 | 0.98 | 0.13 | 0.68 | 0.05 |
| AD-3674 | A-30694 | A-18242 | 0.24 | 0.07 | 0.42 | 0.17 | 0.54 | 0.04 |

Example 14: Silencing Activity of Cholesterol-(GalNAc)3 Conjugated siRNAs Relative to Cholesterol Only Conjugated siRNAs Bolus dosing of formulated siRNAs in C57/BL6 mice (3/group, 8-10 weeks old, Charles River Laboratories, MA) was performed by low volume tail vein injection using a 27G needle. Dosing was carried out on three consecutive days at 100 mg/kg. Mice were wither sacrificed 24 hour post last dose and organs harvested and frozen in liquid nitrogen or blood was withdrawn on days 1, 2, 5, 8, 11 and 15 post last dose. Harvested serum, livers and ileums were stored at −80° C. Total serum cholesterol was measured using the Modified Trinder Methodology Cholesterol Test from Stanbio Laboratory (Boerne, Tex., USA) according to manufacturer's instructions. Measurements were taken on a VERSA Max Tunable microplate reader (Molecular Devices, Sunnyvale, Calif.) using SoftMax Pro software.

bDNA Analysis:

Frozen livers were grinded using 6850 Freezer/Mill Cryogenic Grinder (SPEX CentriPrep, Inc) and powders stored at the protocol and chemiluminescence was read as relative light units (RLUs) on a microplate luminometer Victor2-Light (Perkin Elmer). The ratio of ApoB mRNA to GAPDH mRNA in liver lysates was averaged over each treatment group and compared to a control group treated with PBS Results:

As shown in FIG. 31, as compared to the Cholesterol conjugated siRNA, treatment with cholesterol-(GalNAc)3 conjugated siRNA resulted in significant lowering of ApoB transcript levels (~65% vs ~10%, as indicated by a smaller ApoB to GAPDH transcript ratio when normalized to a PBS control group), indicating that the cholesterol-(GalNAc)3 conjugated siRNAs have superior knockdown compared to just the cholesterol conjugated siRNAs. The silencing activity translated in lowering of total cholesterol by ~50% and ~90% respectively for cholesterol only and cholesterol-(GalNAc)3 conjugated siRNAs as compared to PBS control.

As shown in FIG. 32, the cholesterol-(GalNAc)3 conjugated siRNA (AD-3698) showed improved and longer duration of lowering of total cholesterol than cholesterol only conjugated siRNAs (AD-5544), ~15 days versus ~10 days.

TABLE 5

Sequences for comparison of cholesterol conjugated and cholesterol-(GalNAc)₃ conjugated siRNAs.

| Duplex # | Strand # | Strand Type | SEQ ID NO: | Sequence |
| --- | --- | --- | --- | --- |
| 18117 | 5474 | Sense | 127 | GGAAUCuuAuAuuuGAUCcAAsQ11 |
|  | 31849 | Anti Sense | 128 | Q38uuGGAUcAAAuAuAAGAuUCcscsU |
| 18118 | 30863 | Sense | 129 | GGAAUCuuAuAuuuGAUCcAAsL96 |
|  | 31849 | Anti Sense | 130 | Q38uuGGAUcAAAuAuAAGAuUCcscsU |

TABLE 5-continued

Sequences for comparison of cholesterol conjugated and cholesterol-(GalNAc)₃ conjugated siRNAs.

| Duplex # | Strand # | Strand Type | SEQ ID NO: | Sequence |
|---|---|---|---|---|
| 18119 | 30864 | Sense | 131 | GGAAUCuuAuAuuuGAUCcAAsQ11L96 |
|  | 31849 | Anti Sense | 132 | Q38uuGGAUcAAAuAuAAGAuUCcscsU |
| 3698 | 30864 | Sense | 133 | GGAAUCuuAuAuuuGAUCcAAsQ11L96 |
|  | 5475 | Anti Sense | 134 | uuGGAUcAAAuAuAAGAuUCcscsU |
| 5544 | 5474 | Sense | 135 | GGAAUCuuAuAuuuGAUCcAAsQ11 |
|  | 5475 | Anti Sense | 136 | uuGGAUcAAAuAuAAGAuUCcscsU |

Lower case letters represent 2'-O-Me modified nucleotides; Chol is cholesterol, L96 is N-[tris(GalNAc-alky)-amidodecanoyl]-4-hydroxyprolinol Hyp-(GalNAc-alkyl)3; Q11 is N-(cholesterylcarboxamidocaproyl)prolinol-4-phosphate, s is phosphorothioate linkage, Q38 is Quasar-570 (Cy3 dye).

Example 15. Comparison of Uptake of Cy3 Labeled siRNA with Cholesterol Conjugated siRNA Versus Cholesterol-(GalNAc)3 Conjugated siRNA Bolus dosing of Cy3-labeled siRNAs in C57/BL6 mice (3/group, 16-19 gram body weight, Charles River Laboratories, MA) was performed by tail vein injection. Mice were kept under an infrared lamp for approximately 3 min prior to dosing to ease injection. AD-18117, AD-18118, AD-18119, and PBS dosing was carried out by one single bolus injection at 100 mg/kg. 15 minutes or 3 hour post dose mice were anesthetized with avertin (240 mg/kg), and then perfused with 4% paraformaldehyde/phosphate-buffered saline. The mouse livers were fixed in 4% paraformaldehyde overnight and then in 20% sucrose/phosphate-buffered saline overnight. Tissues were then embedded in O.C.T. compound (Tissue-Tek Optimal Cutting Temperature Compound; Sahura, Torrance, Calif.) and sections were cut at 6 µm with a cryostat maintained at −20° C. The slides were analyzed using Carl Zeiss AxioVision microscopy. As shown in FIG. 32, cholesterol-(GalNAc)3 conjugated siRNA (AD-18119) had superior cellular uptake relative to a cholesterol only (AD-18117) or (GalNAc)3 only (AD-1188) conjugated siRNAs.

Example 16. In Vivo Silencing of FVII with Carbohydrate Conjugated siRNAs

Figure 39:
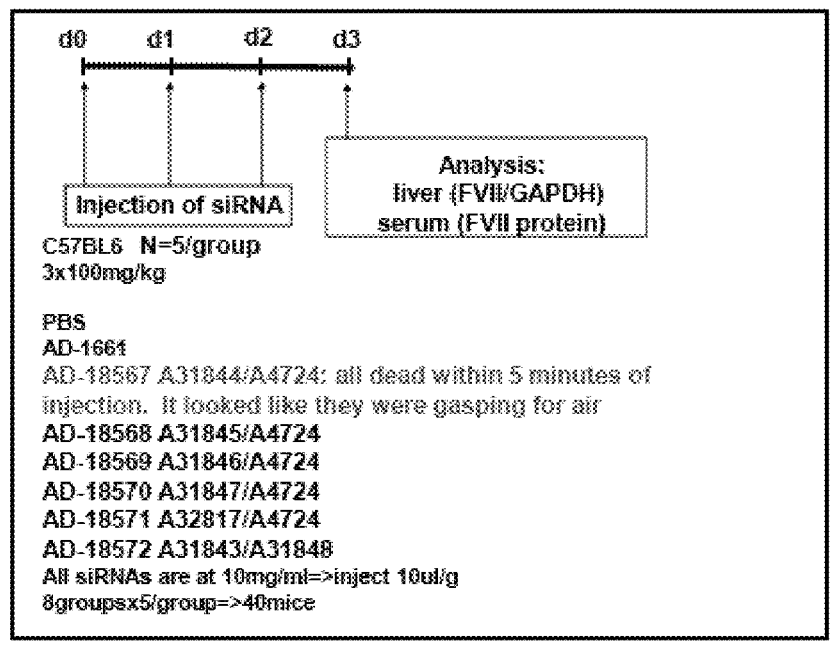
FIGS. 39A-39C. In vivo silencing of FVII with carbohydrate conjugated siRNAs.
Figure 39:
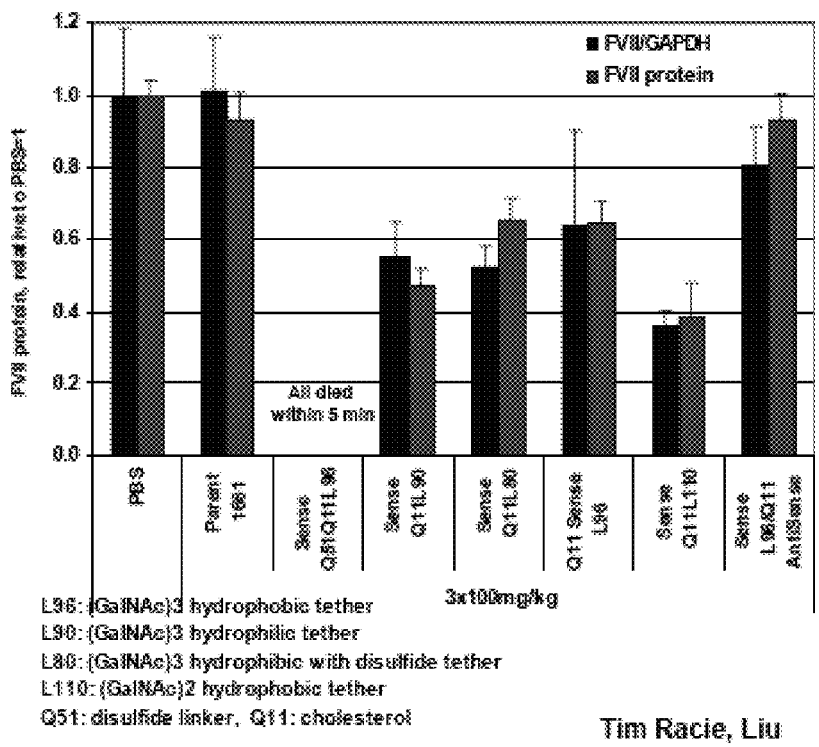
Figure 40:
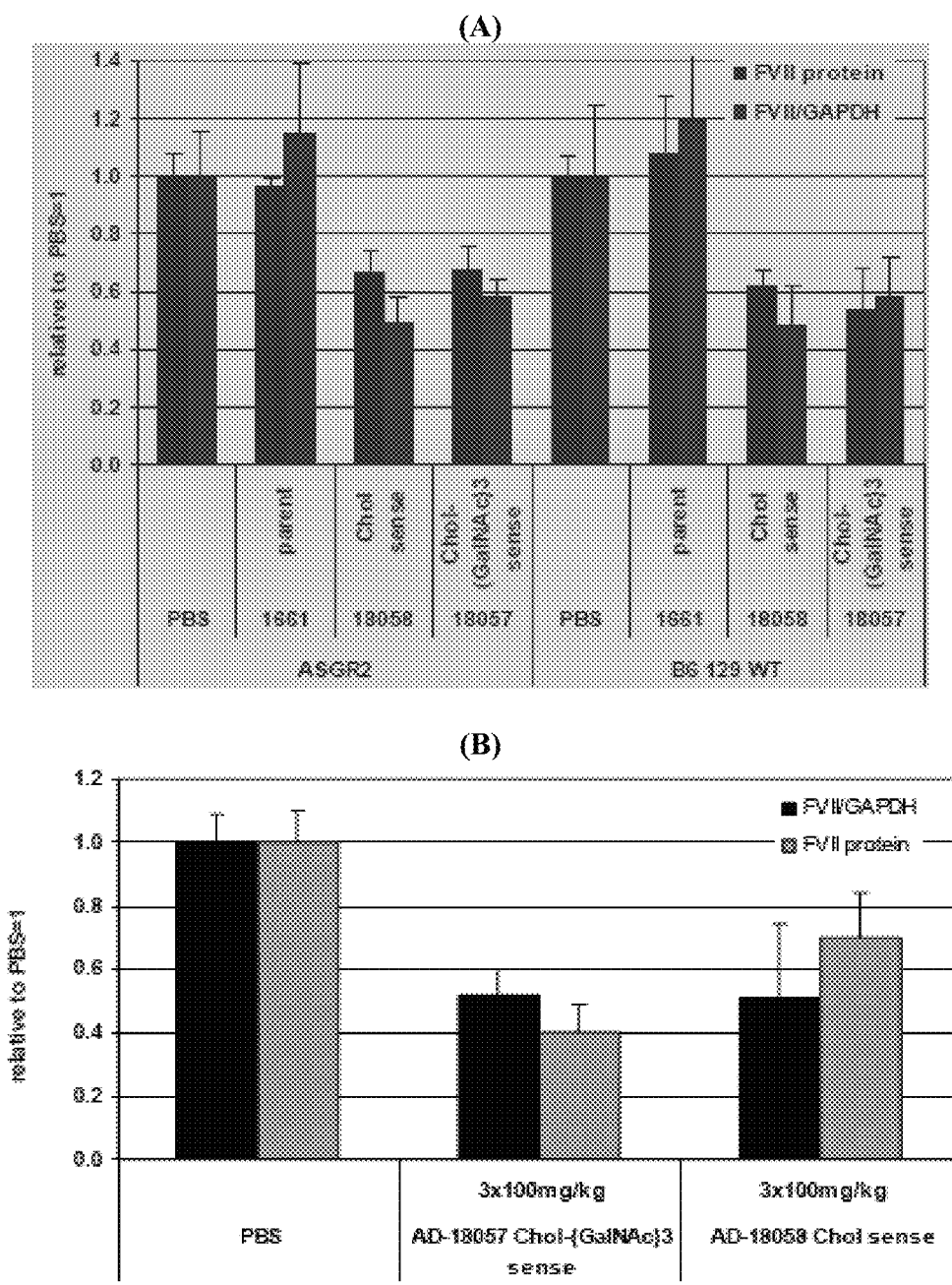
FIG. 40. In vivo silencing of FVII with various carbohydrate-conjugated siRNAs. (A) shows the results of in vivo silencing of FVII with various carbohydrate-conjugated siRNAs; and (B) shows the results of in vivo silencing of FVII with various carbohydrate-conjugated siRNAs.

Experimental design is shown in FIG. 39A.

FIGS. 39A-39C and FIGS. 40 (A and B) show the results of in vivo silencing of FVII with carbohydrate conjugated siRNAs.

Figure 41A:
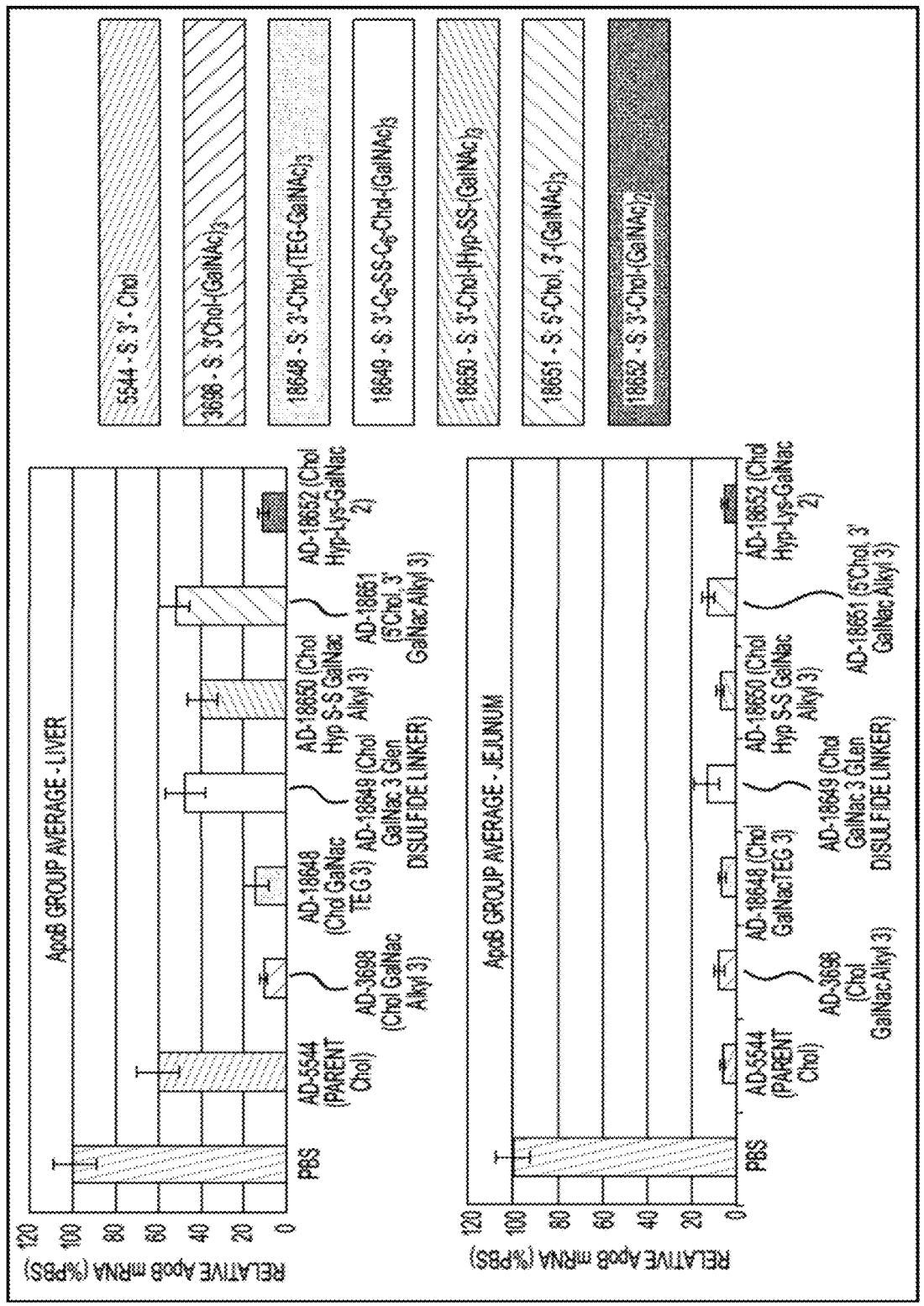
FIGS. 41A-41B. In vivo silencing of ApoB with carbohydrate conjugated siRNAs.
Figure 41B:
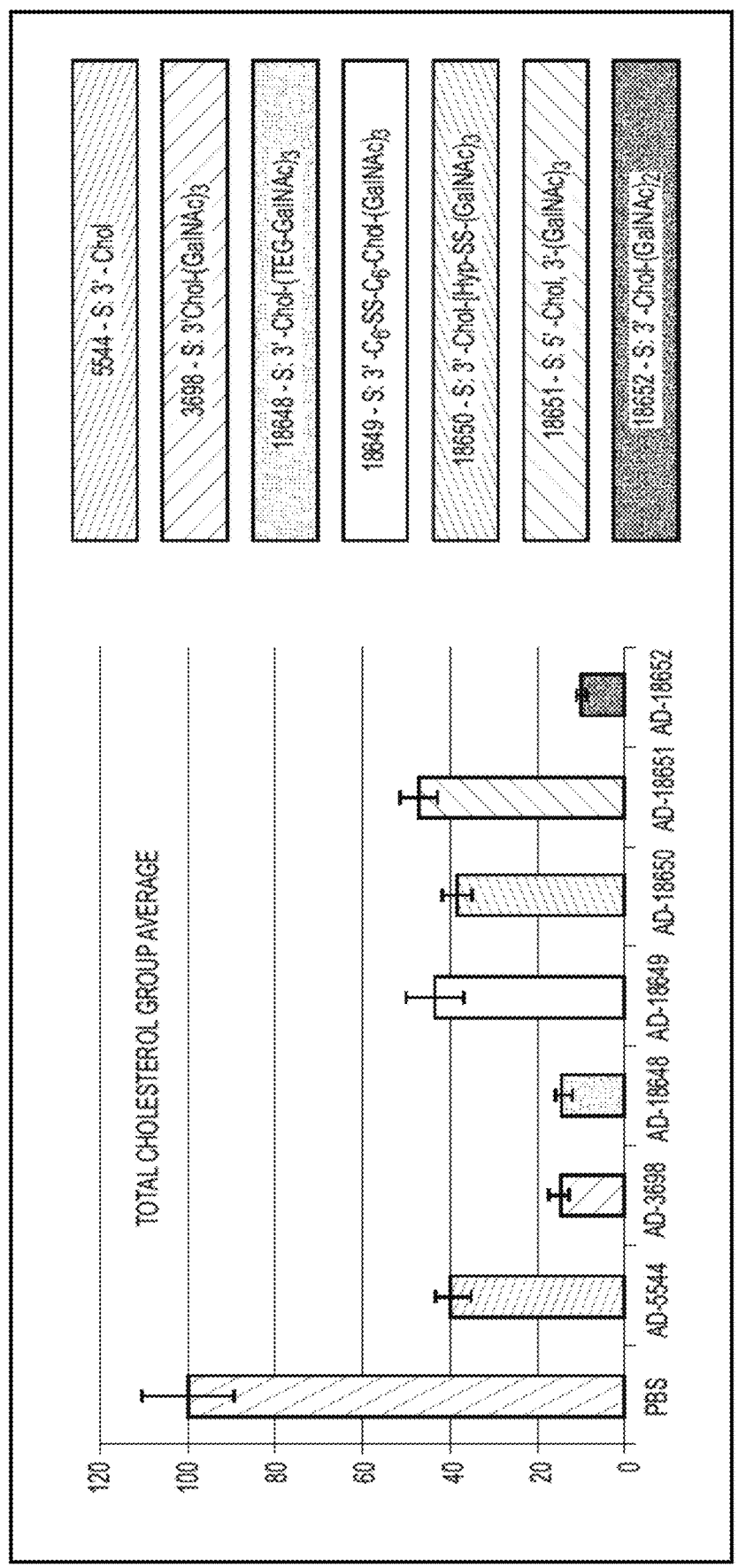

Example 17. Effect of Spacer, Linkage, Valency and Cholesterol Position on In Vivo Silencing with Carbohydrate Conjugated siRNAs Experimental design 100 mg/kg (in PBS), i.v. (bolus) once daily for 3 consecutive days Sac. 24 h after last dose bDNA assay of ApoB (normalized to GAPDH) in liver and jejunum samples total cholesterol in liver was also measured Results are show in FIGS. 41A-41B. Conjugates with a disulfide linkage showed similar inhibition of ApoB levels as with a cholesterol conjugate alone. This was lower than the inhibition seen with conjugates that did not have the disulfide linkage. This effect was seen regardless of where the disulfide linkage was placed. There was a clear preference for placement of cholesterol on the 3'-end of sense strand as when cholesterol was placed at 5'-end of sense strand a lowering of inhibition to cholesterol conjugate only levels was seen. Bivalent conjugates were as effective as the trivalent conjugates.

Example 18. Role of Ligand on In Vivo Gene Silencing (GalNAc Vs. Glucose)

Bivalent GalNAc and glucose conjugates (shown below) were used to confirm involvement of receptor targeting with GalNAc conjugates.

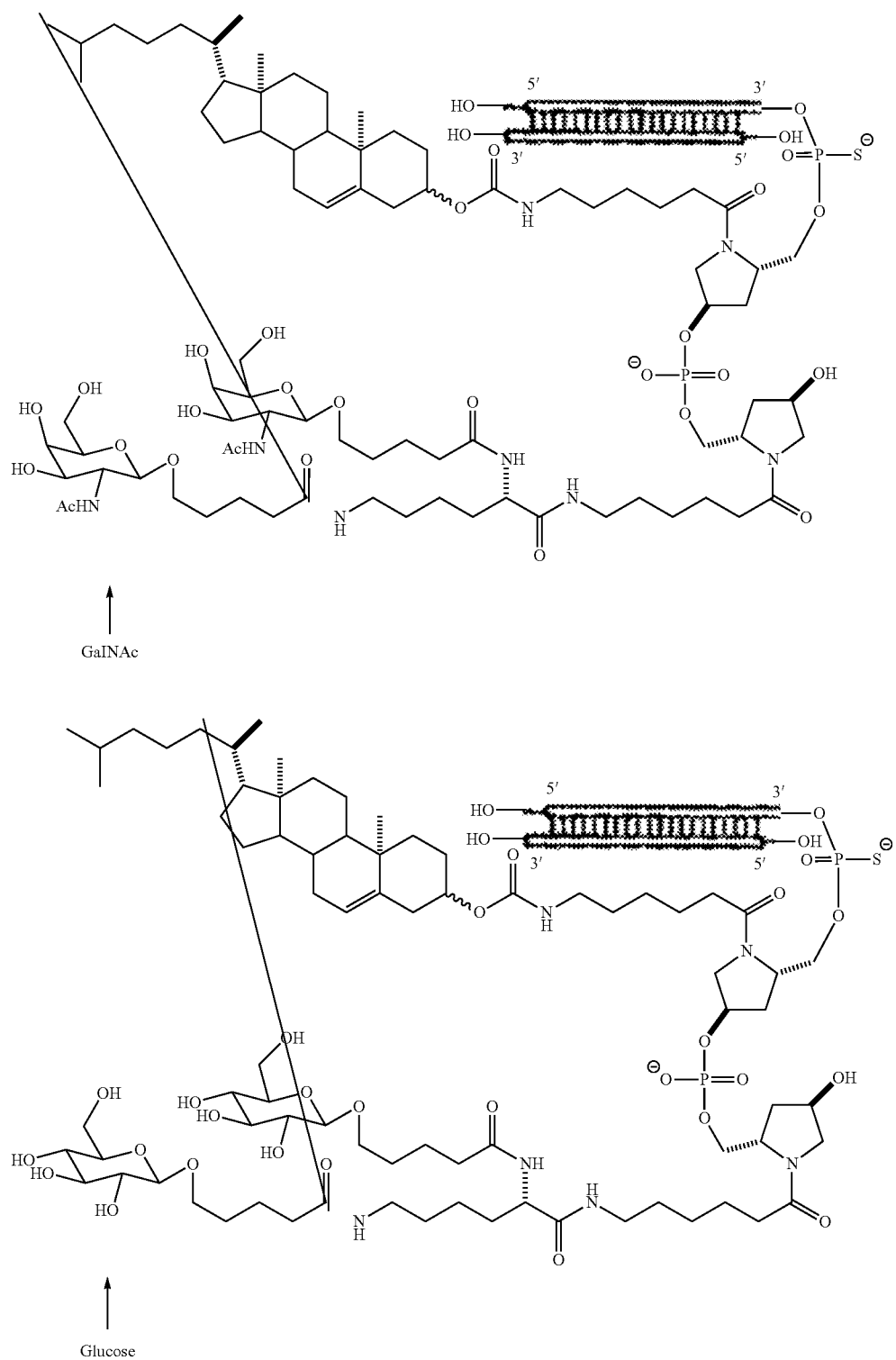

Experimental Design:
100 mg/kg (in PBS), i.v. (bolus) once daily for 3 consecutive days
Sac. 24 h after last dose
bDNA of ApoB (normalized to GAPDH) in liver and jejunum samples
total liver cholesterol levels also measured FIGS. 42 (A and B) shows the results. In the liver, GalNAc conjugate showed a higher inhibition of ApoB than the glucose conjugate or cholesterol only conjugate. However in the jejunum all three conjugates showed similar activity. As there are no ASGP-R1 in jejunum, activity seen could have been due to the presence of cholesterol in all three designs.

Example 19. Silencing Activity of Carbohydrate Conjugates In Vitro

Figure 43:
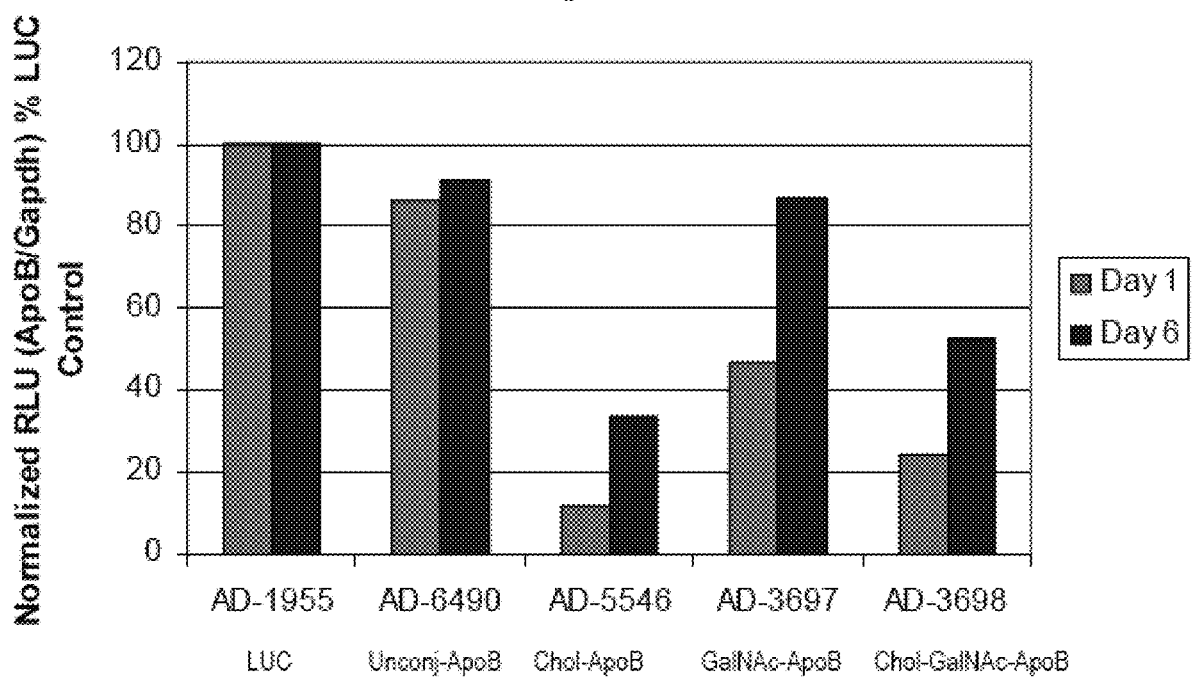
FIG. 43. In vitro silencing of ApoB with carbohydrate conjugated siRNAs.

Primary mouse hepatocytes were seeded in collagen coated 6-well dishes for either 1 or 6 days to down regulate the ASGPR. 5 mM CaCl$_2$) was used to activate the ASGR. ApoB or Luc siRNAs were added at 2 uM in serum free media and uptake allowed to proceed for 24 hours. Cells were lysed and ApoB mRNA knockdown evaluated by bDNA assay. A western blot was done as a control to confirm ASGR downregulation at day 6. FIG. 43 shows that all three conjugates (cholesterol alone, GalNAc alone and cholesterol-GalNac together) showed ApoB mRNA silencing at day 1. After several days in culture, ability of GalNAc conjugates to silence is impaired consistent with downregulation of receptors such as the ASGR known to occur with extended culture times of primary cells. Cholesterol conjugate also showed some reduction in the ability to silence at day 6. The following siRNAs were used:
AD-1955 (control, −/−)
AD-6490 (control, −/Cy3)
AD-5546 (Chol/Cy3)
AD-3697 (GalNAc/Cy3)
AD-3698 (GalNAc+Chol/Cy3)

Figure 44:
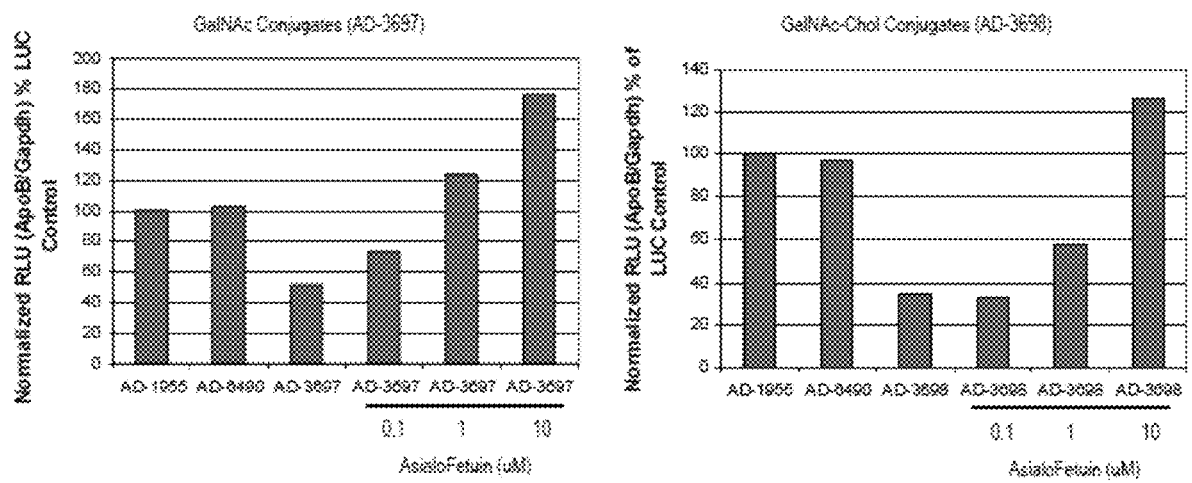
FIG. 44. Competition of carbohydrate conjugated siRNAs with ASGR ligand Asilofetuin (ASF) during in vitro uptake.

Example 20. Competition of Carbohydrate Conjugated siRNAs with ASGR Ligand Asilofetuin (ASF) During In Vitro Uptake Primary mouse hepatocytes were seeded in collagen coated 6-well dishes for 1 day. 5 mM CaCl$_2$) was used to activate the ASGR. The binding of GalNAc conjugated siRNAs was competed with increasing amounts Asialofetuin prior to and during siRNA incubation. ApoB and Luc siRNAs were added at 4 uM in serum free media and uptake allowed to proceed for 24 hours. Cells were lysed and ApoB mRNA knockdown evaluated by bDNA assay. FIG. 44 shows that presence of Asilofetuin competed with uptake of GalNAc and Cholesterol-GalNAc conjugated siRNAs. The ability to outcompete silencing of ApoB with Asilofetuin suggests an interaction between GalNAc and AGSR is important for mediating uptake and activity. The following siRNAs were used:
AD-1955 (control, −/−)
AD-6490 (control, −/Cy3)
AD-3697 (GalNAc/Cy3)
AD-3698 (GalNAc+Chol/Cy3)

Example 21. In Vitro Receptor Binding and Uptake of Carbohydrate Conjugates

Figure 45:
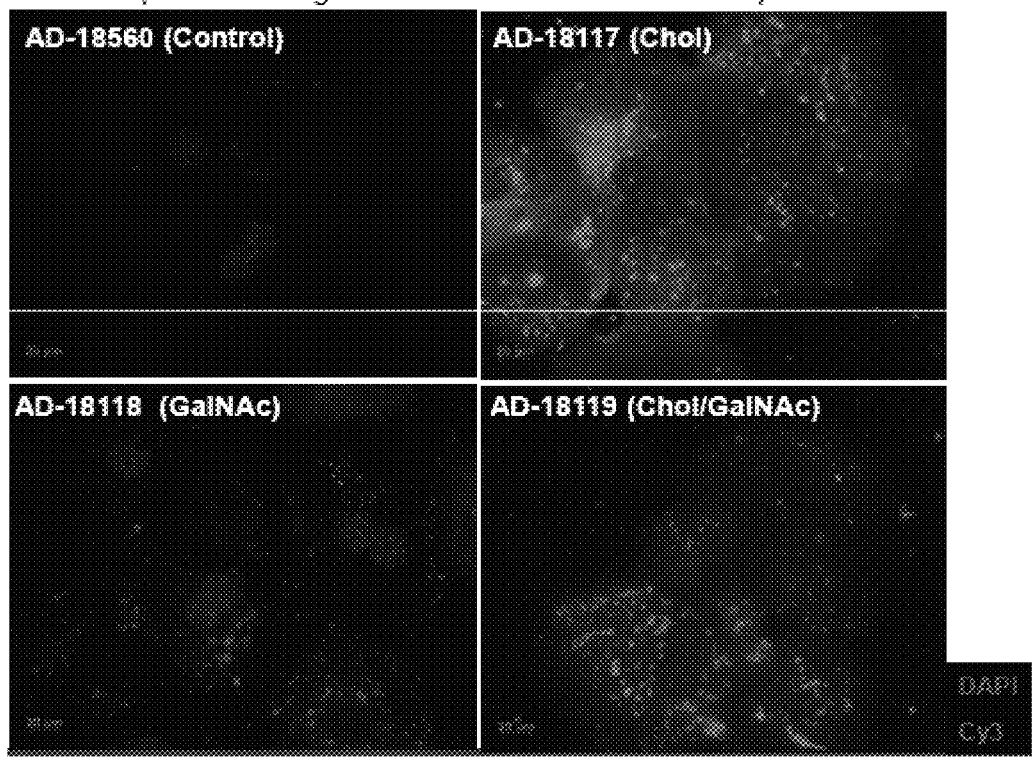
FIG. 45. In vitro receptor binding and uptake of carbohydrate conjugates.

Primary mouse hepatocytes were seeded in collagen coated 6-well dishes for either 1 or 6 days to down regulate the ASGPR. 5 mM CaCl$_2$ was used to activate the ASGR. ApoB duplexes were added at 1 uM in serum free media and uptake allowed to proceed for 6 hours. After uptake was complete, cells were fixed in 3.7% PFA and counter stained with DAPI. As can be seen in FIG. 45, Cy3 labeled siRNAs comprising either a cholesterol conjugate (AD-18117) or a cholsaterol+GalNAc conjugate (AD-18119) were taken up much more effectively than a Cy3 labeled siRNA without a conjugate (AD-18560) or with a GalNAc conjugate only (AD-18118).

Example 22. In Vivo ApoB Gene Silencing with Galactose Conjugated siRNAs

Mice were injected by IV bolus at 50 mg/kg. The galactose conjugated siRNA shown in FIG. 46A was synthesized from compound 207. FIG. 46 B shows that siRNA comprising both a cholesterol and galactose conjugate led to gene silencing in comparison to siRNA comprising only the galactose conjugate.

---

We claim:

1. A modified RNAi agent comprising a sense strand and an antisense strand, wherein:

the antisense strand targets an HBV mRNA;

all of the nucleotide sugars of the RNAi agent are 2'-modified, wherein each 2'-modification is independently selected from the group consisting of 2'-H, 2'-(2-methoxyethoxy), 2'-OCH$_3$, 2'-O-allyl, 2'—C— allyl, and 2'-fluoro; and at least one of the sense and antisense strands is conjugated to at least one targeting ligand that consists of two or more building blocks connected to a biantennary or triantennary branched linker, wherein the two or more building blocks are selected from the group consisting of:

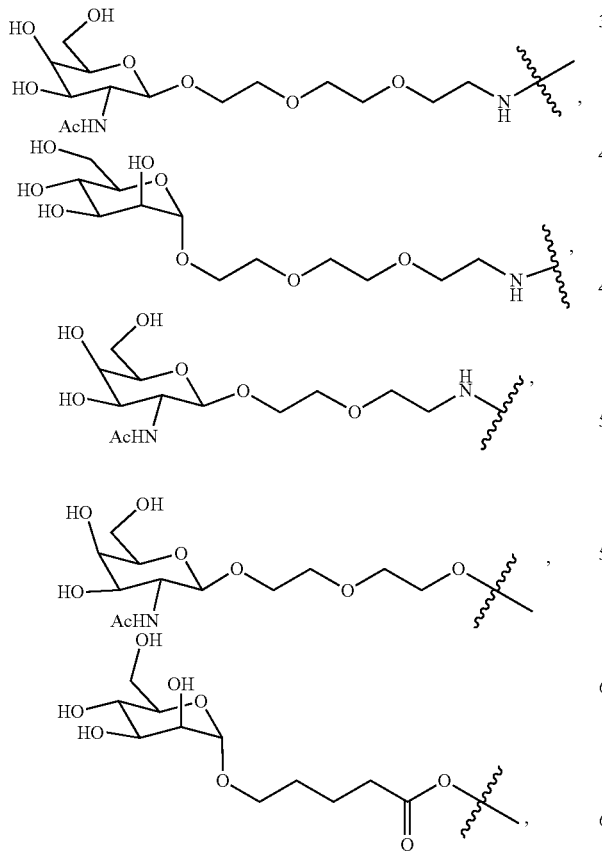

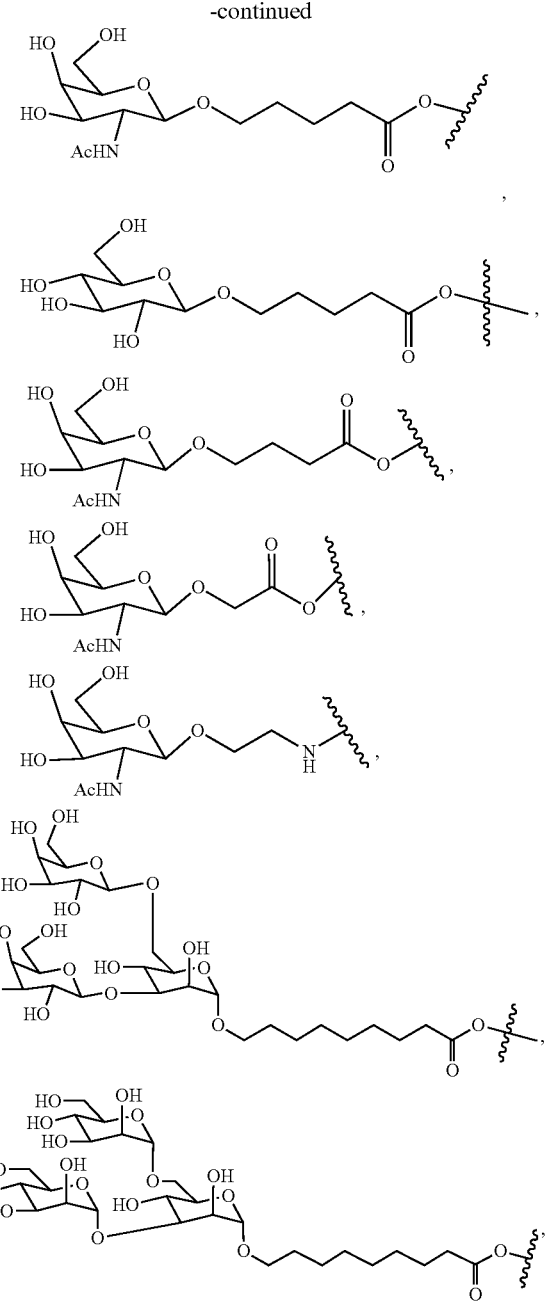

and

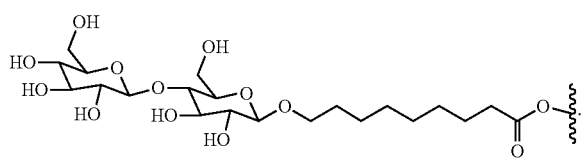 [SMILES: *OC(=O)CCCCCCCCOC1OC(CO)C(OC2OC(CO)C(O)C(O)C2O)C(O)C1O]

wherein the biantennary branched linker consists of a branched carbon atom connected to the building blocks through one or more of —C(O)—, —NH—, —O—, —NHC(O)—, and —(CH$_2$)$_x$— where x is 1-4, and wherein the triantennary branched linker consists of a branched carbon atom connected to the building blocks through one or more of —C(O)—, —NH—, —O—, —NHC(O)—, and —(CH$_2$)$_x$— where x is 1-4.

2. The modified RNAi agent of claim 1, wherein the targeting ligand is at the 3'-end of the sense strand.

3. The modified RNAi agent of claim 1, wherein the targeting ligand is at the 5'-end of the sense strand.

4. The modified RNAi agent of claim 1, wherein each 2'-modification is independently selected from the group consisting of 2'-OCH$_3$ and 2'-fluoro.

5. The modified RNAi agent of claim 1, wherein the targeting ligand consists of three building blocks connected to a biantennary or triantennary branched linker.

6. The modified RNAi agent of claim 5, wherein the targeting ligand is prepared by reacting a building block precursor compound selected from the group consisting of:

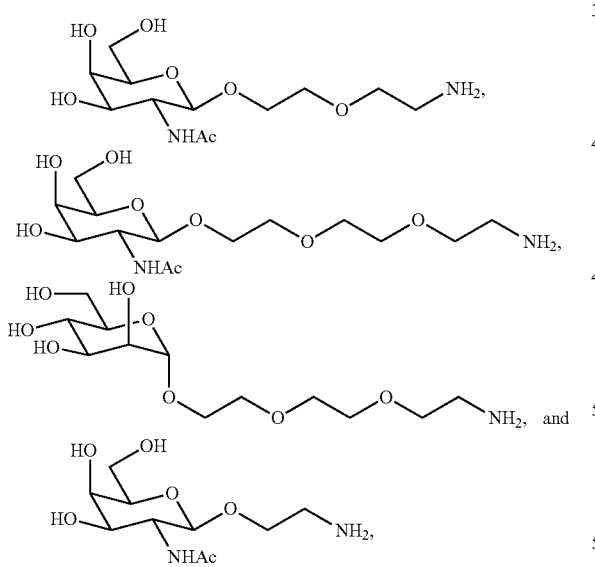

or a salt thereof, wherein each hydroxyl group of the building block precursor compound is protected with a hydroxyl protecting group, with a biantennary or triantennary branched linker compound that contains a terminal carboxylic acid group in each branch of the branched linker compound, via an amidation reaction.

7. The modified RNAi agent of claim 6, wherein the building block precursor compound is selected from the group consisting of:

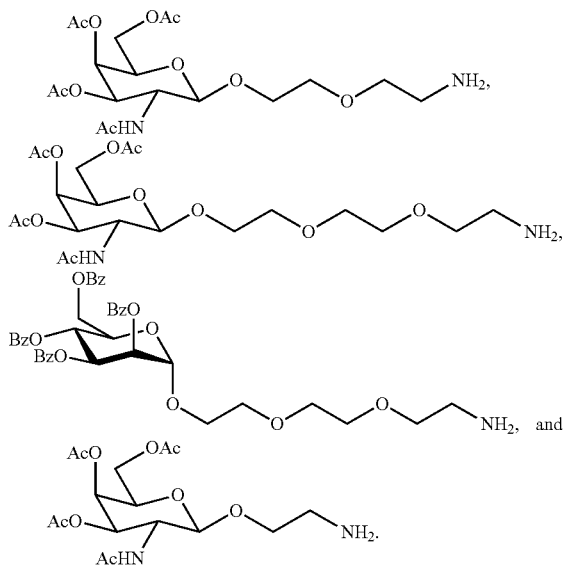

8. The modified RNAi agent of claim 5, wherein the targeting ligand is prepared by reacting a building block precursor compound having the formula,

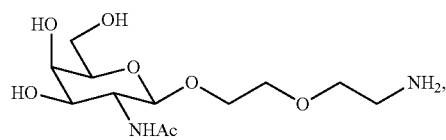 [SMILES: CC(=O)NC1C(OCCOCCN)OC(CO)C(O)C1O]

or a salt thereof, wherein each hydroxyl group of the building block precursor compound is protected with a hydroxyl protecting group, with a biantennary or triantennary branched linker compound that contains a terminal carboxylic acid group in each branch of the branched linker compound, via an amidation reaction.

9. The modified RNAi agent of claim 8, wherein the building block precursor compound is

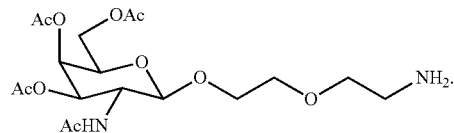 [SMILES: CC(=O)NC1C(OCCOCCN)OC(COC(C)=O)C(OC(C)=O)C1OC(C)=O]

10. The modified RNAi agent of claim 5, wherein the targeting ligand is prepared by reacting a building block precursor compound having the formula,

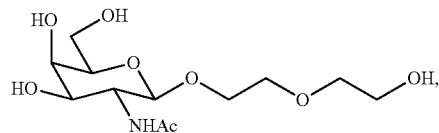 [SMILES: CC(=O)NC1C(OCCOCCO)OC(CO)C(O)C1O]

or a salt thereof, wherein each hydroxyl group of the N-acetyl galactosamine moiety of the building block precursor compound is protected with a hydroxyl protecting group, with a biantennary or triantennary branched linker compound that contains a terminal hydroxyl group in each branch of the branched linker compound, via a dehydration reaction.

11. The modified RNAi agent of claim 10, wherein the building block precursor compound is

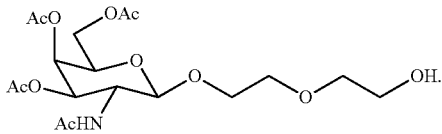 [SMILES: CC(=O)NC1C(OCCOCCO)OC(COC(C)=O)C(OC(C)=O)C1OC(C)=O]

12. The modified RNAi agent of claim 5, wherein the targeting ligand is prepared by reacting a building block precursor compound selected from the group consisting of:

or a salt thereof, wherein each hydroxyl group of the building block precursor compound is protected with a hydroxyl protecting group, with a biantennary or triantennary branched linker compound that contains a terminal amine group in each branch of the branched linker compound, via an amidation reaction.

13. The modified RNAi agent of claim 12, wherein the building block precursor compound is selected from the group consisting of:

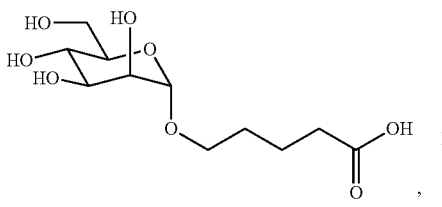
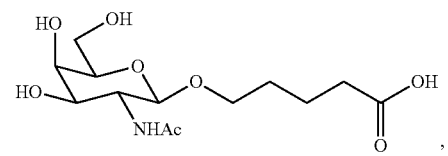
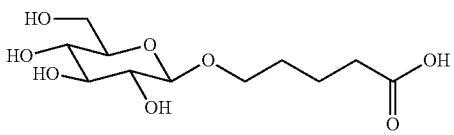
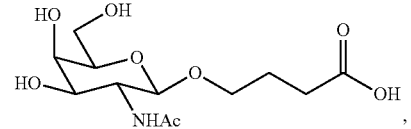
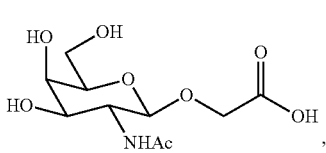
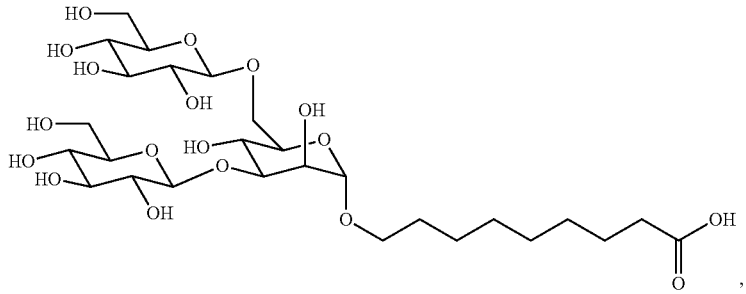
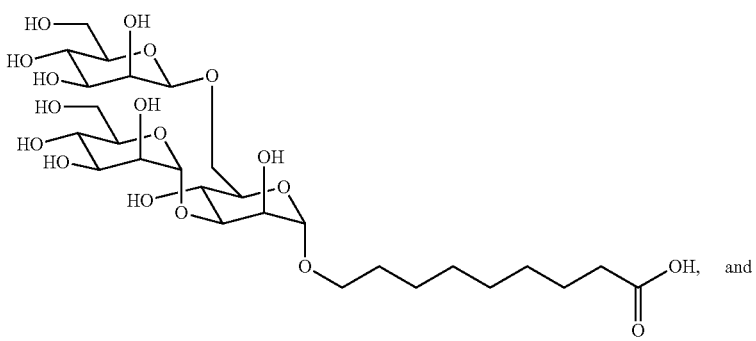, and
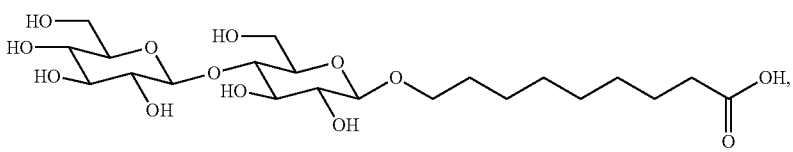

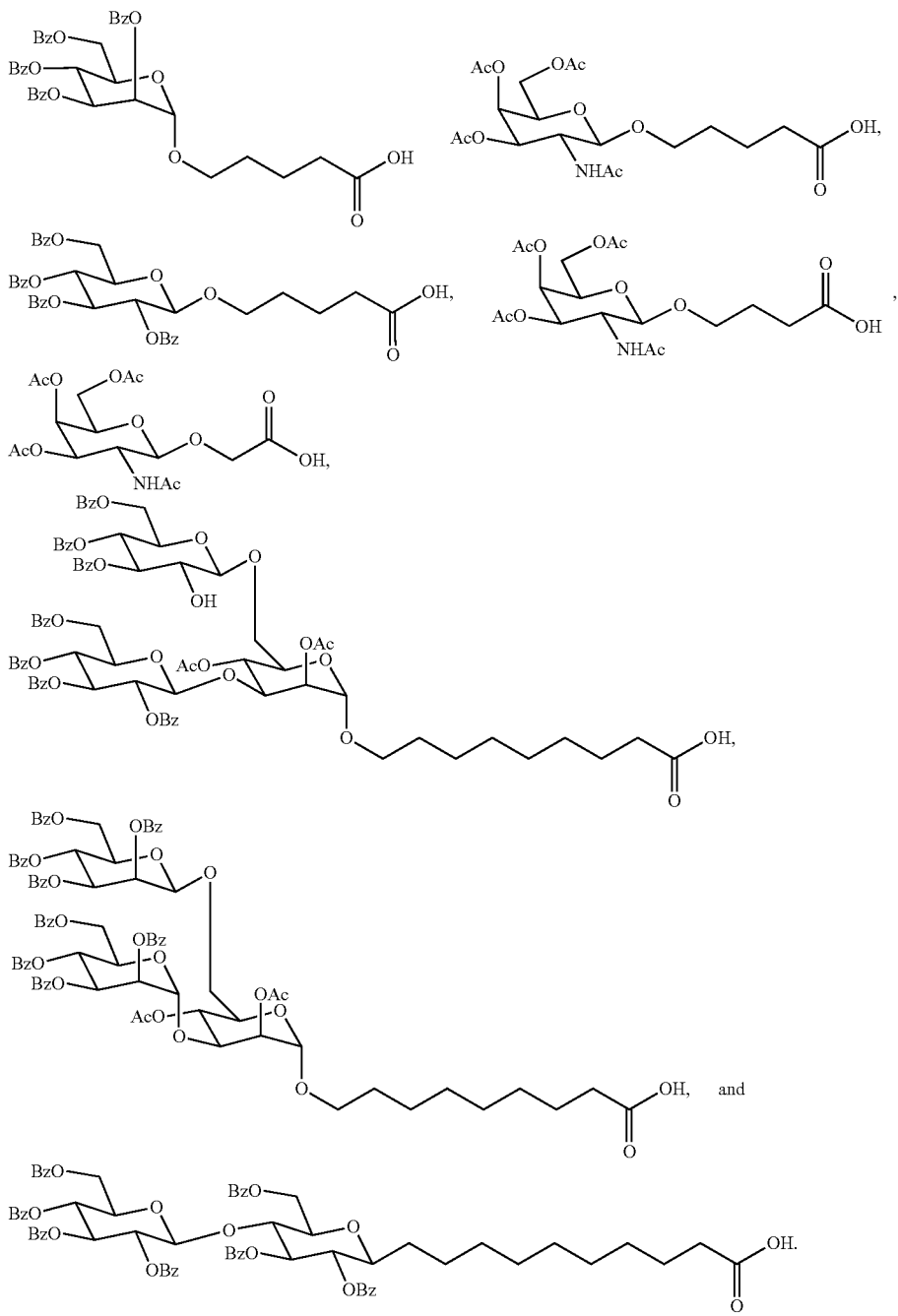

14. The modified RNAi agent of claim 1, wherein the antisense strand has 3 or fewer mismatches with respect to the HBV mRNA; and the sense strand that is sufficiently complementary with the antisense strand to form the double-stranded modified RNAi agent.

15. The modified RNAi agent of claim 14, wherein each of the sense and antisense strands is independently 17 to 25 nucleotides in length.

16. The modified RNAi agent of claim 15, wherein the sense and antisense strands form a duplex region of 17 to 23 nucleotide pairs in length.

17. The modified RNAi agent of claim 15, wherein the sense and antisense strands form a duplex region of 21 nucleotide pairs in length.

18. The modified RNAi agent of claim 16, comprising no overhang, or one or two 3' overhangs of 2 or 3 nucleotides in length.

19. The modified RNAi agent of claim 1, wherein the sense or antisense strand, or both, comprise a terminal modification suitable for modulating resistance to degradation.

20. The modified RNAi agent of claim 1, comprising one or more phosphorothioate modifications within one or both of the 3' or 5' terminal regions of the sense strand, the antisense strand, or both strands.

21. The modified RNAi agent of claim 1, wherein the sense strand is conjugated with a targeting ligand that consists of two or three building blocks connected to a biantennary or triantennary branched linker, wherein the building blocks are selected from the group consisting of:

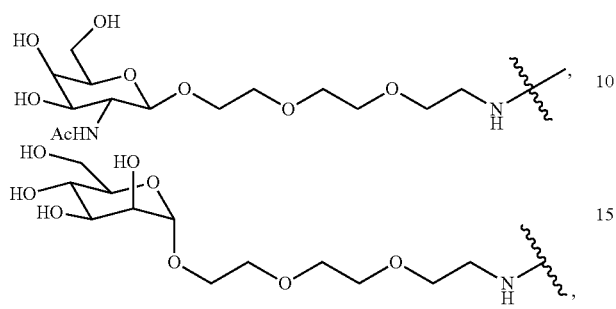

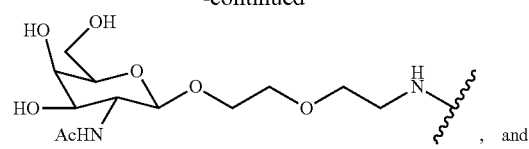

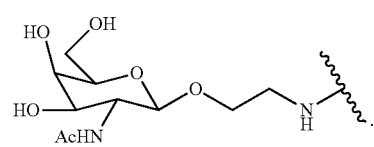

22. A pharmaceutical composition comprising the modified RNAi agent of claim 1 in combination with a pharmaceutically acceptable carrier or excipient.

* * * * *